US010000467B2

(12) United States Patent
Hermanson et al.

(10) Patent No.: US 10,000,467 B2
(45) Date of Patent: Jun. 19, 2018

(54) CYANINE COMPOUNDS

(71) Applicants: Pierce Biotechnology, Inc., Rockford, IL (US); Dyomics GmbH, Jena (DE)

(72) Inventors: Greg Hermanson, Loves Park, IL (US); Peter T. Czerney, Weimar (DE); Surbhi Desai, Rockford, IL (US); Matthias S. Wenzel, Jena (DE); Boguslawa R. Dworecki, Rockford, IL (US); Frank G. Lehmann, Jena (DE); Marie Christine Nlend, Rockford, IL (US)

(73) Assignees: Pierce Biotechnology, Inc., Rockford, IL (US); Dyomics GmbH, Jena (DE)

( * ) Notice: Subject to any disclaimer, the term of this patent is extended or adjusted under 35 U.S.C. 154(b) by 35 days.

(21) Appl. No.: 15/042,328

(22) Filed: Feb. 12, 2016

(65) Prior Publication Data

US 2016/0176852 A1    Jun. 23, 2016
US 2017/0114038 A9    Apr. 27, 2017

Related U.S. Application Data

(63) Continuation of application No. 13/780,338, filed on Feb. 28, 2013, now abandoned.

(60) Provisional application No. 61/718,805, filed on Oct. 26, 2012, provisional application No. 61/606,210, filed on Mar. 2, 2012.

(51) Int. Cl.
| | |
|---|---|
| *C07D 401/14* | (2006.01) |
| *A61K 49/04* | (2006.01) |
| *C07D 209/18* | (2006.01) |
| *C07D 403/06* | (2006.01) |
| *C07D 403/08* | (2006.01) |
| *A61K 49/12* | (2006.01) |
| *A61K 49/14* | (2006.01) |
| *A61K 49/16* | (2006.01) |
| *A61K 49/22* | (2006.01) |
| *C07K 16/40* | (2006.01) |
| *G01N 33/58* | (2006.01) |
| *A61K 47/68* | (2017.01) |

(52) U.S. Cl.
CPC ........ *C07D 401/14* (2013.01); *A61K 47/6871* (2017.08); *A61K 49/04* (2013.01); *A61K 49/12* (2013.01); *A61K 49/143* (2013.01); *A61K 49/16* (2013.01); *A61K 49/221* (2013.01); *C07D 209/18* (2013.01); *C07D 403/06* (2013.01); *C07D 403/08* (2013.01); *C07K 16/40* (2013.01); *G01N 33/582* (2013.01); *C07K 2317/76* (2013.01)

(58) Field of Classification Search
CPC .. C07D 207/18; C07D 207/30; C07D 295/00; C07D 403/06; A61K 49/00
See application file for complete search history.

(56) References Cited

U.S. PATENT DOCUMENTS

| | | |
|---|---|---|
| 1,524,791 A | 2/1925 | Konig |
| 4,839,265 A | 6/1989 | Ohno et al. |
| 4,981,977 A | 1/1991 | Southwick et al. |
| 5,268,486 A | 12/1993 | Waggoner et al. |
| 5,486,616 A | 1/1996 | Waggoner et al. |
| 5,556,959 A | 9/1996 | Brush et al. |
| 5,569,587 A | 10/1996 | Waggoner |
| 5,569,766 A | 10/1996 | Waggoner et al. |
| 5,627,027 A | 5/1997 | Waggoner |
| 5,846,737 A | 12/1998 | Kang |
| 5,972,838 A | 10/1999 | Pearce et al. |
| 5,986,086 A | 11/1999 | Brush et al. |
| 6,048,982 A | 4/2000 | Waggoner |
| 6,083,485 A | 7/2000 | Licha et al. |
| 6,136,612 A | 10/2000 | Della Ciana et al. |
| 6,225,050 B1 | 5/2001 | Waggoner |
| 6,258,340 B1 | 7/2001 | Licha et al. |
| 6,342,326 B1 | 1/2002 | Milton |
| 6,534,041 B1 | 3/2003 | Licha et al. |
| 6,641,093 B2 | 11/2003 | Coudrais |
| 6,939,532 B2 | 9/2005 | Achilefu et al. |
| 6,974,873 B2 | 12/2005 | Leung et al. |
| 6,977,305 B2 | 12/2005 | Leung et al. |
| 7,172,907 B2 | 2/2007 | Chen et al. |
| 7,175,831 B2 * | 2/2007 | Achilefu ................. C09B 23/02 424/1.11 |
| 7,175,835 B1 | 2/2007 | Simouldis et al. |
| 7,566,790 B2 | 7/2009 | Leung et al. |
| 7,671,214 B2 | 3/2010 | Leung et al. |
| 7,745,640 B2 | 6/2010 | Czerney et al. |
| 7,750,163 B2 | 7/2010 | West et al. |
| 7,790,893 B2 | 9/2010 | Leung et al. |
| 7,820,824 B2 | 10/2010 | Leung et al. |
| 7,855,293 B2 | 12/2010 | Haalck et al. |
| 7,927,830 B2 | 4/2011 | Cheung et al. |
| 7,951,959 B2 | 5/2011 | Brush et al. |

(Continued)

FOREIGN PATENT DOCUMENTS

| | | |
|---|---|---|
| AU | 2006200511 A1 | 2/2006 |
| DE | 4445065 A1 | 6/1996 |

(Continued)

OTHER PUBLICATIONS

Second Office Action with English translation issued in Chinese Patent Application No. 201380005497.X (dated Apr. 28, 2016, 21 pages).

(Continued)

*Primary Examiner* — Michael G Hartley
*Assistant Examiner* — Jagadishwar R Samala
(74) *Attorney, Agent, or Firm* — McNeill Baur PLLC

(57) ABSTRACT

Compounds used as labels with properties comparable to known fluorescent compounds. The compounds can be conjugated to proteins and nucleic acids for biological imaging and analysis. Synthesis of the compounds, formation and use of the conjugated compounds, and specific non-limiting examples of each are provided.

11 Claims, 27 Drawing Sheets
(7 of 27 Drawing Sheet(s) Filed in Color)

(56) References Cited

U.S. PATENT DOCUMENTS

| | | | |
|---|---|---|---|
| 8,431,111 | B2 | 4/2013 | Nairne et al. |
| 9,097,667 | B2 * | 8/2015 | Mao .................... C09B 11/08 |
| 2001/0055567 | A1 | 12/2001 | Licha et al. |
| 2002/0064794 | A1 | 5/2002 | Leung et al. |
| 2002/0077487 | A1 | 6/2002 | Leung et al. |
| 2004/0241095 | A1 | 12/2004 | Achilefu et al. |
| 2006/0004188 | A1 | 1/2006 | Leung et al. |
| 2006/0099638 | A1 | 5/2006 | Leung et al. |
| 2007/0128659 | A1 | 6/2007 | Czerney et al. |
| 2007/0178512 | A1 | 8/2007 | Leung et al. |
| 2007/0203343 | A1 | 8/2007 | West et al. |
| 2008/0233050 | A1 | 9/2008 | Achilefu et al. |
| 2009/0035809 | A1 | 2/2009 | Leung et al. |
| 2009/0305410 | A1 | 12/2009 | Mao et al. |
| 2010/0040547 | A1 * | 2/2010 | Frangioni ........... C07D 209/08 424/9.1 |
| 2010/0196282 | A1 | 8/2010 | Nairne |
| 2010/0215585 | A1 | 8/2010 | Frangioni |
| 2010/0267937 | A1 | 10/2010 | West et al. |
| 2010/0303732 | A1 | 12/2010 | Bahner |
| 2011/0065876 | A1 | 3/2011 | Okamoto et al. |
| 2011/0065896 | A1 | 3/2011 | Licha et al. |
| 2011/0171678 | A1 | 7/2011 | Leung et al. |
| 2011/0178397 | A1 | 7/2011 | Bahner |
| 2012/0114563 | A1 | 5/2012 | Carter et al. |
| 2014/0106349 | A1 | 4/2014 | Mao et al. |

FOREIGN PATENT DOCUMENTS

| | | |
|---|---|---|
| DE | 19717904 A1 | 10/1998 |
| DE | 19926460 A1 | 12/1999 |
| DE | 10046215 B4 | 4/2004 |
| EP | 1152008 A2 | 11/2001 |
| EP | 1181940 A2 | 2/2002 |
| EP | 1322710 B1 | 1/2007 |
| EP | 1770129 A2 | 4/2007 |
| EP | 1792949 A2 | 6/2007 |
| EP | 1801165 A2 | 6/2007 |
| EP | 2325263 A1 | 5/2011 |
| GB | 434875 | 9/1935 |
| JP | 03217837 | 9/1991 |
| JP | Hei 5-313304 | 11/1993 |
| WO | 96/17628 A1 | 6/1996 |
| WO | 98/48838 A1 | 11/1998 |
| WO | 00/075237 A2 | 12/2000 |
| WO | 02/26891 A1 | 4/2002 |
| WO | 02/32466 A1 | 4/2002 |
| WO | 2004/065491 | 8/2004 |
| WO | 2004/065491 A1 | 8/2004 |
| WO | 2005/044923 A1 | 5/2005 |
| WO | 2005/103162 A1 | 11/2005 |
| WO | 2006/020947 A2 | 2/2006 |
| WO | 2009/016180 | 2/2009 |
| WO | 2009/016181 | 2/2009 |
| WO | 2009/078970 A1 | 6/2009 |
| WO | 2010/091126 A1 | 8/2010 |
| WO | 2010/106169 | 9/2010 |
| WO | 2012/088007 A1 | 6/2012 |
| WO | 2012/129128 A1 | 9/2012 |

OTHER PUBLICATIONS

Extended European Search Report and Written Opinion issued in European Patent Application No. 16169172.0 (dated Jul. 14, 2016, 7 pages).
Rejection Decision with English translation issued in Chinese Patent Application No. 201380005497.X (dated Nov. 2, 2016, 11 pages).
Extended European Search Report, European Patent Application No. 15198169.3 (dated Mar. 29, 2016, 8 pages).
Alvarez-Maubecin et al. Functional Coupling Between Neurons and Glia. The Journal of Neuroscience. Jun. 1, 2000, 20(11):4091-4098.
Bharaj et al. Rapid sequencing of the p53 gene with a new automated DNA sequencer. Clinical Chemistry. 44:7 1397-1403 (1998).
Product brochure titled CF™ Dyes the next-generation dyes for protein labeling. Apr. 6, 2009.
Burns et al. An Integrated Nanoliter DNA Analysis Device. Science. vol. 282, pp. 484-487, Oct. 16, 1998.
DeRisi et al. Exploring the Metabolic and Genetic Control of Gene Expression on a Genomic Scale. Science. vol. 278, pp. 680-686, Oct. 24, 1997.
Examination Report, Great Britain Application No. 1214580.1, dated May 31, 2013 (4 pages).
Fradelizi et al. Quantitative Measurement of Proteins by Western Blotting with Cy5™-Coupled Secondary Antibodies. BioTechniques. 26:484-494 Mar. 1999.
Gragg. Synthesis of Near-Infrared Heptamethine Cyanine Dyes. Chemistry Theses. Paper 28 (Apr. 26, 2010.). http://digitalarchive.gsu.edu/chemistry_theses/28.
Hermanson, Bioconjugate Techniques, 2nd Ed., London, Elsevier Inc. 2008, pp. 464-474; 690-697.
International Preliminary Report on Patentability, PCT/US/2011/065975, dated Jul. 4, 2013 (8 pages).
International Preliminary Report on Patentability, PCT/US2013/028252, dated Sep. 12, 2014, 8 pages.
International Search Report and Written Opinion for PCT/US2011/065975, dated Mar. 15, 2012 (8 pages).
International Search Report and Written Opinion PCT/US2013/028252, issued by the European Patent Office, and dated Apr. 25, 2013 (12 pages).
Licha et al. Synthesis and Characterization of Cyanine Dye—Poly(ethylene Glycol) Conjugates as Contrast Agents for in Vivo Fluorescence Imaging. SPIE 3196 (1998) 98-102.
MacBeath and Schreiber. Printing Proteins as Microarrays for High-Throughput Function Determination. Science. vol. 289, pp. 1760-1763, Sep. 8, 2000.
Manders et al. Direct Imaging of DNA in Living Cells Reveals the Dynamics of Chromosome Formation. The Journal of Cell Biology. vol. 144, No. 5, Mar. 8, 1999 813-821.
Mank et al., Visible Diode Laser-Induced Fluorescence Detection in Liquid Chromatography after Precolumn Derivatization of Amines. Anal. Chem. vol. 67, pp. 1742-1748, 1995.
Mujumdar et al. Cyanine Dye Labeling Reagents: Sulfoindocyanine Succinimidyl Esters. Bioconjug Chem. vol. 4, No. 2, pp. 105-111, Mar./Apr. 1993.
Patonay et al. Noncovalent Labeling of Biomolecules with Red and Near-Infrared Dyes. Molecules. 9, 40-49, 2004.
Pharmacia Biotech. Table of Contents p. 294 and p. 295 of the Pharmacia Biotech Catalogue. 1994.
Riefke et al. Tumor Detection with Cyanine Dye-Poly(ethylene Glycol) Conjugates as Contrast Agents for Near-Infrared Imaging. SPIE 3196 (1998) 103-110.
Roman et al. Non-Radioisotopic AFLP Method Using PCR Primers Fluorescently Labeled with Cy™ 5. BioTechniques. vol. 26, No. 2, pp. 236-238, Feb. 1999.
Schena et al. Parallel human genome analysis: Microarray-based expression monitoring of 1000 genes. Proc. Natl. Acad. Sci. USA. vol. 93, pp. 10614-10619, Oct. 1996.
Search Report issued by the German Patent Office for App #10 2006 029 454.8 dated Oct. 10, 2006 (with English language summary), 5 pages.
Search Report issued by the German Patent Office for App #10 2006 057 345.5 dated May 21, 2007 (with English language summary), 5 pages.
Shao et al. Monofunctional Carbocyanine Dyes for Bio- and Bioorthogonal Conjugation. Bioconjugate Chemistry. 19(12): 2487-2491, Dec. 2008.
Strekowski (ed.), Heterocyclic Polymethine Dyes: Synthesis, Properties and Applications, (2008) Springer-Verlag, Berlin Heidelberg, pp. 1-241.
United Kingdom Search and Examination Report GB1214580.1, dated Nov. 22, 2012, 4 pages.

(56) References Cited

OTHER PUBLICATIONS

Voss et al. Automated Cycle Sequencing with Taquenase™: Protocols for Internal Labeling, Dye Primer and "Doublex" Simultaneous. BioTechniques. vol. 23, No. 2, pp. 312-318, Aug. 1997.
Wilchek and Miron. Activation of Sepharose with N, N'-disuccinimidyl carbonate. Applied Biochemistry and Biotechnology, vol. 11, pp. 191-193 (1985).

* cited by examiner

A    B

1

2

3

4

A  B

1

2

3

4

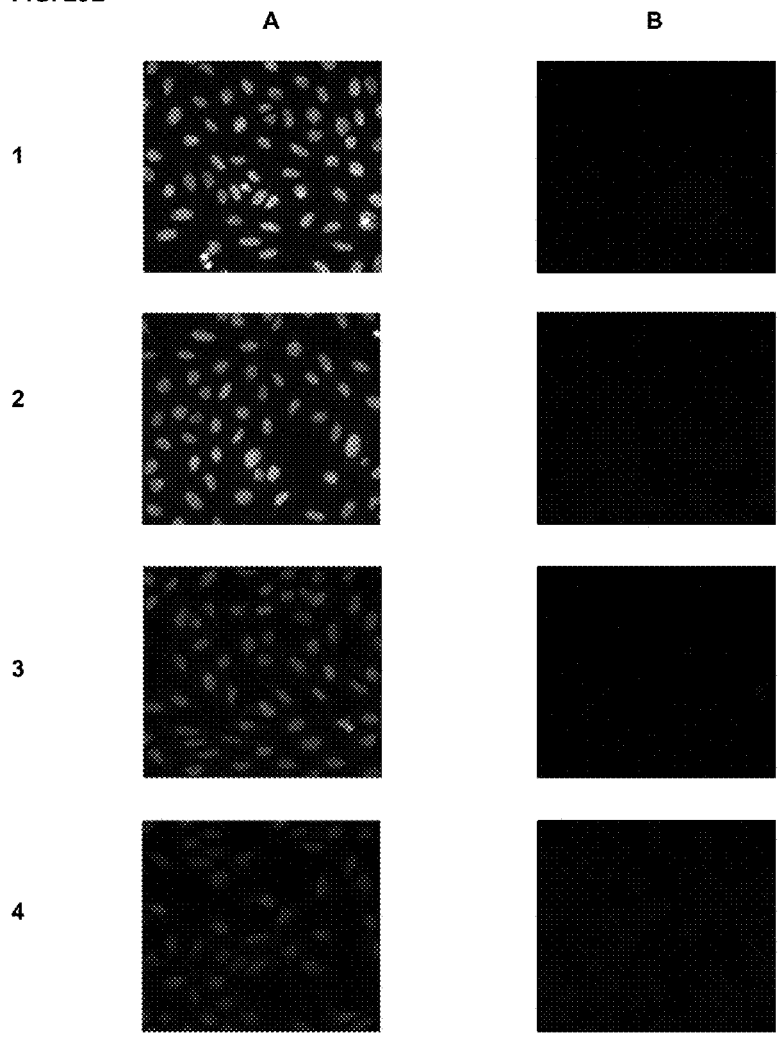

A                             B

1

2

3

4

US 10,000,467 B2

CYANINE COMPOUNDS

This application is a continuation of U.S. application Ser. No. 13/780,338 filed Feb. 28, 2013, which claims priority to U.S. application Ser. Nos. 61/606,210 filed Mar. 2, 2012 and 61/718,805 filed Oct. 26, 2012, each of which is expressly incorporated by reference herein in its entirety.

Compounds useful as labels with properties comparable to known fluorescent compounds are disclosed. The compounds can be conjugated to proteins and nucleic acids for biological imaging and analysis. Synthesis of the compounds, formation and use of the conjugated compounds, and specific non-limiting examples of each are disclosed.

Compounds that react with biomolecules (e.g., antigens, antibodies, DNA-segments with the corresponding complimentary species for measuring enzyme kinetics, receptor-ligand interactions, nucleic acid hybridization kinetics in vitro as well as in vivo, etc.), termed labels or dyes, are useful for, e.g., pharmacological characterization of receptors and drugs, binding data, etc. Compounds such as xanthylium salts (U.S. Pat. No. 5,846,737) and/or cyanines (U.S. Pat. No. 5,627,027) are used for such applications, but aggregate and form dimers, especially in aqueous solution, due to planarity of their π-system. Compounds that have insufficient hydrophilicity undergo non-specific interactions with various surfaces, resulting in problems when attempting purify the corresponding conjugate, and an unsatisfactory signal to noise ratio.

Efforts are directed to reducing undesirable properties by introducing substituents that increase the hydrophilicity of the compounds. For example, sulfonic acid function substituents have been introduced into the cyanine chromophore. U.S. Pat. No. 6,083,485 (Licha) and U.S. Pat. Nos. 6,977,305 and 6,974,873 (Molecular Probes) disclose cyanine compounds having one of the common methyl groups in the 3-position of the terminal indole heterocycle substituted by a ω-carboxyalkyl function, and in which the previously present (e.g. in Cy3 or Cy5) N-alkyl or N-ω-carboxyalkyl functions are replaced by N-w-alkyl sulfonic acid functions. WO 05/044923 discloses cyanine compounds having the common methyl substituent in the 3-position of the terminal indole heterocycle substituted by a N-ω-alkyl sulfonic acid function. In these publications, cyanine compounds having more than two sulfonic acid function substituents exhibited higher solubility and correspondingly a lower tendency to dimer formation, in comparison to cyanine compounds (Cy3, Cy5) described in U.S. Pat. No. 5,627,027.

The disclosed cyanine compounds are useful as labels in optical, especially fluorescence optical, determination and detection methods. The compounds have high hydrophilicity, high molar absorbance, high photo-stability, and high storage stability. These compounds can be excited by monochromatic (e.g., lasers, laser diodes) or polychromatic (e.g., white light sources) light in the ultraviolet (UV), visible, and near infrared (NIR) spectral region to generate emission of fluorescence light.

Typical application methods are based on the reaction of the compounds with biomolecules such as proteins (e.g., antigens, antibodies, etc.), DNA and/or RNA segments, etc. with the corresponding complimentary species. Thus, among other embodiments, the compounds are useful to measure enzyme kinetics, receptor-ligand interactions, and nucleic acid hybridization kinetics in vitro and/or in vivo. The compounds are useful for the pharmacological characterization of receptors and/or drugs.

Applications include, but are not limited to, uses in medicine, pharmacy, biological sciences, materials sciences, environmental control, detection of organic and inorganic micro samples occurring in nature, etc.

The following nomenclature is used to describe embodiments: 550 Compound 1/X, 550 Compound 2/X, 550 Compound 3/X, 550 Compound 4/X, 550 Compound 5/X, 550 Compound 6/X, 650 Compound 1/X, 650 Compound 2/X, 650 Compound 3/X, 650 Compound 4/X, 650 Compound 5/X, 650 Compound 6/X, 755 Compound 1/X, 755 Compound 2/X, 755 Compound 3/X, 755 Compound 4/X, 755 Compound 5/X, 755 Compound 6/X, where 550, 650, and 755 Compounds comprise a polymethine chain of 3 carbon, 5 carbon, and 7 carbon atoms, respectively; the first number is the length of an ethylene glycol, diethylene glycol, or (poly)ethylene glycol (collectively referred to herein as PEG) on an indole N, e.g. 1 is ethylene glycol ($PEG_1$) on an indole N, 2 is diethylene glycol ($PEG_2$) on an indole N, 3 is (poly)ethylene glycol (poly=3, $PEG_3$) on an indole N, 4 is (poly)ethylene glycol (poly=4, $PEG_4$) on an indole N, 5 is (poly)ethylene glycol (poly=5, $PEG_5$) on an indole N, and 6 is (poly)ethylene glycol (poly=6, $PEG_6$) on an indole N; and X is the total number of PEG groups on the compound. For example, 650 Compound 4/4 contains $PEG_4$ on an indole N and a total of four PEG groups on the compound.

In one embodiment, the cyanine compounds have, in an N-position of one heterocycle, ethylene glycol, diethylene glycol, or an ethylene glycol polymer (i.e., poly(ethylene) glycol, abbreviated as PEG), and the other heterocycle has, in a N-position, a function for conjugating the compound to a biomolecule, and an ethylene glycol, diethylene glycol, or an ethylene glycol polymer (i.e., poly(ethylene) glycol, abbreviated as PEG) in another position of the cyanine compound. In one embodiment, the cyanine compound has, in any position of the compound, at least one sulfo and/or sulfoalkyl. In one embodiment, the cyanine compound has, in any position of the compound, a sulfonamide and/or carboxamide comprising an ethylene glycol group or an ethylene glycol polymer (i.e., poly(ethylene) glycol, abbreviated as PEG), either directly or indirectly attached to the compound. Indirect attachment indicates use of a linker, direct attachment indicates lack of such a linker. A linker can be any moiety.

In one embodiment, the cyanine compounds have, in an N-position of one heterocycle, an ethylene glycol, diethylene glycol, or ethylene glycol polymer (i.e., poly(ethylene) glycol, abbreviated as PEG), and the other heterocycle has, in a N-position, an ethylene glycol, diethylene glycol, or ethylene glycol polymer (i.e., poly(ethylene) glycol, abbreviated as PEG) and a function for conjugating the compound to a biomolecule, and an ethylene glycol group or an ethylene glycol polymer (i.e., poly(ethylene) glycol, abbreviated as PEG) in another position of the benzocyanine compound. In one embodiment, the cyanine compound has, in any position of the compound, at least one sulfo and/or sulfoalkyl. In one embodiment, the cyanine compound has, in any position of the compound, a sulfonamide and/or carboxamide comprising an ethylene glycol, diethylene glycol, or ethylene glycol polymer (i.e., poly(ethylene) glycol, abbreviated as PEG), either directly or indirectly attached to the compound. Indirect attachment indicates use of a linker, direct attachment indicates lack of such a linker. A linker can be any moiety.

BRIEF DESCRIPTION OF THE DRAWINGS

The patent of application file contains at least one drawing executed in color. Copies of this patent or patent application publication with color drawing(s) will be provided by the office upon request and payment of the necessary fee.

FIGS. 20A-D show immunofluorescence assay results with inventive compounds and commercial dyes in one embodiment.

Figure 1A:
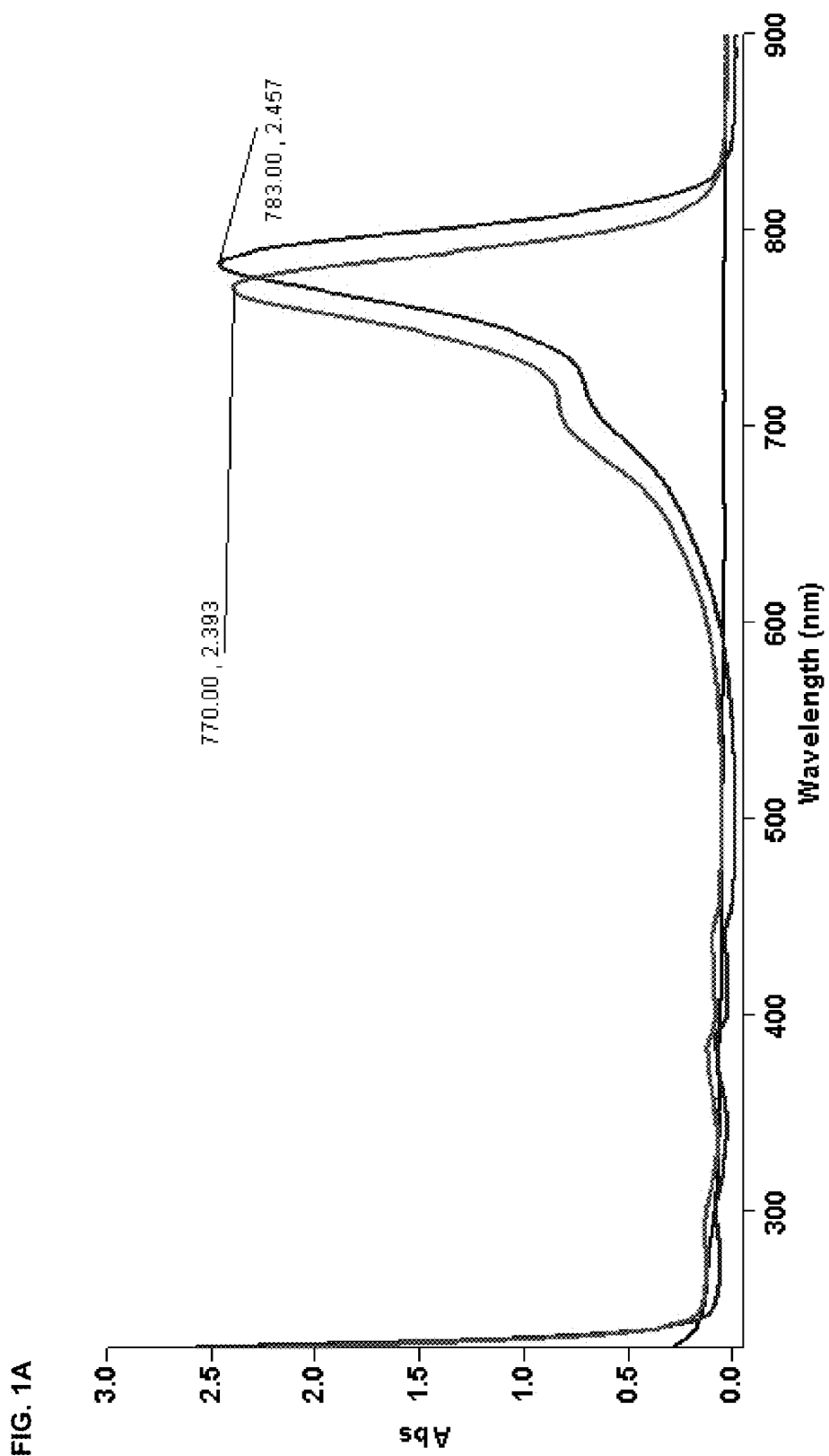
FIGS. 1A-C show the absorption maxima for compounds and conjugated compounds.

Unless otherwise noted, reference to general formulas (e.g., I, II, III, IV, V, and VI, each subsequently described), encompasses their respective a, b, c, etc. structures.

In one embodiment, the compound is a compound according to general formula Ia with "a" indicating the chain from the right indole N terminates in COX:

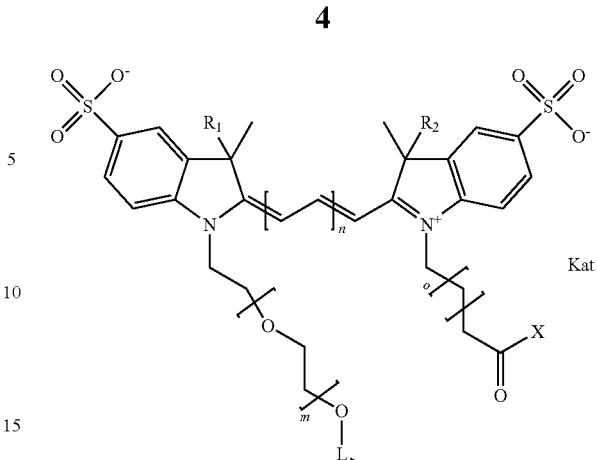

or general formula Ib with "b" indicating the chain from the right indole N terminates in OH:

where each of $R^1$ and $R^2$ is the same or different and is independently selected from the group consisting of an aliphatic, heteroaliphatic, sulfoalkyl, heteroaliphatic with terminal $SO_3$, a PEG group P-L-Z where P is selected from an ethylene glycol group, a diethylene glycol group, and a (poly)ethylene glycol group where the (poly)ethylene glycol group is $(CH_2CH_2O)_s$ where s is an integer from 3-6 inclusive, a sulfonamide group -L-$SO_2$NH—P-L-Z, and a carboxamide group -L-CONH—P-L-Z; where L is selected from the group consisting of a divalent linear (—$(CH_2)_o$—, o=0 to 15), crossed, or cyclic alkane group that can be substituted by at least one atom selected from the group consisting of oxygen, substituted nitrogen, and/or sulfur; where Z is selected from the group consisting of H, $CH_3$, alkyl, heteroalkyl, $NH_2$, —$COO^-$, —COOH, —COSH, CO—NH—$NH_2$, —COF, —COCl, —COBr, —COI, —COO-Su (succinimidyl/sulfo-succinimidyl), —COO-STP (4-sulfo-2,3,5,6-tetrafluorophenyl), —COO-TFP (2,3,5,6-tetrafluorophenyl), —COO-benzotriazole, —CO-benzotriazole, —CONR'—CO—$CH_2$—I, —CONR'R", —CONR'—biomolecule, —CONR'-L-COO, —CONR'-L-COOH, —CONR'-L-COO-Su, —CONR'-L-COO-STP, —CONR'-L-COO-TFP, —CONR'-L-CONR"$_2$, —CONR'-L-CO-biomolecule, —CONR'-L-CO—NH—$NH_2$, —CONR'-L-OH, —CONR'-L-O-phosphoramidite, —CONR'-L-CHO, —CONR'-L-maleimide, and —CONR'-L-NH—CO—$CH_2$—I; R' and R" is selected from the group consisting of H, aliphatic group, and heteroaliphatic group, and the biomolecule is a protein, antibody, nucleotide, oligonucleotide, biotin, or hapten; X is selected from the group consisting of —OH, —SH, —NH$_2$, —NH—NH$_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, and —NR-L-NH—CO—CH2-I, where R is —H or an aliphatic or heteroaliphatic group; Kat is a number of Na$^+$, K$^+$, Ca$^{2+}$, ammonia, or other cation(s) needed to compensate the negative charge brought by the cyanine; m is an integer from 0 to 5 inclusive; o is an integer from 0 to 12 inclusive; and n is an integer from 1 to 3 inclusive; with the proviso that at least one of R$^1$ and R$^2$ contains a PEG group.

In one embodiment, the PEG group is selected from —C—C—O—C (ethylene glycol with terminal methyl), —C—C—O—C—C—O—C (diethylene glycol with terminal methyl), —C—C—O—C—C—O—C—C—O—C ((poly)ethylene glycol (3) with terminal methyl), —C—C—O—C—C—O—C—C—O—C—C—O—C ((poly)ethylene glycol (4) with terminal methyl), —C—C—O—C—C—O—C—C—O—C—C—O—C—C—O—C((poly)ethylene glycol (5) with terminal methyl), or C—C—O—C—C—O—C—C—O—C—C—O—C—C—O—C—C—O—C((poly)ethylene glycol (6) with terminal methyl). In one embodiment, the PEG group P may be either uncapped, e.g., lack a terminal methyl, or may be capped with an atom or group other than a methyl. In one embodiment, the PEG group P terminates with a Z group, where Z is selected from H, CH$_3$, a CH$_3$ group, alkyl, or a heteroalkyl group.

In one embodiment the compound is general formula I where R1 is sulfoalkyl and R2 is a PEG group; X is —OH, —NHS, —O-TFP, or —NR-L-maleimide; m is 0; o is 3; and n is 1. In one embodiment the compound is general formula I where R1 is sulfoalkyl and R2 is a PEG group; X is —OH, —NHS, —O-TFP, or —NR-L-maleimide; m is 1; o is 3; and n is 1. In one embodiment, the compound is general formula I where R1 is sulfoalkyl and R2 is a PEG group; X is —OH, —NHS, —O-TFP, or —NR-L-maleimide; m is 2; o is 3; and n is 1. In one embodiment the compound is general formula I where R1 is sulfoalkyl and R2 is a PEG group; X is —OH, —NHS, —O-TFP, or —NR-L-maleimide; m is 3; o is 3; and n is 1. In one embodiment the compound is general formula I where R1 is sulfoalkyl and R2 is a PEG group; X is —OH, —NHS, —O-TFP, or —NR-L-maleimide; m is 4; o is 3; and n is 1. In one embodiment the compound is general formula I, where R1 is sulfoalkyl and R2 is a PEG group; X is —OH, —NHS, —O-TFP, or —NR-L-maleimide; m is 5; o is 3; and n is 1.

In one embodiment the compound is general formula I where R1 is sulfoalkyl and R2 is a PEG group; X is —OH, —NHS, —O-TFP, or —NR-L-maleimide; m is 0; o is 3; and n is 2. In one embodiment the compound is general formula I where R1 is sulfoalkyl and R2 is a PEG group; X is —OH, —NHS, —O-TFP, or —NR-L-maleimide; m is 1; o is 3; and n is 2. In one embodiment the compound is general formula I, where R1 is sulfoalkyl and R2 is a PEG group; X is —OH, —NHS, —O-TFP, or —NR-L-maleimide; m is 2; o is 3; and n is 2. In one embodiment the compound is general formula I where R1 is sulfoalkyl and R2 is a PEG group; X is —OH, —NHS, —O-TFP, or —NR-L-maleimide; m is 3; o is 3; and n is 2. In one embodiment the compound is general formula I where R1 is sulfoalkyl and R2 is a PEG group; X is —OH, —NHS, —O-TFP, or —NR-L-maleimide; m is 4; o is 3; and n is 2. In one embodiment the compound is general formula I where R1 is sulfoalkyl and R2 is a PEG group; X is —OH, —NHS, —O-TFP, or —NR-L-maleimide; m is 5; o is 3; and n is 2.

In one embodiment the compound is general formula I where R1 is sulfoalkyl and R2 is a PEG group; X is —OH, —NHS, —O-TFP, or —NR-L-maleimide; m is 0; o is 3; and n is 3. In one embodiment the compound is general formula I where R1 is sulfoalkyl and R2 is a PEG group; X is —OH, —NHS, —O-TFP, or —NR-L-maleimide; m is 1; o is 3; and n is 3. In one embodiment the compound is general formula I where R1 is sulfoalkyl and R2 is a PEG group; X is —OH, —NHS, —O-TFP, or —NR-L-maleimide; m is 2; o is 3; and n is 3. In one embodiment the compound is general formula I where R1 is sulfoalkyl and R2 is a PEG group; X is —OH, —NHS, —O-TFP, or —NR-L-maleimide; m is 3; o is 3; and n is 3. In one embodiment, the compound is general formula I, where R1 is sulfoalkyl and R2 is a PEG group; X is —OH, —NHS, —O-TFP, or —NR-L-maleimide; m is 4; o is 3; and n is 3. In one embodiment the compound is general formula I where R1 is sulfoalkyl and R2 is a PEG group; X is —OH, —NHS, —O-TFP, or —NR-L-maleimide; m is 5; o is 3; and n is 3.

In one embodiment the compound is general formula I where R1 is methyl and R2 is a PEG group; X is —OH, —NHS, —O-TFP, or —NR-L-maleimide; m is 0; o is 3; and n is 1. In one embodiment the compound is general formula I where R1 is methyl and R2 is a PEG group; X is —OH, —NHS, —O-TFP, or —NR-L-maleimide; m is 1; o is 3; and n is 1. In one embodiment the compound is general formula I where R1 is methyl and R2 is a PEG group; X is —OH, —NHS, —O-TFP, or —NR-L-maleimide; m is 2; o is 3; and n is 1. In one embodiment the compound is general formula I where R1 is methyl and R2 is a PEG group; X is —OH, —NHS, —O-TFP, or —NR-L-maleimide; m is 3; o is 3; and n is 1. In one embodiment, the compound is general formula I, where R1 is methyl and R2 is a PEG group; X is —OH, —NHS, —O-TFP, or —NR-L-maleimide; m is 4; o is 3; and n is 1. In one embodiment the compound is general formula I where R1 is methyl and R2 is a PEG group; X is —OH, —NHS, —O-TFP, or —NR-L-maleimide; m is 5; o is 3; and n is 1.

In one embodiment the compound is general formula I where R1 is methyl and R2 is a PEG group; X is —OH, —NHS, —O-TFP, or —NR-L-maleimide; m is 0; o is 3; and n is 2. In one embodiment the compound is general formula I where R1 is methyl and R2 is a PEG group; X is —OH, —NHS, —O-TFP, or —NR-L-maleimide; m is 1; o is 3; and n is 2. In one embodiment the compound is general formula I where R1 is methyl and R2 is a PEG group; X is —OH, —NHS, —O-TFP, or —NR-L-maleimide; m is 2; o is 3; and n is 2. In one embodiment the compound is general formula I where R1 is methyl and R2 is a PEG group; X is —OH, —NHS, —O-TFP, or —NR-L-maleimide; m is 3; o is 3; and n is 2. In one embodiment the compound is general formula I where R1 is methyl and R2 is a PEG group; X is —OH, —NHS, —O-TFP, or —NR-L-maleimide; m is 4; o is 3; and n is 2. In one embodiment the compound is general formula I where R1 is methyl and R2 is a PEG group; X is —OH, —NHS, —O-TFP, or —NR-L-maleimide; m is 5; o is 3; and n is 2.

In one embodiment, the compound is general formula I where R1 is methyl and R2 is a PEG group; X is —OH, —NHS, —O-TFP, or —NR-L-maleimide; m is 0; o is 3; and n is 3. In one embodiment the compound is general formula I where R1 is methyl and R2 is a PEG group; X is —OH, —NHS, —O-TFP, or —NR-L-maleimide; m is 1; o is 3; and n is 3. In one embodiment the compound is general formula I where R1 is methyl and R2 is a PEG group; X is —OH, —NHS, —O-TFP, or —NR-L-maleimide; m is 2; o is 3; and n is 3. In one embodiment, the compound is general formula I where R1 is methyl and R2 is a PEG group; X is —OH, —NHS, —O-TFP, or —NR-L-maleimide; m is 3; o is 3; and n is 3. In one embodiment, the compound is general formula I where R1 is methyl and R2 is a PEG group; X is —OH, —NHS, —O-TFP, or —NR-L-maleimide; m is 4; o is 3; and n is 3. In one embodiment, the compound is general formula I where R1 is methyl and R2 is a PEG group; X is —OH, —NHS, —O-TFP, or —NR-L-maleimide; m is 5; o is 3; n is 3.

In one embodiment the compound is general formula I where R1 and R2 are PEG groups; X is —OH, —NHS, —O-TFP, or —NR-L-maleimide; m is 0; o is 3; and n is 1. In one embodiment the compound is general formula I where R1 and R2 are PEG groups; X is —OH, —NHS, —O-TFP, or —NR-L-maleimide; m is 1; o is 3; and n is 1. In one embodiment the compound is general formula I where R1 and R2 are PEG groups; X is —OH, —NHS, —O-TFP, or —NR-L-maleimide; m is 2; o is 3; and n is 1. In one embodiment the compound is general formula I where R1 and R2 are PEG groups; X is —OH, —NHS, —O-TFP, or —NR-L-maleimide; m is 3; o is 3; and n is 1. In one embodiment, the compound is general formula I, where R1 and R2 are PEG groups; X is —OH, —NHS, —O-TFP, or —NR-L-maleimide; m is 4; o is 3; and n is 1. In one embodiment the compound is general formula I where R1 and R2 are PEG groups; X is —OH, —NHS, —O-TFP, or —NR-L-maleimide; m is 5; o is 3; and n is 1.

In one embodiment the compound is general formula I where R1 and R2 are PEG groups; X is —OH, —NHS, —O-TFP, or —NR-L-maleimide; m is 0; o is 3; and n is 2. In one embodiment the compound is general formula I where R1 and R2 are PEG groups; X is —OH, —NHS, —O-TFP, or —NR-L-maleimide; m is 1; o is 3; and n is 2. In one embodiment the compound is general formula I where R1 and R2 are PEG groups; X is —OH, —NHS, —O-TFP, or —NR-L-maleimide; m is 2; o is 3; and n is 2. In one embodiment the compound is general formula I where R1 and R2 are PEG groups; X is —OH, —NHS, —O-TFP, or —NR-L-maleimide; m is 3; o is 3; and n is 2. In one embodiment the compound is general formula I where R1 and R2 are PEG groups; X is —OH, —NHS, —O-TFP, or —NR-L-maleimide; m is 4; o is 3; and n is 2. In one embodiment the compound is general formula I where R1 and R2 are PEG groups; X is —OH, —NHS, —O-TFP, or —NR-L-maleimide; m is 5; o is 3; and n is 2.

In one embodiment the compound is general formula I where R1 and R2 are PEG groups; X is —OH, —NHS, —O-TFP, or —NR-L-maleimide; m is 0; o is 3; and n is 3. In one embodiment the compound is general formula I where R1 and R2 are PEG groups; X is —OH, —NHS, —O-TFP, or —NR-L-maleimide; m is 1; o is 3; and n is 3. In one embodiment the compound is general formula I where R1 and R2 are PEG groups; X is —OH, —NHS, —O-TFP, or —NR-L-maleimide; m is 2; o is 3; and n is 3. In one embodiment the compound is general formula I where R1 and R2 are PEG groups; X is —OH, —NHS, —O-TFP, or —NR-L-maleimide; m is 3; o is 3; and n is 3. In one embodiment, the compound is general formula I, where R1 and R2 are PEG groups; X is —OH, —NHS, —O-TFP, or —NR-L-maleimide; m is 4; o is 3; and n is 3. In one embodiment the compound is general formula I where R1 and R2 are PEG groups; X is —OH, —NHS, —O-TFP, or —NR-L-maleimide; m is 5; o is 3; and n is 3.

In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 0; o is 3; and n is 1. In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 1; o is 3; and n is 1. In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 2; o is 3; and n is 1. In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 3; o is 3; and n is 1. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 4; o is 3; and n is 1. In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 5; o is 3; and n is 1.

In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 0; o is 3; and n is 2. In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 1; o is 3; and n is 2. In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 2; o is 3; and n is 2. In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 3; o is 3; and n is 2. In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 4; o is 3; and n is 2. In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 5; o is 3; and n is 2.

In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 0; o is 3; and n is 3. In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 1; o is 3; and n is 3. In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 2; o is 3; and n is 3. In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 3; o is 3; and n is 3. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 4; o is 3; and n is 3. In one embodiment the compound is general formula I where R1 is sulfoalkyl and R2 is a sulfonamide group -L-SO$_2$NH—P where P is a PEG group; X is —OH, —NHS, —O-TFP, or —NR-L-maleimide; m is 5; o is 3; and n is 3.

In one embodiment, an isolated enantiomeric mixture selected from diastereomer Ia of general formula Ia shown below:

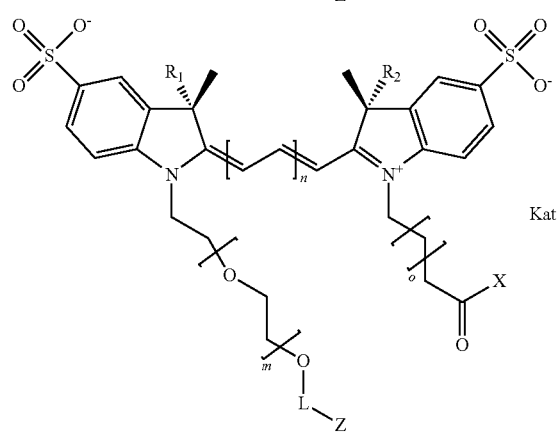

diastereomer Ib of general formula Ia shown below:

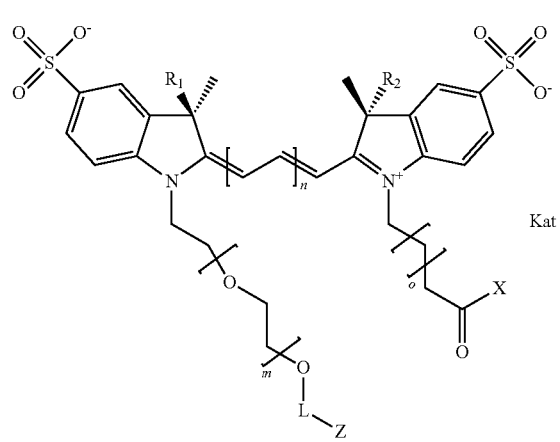

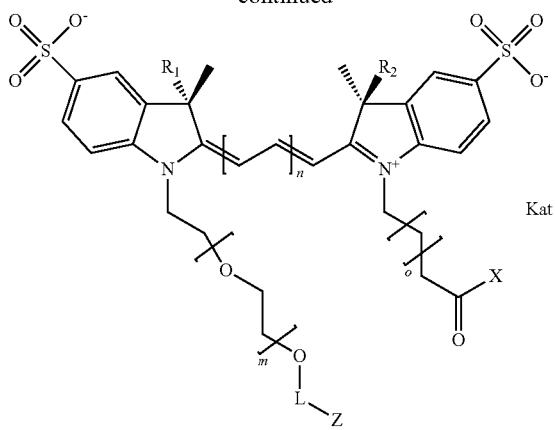

diastereomer Ic of general formula Ib shown below:

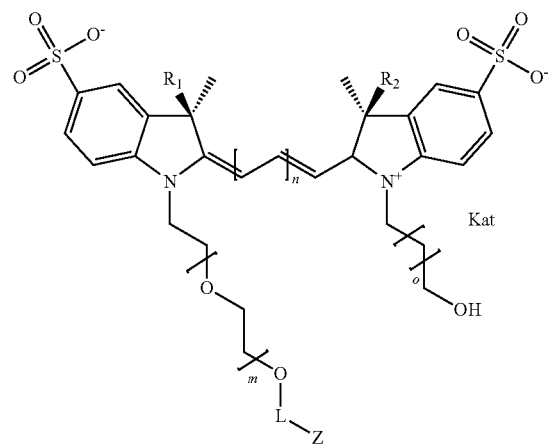

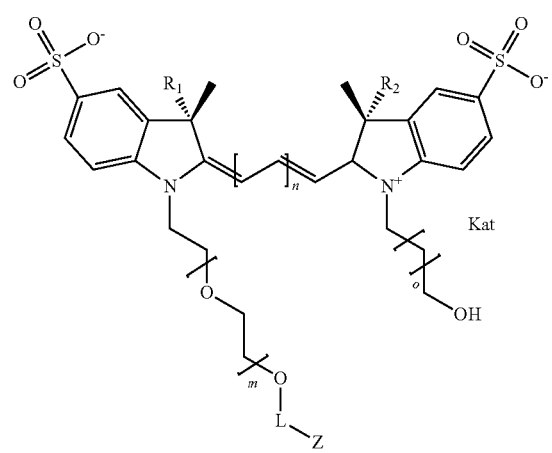

or diastereomer Id of general formula Ib shown below:

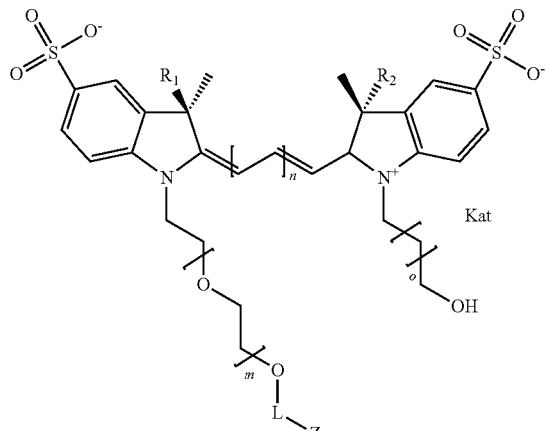

is provided, where each of $R^1$ and $R^2$ is the same or different and is independently selected from the group consisting of aliphatic, heteroaliphatic, sulfoalkyl, heteroaliphatic with terminal $SO_3$, a PEG group P-L-Z where P is selected from an ethylene glycol group, a diethylene glycol group, and a (poly)ethylene glycol group where the (poly)ethylene glycol group is $(CH_2CH_2O)_s$ where s is an integer from 3-6 inclusive, a sulfonamide group -L-$SO_2$NH—P-L-Z, and a carboxamide group -L-CONH—P-L-Z; where L is selected from the group consisting of a divalent linear (—$(CH_2)_o$—, o=0 to 15), crossed, or cyclic alkane group that can be substituted by at least one atom selected from the group consisting of oxygen, substituted nitrogen, and/or sulfur; where Z is selected from the group consisting of H, $CH_3$, alkyl, heteroalkyl, $NH_2$, —COO, —COOH, —COSH, CO—NH—$NH_2$, —COF, —COCl, —COBr, —COI, —COO-Su (succinimidyl/sulfosuccinimidyl), —COO-STP (4-sulfo-2,3,5,6-tetrafluorophenyl), —COO-TFP (2,3,5,6-tetrafluorophenyl), —COO-benzotriazole, —CO-benzotriazole, —CONR'—CO—$CH_2$—I, —CONR'R", —CONR'-biomolecule, —CONR'-L-COO, —CONR'-L-COOH, —CONR'-L-COO-Su, —CONR'-L-COO-STP, —CONR'-L-COO-TFP, —CONR'-CONR"$_2$, —CONR'-CO-biomolecule, —CONR'-CO—NH—$NH_2$, —CONR'-L-OH, —CONR'-L-O-phosphoramidite, —CONR'-L-CHO, —CONR'-L-maleimide, and —CONR'-L-NH—CO—$CH_2$—I; R' and R" is selected from the group consisting of —H, aliphatic, and heteroaliphatic, and the biomolecule is a protein, antibody, nucleotide, oligonucleotide, biotin, or hapten; X is selected from the group consisting of —OH, —SH, —$NH_2$, —NH—$NH_2$, —F, —Cl, —Br, I, —NHS (hydroxysuccinimidyl/sulfo-succinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, and —NR-L-NH—CO—CH2-I, where R is —H or an aliphatic or heteroaliphatic group; Kat is a number of $Na^+$, $K^+$, $Ca^{2+}$, ammonia, or other cation(s) needed to compensate the negative charge brought by the cyanine; m is an integer from 0 to 5 inclusive; o is an integer from 0 to 12 inclusive; and n is an integer from 1 to 3 inclusive; with the proviso that at least one of $R^1$ and $R^2$ contains a PEG group.

In one embodiment, the compound has general formula IIa with "a" indicating the chain from the right indole N terminates in COX:

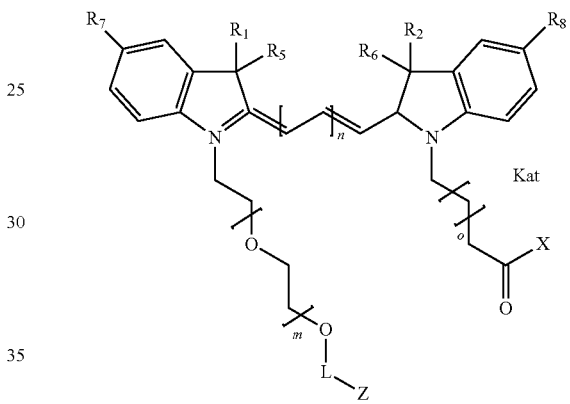

or general formula IIb with "b" indicating the chain from the right indole N terminates in COH:

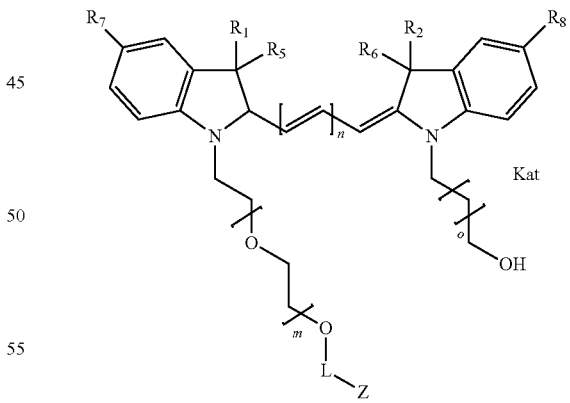

where each of $R^1$, $R^2$, $R^5$, and $R^6$ is the same or different and is independently selected from the group consisting of aliphatic, heteroaliphatic, sulfoalkyl, heteroaliphatic with terminal $SO_3$, a PEG group P-L-Z where P is selected from an ethylene glycol group, a diethylene glycol group, and a (poly)ethylene glycol group where the (poly)ethylene glycol group is $(CH_2CH_2O)_s$ where s is an integer from 3-6 inclusive, a sulfonamide group -L-$SO_2$NH—P-L-Z, and a carboxamide group -L-CONH—P-L-Z; each of $R^7$ and $R^8$ is the

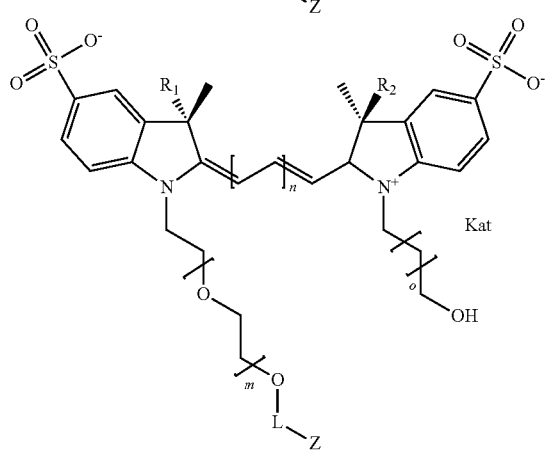

same or different and is independently selected from the group consisting of H, $SO_3$, a PEG group P-L-Z where P is selected from an ethylene glycol group, a diethylene glycol group, and a (poly)ethylene glycol group where the (poly) ethylene glycol group is $(CH_2CH_2O)_s$, where s is an integer from 3-6 inclusive, a sulfonamide group $—SO_2NH—P-L-Z$, and a carboxamide group $—CONH—P-L-Z$; where L is selected from the group consisting of a divalent linear $(—(CH_2)_o—$, o=0 to 15), crossed, or cyclic alkane group that can be substituted by at least one atom selected from the group consisting of oxygen, substituted nitrogen, and/or sulfur; where Z is selected from the group consisting of H, $CH_3$, alkyl, heteroalkyl, $NH_2$, —COO, —COOH, —COSH, CO—NH—$NH_2$, —COF, —COCl, —COBr, —COI, —COO-Su (succinimidyl/sulfosuccinimidyl), —COO-STP (4-sulfo-2,3,5,6-tetrafluorophenyl), —COO-TFP (2,3,5,6-tetrafluorophenyl), —COO-benzotriazole, —CO-benzotriazole, —CONR'—CO—$CH_2$—I, —CONR'R", —CONR'-biomolecule, —CONR'-L-COO, —CONR'-L-COOH, —CONR'-L-COO-Su, —CONR'-L-COO-STP, —CONR'-L-COO-TFP, —CONR'-L-CONR"$_2$, —CONR'-L-CO-biomolecule, —CONR'-L-CO—NH—$NH_2$, —CONR'-L-OH, —CONR'-L-O-phosphoramidite, —CONR'-L-CHO, —CONR'-L-maleimide, and —CONR'-L-NH—CO—$CH_2$—I; R' and R" is selected from the group consisting of H, aliphatic group, and heteroaliphatic group, and the biomolecule is a protein, antibody, nucleotide, oligonucleotide, biotin, or hapten; X is selected from the group consisting of —OH, —SH, $—NH_2$, —NH—$NH_2$, —F, —Cl, —Br, I, —NHS (hydroxysuccinimidyl/sulfo-succinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2H$, —NR-L-CO—NHS, —NR-L-CO-STP, —NR-L-CO-TFP, —NR-L-CO-benzotriazole, —NR-L-CHO, —NR-L-maleimide, and —NR-L-NH—CO—$CH_2$—I, where R is —H or an aliphatic or heteroaliphatic group; Kat is a number of $Na^+$, $K^+$, $Ca^{2+}$, ammonia, or other cation(s) needed to compensate the negative charge brought by the cyanine; m is an integer from 0 to 5 inclusive; o is an integer from 0 to 12 inclusive; and n is an integer from 1 to 3 inclusive; with the proviso that at least one of $R^1$, $R^2$, $R^5$, $R^6$, $R^7$, and $R^8$ contains a PEG group.

In one embodiment the compound is general formula II where R1, R5, and R6 are methyl and R2 is a PEG group; R7 and R8 are sulfo; X is —OH, —NHS, —O-TFP, or —NR-L-maleimide; m is 0; o is 3; and n is 1. In one embodiment the compound is general formula II where R1, R5, and R6 are methyl and R2 is a PEG group; R7 and R8 are sulfo; X is —OH, —NHS, —O-TFP, or —NR-L-maleimide; m is 1; o is 3; and n is 1. In one embodiment the compound is general formula II where R1, R5, and R6 are methyl and R2 is a PEG group; R7 and R8 are sulfo; X is —OH, —NHS, —O-TFP, or —NR-L-maleimide; m is 2; o is 3; and n is 1. In one embodiment the compound is general formula II where R1, R5, and R6 are methyl and R2 is a PEG group; R7 and R8 are sulfo; X is —OH, —NHS, —O-TFP, or —NR-L-maleimide; m is 3; o is 3; and n is 1. In one embodiment the compound is general formula II where R1, R5, and R6 are methyl and R2 is a PEG group; R7 and R8 are sulfo; X is —OH, —NHS, —O-TFP, or —NR-L-maleimide; m is 4; o is 3; and n is 1. In one embodiment the compound is general formula II where R1, R5, and R6 are methyl and R2 is a PEG group; R7 and R8 are sulfo; X is —OH, —NHS, —O-TFP, or —NR-L-maleimide; m is 5; o is 3; and n is 1.

In one embodiment the compound is general formula II where R1, R5, and R6 are methyl and R2 is a PEG group; R7 and R8 are sulfo; X is —OH, —NHS, —O-TFP, or —NR-L-maleimide; m is 0; o is 3; and n is 2. In one embodiment the compound is general formula II where R1, R5, and R6 are methyl and R2 is a PEG group; R7 and R8 are sulfo; X is —OH, —NHS, —O-TFP, or —NR-L-maleimide; m is 1; o is 3; and n is 2. In one embodiment the compound is general formula II where R1, R5, and R6 are methyl and R2 is a PEG group; R7 and R8 are sulfo; X is —OH, —NHS, —O-TFP, or —NR-L-maleimide; m is 2; o is 3; and n is 2. In one embodiment the compound is general formula II where R1, R5, and R6 are methyl and R2 is a PEG group; R7 and R8 are sulfo; X is —OH, —NHS, —O-TFP, or —NR-L-maleimide; m is 3; o is 3; and n is 2. In one embodiment the compound is general formula II where R1, R5, and R6 are methyl and R2 is a PEG group; R7 and R8 are sulfo; X is —OH, —NHS, —O-TFP, or —NR-L-maleimide; m is 4; o is 3; and n is 2. In one embodiment the compound is general formula II where R1, R5, and R6 are methyl and R2 is a PEG group; R7 and R8 are sulfo; X is —OH, —NHS, —O-TFP, or —NR-L-maleimide; m is 5; o is 3; and n is 2.

In one embodiment the compound is general formula II where R1, R5, and R6 are methyl and R2 is a PEG group; R7 and R8 are sulfo; X is —OH, —NHS, —O-TFP, or —NR-L-maleimide; m is 0; o is 3; and n is 3. In one embodiment the compound is general formula II where R1, R5, and R6 are methyl and R2 is a PEG group; R7 and R8 are sulfo; X is —OH, —NHS, —O-TFP, or —NR-L-maleimide; m is 1; o is 3; and n is 3. In one embodiment the compound is general formula II where R1, R5, and R6 are methyl and R2 is a PEG group; R7 and R8 are sulfo; X is —OH, —NHS, —O-TFP, or —NR-L-maleimide; m is 2; o is 3; and n is 3. In one embodiment the compound is general formula II where R1, R5, and R6 are methyl and R2 is a PEG group; R7 and R8 are sulfo; X is —OH, —NHS, —O-TFP, or —NR-L-maleimide; m is 3; o is 3; and n is 3. In one embodiment the compound is general formula II where R1, R5, and R6 are methyl and R2 is a PEG group; R7 and R8 are sulfo; X is —OH, —NHS, —O-TFP, or —NR-L-maleimide; m is 4; o is 3; and n is 3. In one embodiment the compound is general formula II where R1, R5, and R6 are methyl and R2 is a PEG group; R7 and R8 are sulfo; X is —OH, —NHS, —O-TFP, or —NR-L-maleimide; m is 5; o is 3; and n is 3.

In one embodiment the compound is general formula II where R5 and R6 are methyl; R1 and R2 are PEG groups; R7 and R8 are sulfo; X is —OH, —NHS, —O-TFP, or —NR-L-maleimide; m is 0; o is 3; and n is 1. In one embodiment the compound is general formula II where R5 and R6 are methyl; R1 and R2 are PEG groups; R7 and R8 are sulfo; X is —OH, —NHS, —O-TFP, or —NR-L-maleimide; m is 1; o is 3; and n is 1.

In one embodiment the compound is general formula II where R5 and R6 are methyl; R1 and R2 are PEG groups; R7 and R8 are sulfo; X is —OH, —NHS, —O-TFP, or —NR-L-maleimide; m is 2; o is 3; and n is 1. In one embodiment the compound is general formula II where R5 and R6 are methyl; R1 and R2 are PEG groups; R7 and R8 are sulfo; X is —OH, —NHS, —O-TFP, or —NR-L-maleimide; m is 3; o is 3; and n is 1. In one embodiment, the compound is general formula II, where R5 and R6 are methyl; R1 and R2 are PEG groups; R7 and R8 are sulfo; X is —OH, —NHS, —O-TFP, or —NR-L-maleimide; m is 4; o is 3; and n is 1. In one embodiment the compound is general formula II where R5 and R6 are methyl; R1 and R2 are PEG groups; R7 and R8 are sulfo; X is —OH, —NHS, —O-TFP, or —NR-L-maleimide; m is 5; o is 3; and n is 1.

In one embodiment the compound is general formula II where R5 and R6 are methyl; R1 and R2 are PEG groups; R7 and R8 are sulfo; X is —OH, —NHS, —O-TFP, or —NR-L-maleimide; m is 0; o is 3; and n is 2. In one embodiment the compound is general formula II where R5 and R6 are methyl; R1 and R2 are PEG groups; R7 and R8 are sulfo; X is —OH, —NHS, —O-TFP, or —NR-L-maleimide; m is 1; o is 3; and n is 2. In one embodiment the compound is general formula II, where R5 and R6 are methyl; R1 and R2 are PEG groups; R7 and R8 are sulfo; X is —OH, —NHS, —O-TFP, or —NR-L-maleimide; m is 2; o is 3; and n is 2. In one embodiment, the compound is general formula II, where R5 and R6 are methyl; R1 and R2 are PEG groups; R7 and R8 are sulfo; X is —OH, —NHS, —O-TFP, or —NR-L-maleimide; m is 3; o is 3; and n is 2. In one embodiment, the compound is general formula II, where R5 and R6 are methyl; R1 and R2 are PEG groups; R7 and R8 are sulfo; X is —OH, —NHS, —O-TFP, or —NR-L-maleimide; m is 4; o is 3; and n is 2. In one embodiment, the compound is general formula II, where R5 and R6 are methyl; R1 and R2 are PEG groups; R7 and R8 are sulfo; X is —OH, —NHS, —O-TFP, or —NR-L-maleimide; m is 5; o is 3; and n is 2.

In one embodiment the compound is general formula II where R5 and R6 are methyl; R1 and R2 are PEG groups; R7 and R8 are sulfo; X is —OH, —NHS, —O-TFP, or —NR-L-maleimide; m is 0; o is 3; and n is 3. In one embodiment the compound is general formula II where R5 and R6 are methyl; R1 and R2 are PEG groups; R7 and R8 are sulfo; X is —OH, —NHS, —O-TFP, or —NR-L-maleimide; m is 1; o is 3; and n is 3. In one embodiment the compound is general formula II where R5 and R6 are methyl; R1 and R2 are PEG groups; R7 and R8 are sulfo; X is —OH, —NHS, —O-TFP, or —NR-L-maleimide; m is 2; o is 3; and n is 3. In one embodiment the compound is general formula II where R5 and R6 are methyl; R1 and R2 are PEG groups; R7 and R8 are sulfo; X is —OH, —NHS, —O-TFP, or —NR-L-maleimide; m is 3; o is 3; and n is 3. In one embodiment, the compound is general formula II, where R5 and R6 are methyl; R1 and R2 are PEG groups; R7 and R8 are sulfo; X is —OH, —NHS, —O-TFP, or —NR-L-maleimide; m is 4; o is 3; and n is 3. In one embodiment the compound is general formula II where R5 and R6 are methyl; R1 and R2 are PEG groups; R7 and R8 are sulfo; X is —OH, —NHS, —O-TFP, or —NR-L-maleimide; m is 5; o is 3; and n is 3.

In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 0; o is 3; and n is 1. In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 1; o is 3; and n is 1. In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 2; o is 3; and n is 1. In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 3; o is 3; and n is 1. In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 4; o is 3; and n is 1. In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 5; o is 3; and n is 1.

In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 0; o is 3; and n is 2. In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 1; o is 3; and n is 2. In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 2; o is 3; and n is 2. In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 3; o is 3; and n is 2. In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 4; o is 3; and n is 2. In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 5; o is 3; and n is 2.

In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 0; o is 3; and n is 3. In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 1; o is 3; and n is 3. In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 2; o is 3; and n is 3. In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 3; o is 3; and n is 3. In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 4; o is 3; and n is 3. In one embodiment, the compound is general formula II, where R5 and R6 are methyl; R1 and R2 are PEG groups; R7 is sulfo; R8 is sulfonamide -L-SO$_2$NH—P where P is a PEG group; X is —OH, —NHS, —O-TFP, or —NR-L-maleimide; m is 5; o is 3; and n is 3.

In one embodiment, the compound is general formula II, where R5 and R6 are methyl; R1 and R2 are PEG groups;

R7 is sulfo; R8 is a carboxamide group —CONH—P where P is a PEG group; X is —OH, —NHS, —O-TFP, or —NR-L-maleimide; m is 0; o is 3; and n is 1. In one embodiment, the compound is general formula II, where R5 and R6 are methyl; R1 and R2 are PEG groups; R7 is sulfo; R8 is a carboxamide group —CONH—P where P is a PEG group; X is —OH, —NHS, —O-TFP, or —NR-L-maleimide; m is 1; o is 3; and n is 1. In one embodiment, the compound is general formula II, where R5 and R6 are methyl; R1 and R2 are PEG groups; R7 is sulfo; R8 is a carboxamide group —CONH—P where P is a PEG group; X is —OH, —NHS, —O-TFP, or —NR-L-maleimide; m is 2; o is 3; and n is 1. In one embodiment, the compound is general formula II, where R5 and R6 are methyl; R1 and R2 are PEG groups; R7 is sulfo; R8 is a carboxamide group —CONH—P where P is a PEG group; X is —OH, —NHS, —O-TFP, or —NR-L-maleimide; m is 3; o is 3; and n is 1. In one embodiment, the compound is general formula II, where R5 and R6 are methyl; R1 and R2 are PEG groups; R7 is sulfo; R8 is carboxamide —CONH—P where P is a PEG group; X is —OH, —NHS, —O-TFP, or —NR-L-maleimide; m is 4; o is 3; and n is 1. In one embodiment, the compound is general formula II, where R5 and R6 are methyl; R1 and R2 are PEG groups; R7 is sulfo; R8 is a carboxamide group —CONH—P where P is a PEG group; X is —OH, —NHS, —O-TFP, or —NR-L-maleimide; m is 5; o is 3; and n is 1.

In one embodiment, the compound is general formula II, where R5 and R6 are methyl; R1 and R2 are PEG groups; R7 is sulfo; R8 is a carboxamide group —CONH—P where P is a PEG group; X is —OH, —NHS, —O-TFP, or —NR-L-maleimide; m is 0; o is 3; and n is 2. In one embodiment, the compound is general formula II, where R5 and R6 are methyl; R1 and R2 are PEG groups; R7 is sulfo; R8 is a carboxamide —CONH—P where P is a PEG group; X is —OH, —NHS, —O-TFP, or —NR-L-maleimide; m is 1; o is 3; and n is 2. In one embodiment, the compound is general formula II, where R5 and R6 are methyl; R1 and R2 are PEG groups; R7 is sulfo; R8 is carboxamide —CONH—P where P is a PEG group; X is —OH, —NHS, —O-TFP, or —NR-L-maleimide; m is 2; o is 3; and n is 2. In one embodiment, the compound is general formula II, where R5 and R6 are methyl; R1 and R2 are PEG groups; R7 is sulfo; R8 is carboxamide —CONH—P where P is a PEG group; X is —OH, —NHS, —O-TFP, or —NR-L-maleimide; m is 3; o is 3; and n is 2. In one embodiment, the compound is general formula II, where R5 and R6 are methyl; R1 and R2 are PEG groups; R7 is sulfo; R8 is carboxamide —CONH—P where P is a PEG group; X is —OH, —NHS, —O-TFP, or —NR-L-maleimide; m is 4; o is 3; and n is 2. In one embodiment, the compound is general formula II, where R5 and R6 are methyl; R1 and R2 are PEG groups; R7 is sulfo; R8 is a carboxamide group —CONH—P where P is a PEG group; X is —OH, —NHS, —O-TFP, or —NR-L-maleimide; m is 5; o is 3; and n is 2.

In one embodiment, the compound is general formula II, where R5 and R6 are methyl; R1 and R2 are PEG groups; R7 is sulfo; R8 is a carboxamide group —CONH—P where P is a PEG group; X is —OH, —NHS, —O-TFP, or —NR-L-maleimide; m is 0; o is 3; and n is 3. In one embodiment, the compound is general formula II, where R5 and R6 are methyl; R1 and R2 are PEG groups; R7 is sulfo; R8 is a carboxamide group —CONH—P where P is a PEG group; X is —OH, —NHS, —O-TFP, or —NR-L-maleimide; m is 1; o is 3; and n is 3. In one embodiment, the compound is general formula II, where R5 and R6 are methyl; R1 and R2 are PEG groups; R7 is sulfo; R8 is carboxamide —CONH—P where P is a PEG group; X is —OH, —NHS, —O-TFP, or —NR-L-maleimide; m is 2; o is 3; and n is 3. In one embodiment, the compound is general formula II, where R5 and R6 are methyl; R1 and R2 are PEG groups; R7 is sulfo; R8 is carboxamide —CONH—P where P is a PEG group; X is —OH, —NHS, —O-TFP, or —NR-L-maleimide; m is 3; o is 3; and n is 3. In one embodiment, the compound is general formula II, where R5 and R6 are methyl; R1 and R2 are PEG groups; R7 is sulfo; R8 is carboxamide —CONH—P where P is a PEG group; X is —OH, —NHS, —O-TFP, or —NR-L-maleimide; m is 4; o is 3; and n is 3. In one embodiment, the compound is general formula II, where R5 and R6 are methyl; R1 and R2 are PEG groups; R7 is sulfo; R8 is a carboxamide group —CONH—P where P is a PEG group; X is —OH, —NHS, —O-TFP, or —NR-L-maleimide; m is 5; o is 3; and n is 3.

In one embodiment, the compound has general formula IIIa with "a" indicating the chain from the right indole N terminates in COX:

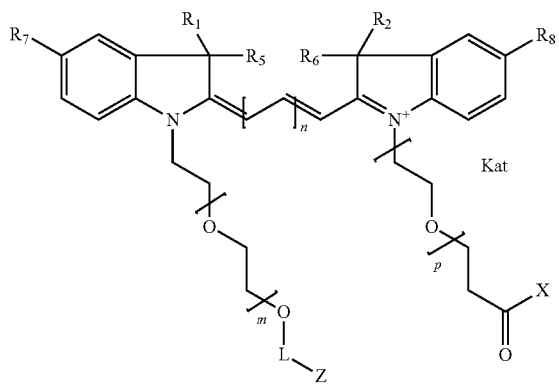

or general formula IIIb with "b" indicating the chain from the right indole N terminates in COH:

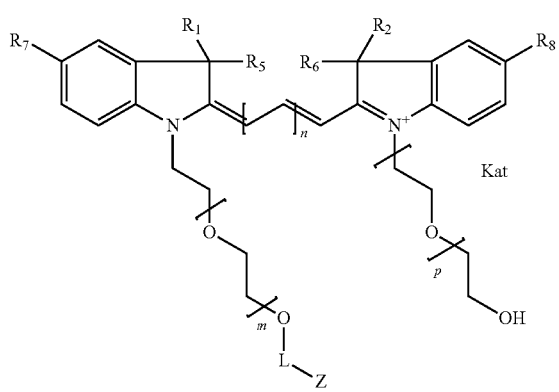

where each of $R^1$, R2, $R^5$, and $R^6$ is the same or different and is independently selected from the group consisting of an aliphatic, heteroaliphatic, sulfoalkyl group, heteroaliphatic with terminal $SO_3$, a PEG group P-L-Z where P is selected from an ethylene glycol group, a diethylene glycol group, and a (poly)ethylene glycol group where the (poly)ethylene glycol group is $(CH_2CH_2O)_s$ where s is an integer from 3-6 inclusive, a sulfonamide group -L-$SO_2$NH—P-L-Z, and a carboxamide group -L-CONH—P-L-Z; each of $R^7$ and $R^8$ is the same or different and is independently selected from the group consisting of H, $SO_3$, a PEG group P-L-Z where P is selected from an ethylene glycol group, a diethylene glycol group, and a (poly)ethylene glycol group where the (poly) ethylene glycol group is $(CH_2CH_2O)_s$ where s is an integer from 3-6 inclusive, a sulfonamide group —$SO_2NH$—P-L-Z, and a carboxamide group —CONH—P-L-Z; where L is selected from the group consisting of a divalent linear (—$(CH_2)_o$—, o=0 to 15), crossed, or cyclic alkane group that can be substituted by at least one atom selected from the group consisting of oxygen, substituted nitrogen, and/or sulfur; where Z is selected from the group consisting of H, $CH_3$, alkyl, heteroalkyl, $NH_2$, —COO⁻, —COOH, —COSH, CO—NH—$NH_2$, —COF, —COCl, —COBr, —COI, —COO-Su (succinimidyl/sulfosuccinimidyl), —COO-STP (4-sulfo-2,3,5,6-tetrafluorophenyl), —COO-TFP (2,3,5,6-tetrafluorophenyl), —COO-benzotriazole, —CO-benzotriazole, —CONR'—CO—$CH_2$—I, —CONR'R", —CONR'-biomolecule, —CONR'-L-COO, —CONR'-L-COOH, —CONR'-L-COO-Su, —CONR'-L-COO-STP, —CONR'-L-COO-TFP, —CONR'-L-CONR"$_2$, —CONR'-L-CO-biomolecule, —CONR'-L-CO—NH—$NH_2$, —CONR'-L-OH, —CONR'-L-O-phosphoramidite, —CONR'-L-CHO, —CONR'-L-maleimide, and —CONR'-L-NH—CO—$CH_2$—I; R' and R" is selected from the group consisting of H, aliphatic group, and heteroaliphatic group, and the biomolecule is a protein, antibody, nucleotide, oligonucleotide, biotin, or hapten; X is selected from the group consisting of —OH, —SH, —$NH_2$, —NH—$NH_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2H$, —NR-L-CO—NHS, —NR-L-CO-STP, —NR-L-CO-TFP, —NR-L-CO-benzotriazole, —NR-L-CHO, —NR-L-maleimide, and —NR-L-NH—CO—CH2-I, where R is —H or an aliphatic or heteroaliphatic group; Kat is a number of $Na^+$, $K^+$, $Ca^{2+}$, ammonia, or other cation(s) needed to compensate the negative charge brought by the cyanine; m is an integer from 0 to 5 inclusive; p is an integer from 1 to 6 inclusive; and n is an integer from 1 to 3 inclusive; and at least one of $R^1$, $R^2$, $R^5$, $R^6$, $R^7$, and $R^8$ contains a PEG group.

In one embodiment, the compound is general formula III, where R1, R5, and R6 are methyl; R2 is a PEG group; R7 and R8 are sulfo; X is —OH, —NHS, —O-TFP, or —NR-L-maleimide; m is 0; p is 1; and n is 1. In one embodiment, the compound is general formula III, where R1, R5, and R6 are methyl; R2 is a PEG group; R7 and R8 are sulfo; X is —OH, —NHS, —O-TFP, or —NR-L-maleimide; m is 1; p is 2; and n is 1. In one embodiment, the compound is general formula III, where R1, R5, and R6 are methyl; R2 is a PEG group; R7 and R8 are sulfo; X is —OH, —NHS, —O-TFP, or —NR-L-maleimide; m is 2; p is 3; and n is 1. In one embodiment, the compound is general formula III, where R1, R5, and R6 are methyl; R2 is a PEG group; R7 and R8 are sulfo; X is —OH, —NHS, —O-TFP, or —NR-L-maleimide; m is 3; p is 4; and n is 1. In one embodiment, the compound is general formula III, where R1, R5, and R6 are methyl; R2 is a PEG group; R7 and R8 are sulfo; X is —OH, —NHS, —O-TFP, or —NR-L-maleimide; m is 4; p is 5; and n is 1. In one embodiment, the compound is general formula III, where R1, R5, and R6 are methyl; R2 is a PEG group; R7 and R8 are sulfo; X is —OH, —NHS, —O-TFP, or —NR-L-maleimide; m is 5; p is 6; and n is 1.

In one embodiment, the compound is general formula III, where R1, R5, and R6 are methyl; R2 is a PEG group; R7 and R8 are sulfo; X is —OH, —NHS, —O-TFP, or —NR-L-maleimide; m is 0; p is 1; and n is 2. In one embodiment, the compound is general formula III, where R1, R5, and R6 are methyl; R2 is a PEG group; R7 and R8 are sulfo; X is —OH, —NHS, —O-TFP, or —NR-L-maleimide; m is 1; p is 2; and n is 2. In one embodiment, the compound is general formula III, where R1, R5, and R6 are methyl; R2 is a PEG group; R7 and R8 are sulfo; X is —OH, —NHS, —O-TFP, or —NR-L-maleimide; m is 2; p is 3; and n is 2. In one embodiment, the compound is general formula III, where R1, R5, and R6 are methyl; R2 is a PEG group; R7 and R8 are sulfo; X is —OH, —NHS, —O-TFP, or —NR-L-maleimide; m is 3; p is 4; and n is 2. In one embodiment, the compound is general formula III, where R1, R5, and R6 are methyl; R2 is a PEG group; R7 and R8 are sulfo; X is —OH, —NHS, —O-TFP, or —NR-L-maleimide; m is 4; p is 5; and n is 2. In one embodiment, the compound is general formula III, where R1, R5, and R6 are methyl; R2 is a PEG group; R7 and R8 are sulfo; X is —OH, —NHS, —O-TFP, or —NR-L-maleimide; m is 5; p is 6; and n is 2.

In one embodiment, the compound is general formula III, where R1, R5, and R6 are methyl; R2 is a PEG group; R7 and R8 are sulfo; X is —OH, —NHS, —O-TFP, or —NR-L-maleimide; m is 0; p is 1; and n is 3. In one embodiment, the compound is general formula III, where R1, R5, and R6 are methyl; R2 is a PEG group; R7 and R8 are sulfo; X is —OH, —NHS, —O-TFP, or —NR-L-maleimide; m is 1; p is 2; and n is 3. In one embodiment, the compound is general formula III, where R1, R5, and R6 are methyl; R2 is a PEG group; R7 and R8 are sulfo; X is —OH, —NHS, —O-TFP, or —NR-L-maleimide; m is 2; p is 3; and n is 3. In one embodiment, the compound is general formula III, where R1, R5, and R6 are methyl; R2 is a PEG group; R7 and R8 are sulfo; X is —OH, —NHS, —O-TFP, or —NR-L-maleimide; m is 3; p is 4; and n is 3. In one embodiment, the compound is general formula III, where R1, R5, and R6 are methyl; R2 is a PEG group; R7 and R8 are sulfo; X is —OH, —NHS, —O-TFP, or —NR-L-maleimide; m is 4; p is 5; and n is 3. In one embodiment, the compound is general formula III, where R1, R5, and R6 are methyl; R2 is a PEG group; R7 and R8 are sulfo; X is —OH, —NHS, —O-TFP, or —NR-L-maleimide; m is 5; p is 6; and n is 3.

In one embodiment the compound is general formula III where R5 and R6 are methyl; R1 and R2 are a PEG group; R7 and R8 are sulfo; X is —OH, —NHS, —O-TFP, or —NR-L-maleimide; m is 0; p is 1; and n is 1. In one embodiment the compound is general formula III where R5 and R6 are methyl; R1 and R2 are a PEG group; R7 and R8 are sulfo; X is —OH, —NHS, —O-TFP, or —NR-L-maleimide; m is 1; p is 2; and n is 1. In one embodiment the compound is general formula III where R5 and R6 are methyl; R1 and R2 are a PEG group; R7 and R8 are sulfo; X is —OH, —NHS, —O-TFP, or —NR-L-maleimide; m is 2; p is 3; and n is 1. In one embodiment the compound is general formula III where R5 and R6 are methyl; R1 and R2 are a PEG group; R7 and R8 are sulfo; X is —OH, —NHS, —O-TFP, or —NR-L-maleimide; m is 3; p is 4; and n is 1. In one embodiment the compound is general formula III where R5 and R6 are methyl; R1 and R2 are a PEG group; R7 and R8 are sulfo; X is —OH, —NHS, —O-TFP, or —NR-L-maleimide; m is 4; p is 5; n is 1. In one embodiment the compound is general formula III where R5 and R6 are methyl; R1 and R2 are a PEG group; R7 and R8 are sulfo; X is —OH, —NHS, —O-TFP, or —NR-L-maleimide; m is 5; p is 6; n is 1.

In one embodiment, the compound is general formula III, where R5 and R6 are methyl; R1 and R2 are a PEG group; R7 and R8 are sulfo; X is —OH, —NHS, —O-TFP, or —NR-L-maleimide; m is 0; p is 1; and n is 2. In one embodiment, the compound is general formula III, where R5 and R6 are methyl; R1 and R2 are a PEG group; R7 and R8 are sulfo; X is —OH, —NHS, —O-TFP, or —NR-L-maleimide; m is 1; p is 2; and n is 2. In one embodiment, the compound is general formula III, where R5 and R6 are methyl; R1 and R2 are a PEG group; R7 and R8 are sulfo; X is —OH, —NHS, —O-TFP, or —NR-L-maleimide; m is 2; p is 3; and n is 2. In one embodiment, the compound is general formula III, where R5 and R6 are methyl; R1 and R2 are a PEG group; R7 and R8 are sulfo; X is —OH, —NHS, —O-TFP, or —NR-L-maleimide; m is 3; p is 4; and n is 2. In one embodiment, the compound is general formula III, where R5 and R6 are methyl; R1 and R2 are a PEG group; R7 and R8 are sulfo; X is —OH, —NHS, —O-TFP, or —NR-L-maleimide; m is 4; p is 5; and n is 2. In one embodiment, the compound is general formula III, where R5 and R6 are methyl; R1 and R2 are a PEG group; R7 and R8 are sulfo; X is —OH, —NHS, —O-TFP, or —NR-L-maleimide; m is 5; p is 6; and n is 2.

In one embodiment, the compound is general formula III, where R5 and R6 are methyl; R1 and R2 are a PEG group; R7 and R8 are sulfo; X is —OH, —NHS, —O-TFP, or —NR-L-maleimide; m is 0; p is 1; and n is 3. In one embodiment, the compound is general formula III, where R5 and R6 are methyl; R1 and R2 are a PEG group; R7 and R8 are sulfo; X is —OH, —NHS, —O-TFP, or —NR-L-maleimide; m is 1; p is 2; and n is 3. In one embodiment, the compound is general formula III, where R5 and R6 are methyl; R1 and R2 are a PEG group; R7 and R8 are sulfo; X is —OH, —NHS, —O-TFP, or —NR-L-maleimide; m is 2; p is 3; and n is 3. In one embodiment, the compound is general formula III, where R5 and R6 are methyl; R1 and R2 are a PEG group; R7 and R8 are sulfo; X is —OH, —NHS, —O-TFP, or —NR-L-maleimide; m is 3; p is 4; and n is 3. In one embodiment, the compound is general formula III, where R5 and R6 are methyl; R1 and R2 are a PEG group; R7 and R8 are sulfo; X is —OH, —NHS, —O-TFP, or —NR-L-maleimide; m is 4; p is 5; and n is 3. In one embodiment, the compound is general formula III, where R5 and R6 are methyl; R1 and R2 are a PEG group; R7 and R8 are sulfo; X is —OH, —NHS, —O-TFP, or —NR-L-maleimide; m is 5; p is 6; and n is 3.

In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 0; p is 1; and n is 1. In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 1; p is 2; and n is 1. In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 2; p is 3; and n is 1. In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 3; p is 4; and n is 1. In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 4; p is 5; and n is 1. In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 5; p is 6; and n is 1.

In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 0; p is 1; and n is 2. In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 1; p is 2; and n is 2. In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 2; p is 3; and n is 2. In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 3; p is 4; and n is 2. In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 4; p is 5; and n is 2. In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 5; p is 6; and n is 2.

In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 0; p is 1; and n is 3. In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 1; p is 2; and n is 3. In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 2; p is 3; and n is 3. In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 3; p is 4; and n is 3. In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 4; p is 5; and n is 3. In one embodiment, the compound is general formula III, where R5 and R6 are methyl; R1 and R2 are a PEG group; R7 is sulfo; R8 is sulfonamide —SO$_2$NH—P where P is a PEG group; X is —OH, —NHS, —O-TFP, or —NR-L-maleimide; m is 5; p is 6; and n is 3.

In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 0; p is 1; and n is 1. In one embodiment, the compound is general formula III, where R5 and R6 are methyl; R1 and R2 are a PEG group; R7 is sulfo;

R8 is a carboxamide group —CONH—P where P is a PEG group; X is —OH, —NHS, —O-TFP, or —NR-L-maleimide; m is 1; p is 2; and n is 1. In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 2; p is 3; and n is 1. In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 3; p is 4; and n is 1. In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 4; p is 5; and n is 1. In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 5; p is 6; and n is 1.

In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 0; p is 1; and n is 2. In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 1; p is 2; and n is 2. In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 2; p is 3; and n is 2. In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 3; p is 4; and n is 2. In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 4; p is 5; and n is 2. In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 5; p is 6; and n is 2.

In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 0; p is 1; and n is 3. In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 1; p is 2; and n is 3. In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 2; p is 3; and n is 3. In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 3; p is 4; and n is 3. In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 4; p is 5; and n is 3. In one embodiment, the compound is general formula III, where R5 and R6 are methyl; R1 and R2 are a PEG group; R7 is sulfo; R8 is a carboxamide group —CONH—P where P is a PEG group; X is —OH, —NHS, —O-TFP, or —NR-L-maleimide; m is 5; p is 6; and n is 3.

In one embodiment, the compound is 550 Compound 1/2

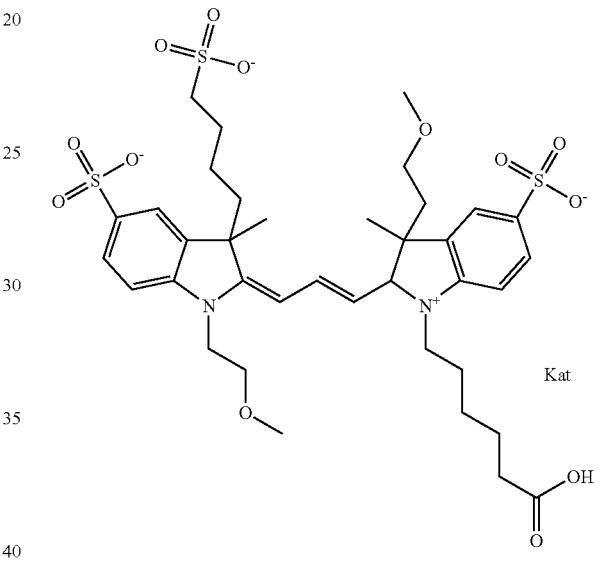

550 Compound 1/2 (1-(5-carboxypentyl)-3-(2-methoxyethyl)-2-((1E,3E)-3-(1-(2-methoxyethyl)-3-methyl-5-sulfonato-3-(3-sulfonatopropyl)indolin-2-ylidene)prop-1-enyl)-3-methyl-3H-indolium-5-sulfonate) contains an ethylene glycol on the indole N of the left heterocycle, i.e., a methylated ethylene glycol, as shown in the structure above, and the ethylene glycol can be represented in abbreviated format as —[C—C—O]$_1$—, which is used throughout. The methyl group on the ethylene glycol prevents the terminal —OH from oxidation. Oxidation is known to occur, overtime, on an unprotected terminus of an ethylene glycol group, diethylene glycol group, or (poly)ethylene glycol group, collectively referred to herein as an unprotected PEG terminus. Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 550 Compound 1, but one skilled in the art appreciates that activation is not limited to these examples. One non-limiting example of an activated compound is the NHS-ester of 550 Compound 1/2, shown below:

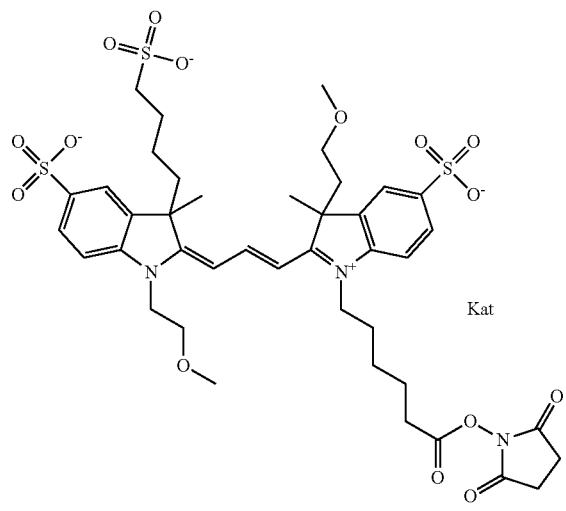 [SMILES: COCCN1/C(=C/C=C/C2=[N+](CCCCCC(=O)ON3C(=O)CCC3=O)c3ccc(S(=O)(=O)[O-])cc3C2(C)CCOC)C(C)(CCCCS(=O)(=O)[O-])c2cc(S(=O)(=O)[O-])ccc21]

In one embodiment, the compound is a NHS-ester of 550 Compound 1/2 where, according to general formula I, o is 1, shown below:

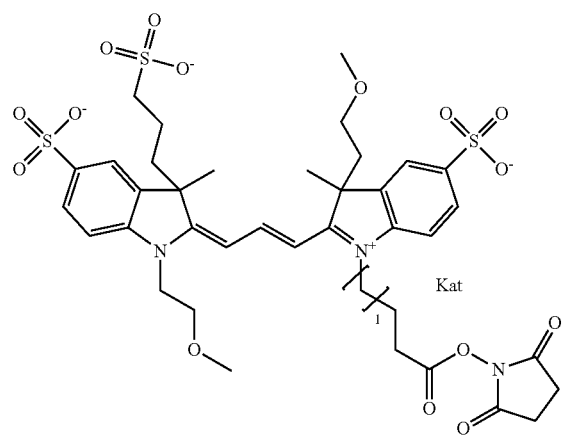

In one embodiment, the compound is an NHS-ester of 550 Compound 1/2 where, according to general formula I, o is 5, shown below:

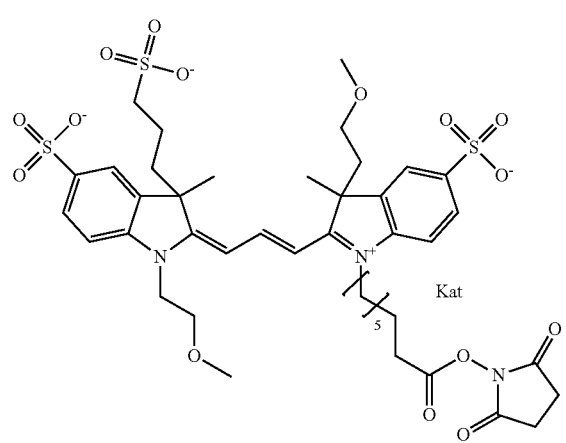

One non-limiting example of a NHS-ester of 550 Compound 1/3, according to general formula III, where m=1 and p=1, is shown below:

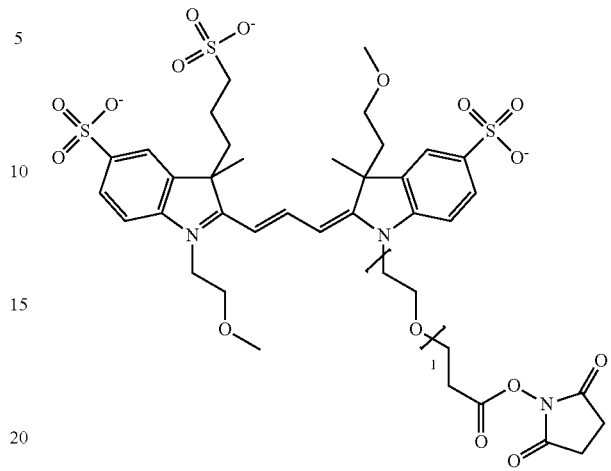

One non-limiting example of a NHS-ester of 550 Compound 1/3, according to general formula III, where m=1 and p=2, is shown below:

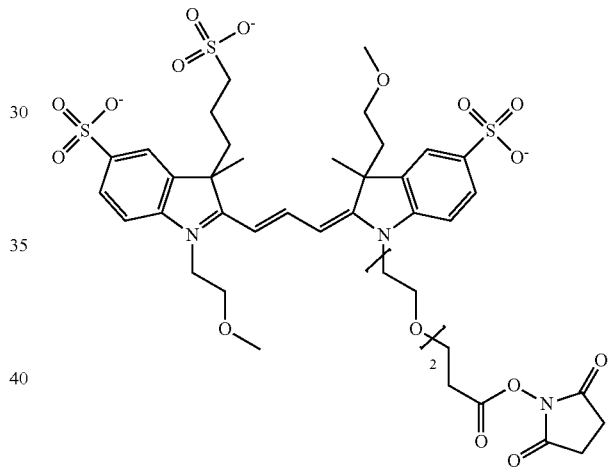

One non-limiting example of a NHS-ester of 550 Compound 1/3, according to general formula III, where One non-limiting example of a NHS-ester of 550 Compound 1/3, according to general formula III, where m=1 and p=4, is shown below:

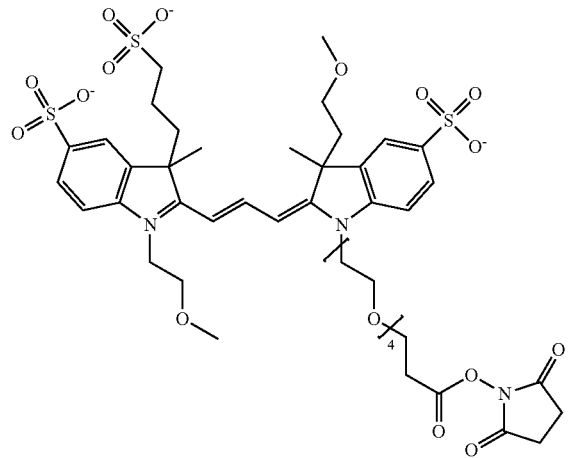

One non-limiting example of a NHS-ester of 550 Compound 1/3, according to general formula III, where m=1 and p=5, is shown below:

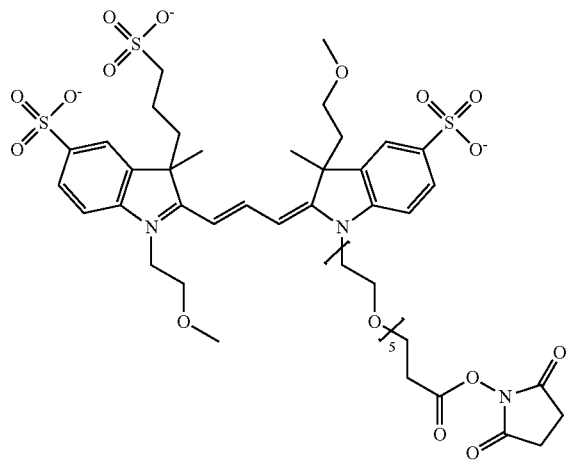

One non-limiting example of a NHS-ester of 550 Compound 1/3, according to general formula III, where m=1 and p=6, is shown below:

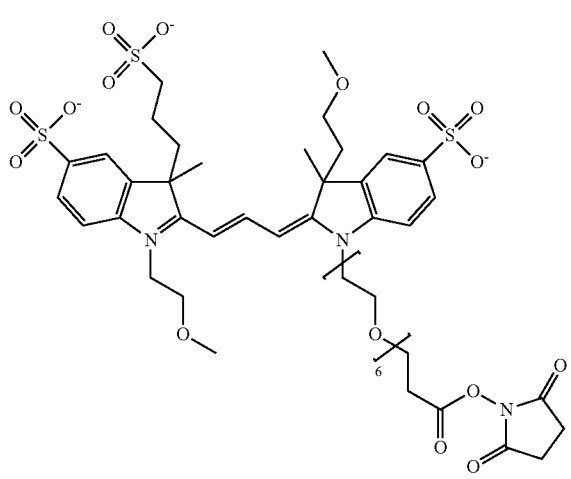

One non-limiting example of a NHS-ester of 550 Compound 2/3, according to general formula III, where m=2 and p=1, is shown below:

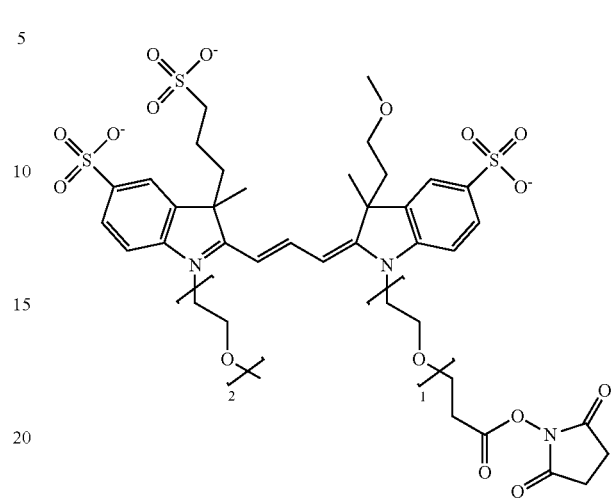

One non-limiting example of a NHS-ester of 550 Compound 2/3, according to general formula III, where m=2 and p=2, is shown below:

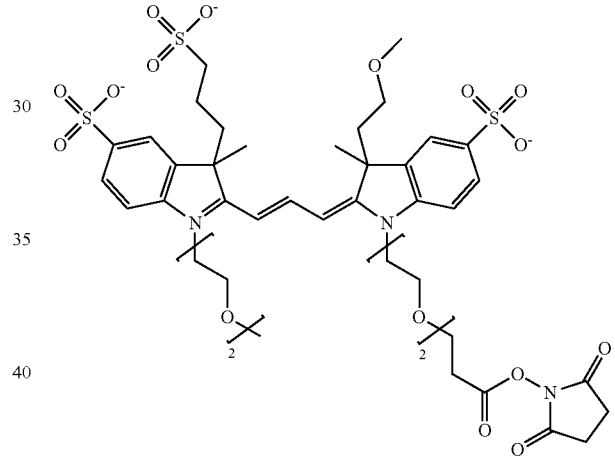

One non-limiting example of a NHS-ester of 550 Compound 2/3, according to general formula III, where m=2 and p=3, is shown below:

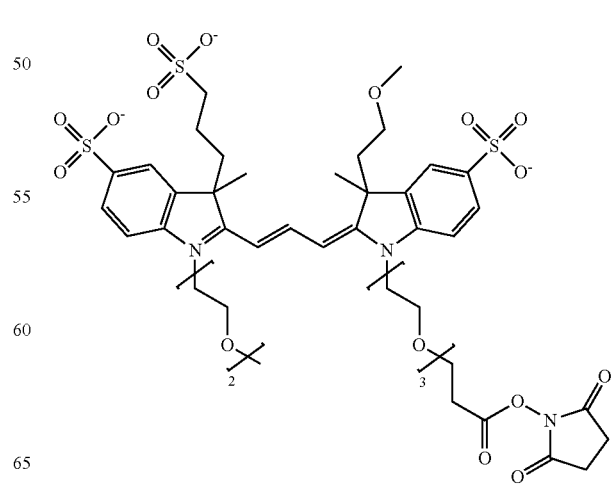

One non-limiting example of a NHS-ester of 550 Compound 3/3, according to general formula III, where m=3 and p=1, is shown below:

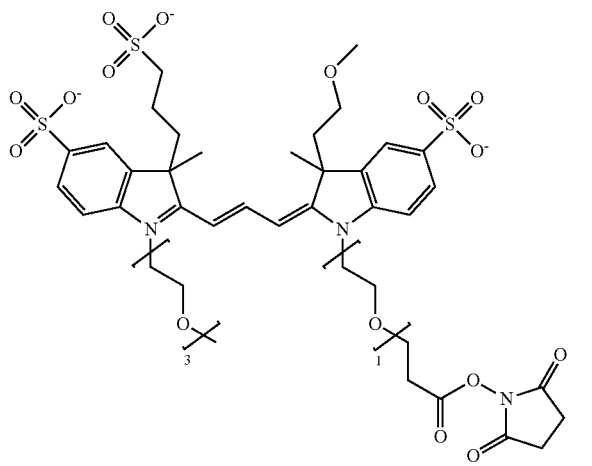

One non-limiting example of a NHS-ester of 550 Compound 4/3, according to general formula III, where m=4 and p=1, is shown below:

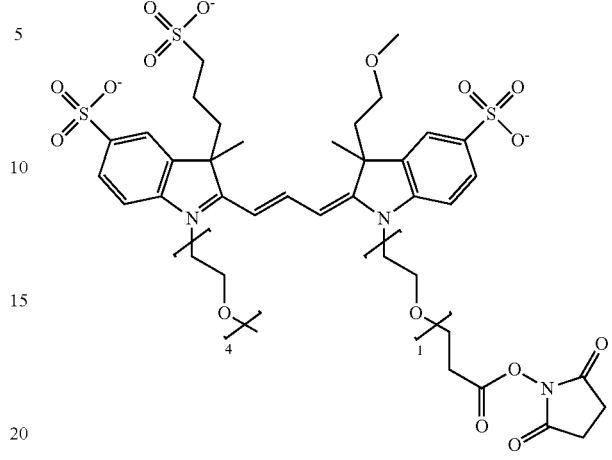

One non-limiting example of a NHS-ester of 550 Compound 3/3, according to general formula III, where

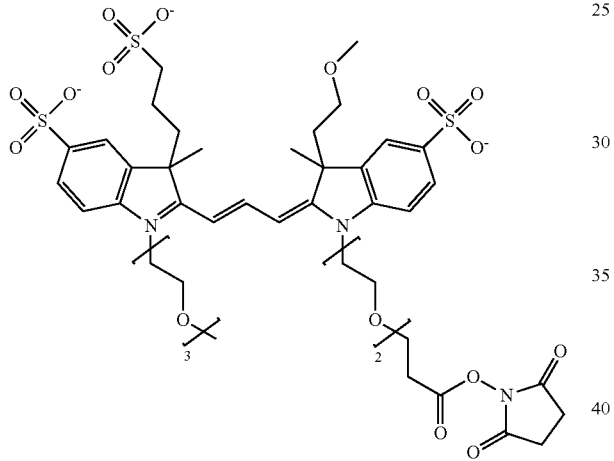

One non-limiting example of a NHS-ester of 550 Compound 5/3, according to general formula III, where m=5 and p=1, is shown below:

One non-limiting example of a NHS-ester of 550 Compound 3/3, according to general formula III, where m=3 and p=3, is shown below:

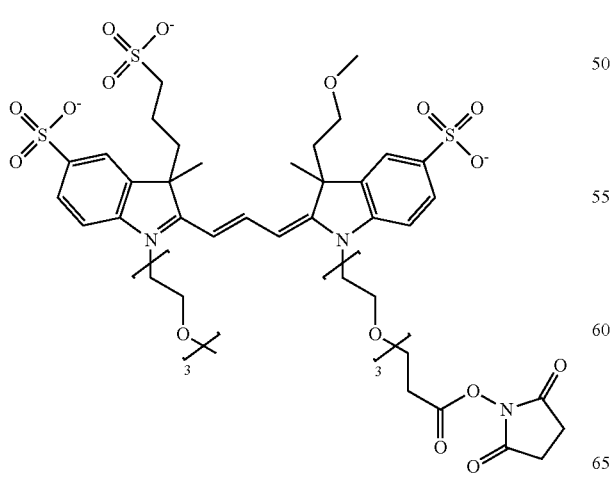

One non-limiting example of a NHS-ester of 550 Compound 6/3, according to general formula III, where m=6 and p=1, is shown below:

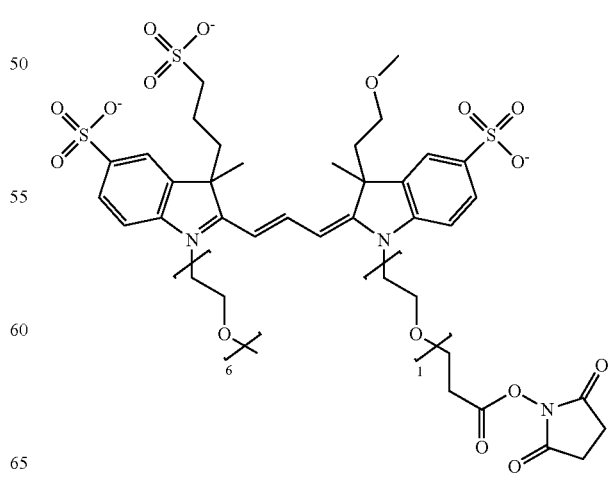

One non-limiting example of an activated 550 Compound 1/2 is a tetrafluorophenyl (TFP)-ester form of 550 Compound 1, shown below:

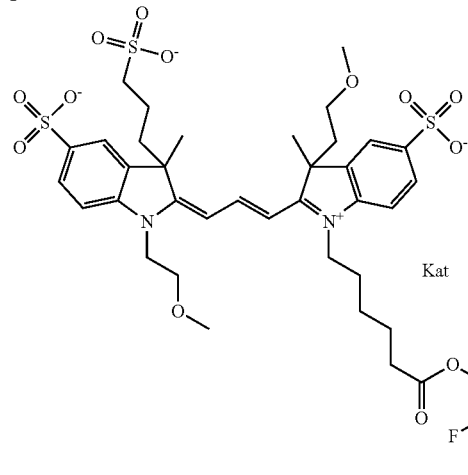

One non-limiting example of an activated 550 Compound 1/2 is a sulfotetrafluorophenyl (STP)-ester form of 550 Compound 1, shown below:

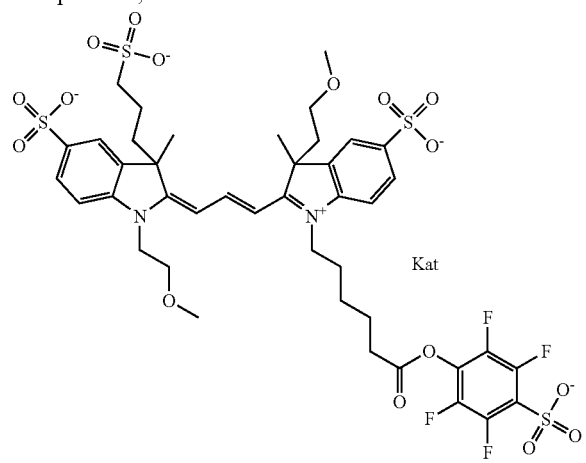

One non-limiting example of an activated 550 Compound 1/2 is a hydrazide form of 550 Compound 1,

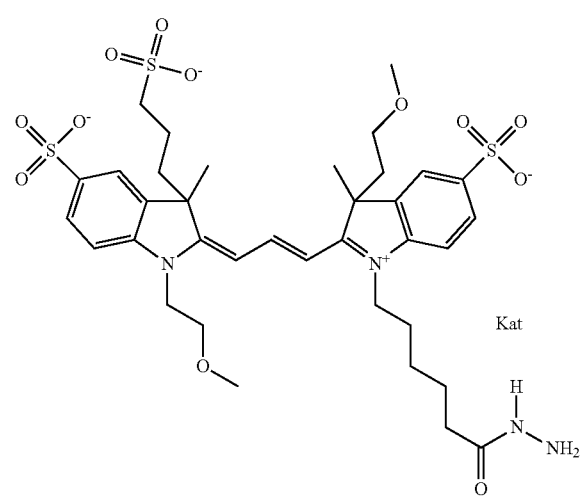 [SMILES: COCCN1/C(=C/C=C/C2=[N+](CCCCCC(=O)NN)c3ccc(S(=O)(=O)[O-])cc3C2(C)CCOC)C(C)(CCCS(=O)(=O)[O-])c2cc(S(=O)(=O)[O-])ccc21]

One non-limiting example of an activated 550 Compound 1/2 is a maleimide form of 550 Compound 1, shown below:

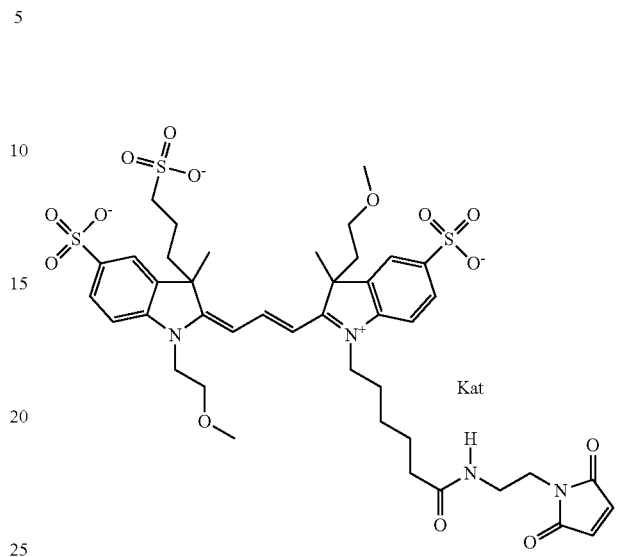

In one embodiment, the compound is 550 Compound 2/2

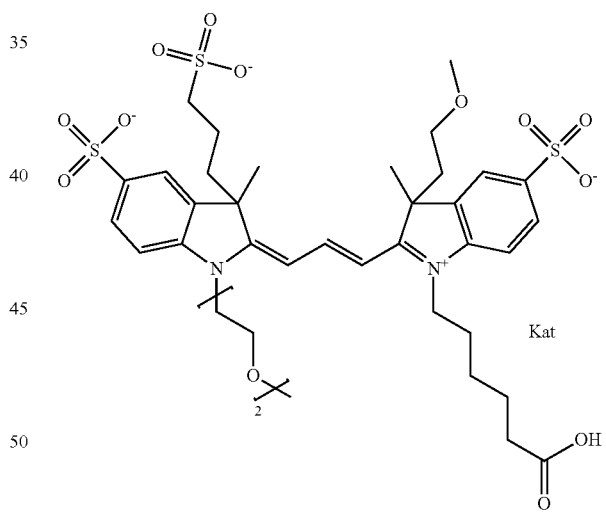

550 Compound 2/2 (1-(5-carboxypentyl)-2-((1E,3E)-3-(1-(2-(2-methoxyethoxy)ethyl)-3-methyl-5-sulfonato-3-(3-sulfonatopropyl)indolin-2-ylidene)prop-1-enyl)-3-(2-methoxyethyl)-3-methyl-3H-indolium-5-sulfonate) contains a diethylene glycol on the indole N of the left heterocycle. 550 Compound 2/2, with the diethylene glycol shown in abbreviated notation used throughout, represents the following structure.

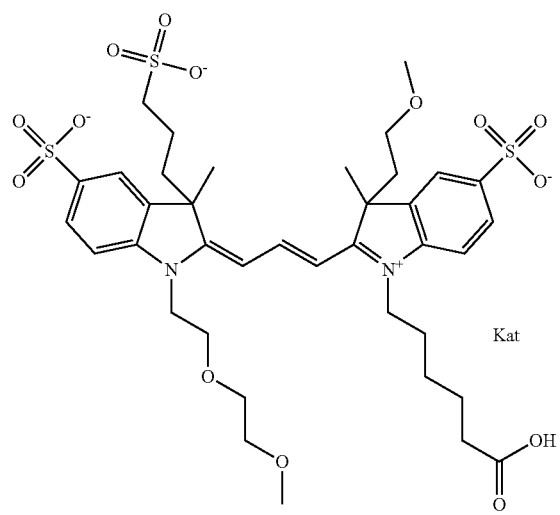 [SMILES: COCCOCCN1/C(=C/C=C/C2=[N+](CCCCCC(=O)O)c3ccc(S(=O)(=O)[O-])cc3C2(C)CCOC)C(C)(CCCS(=O)(=O)[O-])c2cc(S(=O)(=O)[O-])ccc21]

The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 550 Compound 2/2 is activated as described above, one non-limiting example of which is the NHS-ester form of 550 Compound 2/2, shown below.

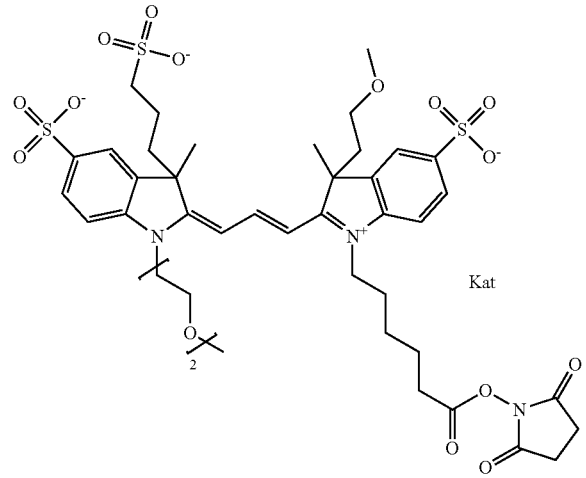

In one embodiment, the compound is 550 Compound 3/2

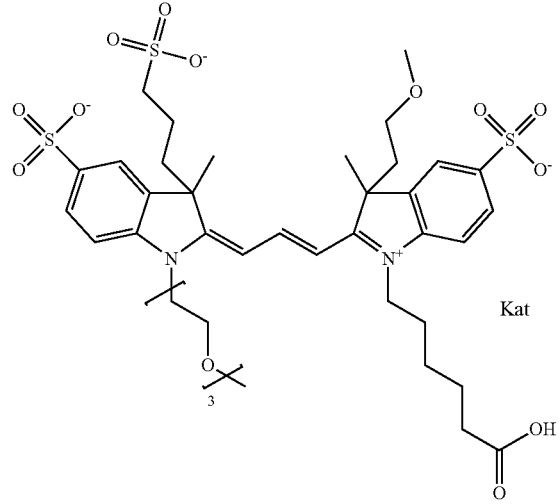

550 Compound 3/2 (1-(5-carboxypentyl)-2-((1E,3E)-3-(1-(2-(2-(2-methoxyethoxy)ethoxy)ethyl)-3-methyl-5-sulfonato-3-(3-sulfonatopropyl)indolin-2-ylidene)prop-1-enyl)-3-(2-methoxyethyl)-3-methyl-3H-indolium-5-sulfonate) contains a (poly)ethylene glycol on the indole N of the left heterocycle. 550 Compound 3/2, with the (poly)ethylene glycol shown in abbreviated notation used throughout, represents the following structure.

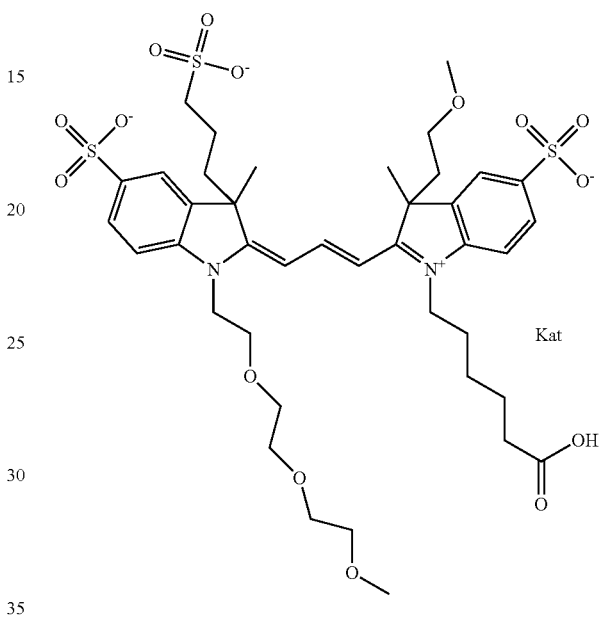

The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 550 Compound 3/2 is activated as described above.

In one embodiment, the compound is 550 Compound 4/2

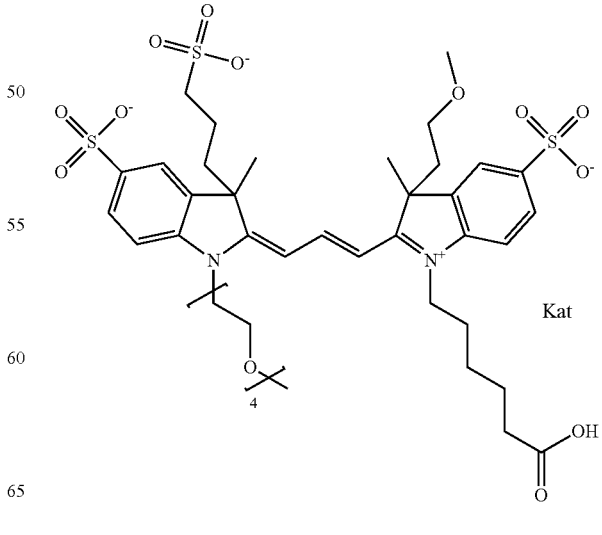

550 Compound 4/2 (1-(5-carboxypentyl)-3-(2-methoxyethyl)-3-methyl-2-((1E,3E)-3-(3-methyl-5-sulfonato-3-(3-sulfonatopropyl)-1-(2,5,8,11-tetraoxatridecan-13-yl)indolin-2-ylidene)prop-1-enyl)-3H-indolium-5-sulfonate) contains a (poly)ethylene glycol on the indole N of the left heterocycle. 550 Compound 4/2, with the (poly)ethylene glycol shown in abbreviated notation used throughout, represents the following structure.

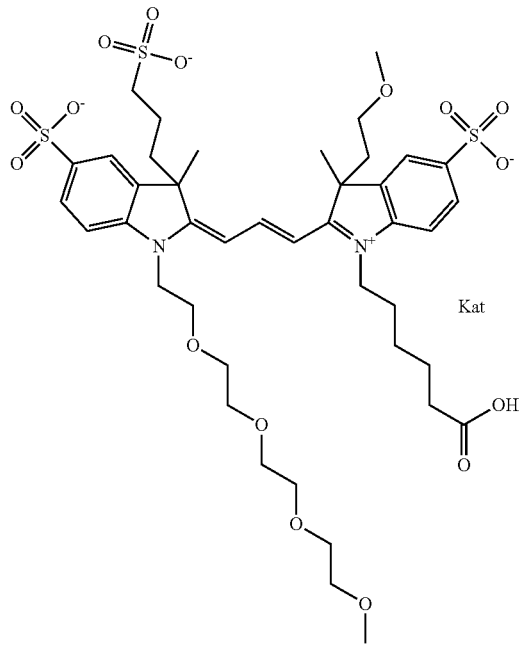 [SMILES: COCCOCCOCCOCCN1/C(=C/C=C/C2=[N+](CCCCCC(=O)O)c3ccc(S(=O)(=O)[O-])cc3C2(C)CCOC)C(C)(CCCS(=O)(=O)[O-])c2cc(S(=O)(=O)[O-])ccc21]

The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 550 Compound 4/2 is activated as described above.

In one embodiment, the compound is 550 Compound 5/2

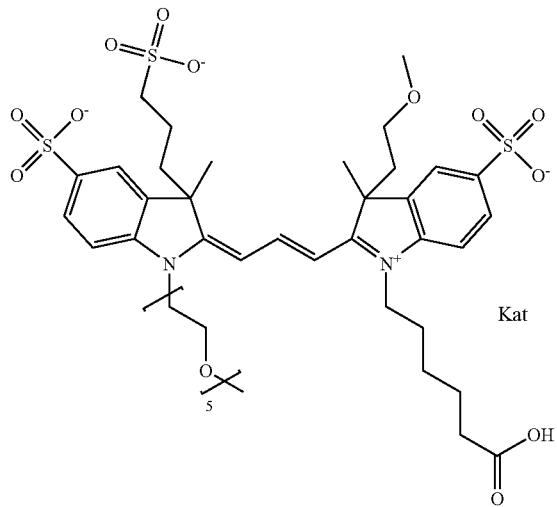

550 Compound 5/2 (2-((1E,3E)-3-(1-(2,5,8,11,14-pentaoxahexadecan-16-yl)-3-methyl-5-sulfonato-3-(3-sulfonatopropyl)indolin-2-ylidene)prop-1-enyl)-1-(5-carboxypentyl)-3-(2-methoxyethyl)-3-methyl-3H-indolium-5-sulfonate) contains a (poly)ethylene glycol on the indole N of the left heterocycle. 550 Compound 5/2, with the (poly)ethylene glycol shown in abbreviated notation used throughout, represents the following structure.

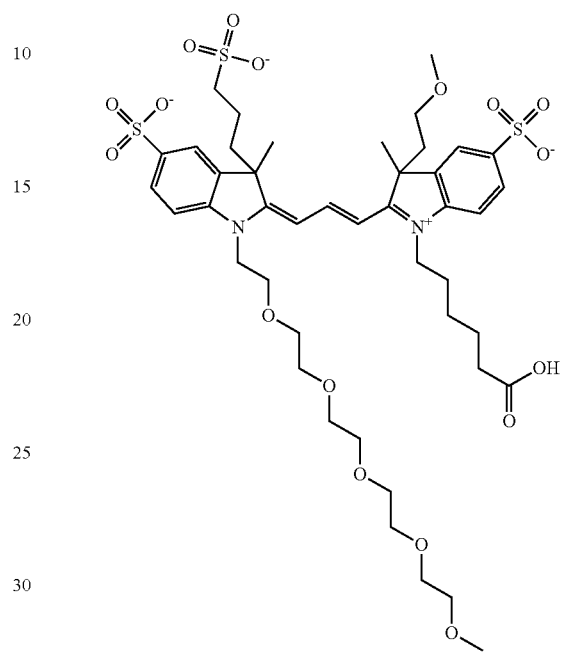

The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 550 Compound 5/2 is activated as described above.

In one embodiment, the compound is 550 Compound 6/2

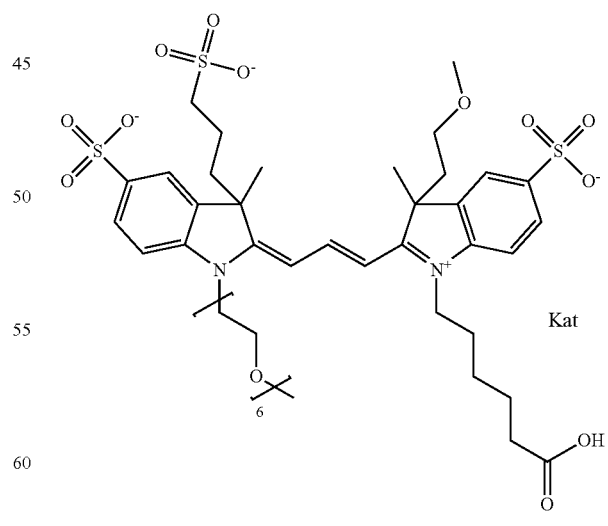

550 Compound 6/2 (1-(5-carboxypentyl)-3-(2-methoxyethyl)-3-methyl-2-((1E,3E)-3-(3-methyl-1-(2,5,8,11,14,17-hexaoxanonadecan-19-yl)-5-sulfonato-3-(3-sulfonatopropyl)indolin-2-ylidene)prop-1-enyl)-3H-indolium-5- sulfonate) contains a (poly)ethylene glycol on the indole N of the left heterocycle. 550 Compound 6/2, with the (poly) ethylene glycol shown in abbreviated notation used throughout, represents the following structure.

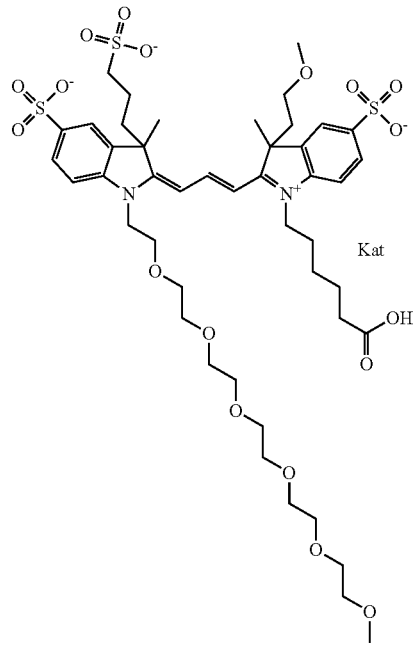 [SMILES: COCCOCCOCCOCCOCCOCCN1/C(=C/C=C/C2=[N+](CCCCCC(=O)O)c3ccc(S(=O)(=O)[O-])cc3C2(C)CCOC)C(C)(CCCS(=O)(=O)[O-])c2cc(S(=O)(=O)[O-])ccc21]

The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 550 Compound 6/2 is activated as described above.

In embodiments, the degree of sulfonation is varied to, e.g., vary the compound's degree of hydrophilicity or hydrophobicity. One non-limiting example is a monosulfonate form of 550 Compound 1/2, shown below, but it is understood that the single sulfo group can be at any of the described positions:

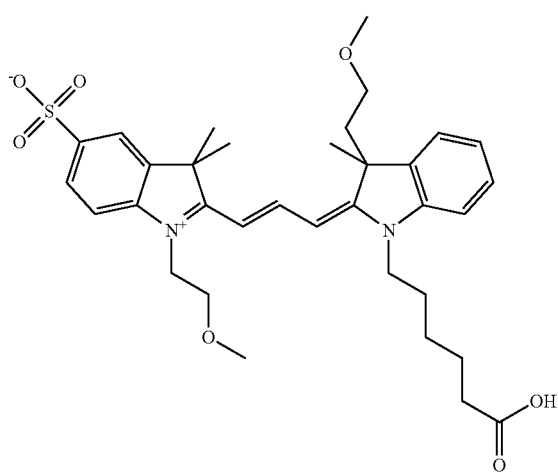

One non-limiting example is a disulfonate form of 550 Compound 1/2, shown below, but it is understood that each of the two sulfo groups can be at any of the described positions:

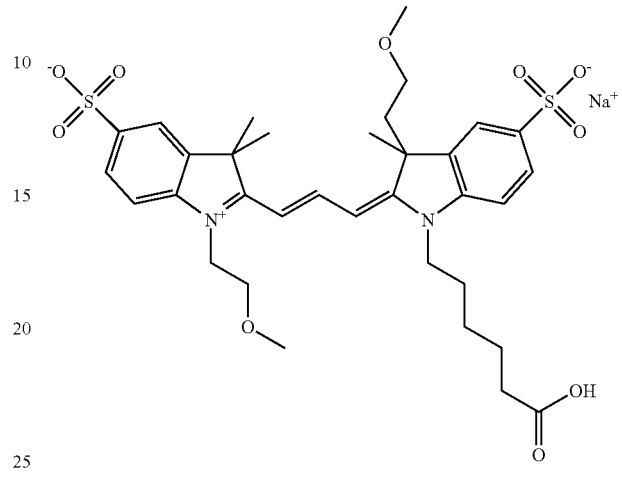

One non-limiting example is a trisulfonate form of 550 Compound 1/2, shown below, but it is understood that each of the three sulfo groups can be at any of the described positions:

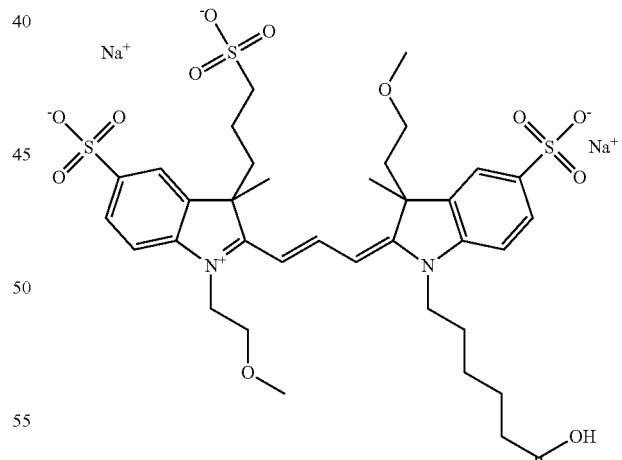

One non-limiting example is a tetrasulfonate form of 550 Compound 1/2, shown below, but it is understood that each of the four sulfo groups can be at any of the described positions:

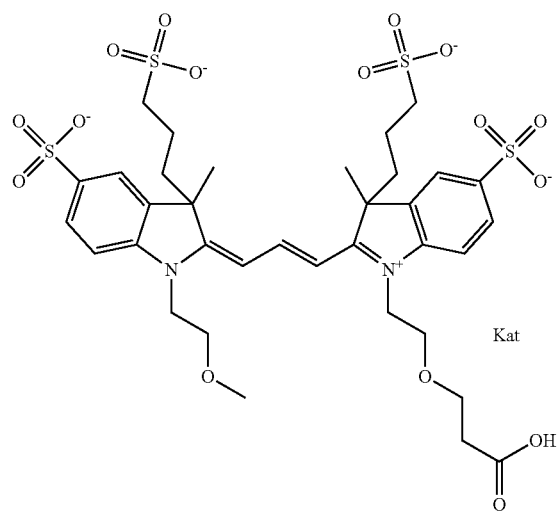 [SMILES: COCCN1/C(=C/C=C/C2=[N+](CCOCCC(=O)O)c3ccc(S(=O)(=O)[O-])cc3C2(C)CCCS(=O)(=O)[O-])C(C)(CCCS(=O)(=O)[O-])c2cc(S(=O)(=O)[O-])ccc21]

In embodiments, the compound contains one or more substitutions of the polymethine linker. In one embodiment, the compound has general formula IVa with "a" indicating an ethylene glycol, diethylene glycol, or (poly)ethylene glycol group on the left indole N, and the chain on the right indole N terminating in COX:

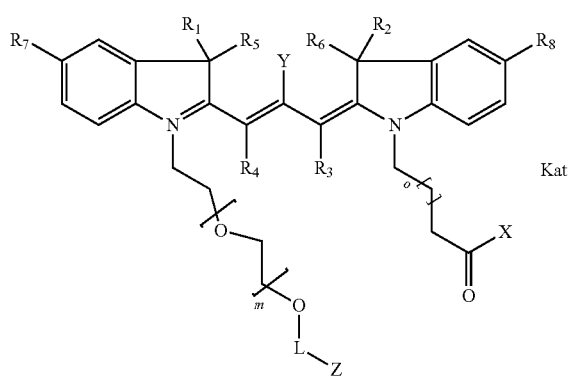

general formula IVb with "b" indicating an ethylene glycol, diethylene glycol, or (poly)ethylene glycol group on the left indole N, and the chain on the right indole N terminating in COH:

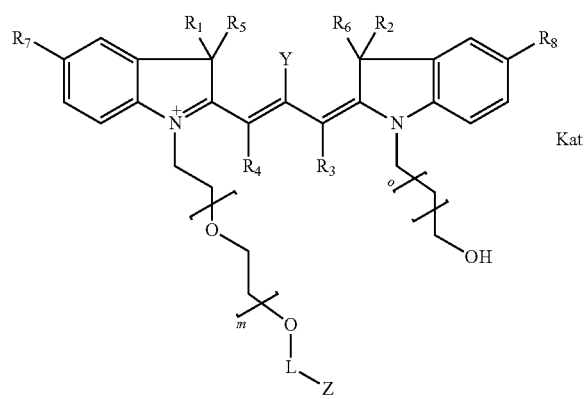

general formula IVc with "c" indicating an ethylene glycol, diethylene glycol, or (poly)ethylene glycol group on the left and right indole N, and the chain on the right indole N terminating in COX:

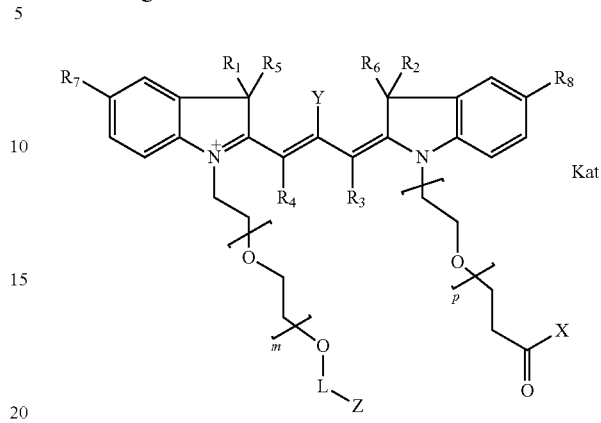

or general formula IVd with "d" indicating an ethylene glycol, diethylene glycol, or (poly)ethylene glycol group on the left indole N, and the chain on the right indole N terminating in COH:

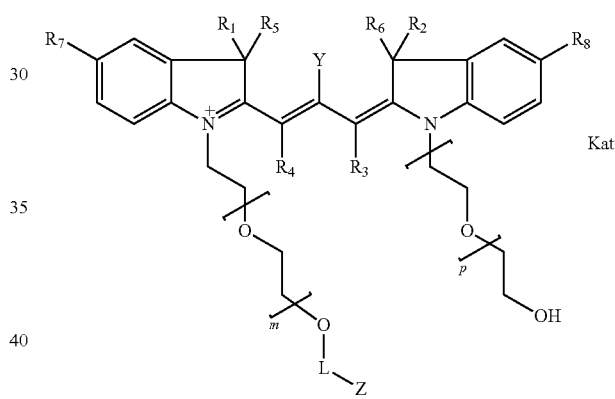

where each of $R^1$, $R^2$, $R^5$, and $R^6$ is the same or different and is independently selected from the group consisting of an aliphatic, heteroaliphatic, sulfoalkyl, heteroaliphatic with terminal $SO_3$, a PEG group P-L-Z where P is selected from an ethylene glycol group, a diethylene glycol group, and a (poly)ethylene glycol group where the (poly)ethylene glycol group is $(CH_2CH_2O)_s$ where s is an integer from 3-6 inclusive, a sulfonamide group -L-$SO_2$NH—P-L-Z, and a carboxamide group -L-CONH—P-L-Z; each of $R^7$ and $R^8$ is the same or different and is independently selected from either H, $SO_3$, a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group —$SO_2$NH—P-L-Z, or a carboxamide group —CONH—P-L-Z; where L is selected from the group consisting of a divalent linear (—$(CH_2)_o$—, o=0 to 15), crossed, or cyclic alkane group that can be substituted by at least one atom selected from the group consisting of oxygen, substituted nitrogen, and/or sulfur;

where Z is selected from the group consisting of H, CH$_3$, alkyl, a heteroalkyl group, NH$_2$, —COO, —COOH, —COSH, CO—NH—NH$_2$, —COF, —COCl, —COBr, —COI, —COO-Su (succinimidyl/sulfosuccinimidyl), —COO-STP (4-sulfo-2,3,5,6-tetrafluorophenyl), —COO-TFP (2,3,5,6-tetrafluorophenyl), —COO-benzotriazole, —CO-benzotriazole, —CONR'—CO—CH$_2$—I, —CONR'R", —CONR'-biomolecule, —CONR'-L-COO, —CONR'-L-COOH, —CONR'-L-COO-Su, —CONR'-L-COO-STP, —CONR'-L-COO-TFP, —CONR'-L-CONR"$_2$, —CONR'-L-CO-biomolecule, —CONR'-L-CO—NH—NH$_2$, —CONR'-L-OH, —CONR'-L-O-phosphoramidite, —CONR'-L-CHO, —CONR'-L-maleimide, and —CONR'-L-NH—CO—CH$_2$—I; R' and R" is selected from the group consisting of H, aliphatic group, and heteroaliphatic group, and the biomolecule is a protein, antibody, nucleotide, oligonucleotide, biotin, or hapten; X is selected from the group consisting of —OH, —SH, —NH$_2$, —NH—NH$_2$, —F, —Cl, —Br, I, —NHS hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, and —NR-L-NH—CO—CH2-I, where R is —H or an aliphatic or heteroaliphatic group; Kat is a number of Na$^+$, K$^+$, Ca$^{2+}$, ammonia, or other cation(s) needed to compensate the negative charge brought by the cyanine; m is an integer from 0 to 5 inclusive; p is an integer from 1 to 6 inclusive; each of R3 and R4 is the same or different and is independently hydrogen, an aliphatic group, a heteroaliphatic group, or a PEG group P-L-Z where P is selected from an ethylene glycol group, a diethylene glycol group, and a (poly)ethylene glycol group where the (poly)ethylene glycol group is (CH$_2$CH$_2$O)$_s$ where s is an integer from 3-6 inclusive; or R3 and R4 together form a cyclic structure where R3 and R4 are joined using a divalent structural element selected from the group consisting of —(CH$_2$)$_q$—, —(CH$_2$)$_q$O(CH$_2$)$_{q'}$—, —(CH$_2$)$_q$S(CH$_2$)$_{q'}$—, —(CH$_2$)$_q$CH=CH—, —OCH=CH— where each of q and q' is the same or different and is a integer from 2 to 6 inclusive; and Y is selected from the group consisting of hydrogen, alkyl, sulfoalkyl, fluorine, chlorine, bromine, a substituted or unsubstituted aryl-, phenoxy- or phenylmercapto function; and Y is selected from the group consisting of hydrogen, alkyl, sulfoalkyl, fluorine, chlorine, bromine, and a PEG group P-L-Z where P is selected from an ethylene glycol group, a diethylene glycol group, and a (poly)ethylene glycol group where the (poly)ethylene glycol group is (CH$_2$CH$_2$O)$_s$ where s is an integer from 3-6 inclusive; with the proviso that at least one of R$^1$, R$^2$, R$^3$, R$^4$, R$^5$, R$^6$, R$^7$, and R$^8$ contains a PEG group.

In one embodiment, the compound of general formula IV wherein each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of —(CH$_2$)$_q$— and CH=CH, where q is an integer from 1 to 2 inclusive, to result in a 3-, 4-, or 5-membered ring.

One non-limiting example is a substituted polymethine form of 550 Compound 1/2, shown below:

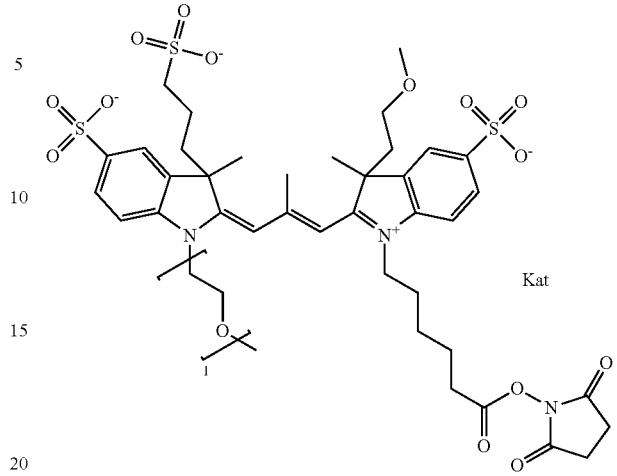

One non-limiting example is a substituted polymethine form of 550 Compound 2/2, shown below:

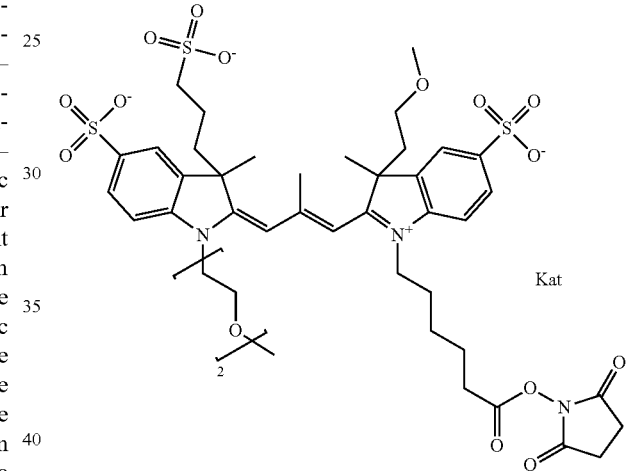

One non-limiting example is a substituted polymethine form of 550 Compound 3/2, shown below:

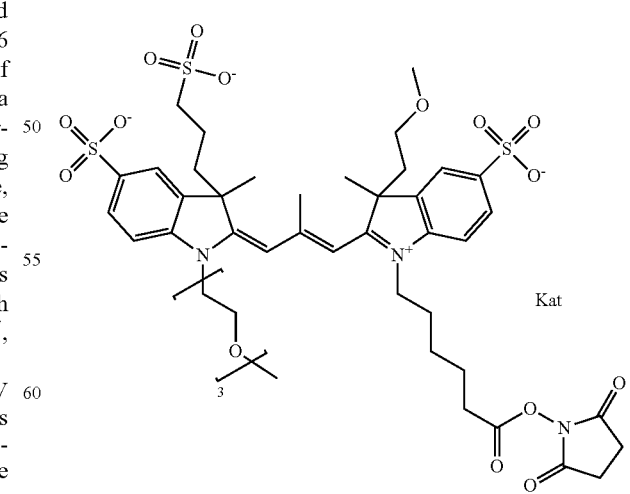

One non-limiting example is a substituted polymethine form of 550 Compound 4/2, shown below:

One non-limiting example is a substituted polymethine form of 550 having an ethylene glycol, diethylene glycol, or (poly)ethylene glycol as described for general formula IV, such as the compound shown below:

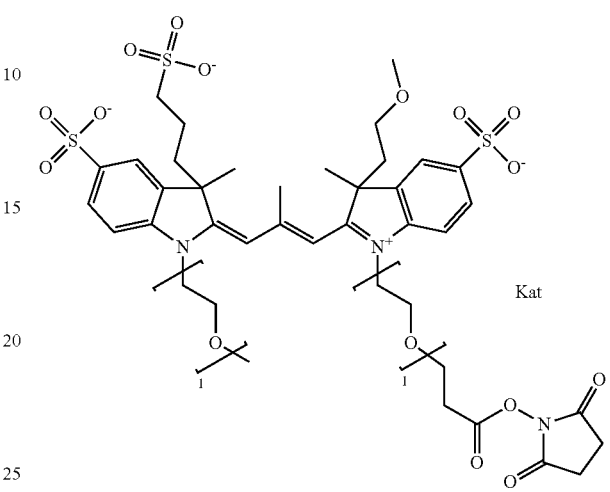

In embodiments, an ethylene glycol group, diethylene glycol group, and/or a (poly)ethylene glycol group, which will collectively be referred to as a PEG group, unless specifically defined, may be present at position(s) in addition to such groups being present on the indole N atom(s).

One non-limiting example of an additionally PEG-substituted compound is a 550 Compound 1/2 according to general formula II where R1 is an ethylene glycol group terminating with a methyl group, shown below:

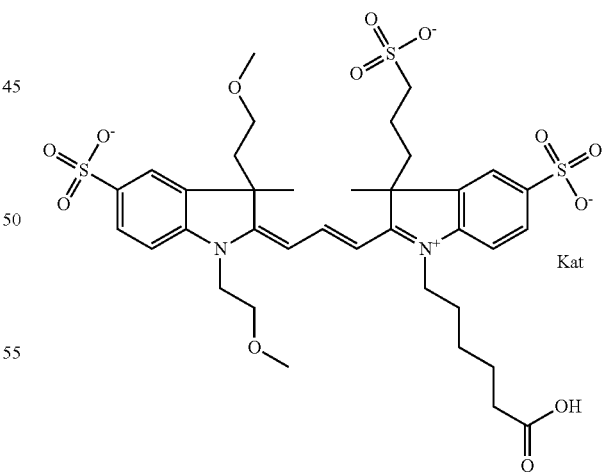

One non-limiting example of an additionally PEG-substituted compound is a 550 Compound 1/2 according to general formula II where R1 is a diethylene glycol group terminating with a methyl group, shown below:

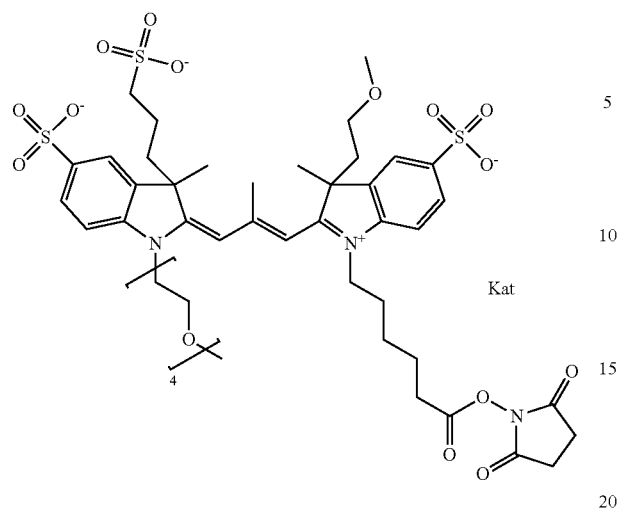

One non-limiting example is a substituted polymethine form of 550 Compound 5/2, shown below:

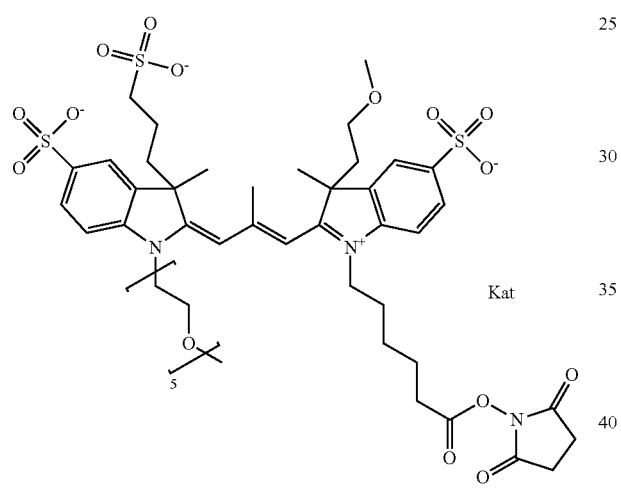

One non-limiting example is a substituted polymethine form of 550 Compound 6/2, shown below:

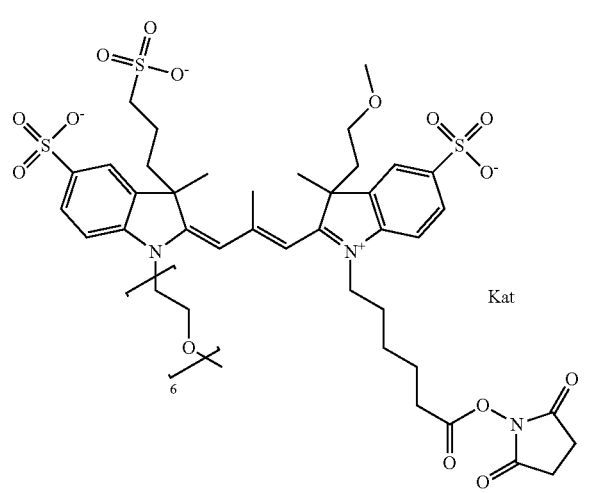

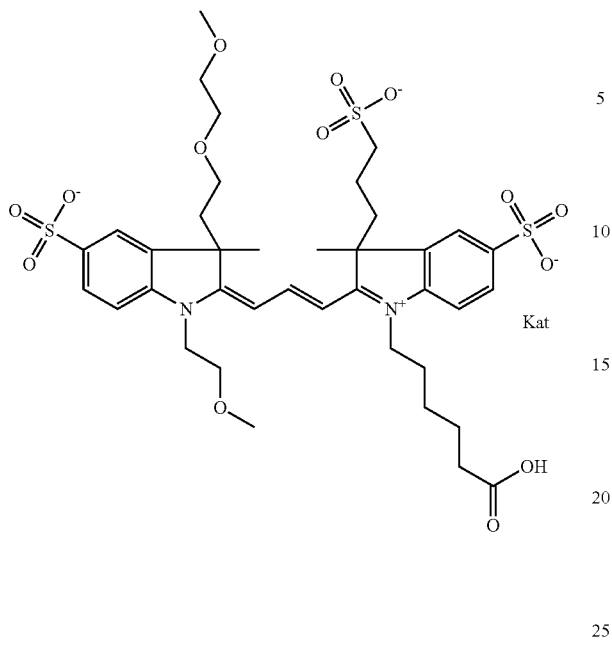

One non-limiting example of an additionally PEG-substituted compound is a 550 Compound 1/2 according to general formula II where R1 is a (poly)ethylene glycol (3) group terminating with a methyl group, shown below:

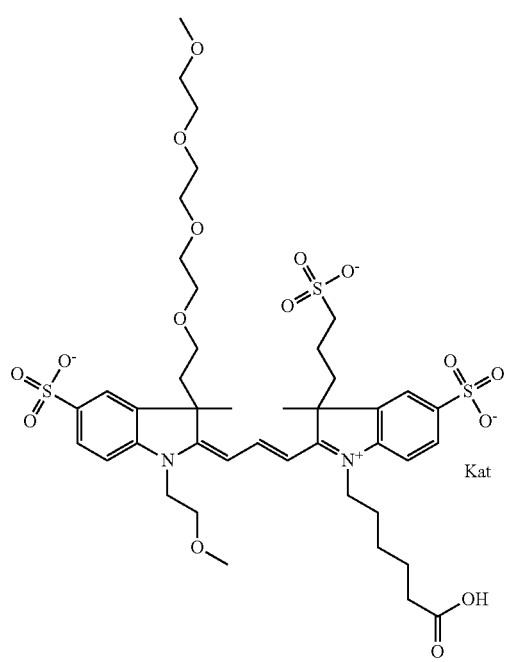

One non-limiting example of an additionally PEG-substituted compound is a 550 Compound 1/2 according to general formula II where R1 is a (poly)ethylene glycol (5) group terminating with a methyl group, shown below:

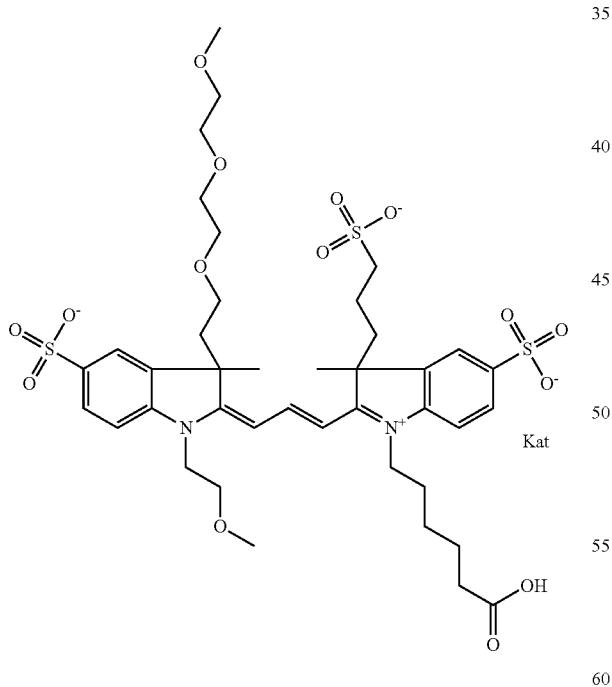

One non-limiting example of an additionally PEG-substituted compound is a 550 Compound 1/2 according to general formula II where R1 is a (poly)ethylene glycol (4) group terminating with a methyl group, shown below:

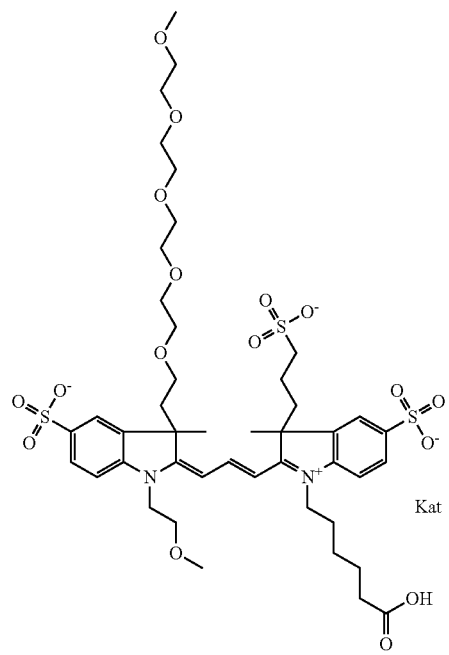

One non-limiting example of an additionally PEG-substituted compound is a 550 Compound 1/2 according to general formula II where R1 is a (poly)ethylene glycol (6) group terminating with a methyl group, shown below:

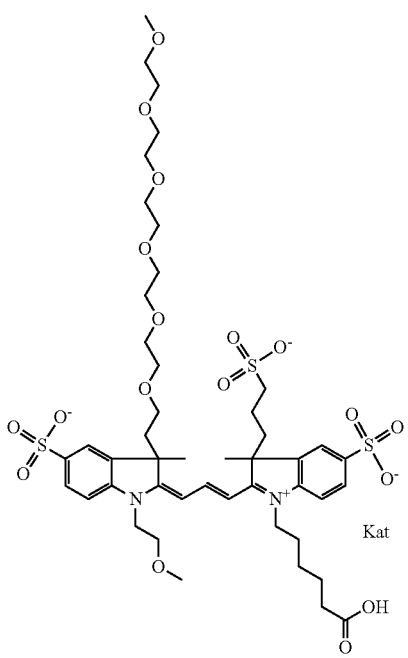

One non-limiting example of an additionally PEG-substituted compound is a 550 Compound 1/2 according to general formula II where R1 is a sulfonamide group -L-SO$_2$NH—P—Z where Z is a methyl group, shown below:

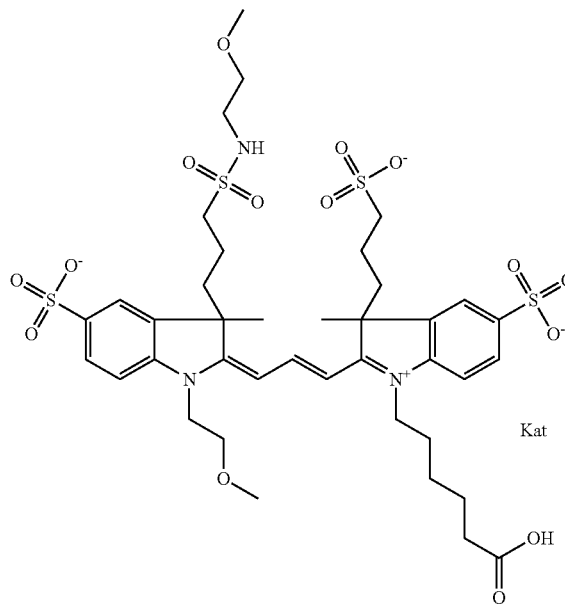

One non-limiting example of an additionally PEG-substituted compound is a 550 Compound 1/2 according to general formula II where R1 is a carboxamide group -L-CONH—P—Z where Z is a methyl group, shown below:

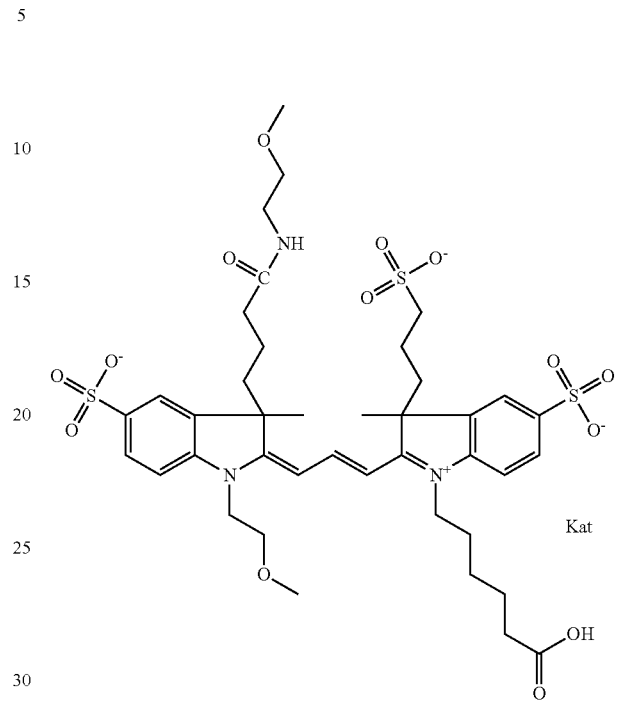

One non-limiting example of an additionally PEG-substituted compound is a 550 Compound 1/2 according to general formula II where R2 is an ethylene glycol group terminating with a methyl group, shown below:

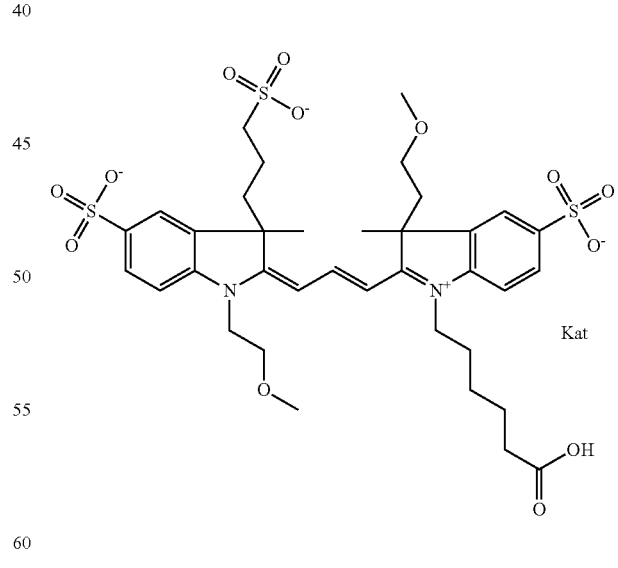

One non-limiting example of an additionally PEG-substituted compound is a 550 Compound 1/2 according to general formula II where R2 is a diethylene glycol group terminating with a methyl group, shown below:

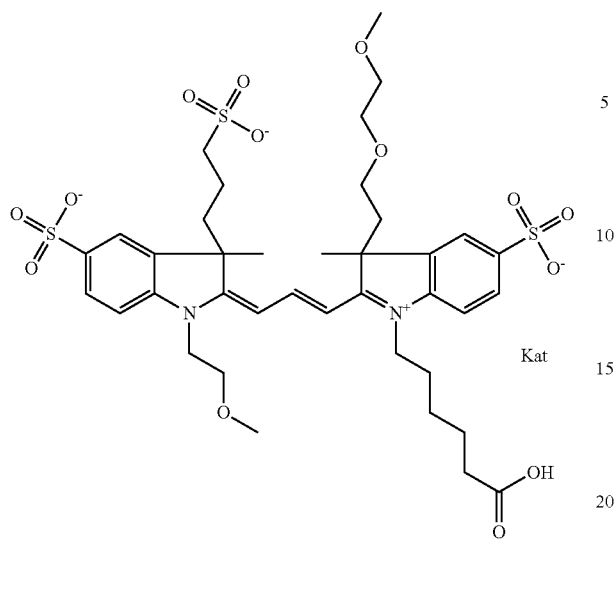

One non-limiting example of an additionally PEG-substituted compound is a 550 Compound 1/2 according to general formula II where R2 is a (poly)ethylene glycol (3) group terminating with a methyl group, shown below:

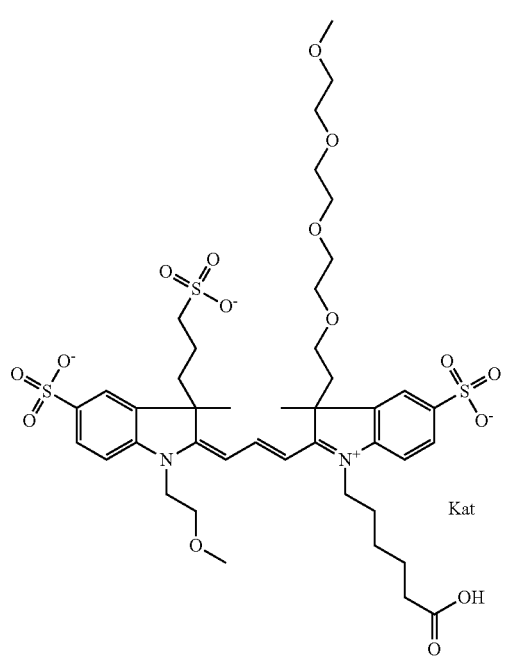

One non-limiting example of an additionally PEG-substituted compound is a 550 Compound 1/2 according to general formula II where R2 is a (poly)ethylene glycol (5) group terminating with a methyl group, shown below:

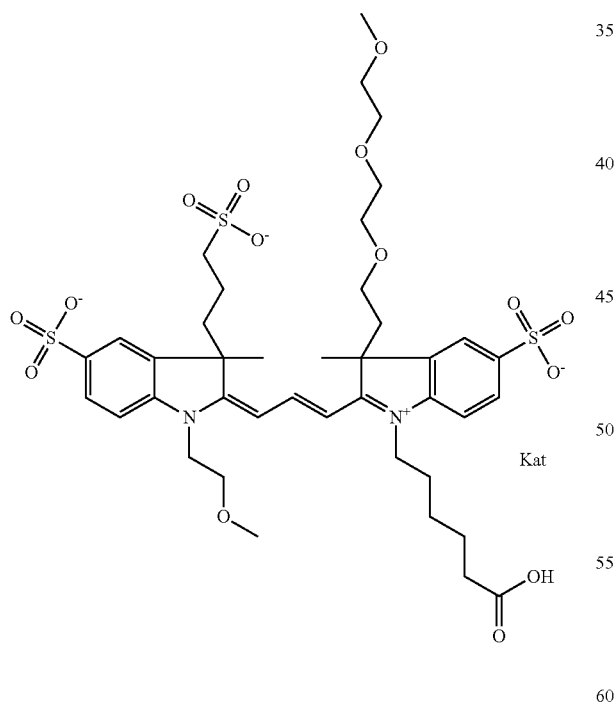

One non-limiting example of an additionally PEG-substituted compound is a 550 Compound 1/2 according to general formula II where R2 is a (poly)ethylene glycol (4) group terminating with a methyl group, shown below:

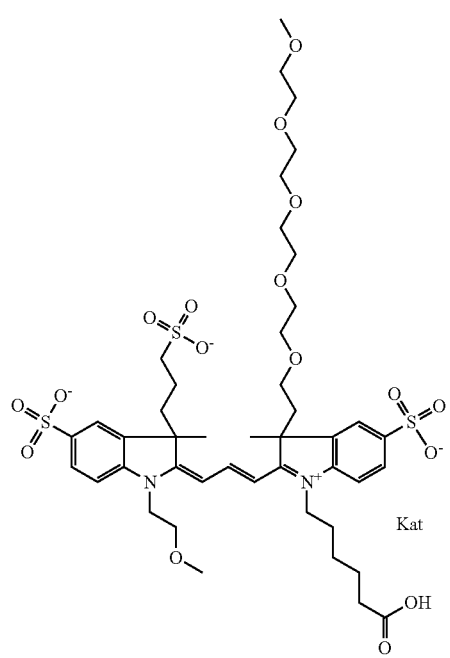

One non-limiting example of an additionally PEG-substituted compound is a 550 Compound 1/2 according to general formula II where R2 is a (poly)ethylene glycol (6) group terminating with a methyl group, shown below:

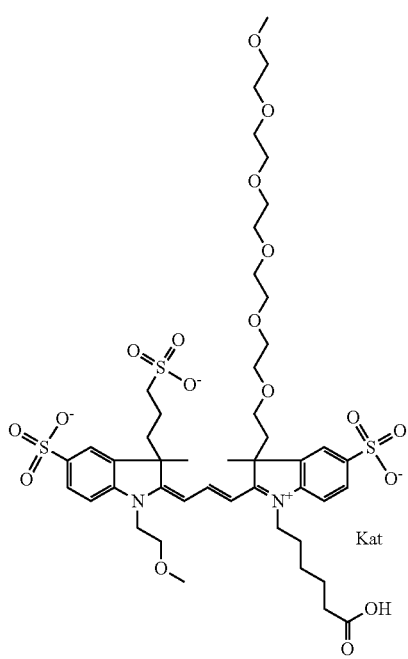

One non-limiting example of an additionally PEG-substituted compound is a 550 Compound 1/2 according to general formula II where R2 is a sulfonamide group -L-SO₂NH—P—Z where Z is a methyl group, shown below:

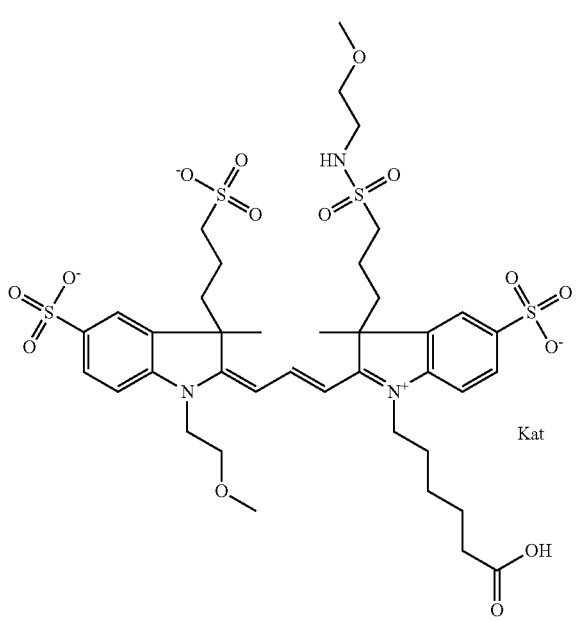

One non-limiting example of an additionally PEG-substituted compound is a 550 Compound 1/2 according to general formula II where R2 is a carboxamide group -L-CONH—P—Z where Z is a methyl group, shown below:

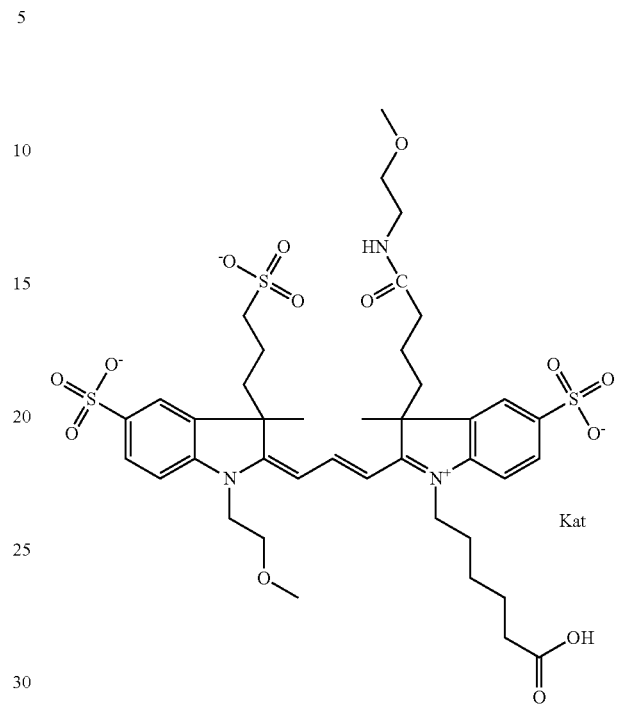

One non-limiting example of an additionally PEG-substituted compound is a 550 Compound 1/3 according to general formula II where both R1 and R2 are an ethylene glycol group terminating with a methyl group, shown below:

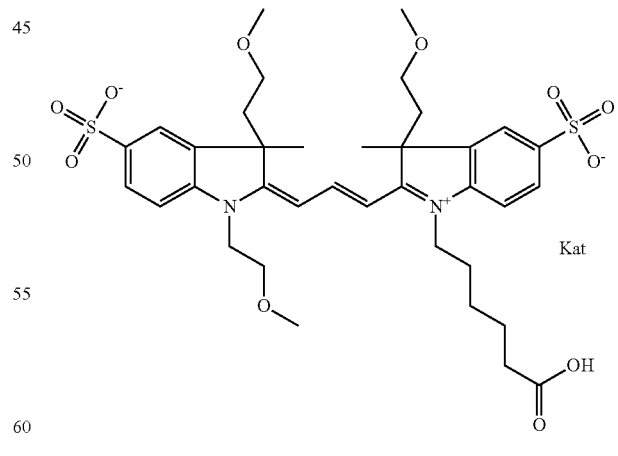

One non-limiting example of an additionally PEG-substituted compound is a 550 Compound 1/3 according to general formula II where both R1 and R2 are a diethylene glycol group terminating with a methyl group, shown below:

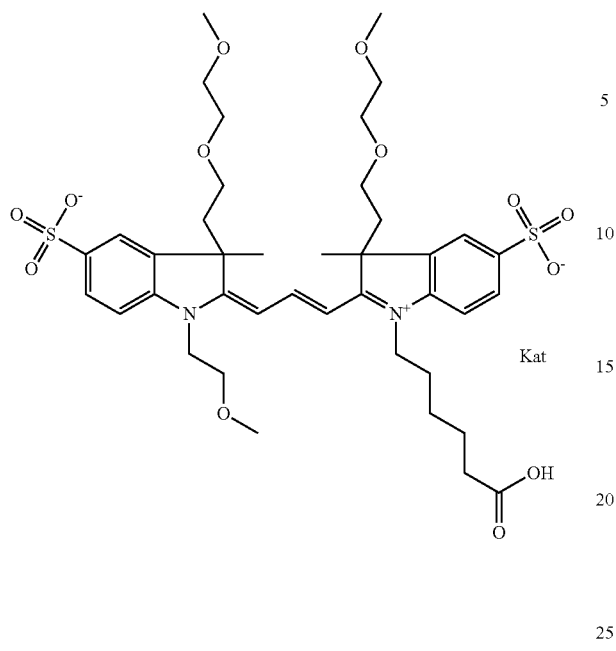

One non-limiting example of an additionally PEG-substituted compound is a 550 Compound 1/3 according to general formula II where both R1 and R2 are a (poly) ethylene glycol (3) group terminating with a methyl group, shown below:

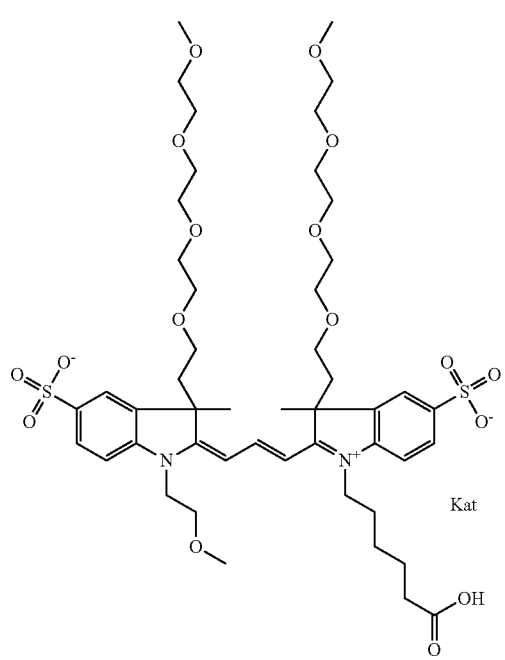

One non-limiting example of an additionally PEG-substituted compound is a 550 Compound 4/4 according to general formula III where both R1 and R2 are a (poly) ethylene glycol (4) group terminating with a methyl group, and R7 and R8 are sulfo, shown below:

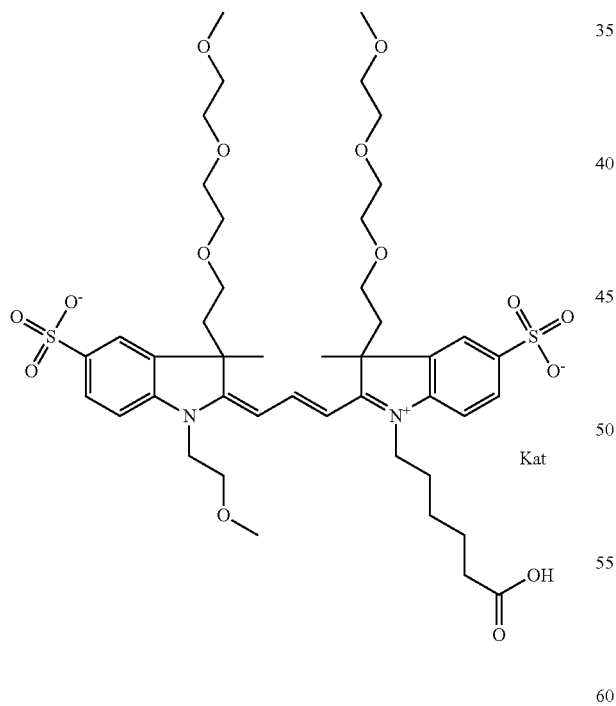

One non-limiting example of an additionally PEG-substituted compound is a 550 Compound 1/3 according to general formula II where both R1 and R2 are a (poly) ethylene glycol (4) group terminating with a methyl group, shown below:

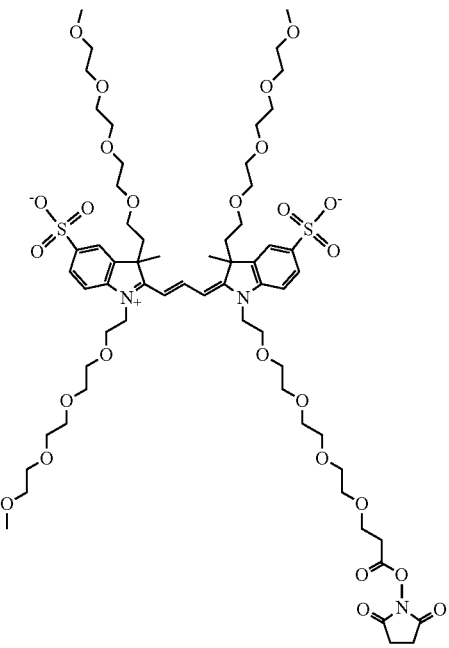

One non-limiting example of an additionally PEG-substituted compound is a 550 Compound 4/4 according to general formula III where both R1 and R2 are a (poly) ethylene glycol (4) group terminating with a methyl group, and R7 and R8 are H, shown below:

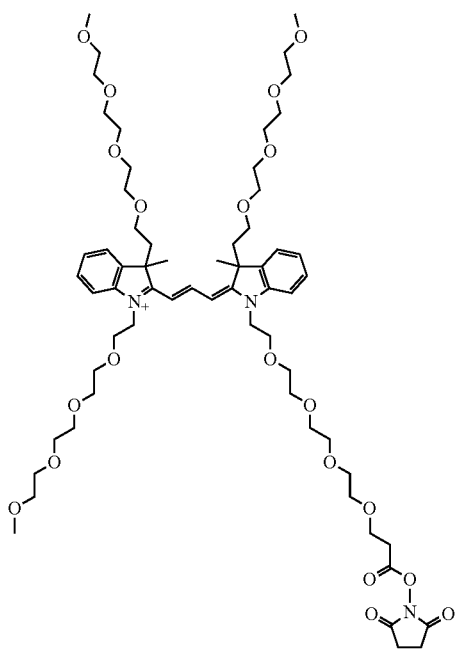

One non-limiting example of an additionally PEG-substituted compound is a 550 Compound 1/3 according to general formula II where both R1 and R2 are a (poly)ethylene glycol (5) group terminating with a methyl group, shown below:

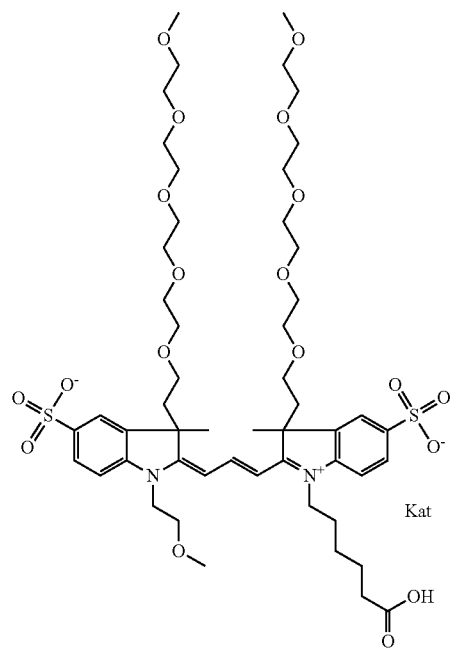

One non-limiting example of an additionally PEG-substituted compound is a 550 Compound 1/3 according to general formula II where both R1 and R2 are a (poly)ethylene glycol (6) group terminating with a methyl group, shown below:

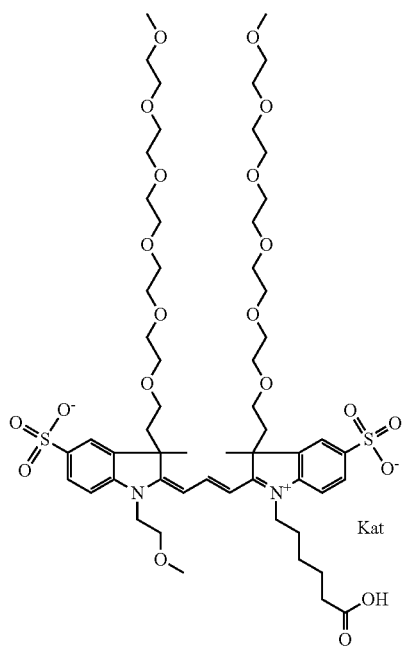

One non-limiting example of an additionally PEG-substituted compound is a 550 Compound 1/2 according to general formula II where R8 is an ethylene glycol group terminating with a methyl group, shown below:

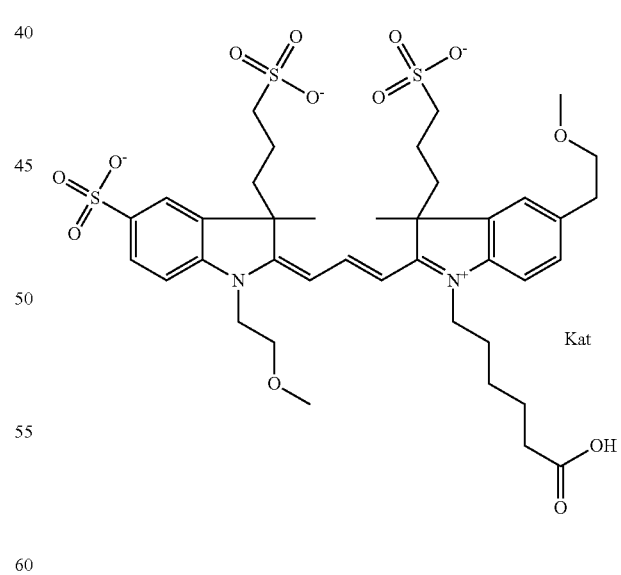

One non-limiting example of an additionally PEG-substituted compound is a 550 Compound 1/2 according to general formula II where R8 is sulfonamide —SO$_2$NH—P—Z where Z is a methyl group, shown below:

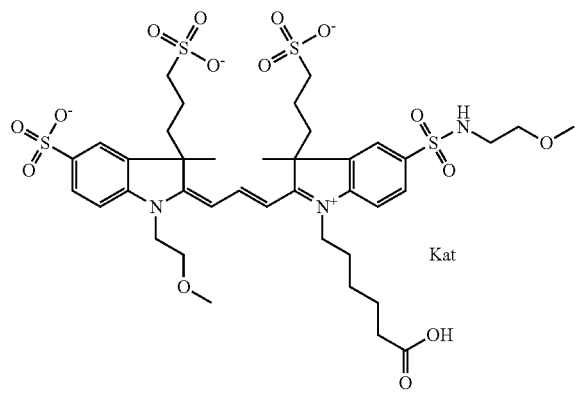

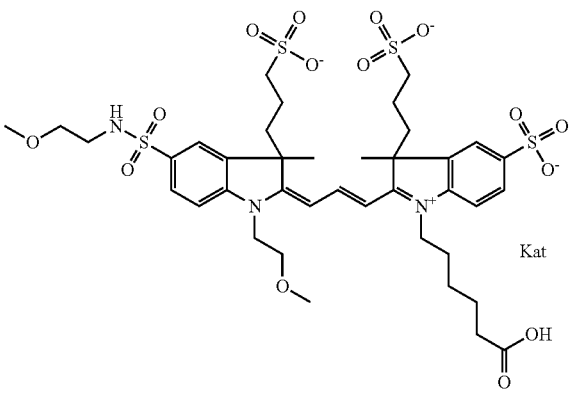

One non-limiting example of an additionally PEG-substituted compound is a 550 Compound 1/2 according to general formula II where R8 is carboxamide —CONH—P—Z where Z is a methyl group, shown below:

One non-limiting example of an additionally PEG-substituted compound is a 550 Compound 1/2 according to general formula II where R7 is a carboxamide group —CONH—P—Z where Z is a methyl group, shown below:

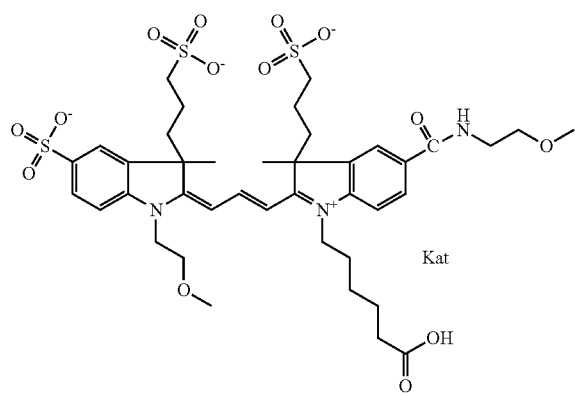

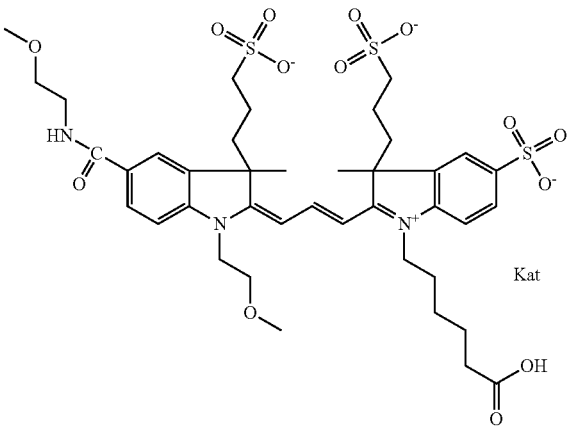

One non-limiting example of an additionally PEG-substituted compound is a 550 Compound 1/2 according to general formula II where R7 is an ethylene glycol group terminating with a methyl group, shown below:

One non-limiting example of an additionally PEG-substituted compound is a 550 Compound 1/3 according to general formula II where both R7 and R8 are an ethylene glycol group terminating with a methyl group, shown below:

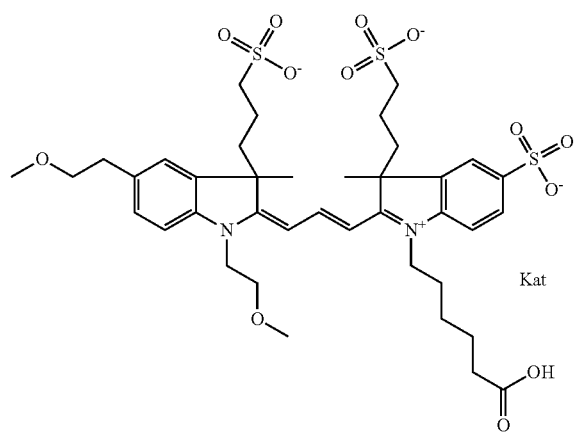

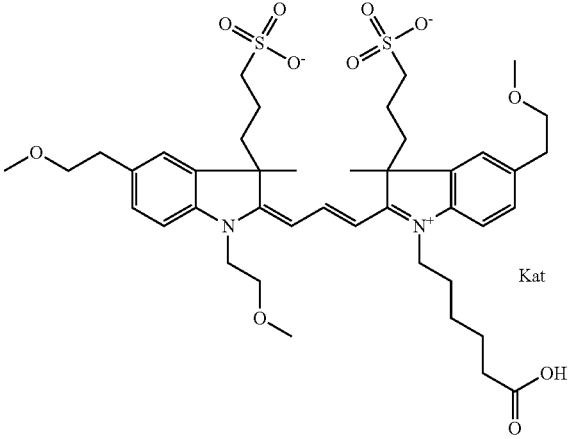

One non-limiting example of an additionally PEG-substituted compound is a 550 Compound 1/2 according to general formula II where R7 is a sulfonamide group —SO₂NH—P—Z where Z is a methyl group, shown below:

One non-limiting example of an additionally PEG-substituted compound is a 550 Compound 1/3 according to general formula II where both R7 and R8 are a sulfonamide group —SO₂NH—P—Z where Z is a methyl group, shown below:

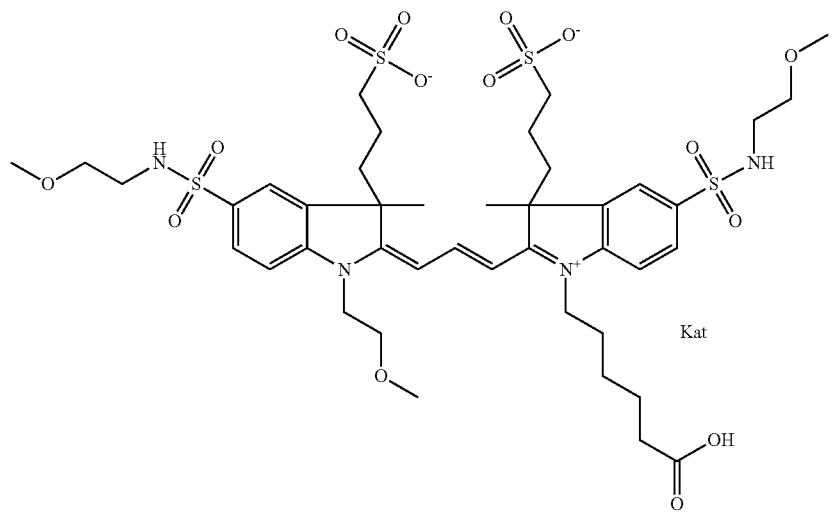

One non-limiting example of an additionally PEG-substituted compound is a 550 Compound 1/3 according to general formula II where both R7 and R8 are a carboxamide group —CONH—P—Z where Z is a methyl group, shown below:

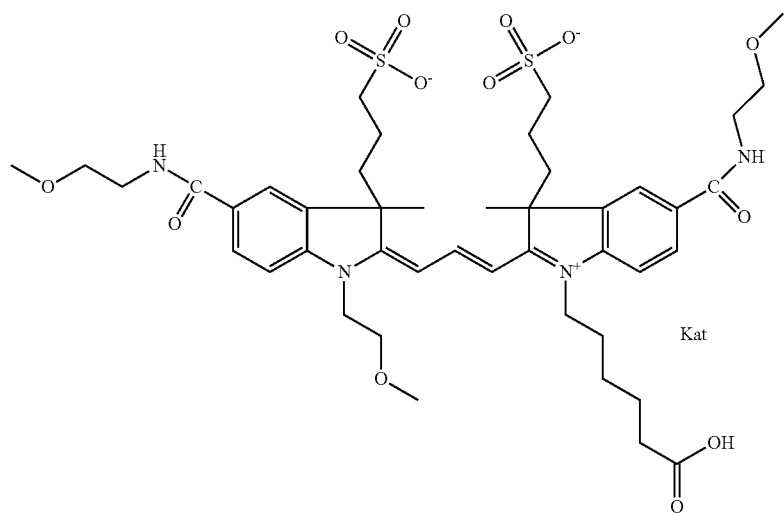

In one embodiment, the compound is 650 Compound 1/2

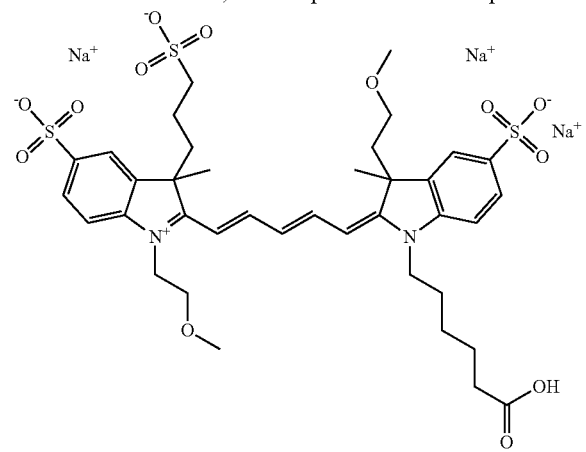

650 Compound 1/2 ((2-((1E,3E,5E)-5-(1-(5-carboxypentyl)-3-(2-methoxyethyl)-3-methyl-5-sulfonatoindolin-2-ylidene)penta-1,3-dienyl)-1-(2-methoxyethyl)-3-methyl-3-(3-sulfonatopropyl)-3H-indolium-5-sulfonate tri sodium salt) contains an ethylene glycol on the indole N of the left heterocycle, i.e., a methylated ethylene glycol. The methyl group on the ethylene glycol prevents the terminal —OH from oxidation. Oxidation is known to occur, over time, on an unprotected PEG terminus (i.e., an unprotected ethylene glycol group, diethylene glycol group, or (poly)ethylene glycol group). Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 650 Compound 1, but one skilled in the art appreciates that activation is not limited to these examples. One non-limiting example of an activated compound is the NHS-ester of 650 Compound 1/2, shown below:

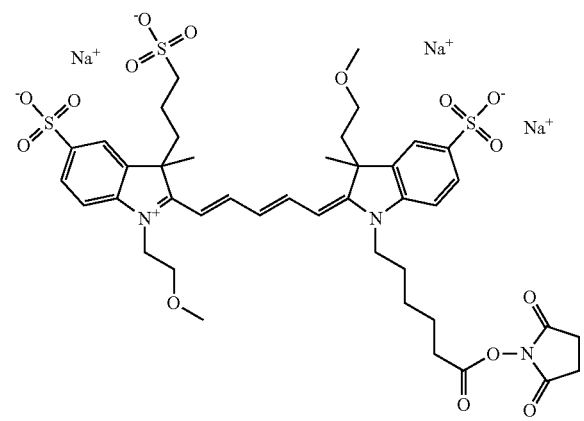

In one embodiment, the compound is a NHS-ester of 650 Compound 1/2 where, according to general formula I, o is 1, shown below:

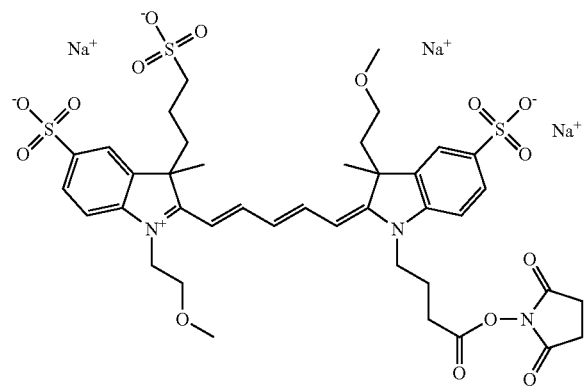

In one embodiment, the compound is an NHS-ester of 650 Compound 1/2 where, according to general formula I, o is 5, shown below:

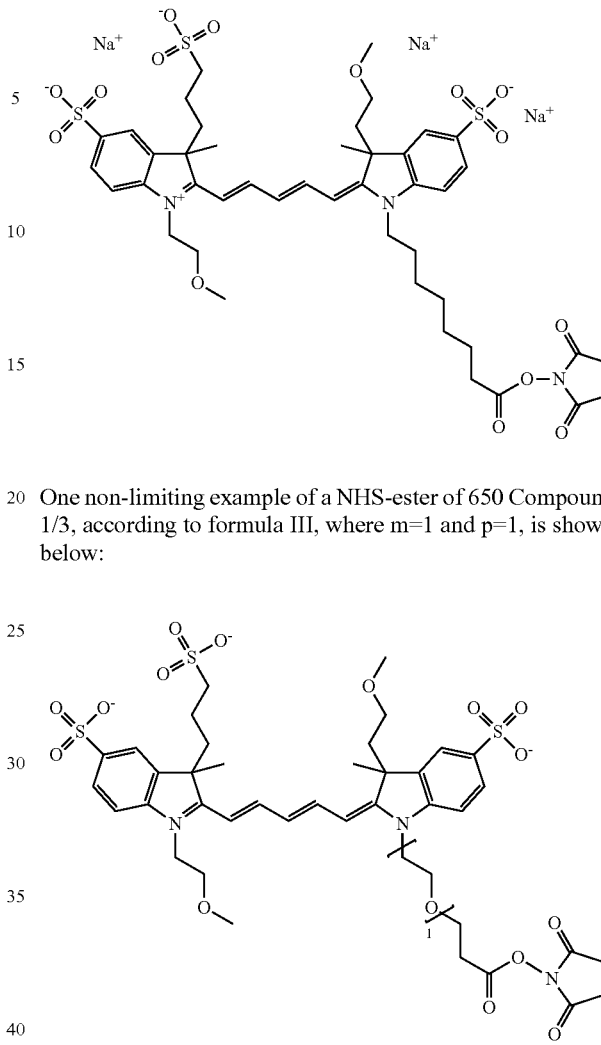

One non-limiting example of a NHS-ester of 650 Compound 1/3, according to formula III, where m=1 and p=1, is shown below:

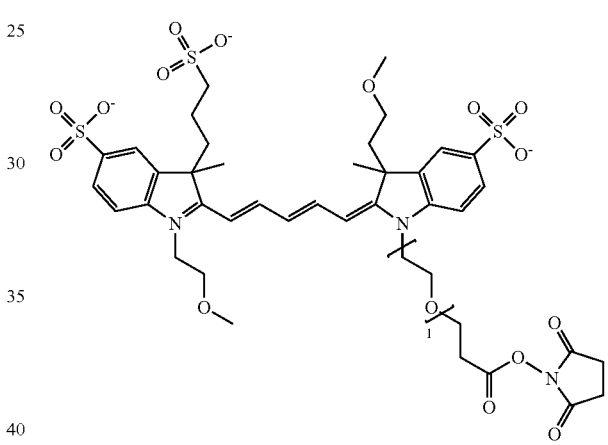

One non-limiting example of a NHS-ester of 650 Compound 1/3, according to general formula III, where m=1 and p=2, is shown below:

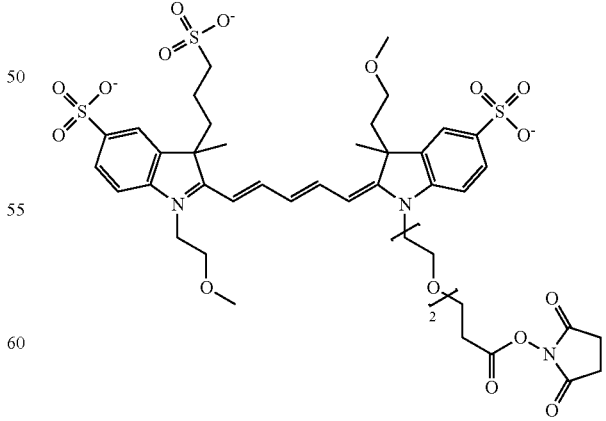

One non-limiting example of a NHS-ester of 650 Compound 1/3, according to general formula III, where m=1 and p=3, is shown below:

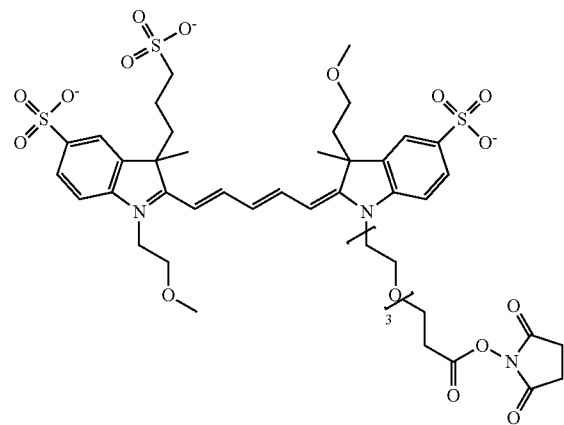

One non-limiting example of a NHS-ester of 650 Compound 1/3, according to general formula III, where m=1 and p=4, is shown below:

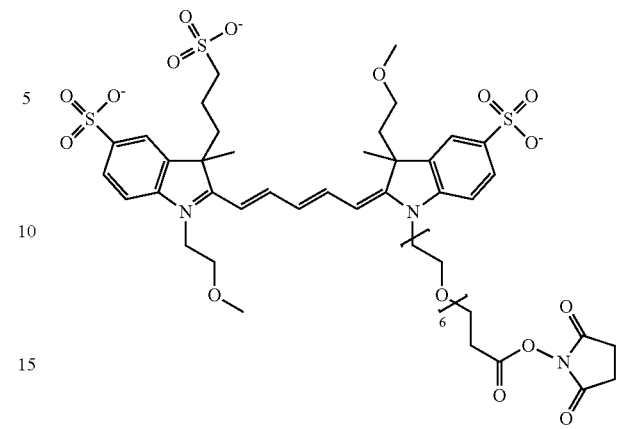

One non-limiting example of a NHS-ester of 650 Compound 2/3, according to general formula III, where m=2 and p=1, is shown below:

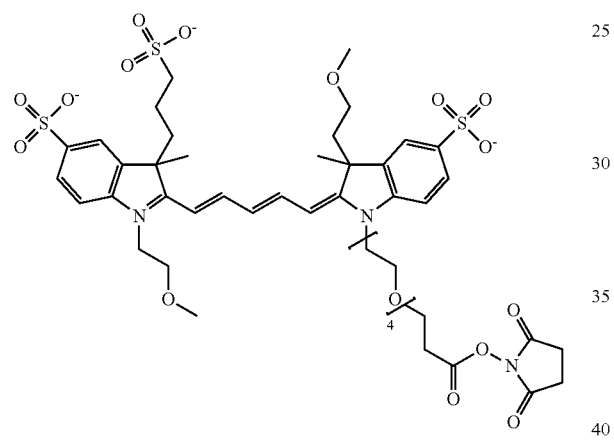

One non-limiting example of a NHS-ester of 650 Compound 1/3, according to general formula III, where m=1 and p=5, is shown below:

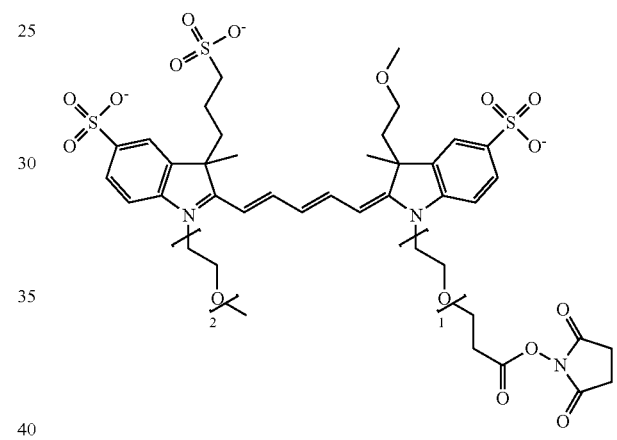

One non-limiting example of a NHS-ester of 650 Compound 2/3, according to general formula III, where m=2 and p=2, is shown below:

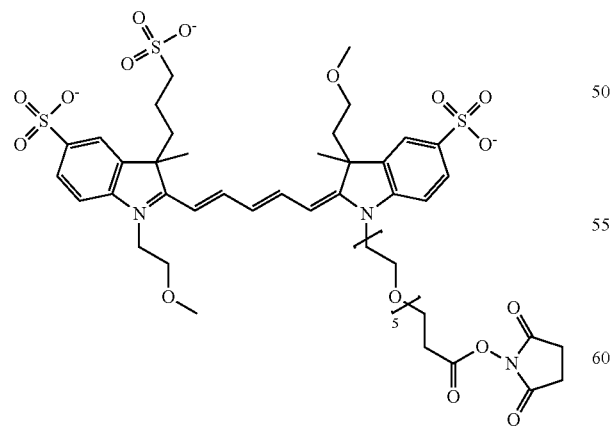

One non-limiting example of a NHS-ester of 650 Compound 1/3, according to general formula III, where m=1 and p=6, is shown below:

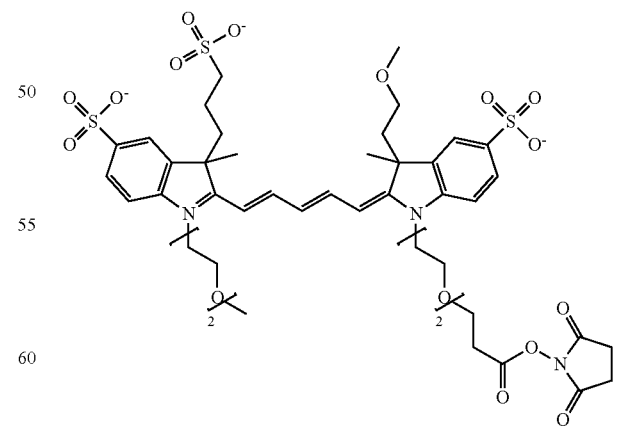

One non-limiting example of a NHS-ester of 650 Compound 2/3, according to general formula III, where m=2 and p=3, is shown below:

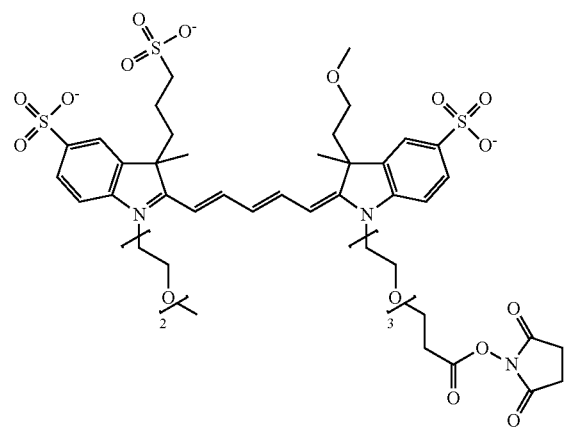

One non-limiting example of a NHS-ester of 650 Compound 3/3, according to general formula III, where m=3 and p=1, is shown below:

One non-limiting example of a NHS-ester of 650 Compound 4/3, according to general formula III, where m=4 and p=1, is shown below:

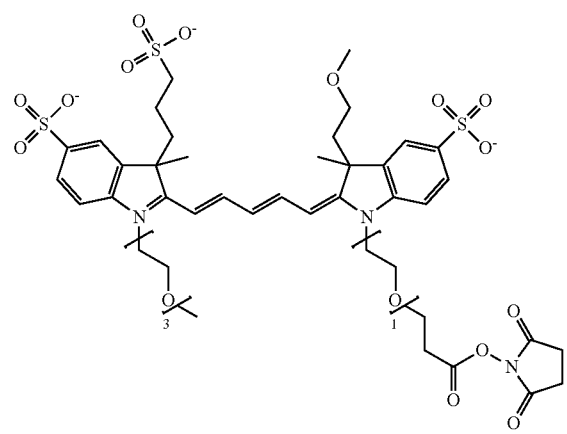

One non-limiting example of a NHS-ester of 650 Compound 3/3, according to general formula III, where m=3 and p=2, is shown below:

One non-limiting example of a NHS-ester of 650 Compound 5/3, according to general formula III, where m=5 and p=1, is shown below:

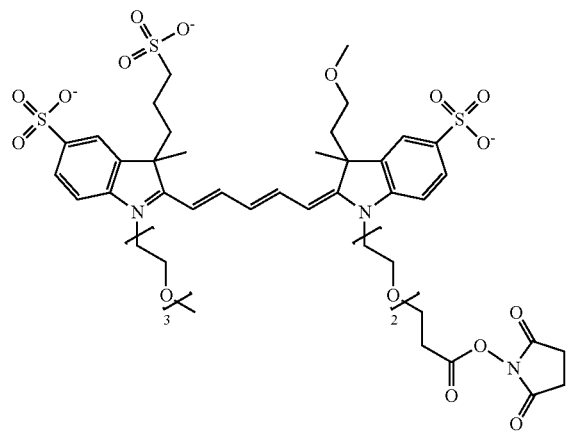

One non-limiting example of a NHS-ester of 650 Compound 3/3, according to general formula III, where m=3 and p=3, is shown below:

One non-limiting example of a NHS-ester of 650 Compound 6/3, according to general formula III, where m=6 and p=1, is shown below:

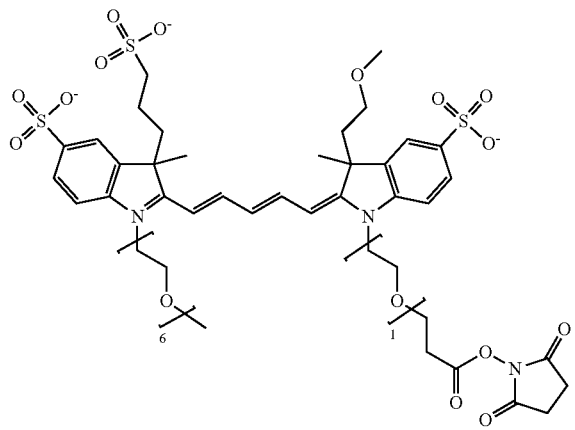

One non-limiting example of an activated 650 Compound 1/2 is the tetrafluorophenyl (TFP)-ester of 650 Compound 1/2, shown below:

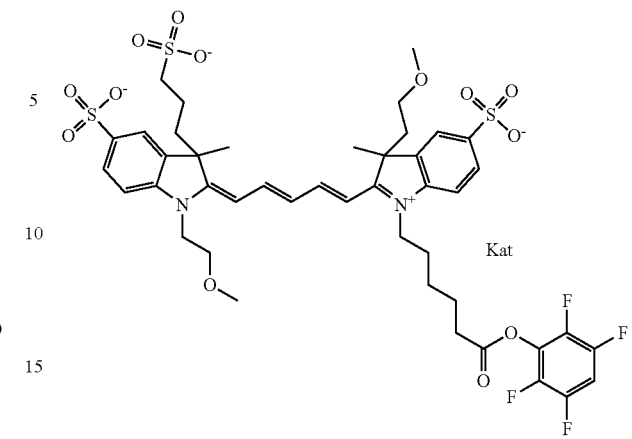

One non-limiting example of an activated 650 Compound 1/2 is the sulfotetrafluorophenyl (STP)-ester of 650 Compound 1/2, shown below:

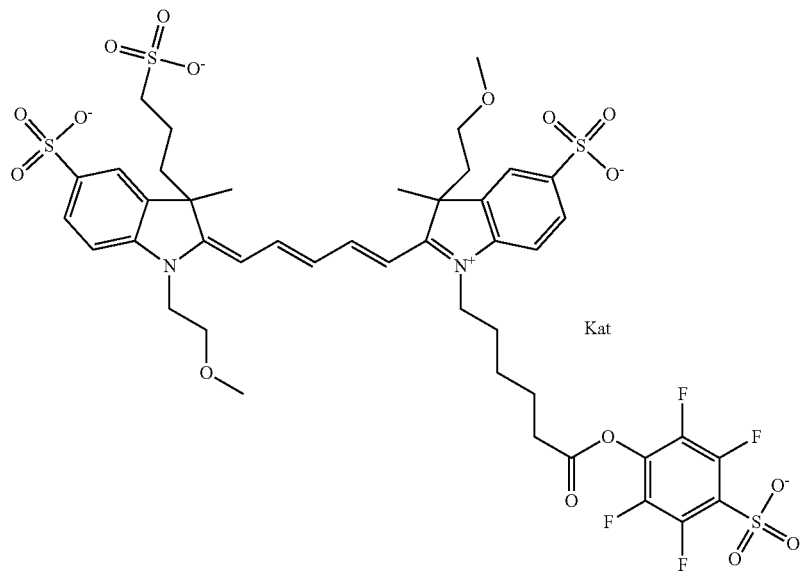 [SMILES: COCCN1/C(=C/C=C/C=C/C2=[N+](CCCCCC(=O)Oc3c(F)c(F)c(S(=O)(=O)[O-])c(F)c3F)c3ccc(S(=O)(=O)[O-])cc3C2(C)CCOC)C(C)(CCCS(=O)(=O)[O-])c2cc(S(=O)(=O)[O-])ccc21]

One non-limiting example of an activated 650 Compound 1/2 is the hydrazide of 650 Compound 1, shown below:

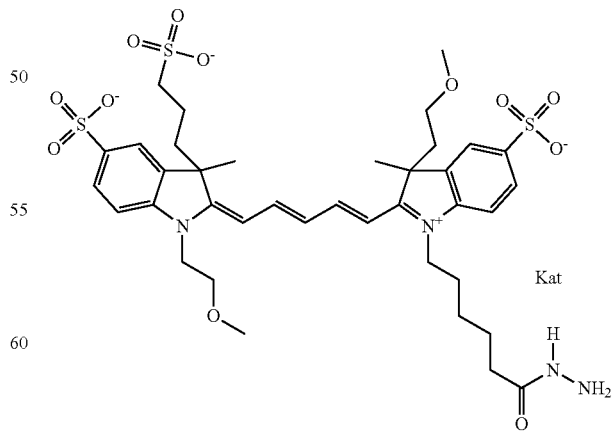

One non-limiting example of an activated 650 Compound 1/2 is the maleimide of 650 Compound 1, shown below:

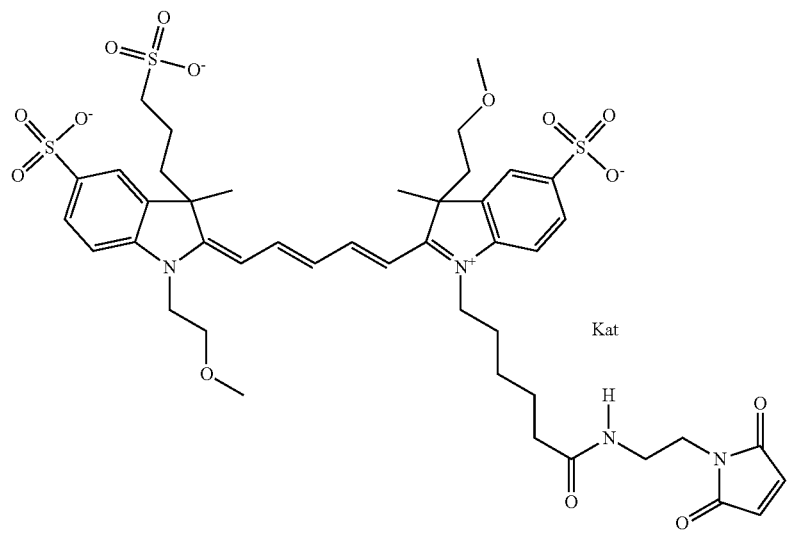 [SMILES: COCCN1/C(=C/C=C/C=C/C2=[N+](CCCCCC(=O)NCCN3C(=O)C=CC3=O)c3ccc(S(=O)(=O)[O-])cc3C2(C)CCOC)C(C)(CCCS(=O)(=O)[O-])c2cc(S(=O)(=O)[O-])ccc21]

Kat

In one embodiment, the compound is 650 Compound 2/2

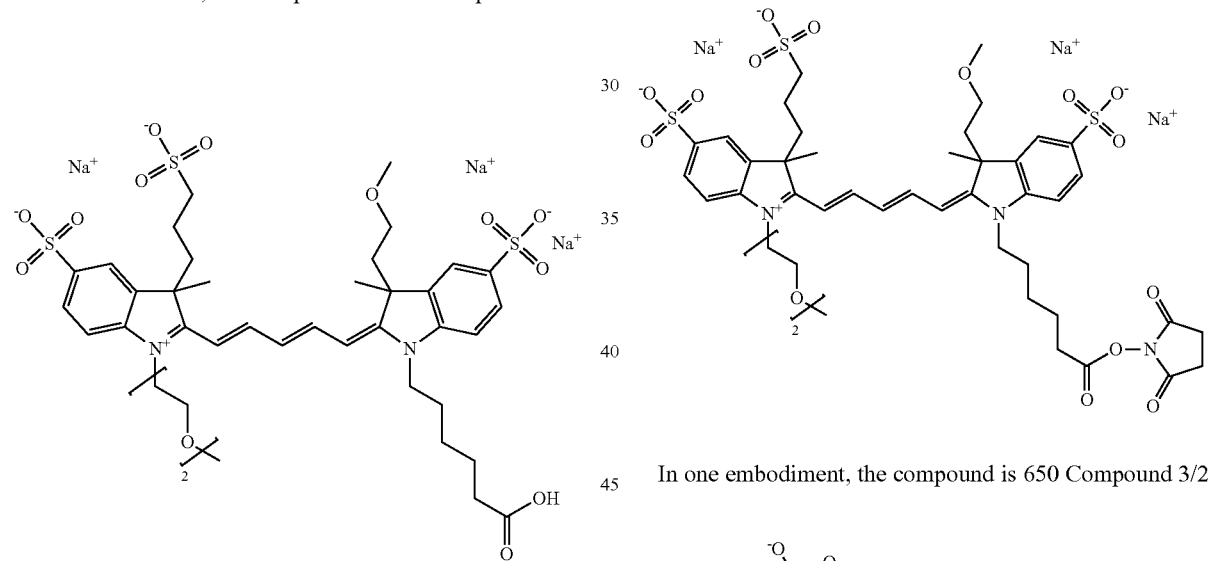

650 Compound 2/2 (2-((1E,3E,5E)-5-(1-(5-carboxypentyl)-3-(2-methoxyethyl)-3-methyl-5-sulfonatoindolin-2-ylidene)penta-1,3-dienyl)-1-(2-(2-methoxyethoxy)ethyl)-3-methyl-3-(3-sulfonatopropyl)-3H-indolium-5-sulfonate tri sodium salt.) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 650 Compound 2/2 is activated as described above, one non-limiting example of which is the NHS-ester form of 650 Compound 2/2, shown below.

In one embodiment, the compound is 650 Compound 3/2

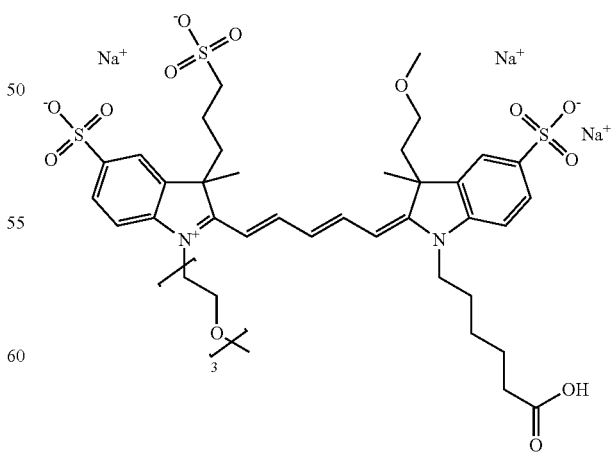

650 Compound 3/2 (2-((1E,3E,5E)-5-(1-(5-carboxypentyl)-3-(2-methoxyethyl)-3-methyl-5-sulfonatoindolin-2- ylidene)penta-1,3-dienyl)-1-(2-(2-(2-methoxyethoxy)ethoxy)ethyl)-3-methyl-3-(3-sulfonatopropyl)-3H-indolium-5-sulfonate tri sodium salt) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 650 Compound 3/2 is activated as described above, one non-limiting example of which is the NHS-ester form of 650 Compound 3/2, shown below.

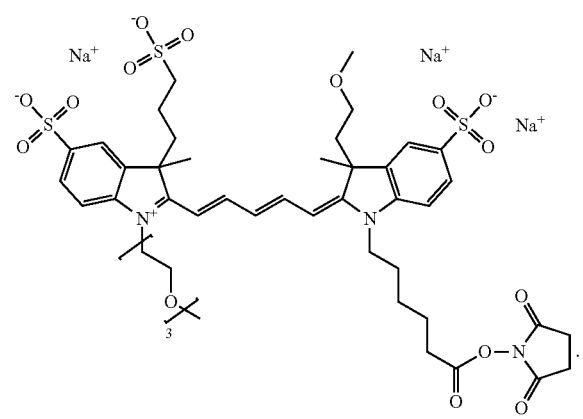

In one embodiment, the compound is 650 Compound 4/2

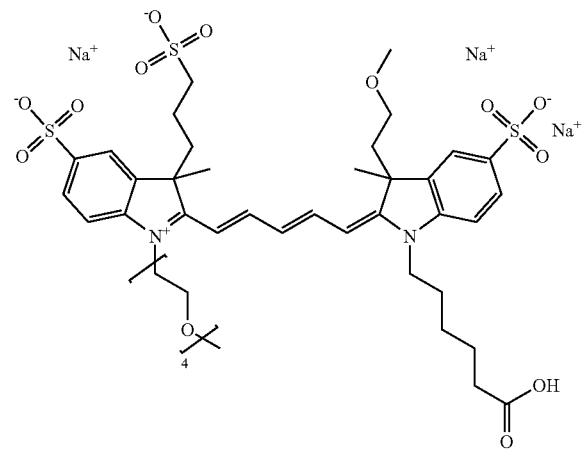

650 Compound 4/2 (2-((1E,3E,5E)-5-(1-(5-carboxypentyl)-3-(2-methoxyethyl)-3-methyl-5-sulfonatoindolin-2-ylidene)penta-1,3-dienyl)-3-methyl-3-(3-sulfonatopropyl)-1-(2,5,8,11-tetraoxatridecan-13-yl)-3H-indolium-5-sulfonate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 650 Compound 4/2 is activated as described above.

In one embodiment, the compound is 650 Compound 5/2

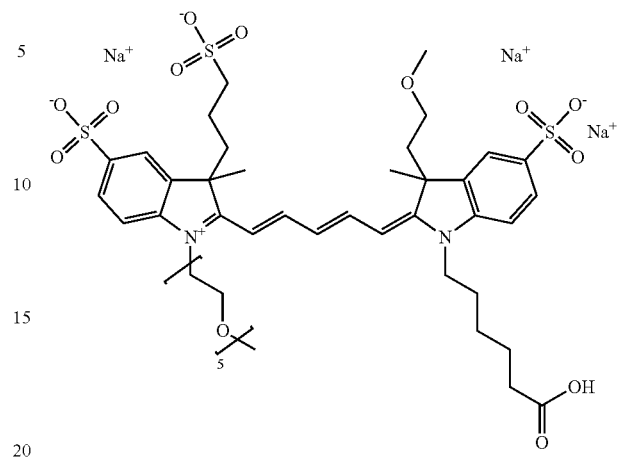

650 Compound 5/2 (2-((1E,3E,5E)-5-(1-(5-carboxypentyl)-3-(2-methoxyethyl)-3-methyl-5-sulfonatoindolin-2-ylidene)penta-1,3-dienyl)-1-(2,5,8,11,14-pentaoxahexadecan-16-yl)-3-methyl-3-(3-sulfonatopropyl)-3H-indolium-5-sulfonate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 650 Compound 5/2 is activated as described above.

In one embodiment, the compound is 650 Compound 6/2

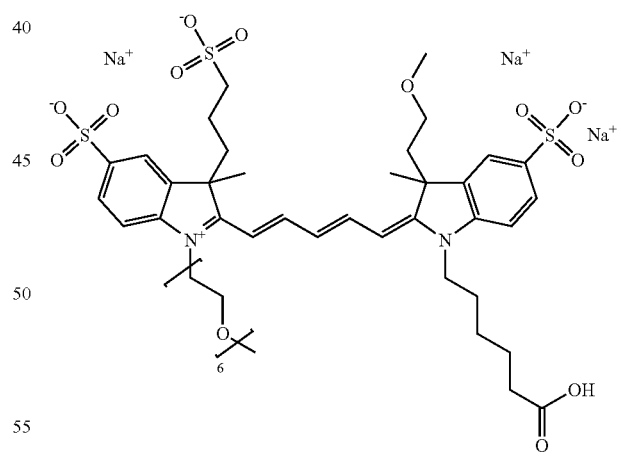

650 Compound 6/2 (2-((1E,3E,5E)-5-(1-(5-carboxypentyl)-3-(2-methoxyethyl)-3-methyl-5-sulfonatoindolin-2-ylidene)penta-1,3-dienyl)-3-methyl-1-(2,5,8,11,14,17-hexaoxanonadecan-19-yl)-3-(3-sulfonatopropyl)-3H-indolium-5-sulfonate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 650 Compound 6/2 is activated as described above.

In embodiments, the compound contains one or more substitutions of the polymethine linker. In one embodiment, the compound has general formula Va

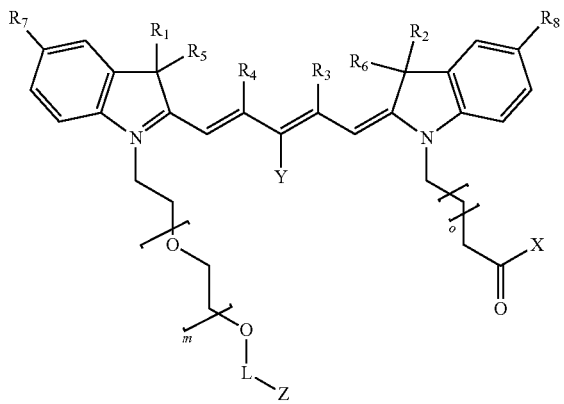

general formula Vb

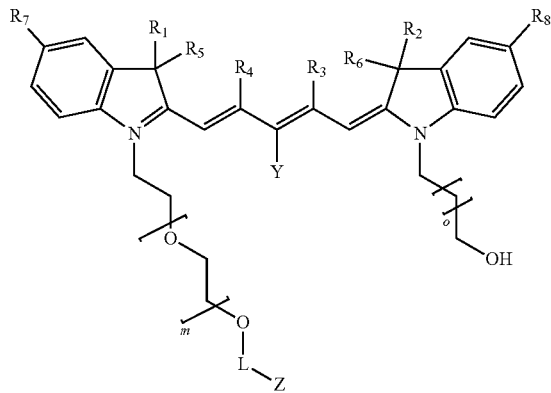

general formula Vc

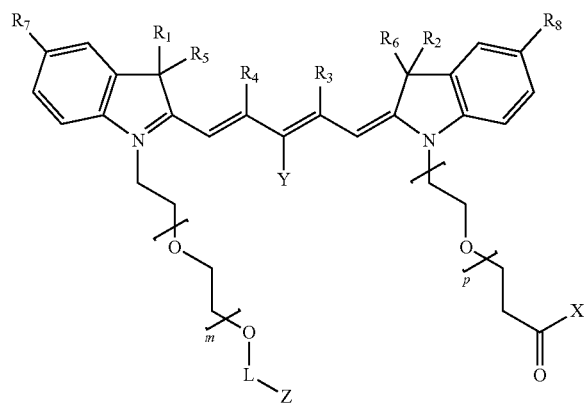

or general formula Vd

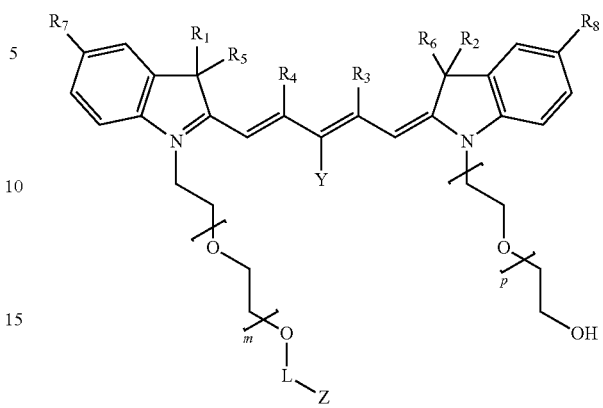

where each of $R^1$, $R^2$, $R^5$, and $R^6$ is the same or different and is independently selected from the group consisting of an aliphatic, heteroaliphatic, sulfoalkyl group, heteroaliphatic with terminal $SO_3$, a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group -L-$SO_2$NH—P-L-Z, and a carboxamide group -L-CONH—P-L-Z; each of $R^7$ and $R^8$ is the same or different and is independently selected from either H, $SO_3$, a PEG group P-L-Z where P is selected from an ethylene glycol group, a diethylene glycol group, and a (poly)ethylene glycol group where the (poly)ethylene glycol group is $(CH_2CH_2O)_s$ where s is an integer from 3-6 inclusive, a sulfonamide group —$SO_2$NH—P-L-Z, or a carboxamide group —CONH—P-L-Z; where L is selected from the group consisting of a divalent linear (—$(CH_2)_o$—, o=0 to 15), crossed, or cyclic alkane group that can be substituted by at least one atom selected from the group consisting of oxygen, substituted nitrogen, and/or sulfur; where Z is selected from the group consisting of H, $CH_3$, alkyl, a heteroalkyl group, $NH_2$, —COO, —COOH, —COSH, CO—NH—$NH_2$, —COF, —COCl, —COBr, —COI, —COO-Su (succinimidyl/sulfosuccinimidyl), —COO-STP (4-sulfo-2,3,5,6-tetrafluorophenyl), —COO-TFP (2,3,5,6-tetrafluorophenyl), —COO-benzotriazole, —CO-benzotriazole, —CONR'—CO—$CH_2$—I, —CONR'R", —CONR'-biomolecule, —CONR'-L-COO$^-$, —CONR'-L-COOH, —CONR'-L-COO-Su, —CONR'-L-COO-STP, —CONR'-L-COO-TFP, —CONR'-L-CONR"$_2$, —CONR'-L-CO-biomolecule, —CONR'-L-CO—NH—$NH_2$, —CONR'-L-OH, —CONR'-L-O-phosphoramidite, —CONR'-L-CHO, —CONR'-L-maleimide, and —CONR'-L-NH—CO—$CH_2$—I; R' and R" is selected from the group consisting of H, aliphatic group, and heteroaliphatic group, and the biomolecule is a protein, antibody, nucleotide, oligonucleotide, biotin, or hapten; X is selected from the group consisting of —OH, —SH, —$NH_2$, —NH—$NH_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, and —NR-L-NH—CO—CH2-I, where R is —H or an aliphatic or heteroaliphatic group; Kat is a number of Na$^+$, K$^+$, Ca$^{2+}$, ammonia, or other cation(s) needed to compensate the negative charge brought by the cyanine; m is an integer from 0 to 5 inclusive; p is an integer from 1 to 6 inclusive; each of R3 and R4 is the same or different and is independently hydrogen, an aliphatic group, a heteroaliphatic group, or a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive; or R3 and R4 together form a cyclic structure where R3 and R4 are joined using a divalent structural element selected from the group consisting of $—(CH_2)_q—$, $—(CH_2)_qO(CH_2)_{q'}—$, $—(CH_2)_qS(CH_2)_{q'}—$, $—(CH_2)_q CH=CH—$, $—OCH=CH—$ where each of q and q' is the same or different and is a integer from 2 to 6 inclusive; and Y is selected from the group consisting of hydrogen, alkyl, sulfoalkyl, fluorine, chlorine, bromine, and a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive; with the proviso that at least one of $R^1$, $R^2$, $R^3$, $R^4$, $R^5$, $R^6$, $R^7$, and $R^8$ contains a PEG group.

In one embodiment, the compound of general formula V wherein each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of $—(CH_2)_q—$ and $CH=CH$, where q is an integer from 1 to 2 inclusive, to result in a 3-, 4-, or 5-membered ring.

In one embodiment, an isolated enantiomeric mixture selected from diastereomer Ia of general formula Va

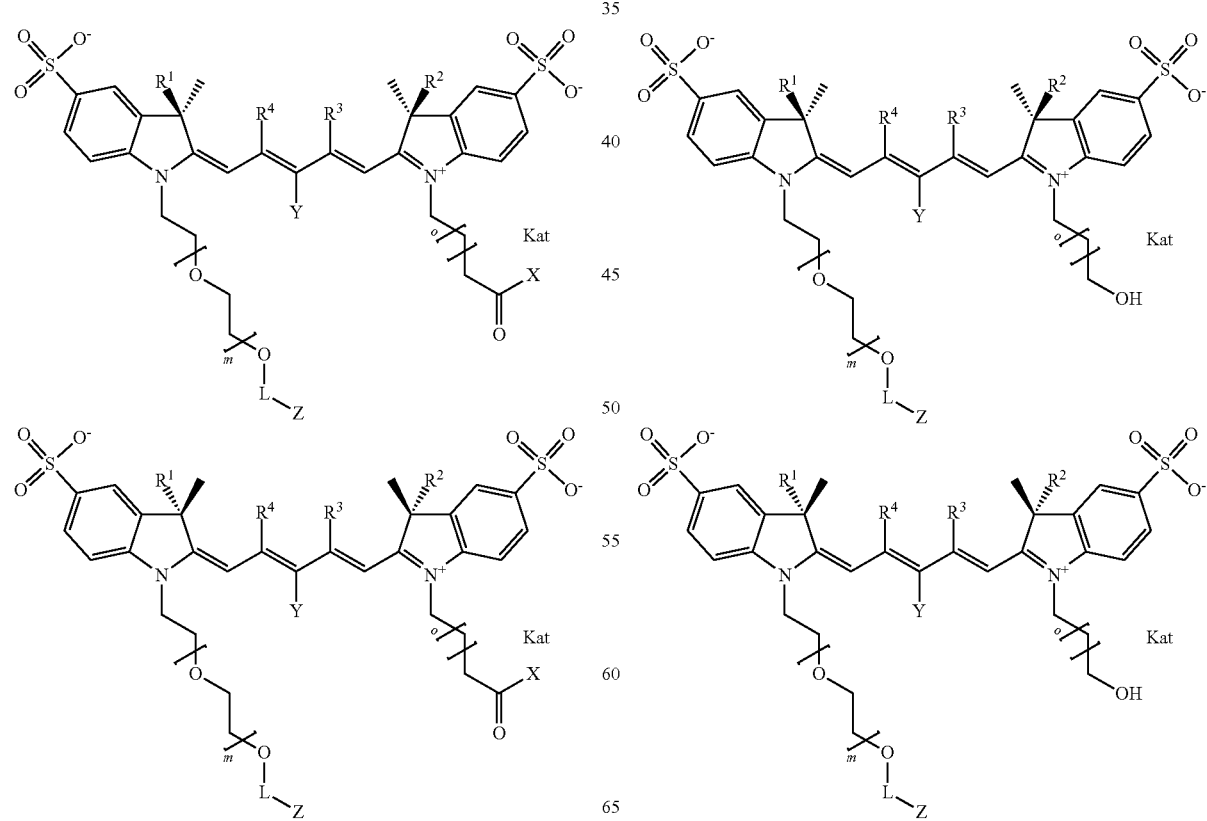

diastereomer Ib of general formula Va

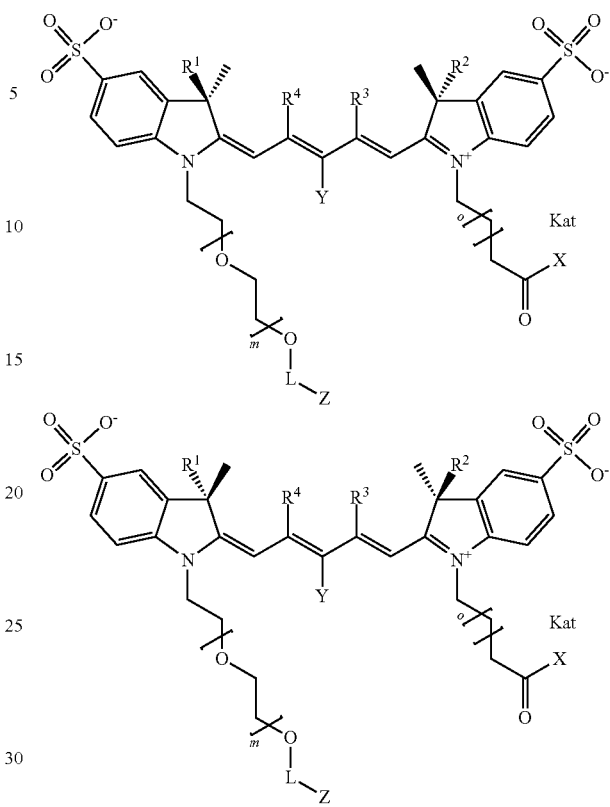

diastereomer Ic of general formula Vb or diastereomer of general formula Vb

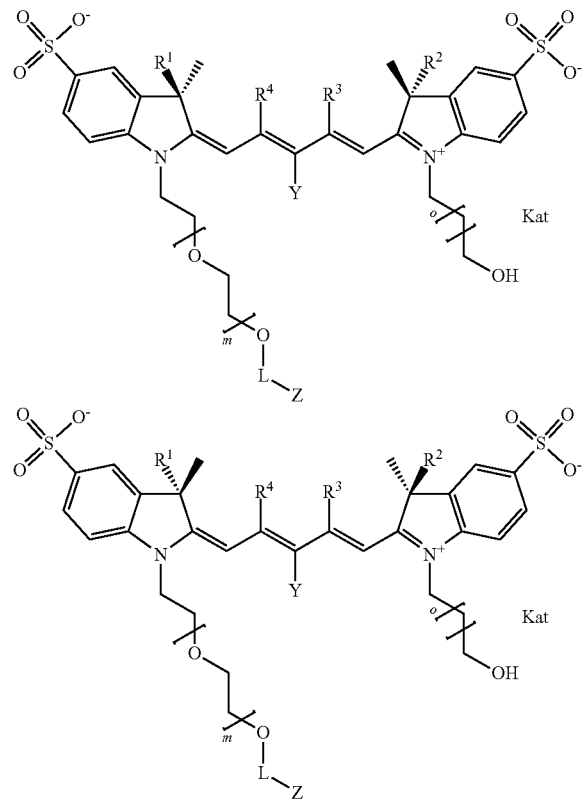

is provided, where each of $R^1$, $R^2$, $R^5$, and $R^6$ is the same or different and is independently selected from the group consisting of an aliphatic, heteroaliphatic, sulfoalkyl group, heteroaliphatic with terminal $SO_3$, a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group -L-$SO_2NH$—P-L-Z, and a carboxamide group -L-CONH—P-L-Z; each of $R^7$ and $R^8$ is the same or different and is independently selected from either H, $SO_3$, a PEG group P-L-Z where P is selected from an ethylene glycol group, a diethylene glycol group, and a (poly)ethylene glycol group where the (poly)ethylene glycol group is $(CH_2CH_2O)_s$ where s is an integer from 3-6 inclusive, a sulfonamide group —$SO_2NH$—P-L-Z, or a carboxamide group —CONH—P-L-Z; where L is selected from the group consisting of a divalent linear (—$(CH_2)_o$—, o=0 to 15), crossed, or cyclic alkane group that can be substituted by at least one atom selected from the group consisting of oxygen, substituted nitrogen, and/or sulfur; where Z is selected from the group consisting of H, $CH_3$, alkyl, a heteroalkyl group, $NH_2$, —$COO^-$, —COOH, —COSH, CO—NH—$NH_2$, —COF, —COCl, —COBr, —COI, —COO-Su (succinimidyl/sulfosuccinimidyl), —COO-STP (4-sulfo-2,3,5,6-tetrafluorophenyl), —COO-TFP (2,3,5,6-tetrafluorophenyl), —COO-benzotriazole, —CO-benzotriazole, —CONR'—CO—$CH_2$—I, —CONR'R", —CONR'-biomolecule, —CONR'-L-$COO^-$, —CONR'-L-COOH, —CONR'-L-COO-Su, —CONR'-L-COO-STP, —CONR'-L-COO-TFP, —CONR'-L-CONR"$_2$, —CONR'-L-CO-biomolecule, —CONR'-L-CO—NH—$NH_2$, —CONR'-L-OH, —CONR'-L-O-phosphoramidite, —CONR'-L-CHO, —CONR'-L-maleimide, and —CONR'-L-NH—CO—$CH_2$-I; R' and R" is selected from the group consisting of H, aliphatic group, and heteroaliphatic group, and the biomolecule is a protein, antibody, nucleotide, oligonucleotide, biotin, or hapten; X is selected from the group consisting of —OH, —SH, —$NH_2$, —NH—$NH_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2H$, —NR-L-CO—NHS, —NR-L-CO-STP, —NR-L-CO-TFP, —NR-L-CO-benzotriazole, —NR-L-CHO, —NR-L-maleimide, and —NR-L-NH—CO—CH2-I, where R is —H or an aliphatic or heteroaliphatic group; Kat is a number of $Na^+$, $K^+$, $Ca^{2+}$, ammonia, or other cation(s) needed to compensate the negative charge brought by the cyanine; m is an integer from 0 to 5 inclusive; o is an integer from 0 to 12 inclusive; each of R3 and R4 is the same or different and is independently hydrogen, an aliphatic group, a heteroaliphatic group, or a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive; or R3 and R4 together form a cyclic structure where R3 and R4 are joined using a divalent structural element selected from the group consisting of —$(CH_2)_q$—, —$(CH_2)_qO(CH_2)_{q'}$—, —$(CH_2)_qS(CH_2)_{q'}$—, —$(CH_2)_q$CH=CH—, —OCH=CH— where each of q and q' is the same or different and is a integer from 2 to 6 inclusive; and Y is selected from the group consisting of hydrogen, alkyl, sulfoalkyl, fluorine, chlorine, bromine, and a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive; with the proviso that at least one of $R^1$, $R^2$, $R^3$, and $R^4$ contains a PEG group.

In one embodiment, the compound of general formula V wherein each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of —$(CH_2)_q$— and CH=CH, where q is an integer from 1 to 2 inclusive, to result in a 3-, 4-, or 5-membered ring.

One non-limiting example is a substituted polymethine form of 650 Compound 1/2, shown below:

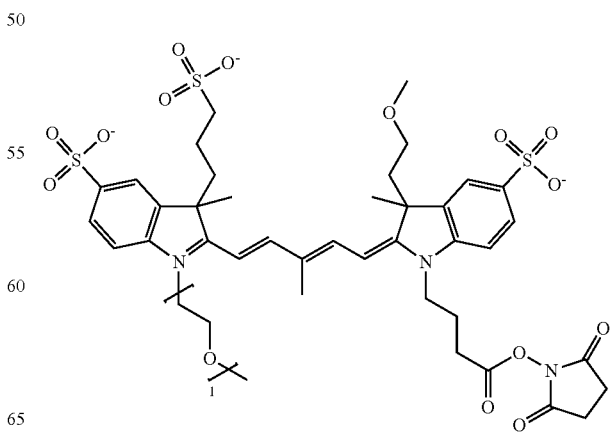

One non-limiting example is a substituted polymethine form of 650 Compound 2/2, shown below:

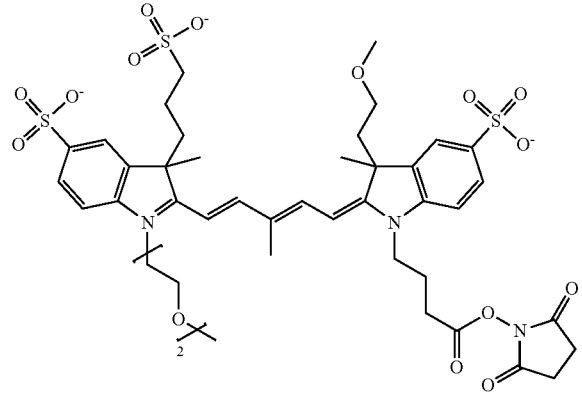

One non-limiting example is a substituted polymethine form of 650 Compound 3/2, shown below:

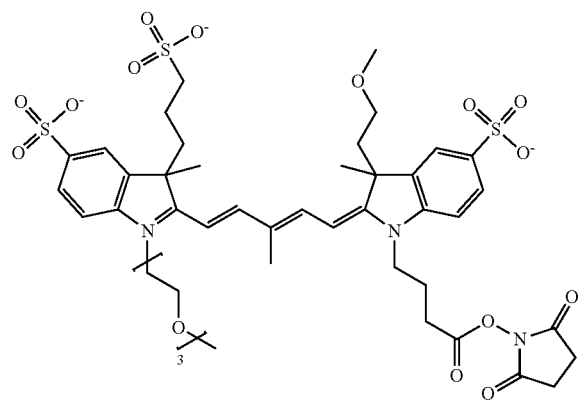

One non-limiting example is a substituted polymethine form of 650 Compound 4/2, shown below:

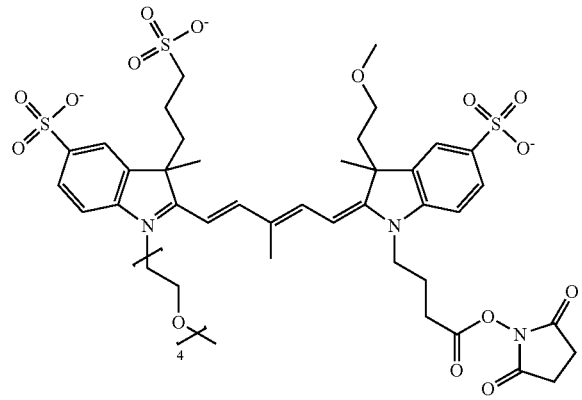

One non-limiting example is a substituted polymethine form of 650 Compound 5/2, shown below:

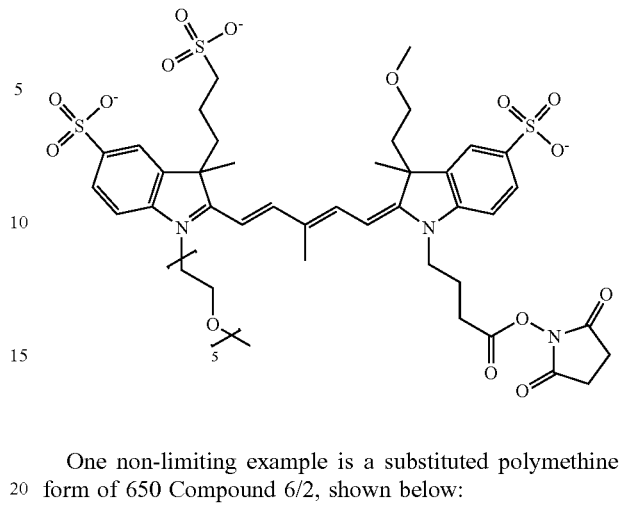

One non-limiting example is a substituted polymethine form of 650 Compound 6/2, shown below:

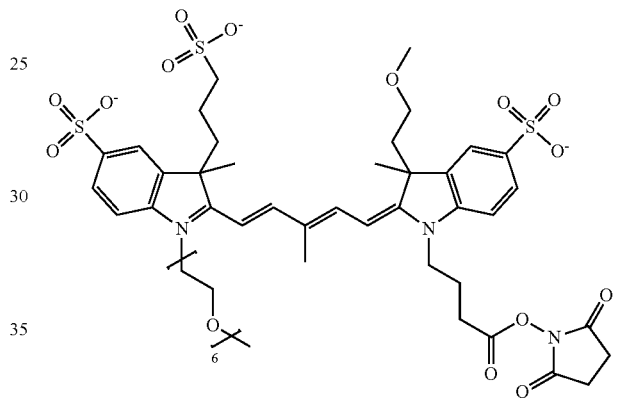

One non-limiting example is a substituted polymethine form of 650 Compound 1/3 having an ethylene glycol, diethylene glycol, or (poly)ethylene glycol as described for general formula V, such as the compound shown below:

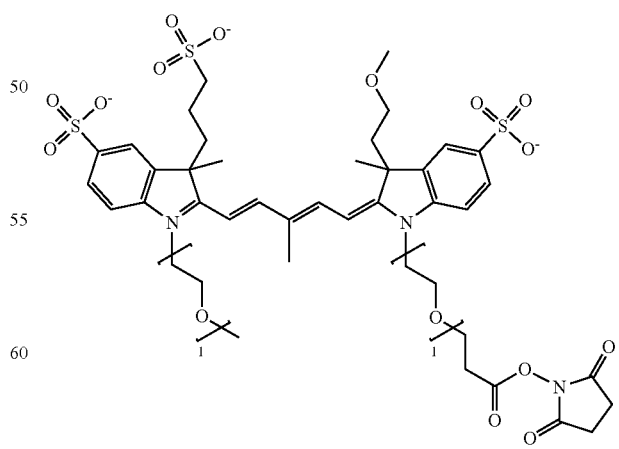

One non-limiting example is a substituted polymethine form of 650 Compound 1/2, shown below:

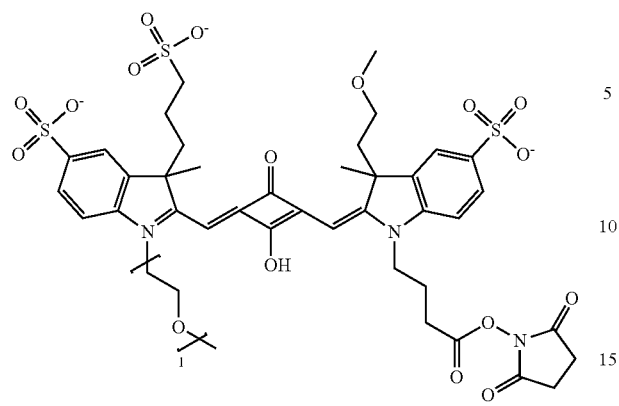

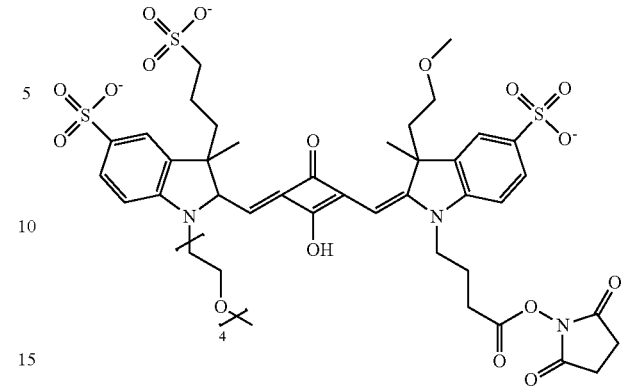

One non-limiting example is a substituted polymethine form of 650 Compound 5/2, shown below:

One non-limiting example is a substituted polymethine form of 650 Compound 2/2, shown below:

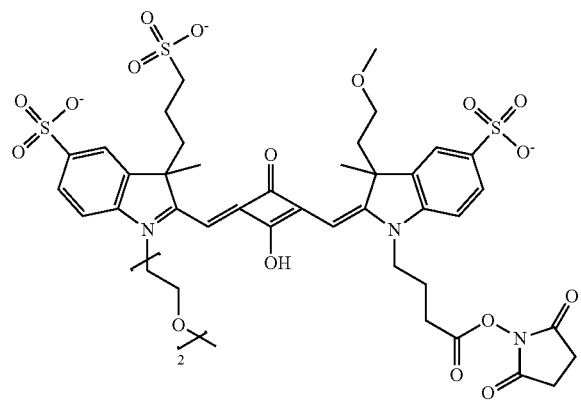

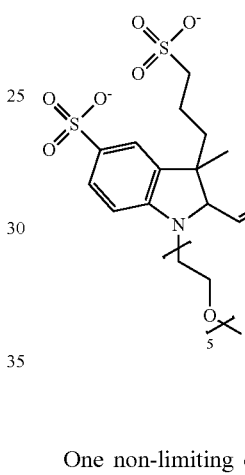

One non-limiting example is a substituted polymethine form of 650 Compound 6/2, shown below:

One non-limiting example is a substituted polymethine form of 650 Compound 3/2, shown below:

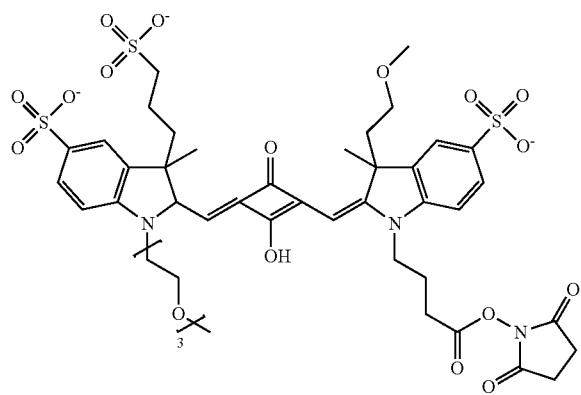

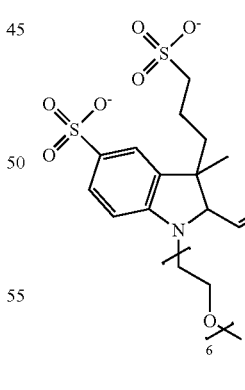

One non-limiting example is a substituted polymethine form of 650 Compound 1/3 having an ethylene glycol, diethylene glycol, or (poly)ethylene glycol as described for general formula V, such as the compound shown below:

One non-limiting example is a substituted polymethine form of 650 Compound 4/2, shown below:

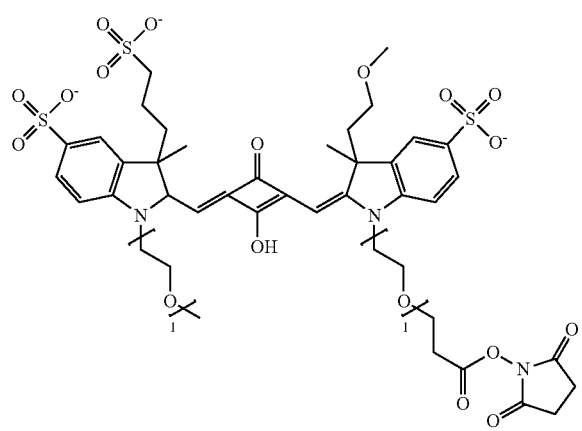

In embodiments, the degree of sulfonation is varied to, e.g., vary the compound's degree of hydrophilicity or hydrophobicity. One non-limiting example is a monosulfonate form of 650 Compound 1/2, shown below, but it is understood that the single sulfo group can be at any of the described positions:

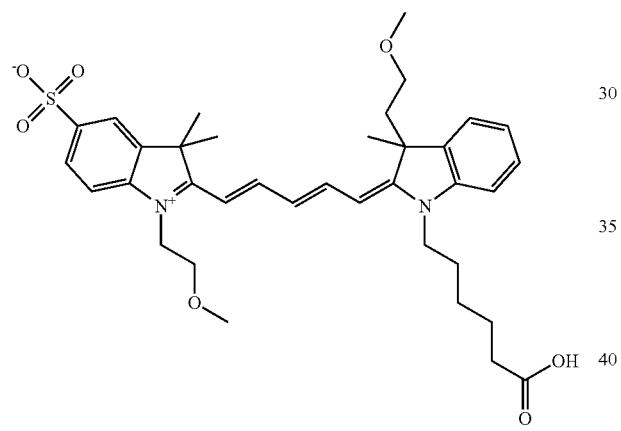

One non-limiting example is a disulfonate form of 650 Compound 1/2, shown below, but it is understood that each of the two sulfo groups can be at any of the described positions:

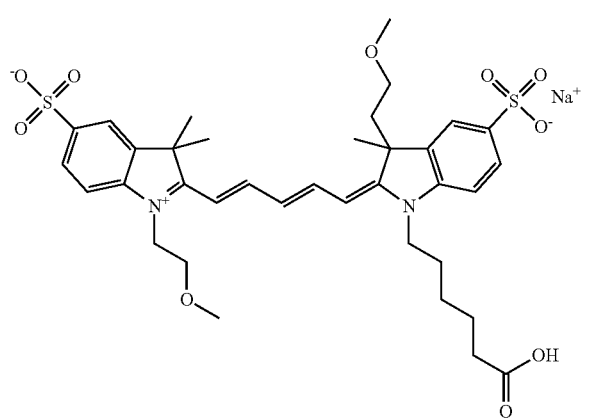

One non-limiting example is a trisulfonate form of 650 Compound 1/2, shown below, but it is understood that each of the three sulfo groups can be at any of the described positions:

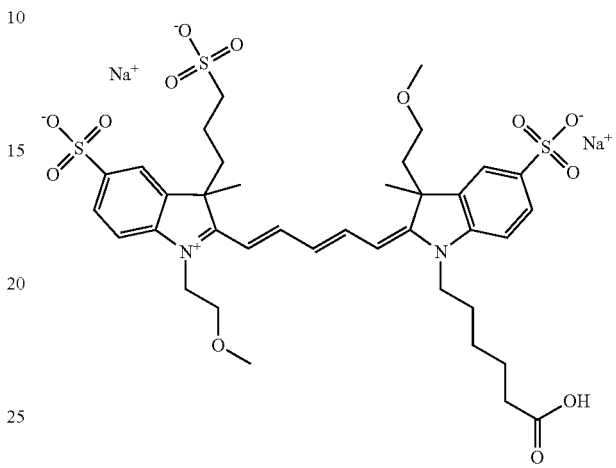

One non-limiting example is a tetrasulfonate form of 650 Compound 1/2, shown below, but it is understood that each of the four sulfo groups can be at any of the described positions:

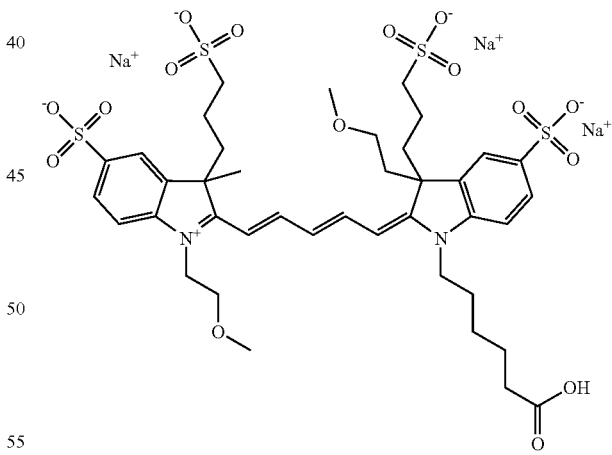

In various embodiments, an ethylene glycol group, diethylene glycol group, and/or a (poly)ethylene glycol group, which will collectively be referred to as a PEG group, unless specifically defined, may be present at position(s) in addition to such groups being present on the N atom(s) of the indole structure.

One non-limiting example of an additionally PEG-substituted compound is a 650 Compound 1/2 according to general formula II where R1 is an ethylene glycol group terminating with a methyl group, shown below:

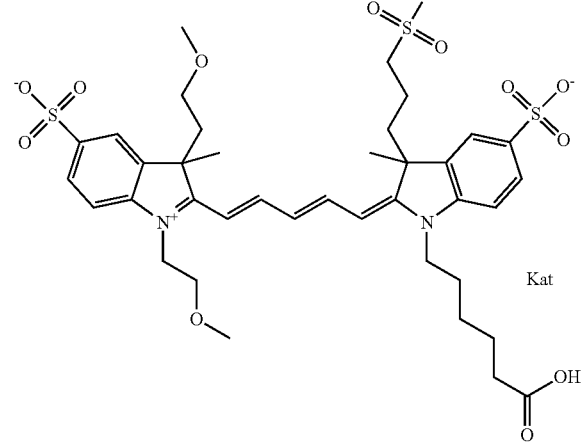

One non-limiting example of an additionally PEG-substituted compound is a 650 Compound 1/2 according to general formula II where R1 is a diethylene glycol group terminating with a methyl group, shown below:

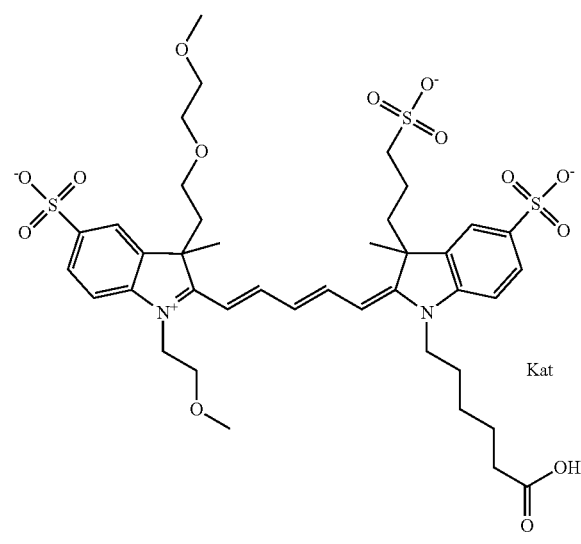

One non-limiting example of an additionally PEG-substituted compound is a 650 Compound 1/2 according to general formula II where R1 is a (poly)ethylene glycol (3) group terminating with a methyl One non-limiting example of an additionally PEG-substituted compound is a 650 Compound 1/2 according to general formula II where R1 is a (poly)ethylene glycol (4) group terminating with a methyl group, shown below:

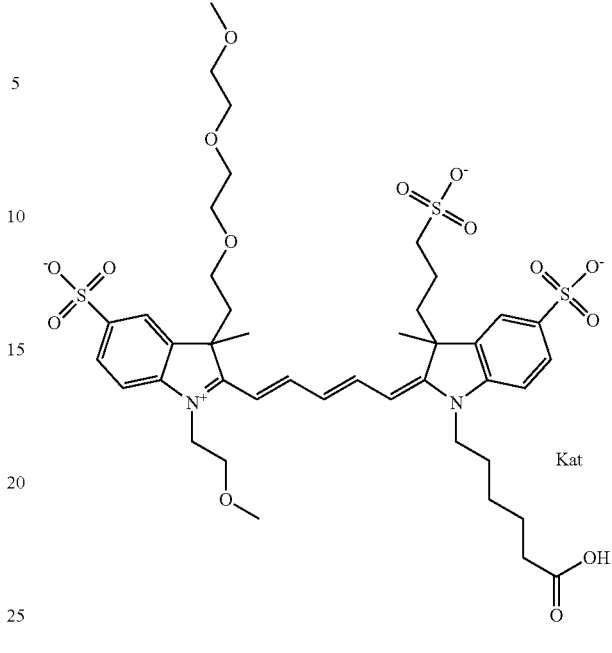

One non-limiting example of an additionally PEG-substituted compound is a 650 Compound 1/2 according to general formula II where R1 is a (poly)ethylene glycol (5) group terminating with a methyl group, shown below:

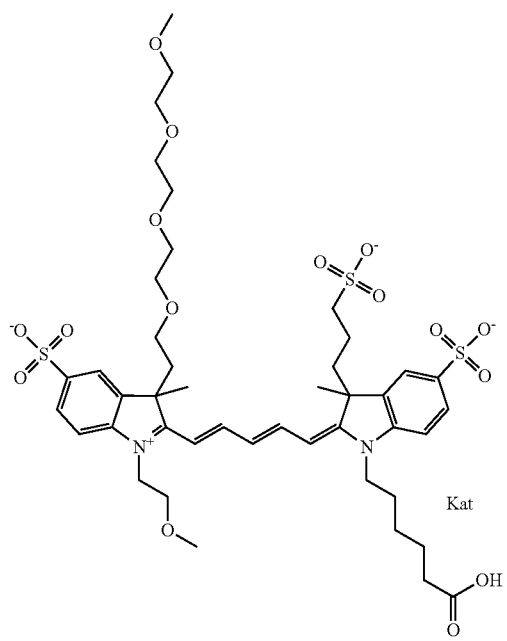

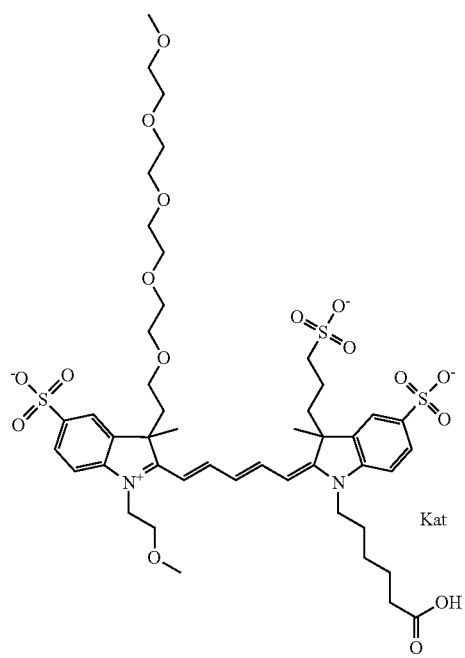

One non-limiting example of an additionally PEG-substituted compound is a 650 Compound 1/2 according to general formula II where R1 is a (poly)ethylene glycol (6) group terminating with a methyl group, shown below:

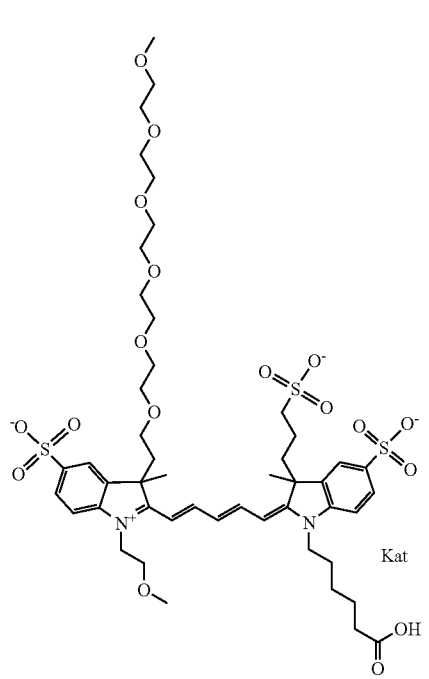

One non-limiting example of an additionally PEG-substituted compound is a 650 Compound 1/2 according to general formula II where R1 is a sulfonamide group -L-SO₂NH—P—Z where Z is a methyl group, shown below:

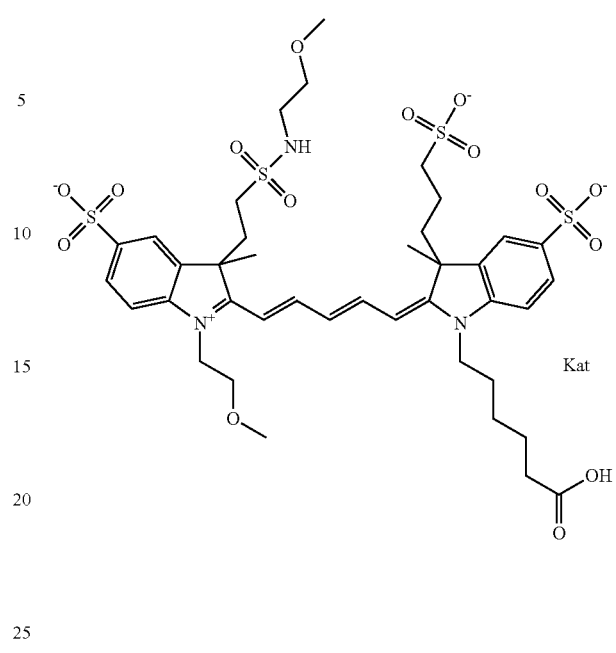

One non-limiting example of an additionally PEG-substituted compound is a 650 Compound 1/2 according to general formula II where R1 is a carboxamide group -L-CONH—P—Z where Z is a methyl group, shown below:

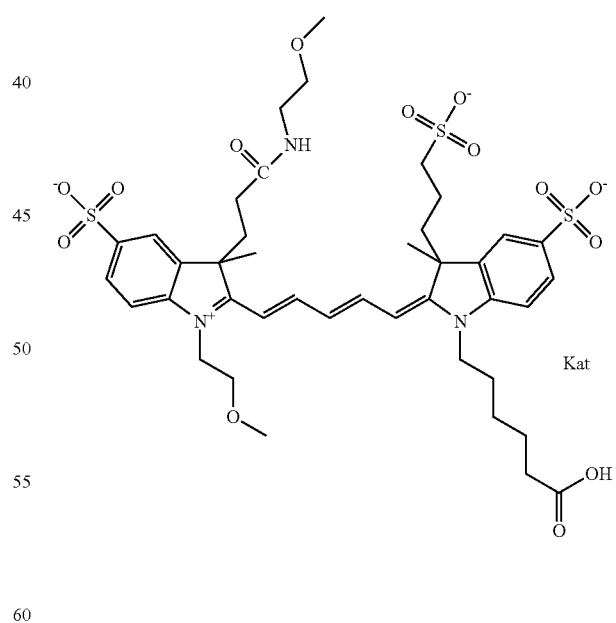

One non-limiting example of an additionally PEG-substituted compound is a 650 Compound 1/2 according to general formula II where R2 is an ethylene glycol group terminating with a methyl group, shown below:

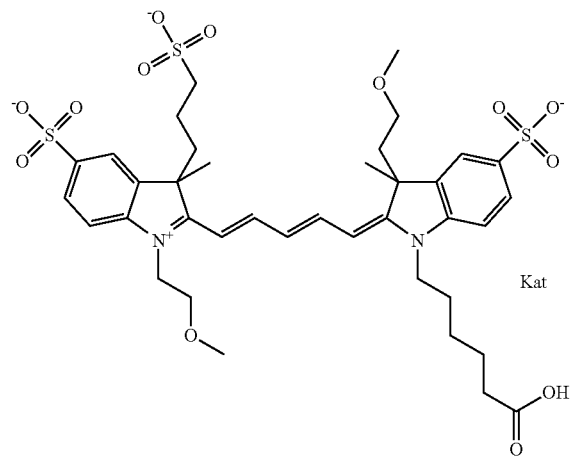

One non-limiting example of an additionally PEG-substituted compound is a 650 Compound 1/2 according to general formula II where R2 is a diethylene glycol group terminating with a methyl group, shown below:

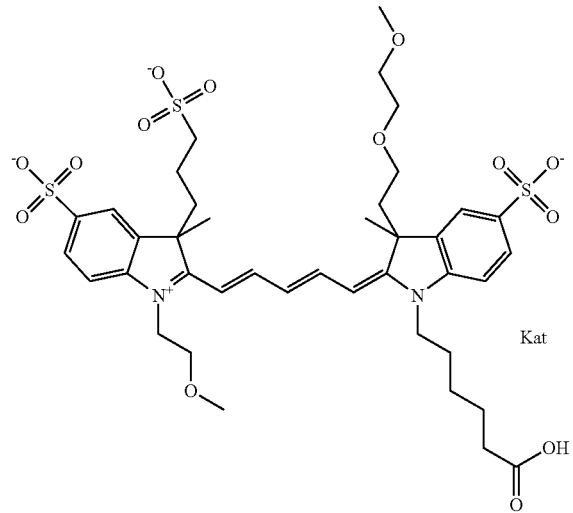

One non-limiting example of an additionally PEG-substituted compound is a 650 Compound 1/2 according to general formula II where R2 is a (poly)ethylene glycol (3) group terminating with a methyl group, shown below:

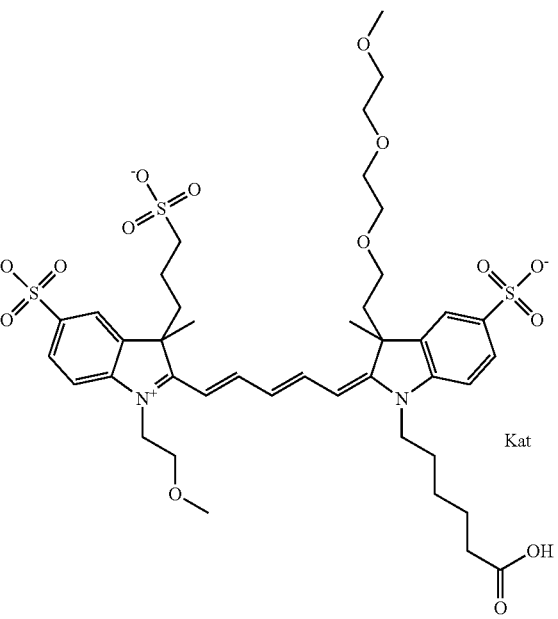

One non-limiting example of an additionally PEG-substituted compound is a 650 Compound 1/2 according to general formula II where R2 is a (poly)ethylene glycol (4) group terminating with a methyl group, shown below:

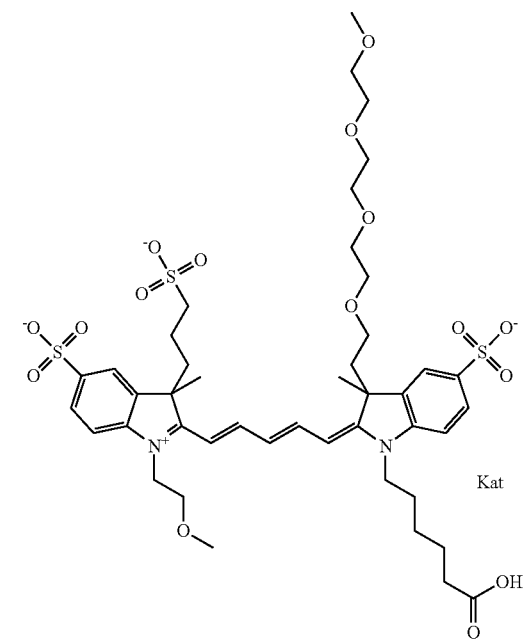

One non-limiting example of an additionally PEG-substituted compound is a 650 Compound 1/2 according to general formula II where R2 is a (poly)ethylene glycol (5) group terminating with a methyl group, shown below:

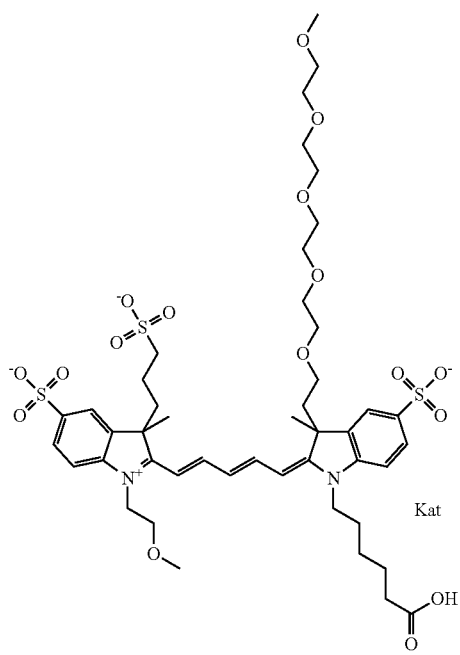

One non-limiting example of an additionally PEG-substituted compound is a 650 Compound 1/2 according to general formula II where R2 is a (poly)ethylene glycol (6) group terminating with a methyl group, shown below:

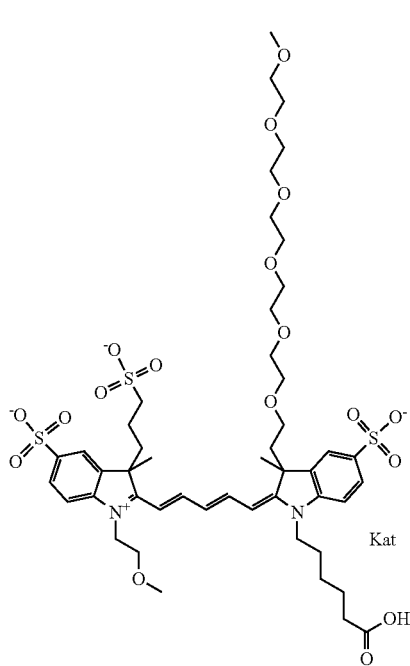

One non-limiting example of an additionally PEG-substituted compound is a 650 Compound 1/2 according to general formula II where R2 is a sulfonamide group -L-SO$_2$NH—P—Z where Z is a methyl group, shown below:

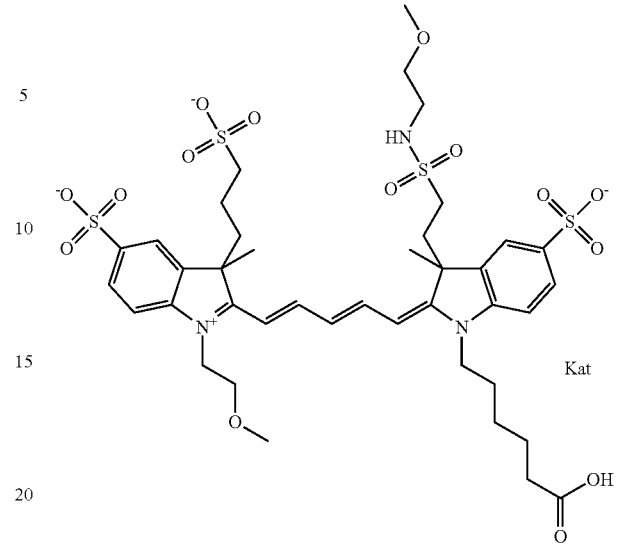

One non-limiting example of an additionally PEG-substituted compound is a 650 Compound 1/2 according to general formula II where R2 is a carboxamide group -L-CONH—P—Z where Z is a methyl group, shown below:

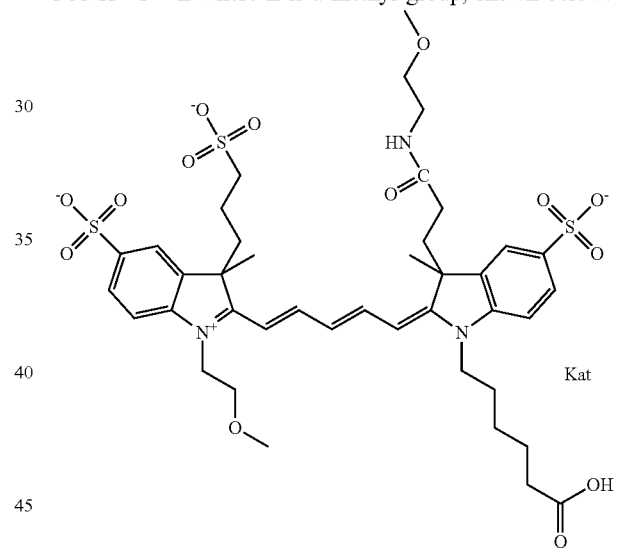

One non-limiting example of an additionally PEG-substituted compound is a 650 Compound 1/3 according to general formula II where both R1 and R2 are an ethylene glycol group terminating with a methyl group, shown below:

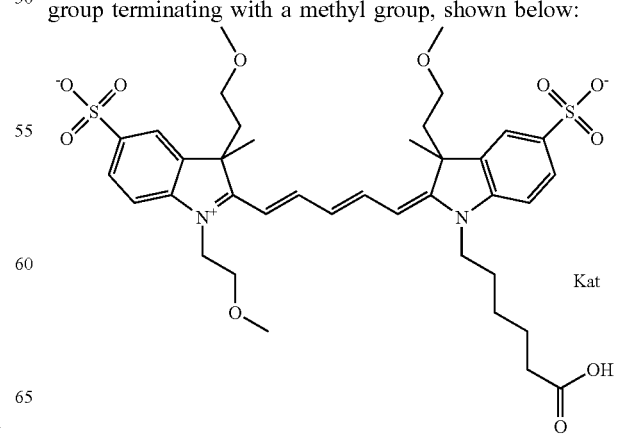

One non-limiting example of an additionally PEG-substituted compound is a 650 Compound 1/3 according to general formula II where both R1 and R2 are a diethylene glycol group terminating with a methyl group, shown below:

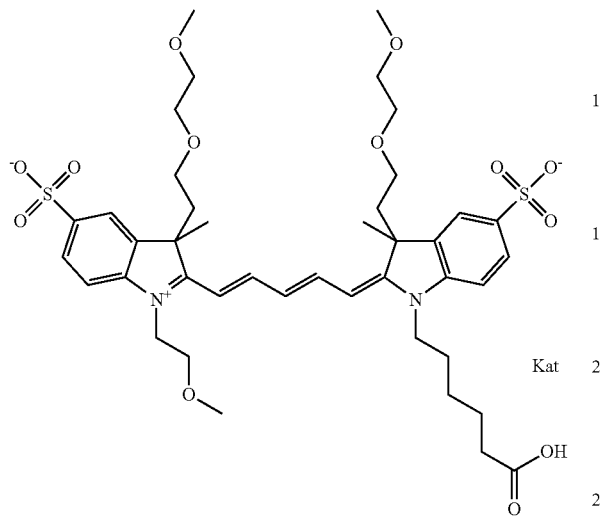

One non-limiting example of an additionally PEG-substituted compound is a 650 Compound 1/3 according to general formula II where both R1 and R2 are a (poly)ethylene glycol (3) group terminating with a methyl group, shown below:

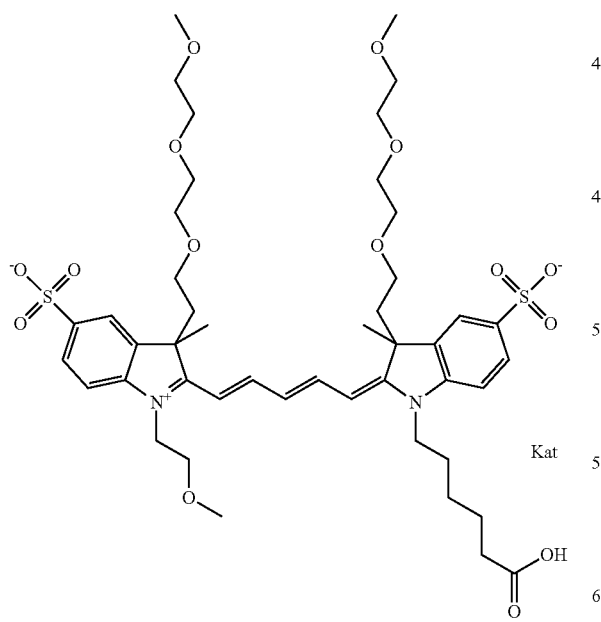

One non-limiting example of an additionally PEG-substituted compound is a 650 Compound 1/3 according to general formula II where both R1 and R2 are a (poly)ethylene glycol (4) group terminating with a methyl group, shown below:

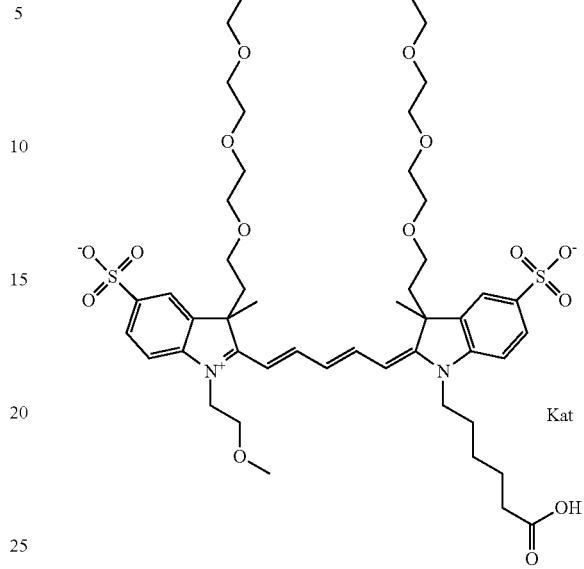

One non-limiting example of an additionally PEG-substituted compound is a 650 Compound 4/4 according to general formula III where both R1 and R2 are a (poly)ethylene glycol (4) group terminating with a methyl group, and R7 and R8 are sulfo, shown below:

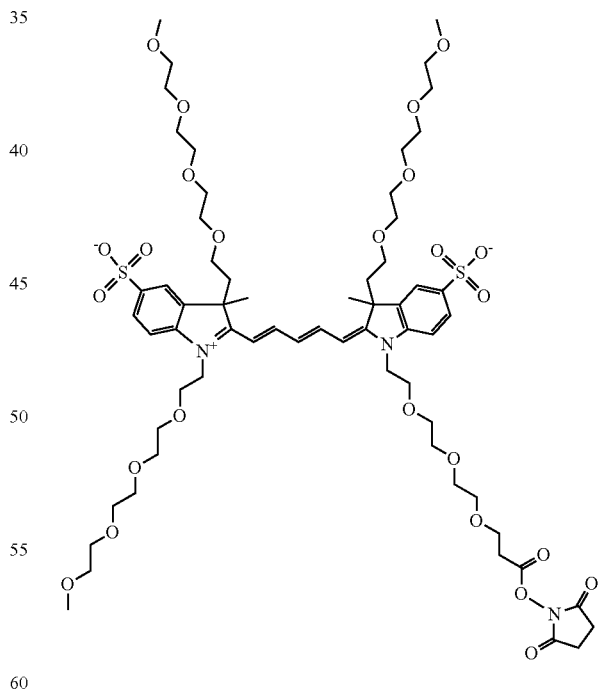

One non-limiting example of an additionally PEG-substituted compound is a 650 Compound 4/4 according to general formula III (V19-03005) where both R1 and R2 are a (poly)ethylene glycol (4) group terminating with a methyl group, and R7 and R8 are sulfo, shown below:

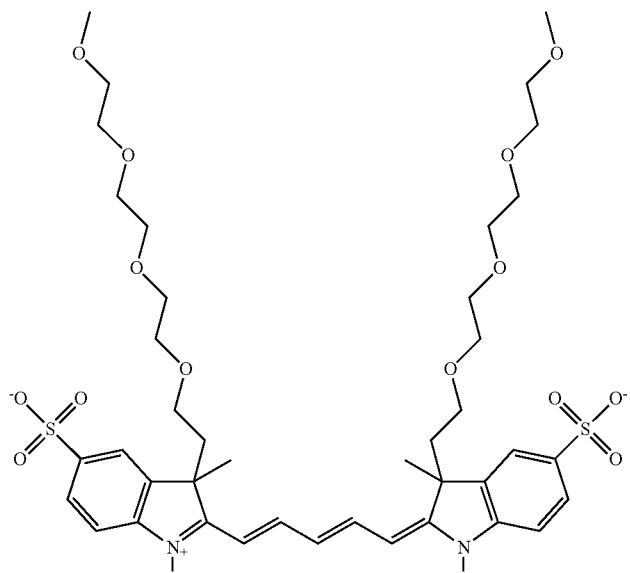
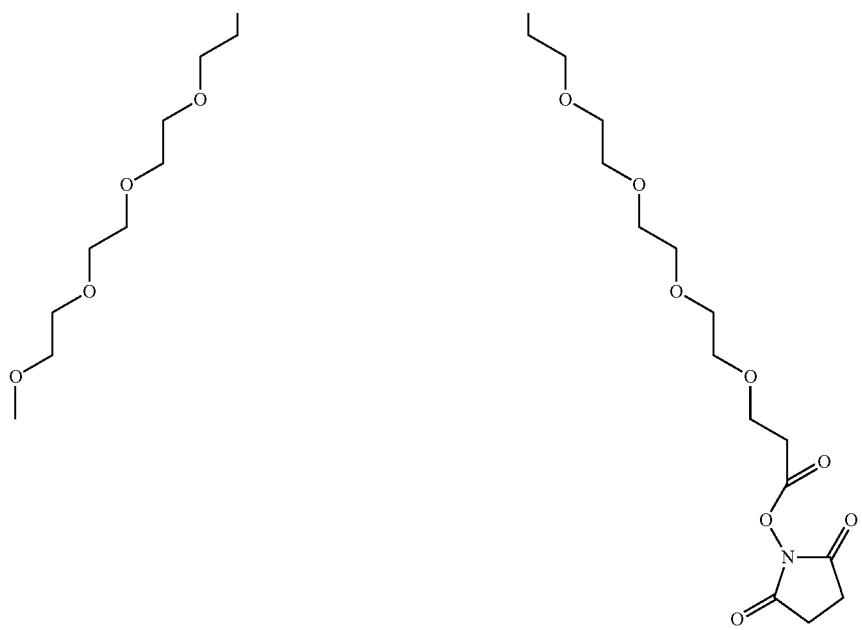
One non-limiting example of an additionally PEG-substituted compound is a 650 Compound 4/4 according to general formula III where both R1 and R2 are a (poly) ethylene glycol (4) group terminating with a methyl group, and R7 and R8 are H, shown below:

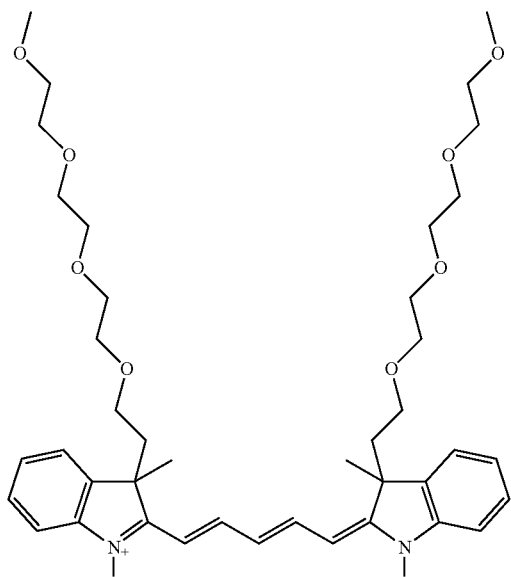
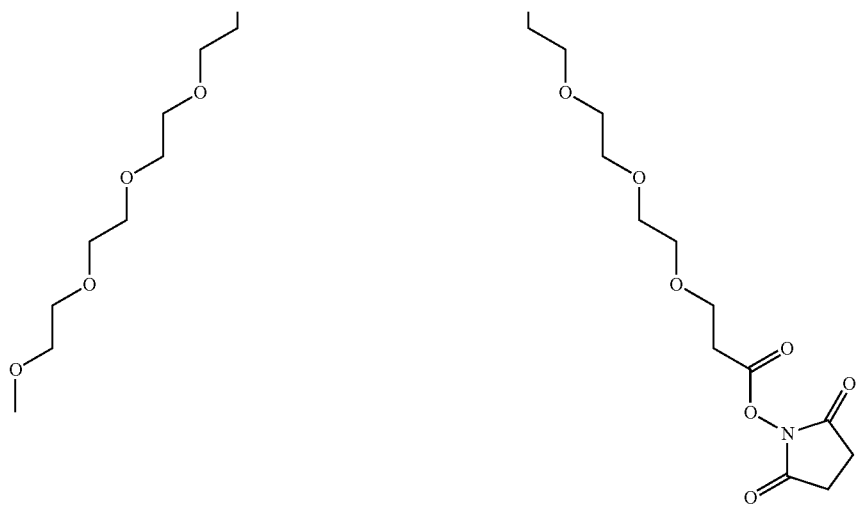
One non-limiting example of an additionally PEG-substituted compound is a 650 Compound 4/4 according to general formula III where both R1 and R2 are a (poly) ethylene glycol (4) group terminating with a methyl group, and R7 and R8 are H, shown below:

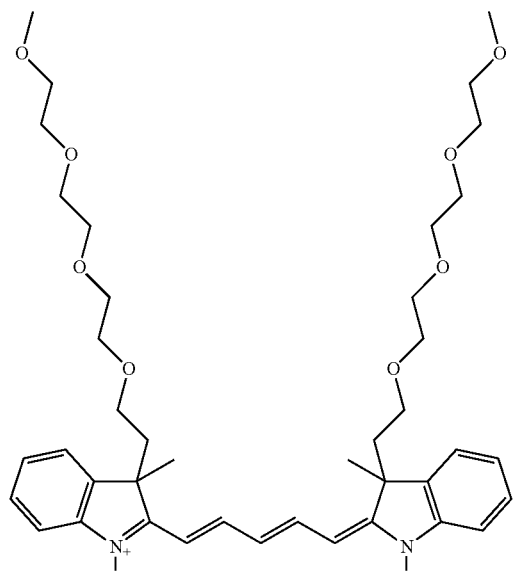
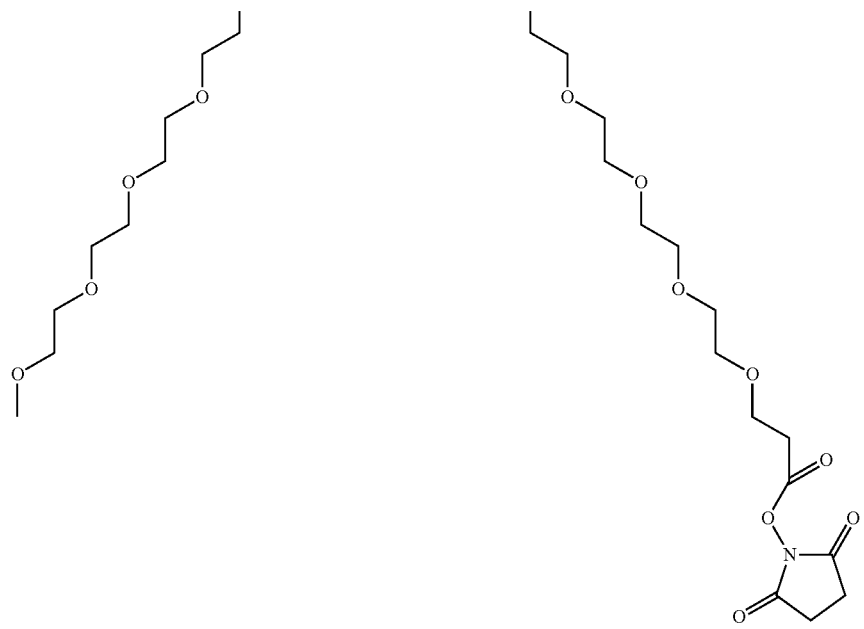

One non-limiting example of an additionally PEG-substituted compound is a 650 Compound 1/3 according to general formula II where both R1 and R2 are a (poly) ethylene glycol (5) group terminating with a methyl group, shown below:

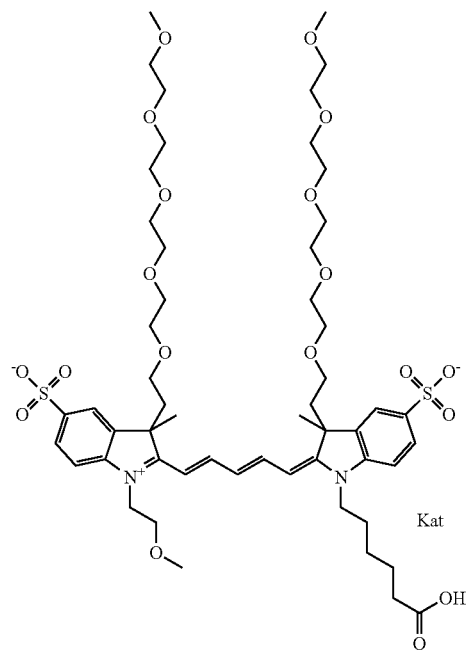

One non-limiting example of an additionally PEG-substituted compound is a 650 Compound 1/3 according to general formula II where both R1 and R2 are a (poly) ethylene glycol (6) group terminating with a methyl group, shown below:

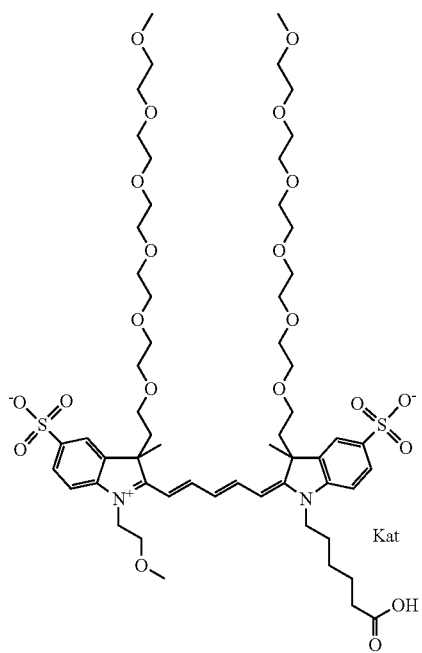

One non-limiting example of an additionally PEG-substituted compound is a 650 Compound 1/3 according to general formula II where both R1 and R2 are a sulfonamide group -L-SO$_2$NH—P—Z where Z is a methyl group, shown below:

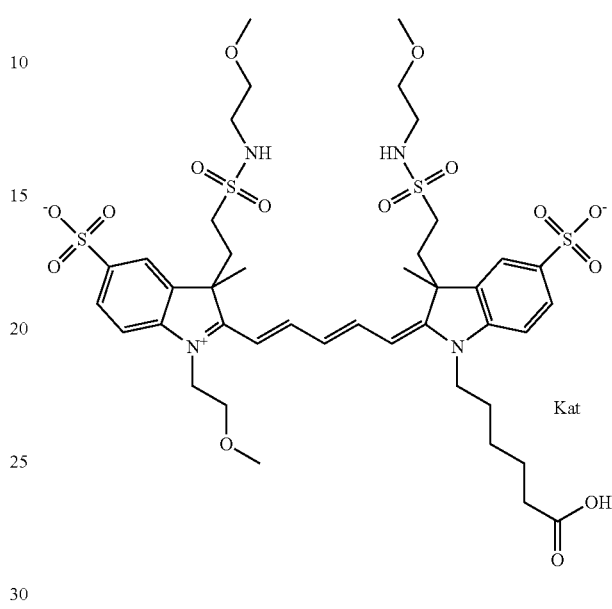

One non-limiting example of an additionally PEG-substituted compound is a 650 Compound 1/3 according to general formula II where both R1 and R2 are a carboxamide group -L-CONH—P—Z where Z is a methyl group, shown below:

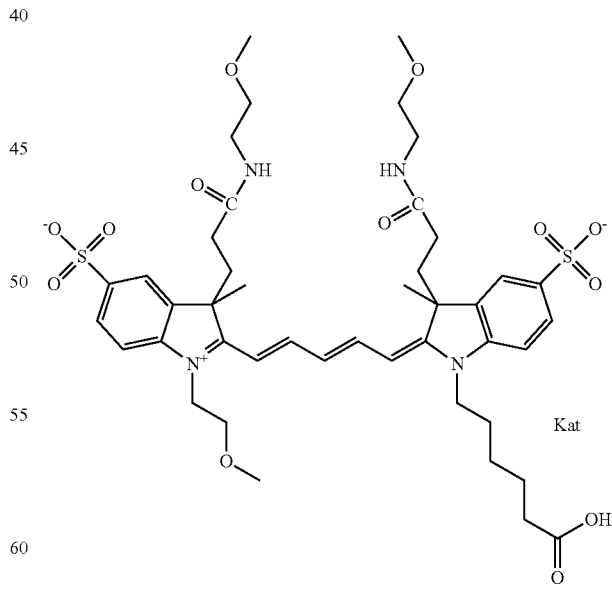

One non-limiting example of an additionally PEG-substituted compound is a 650 Compound 1/2 according to general formula II where R8 is an ethylene glycol group terminating with a methyl group, shown below:

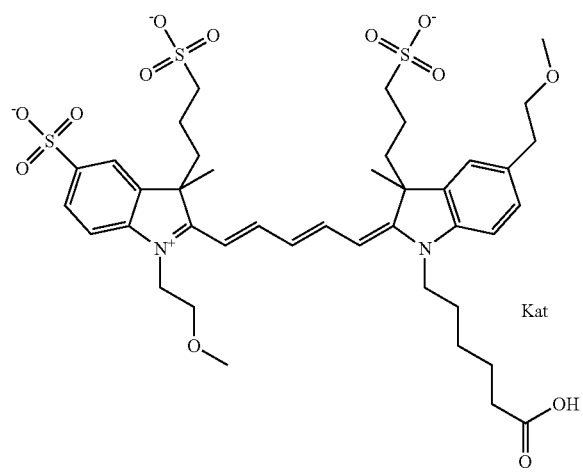

One non-limiting example of an additionally PEG-substituted compound is a 650 Compound 1/2 according to general formula II where R8 is sulfonamide —SO₂NH—P—Z where Z is a methyl group, shown below:

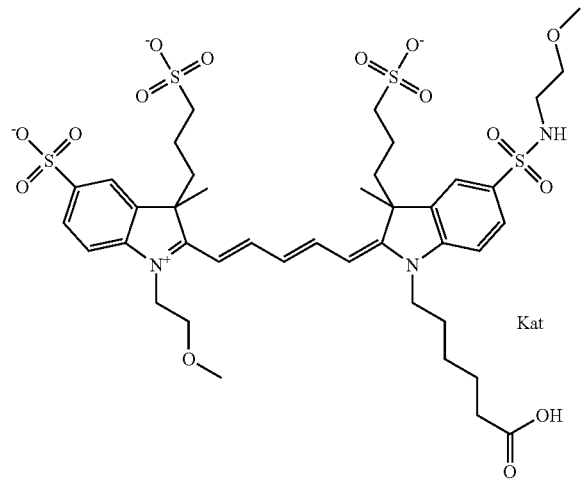

One non-limiting example of an additionally PEG-substituted compound is a 650 Compound 1/2 according to general formula II where R8 is carboxamide —CONH—P—Z where Z is a methyl group, shown below:

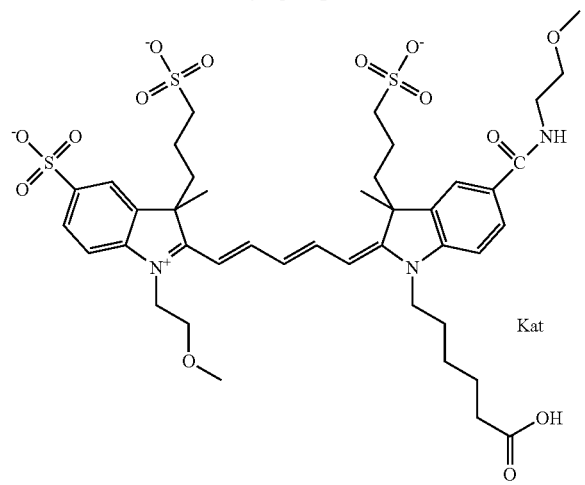

One non-limiting example of an additionally PEG-substituted compound is a 650 Compound 1/2 according to general formula II where R7 is an ethylene glycol group terminating with a methyl group, shown below:

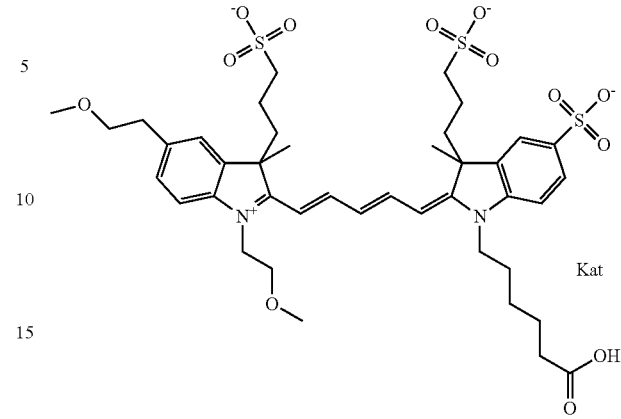

One non-limiting example of an additionally PEG-substituted compound is a 650 Compound 1/2 according to general formula II where R7 is a sulfonamide group —SO₂NH—P—Z where Z is a methyl group, shown below:

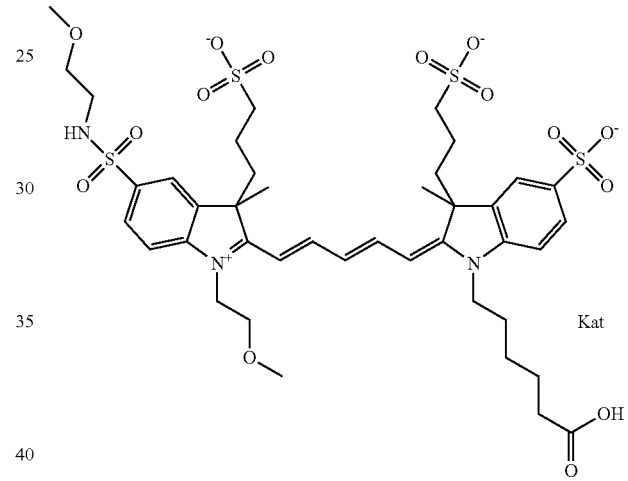

One non-limiting example of an additionally PEG-substituted compound is a 650 Compound 1/2 according to general formula II where R7 is a carboxamide group —CONH—P—Z where Z is a methyl group, shown below:

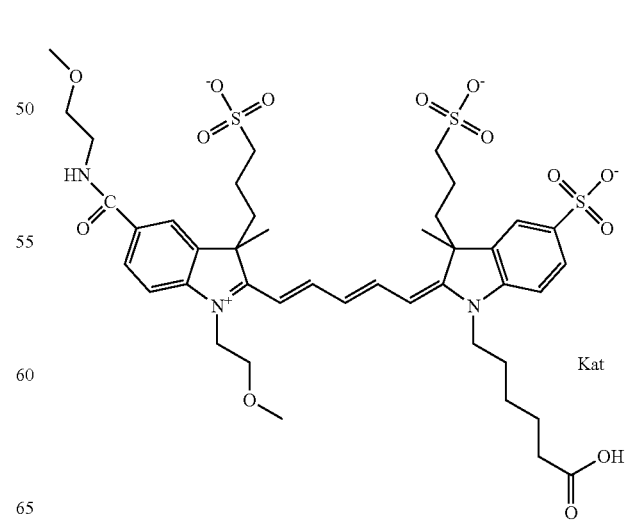

One non-limiting example of an additionally PEG-substituted compound is a 650 Compound 1/3 according to general formula II where both R7 and R8 are an ethylene glycol group terminating with a methyl group, shown below:

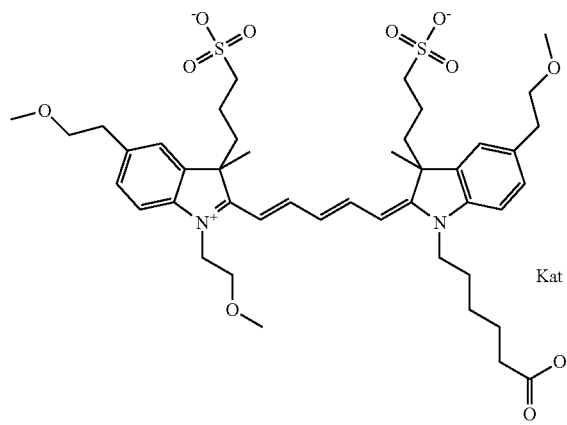

One non-limiting example of an additionally PEG-substituted compound is a 650 Compound 1/3 according to general formula II where both R7 and R8 are a sulfonamide group —SO₂NH—P—Z where Z is a methyl group, shown below:

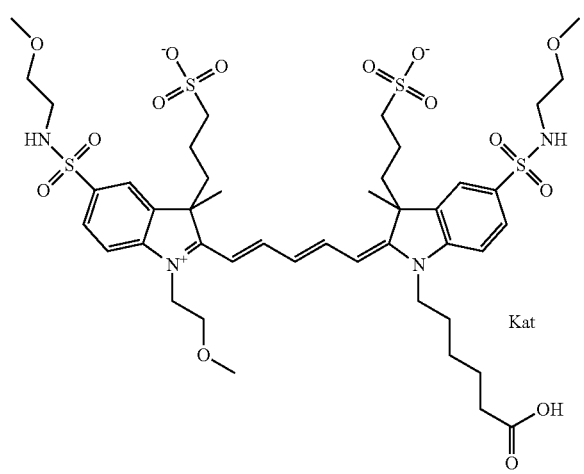

One non-limiting example of an additionally PEG-substituted compound is a 650 Compound 1/3 according to general formula II where both R7 and R8 are a carboxamide group —CONH—P—Z where Z is a methyl group, shown below:

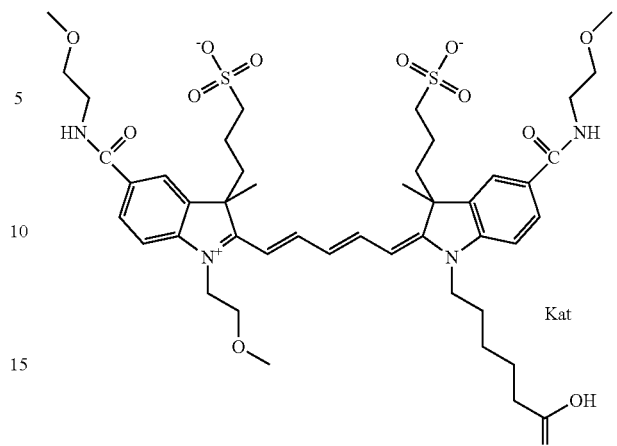

In one embodiment, the compound is 755 Compound 1/2

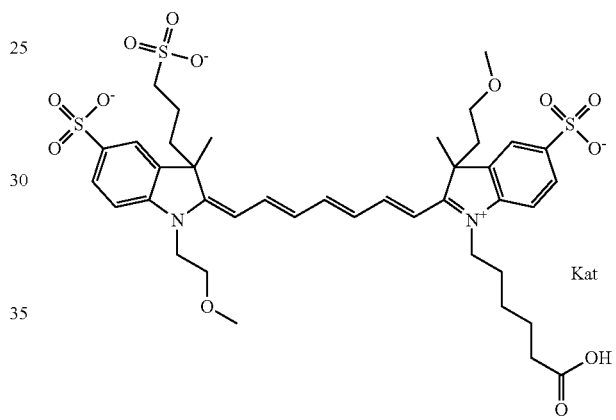

755 Compound 1/2 (1-(5-carboxypentyl)-3-(2-methoxyethyl)-2-((1E,3E,5E,7E)-7-(1-(2-methoxyethyl)-3-methyl-5-sulfonato-3-(3-sulfonatopropyl)indolin-2-ylidene)hepta-1,3,5-trienyl)-3-methyl-3H-indolium-5-sulfonate tri sodium salt) contains an ethylene glycol on the indole N of the left heterocycle, i.e., a methylated ethylene glycol. The methyl group on the ethylene glycol prevents the terminal —OH from oxidation. Oxidation is known to occur, over time, on an unprotected PEG terminus (i.e., an unprotected terminus of an ethylene glycol group, diethylene glycol group, or (poly)ethylene glycol group). Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 755 Compound 1/2, but one skilled in the art appreciates that activation is not limited to these examples. One non-limiting example of an activated compound is the NHS-ester of 755 Compound 1/2, shown below:

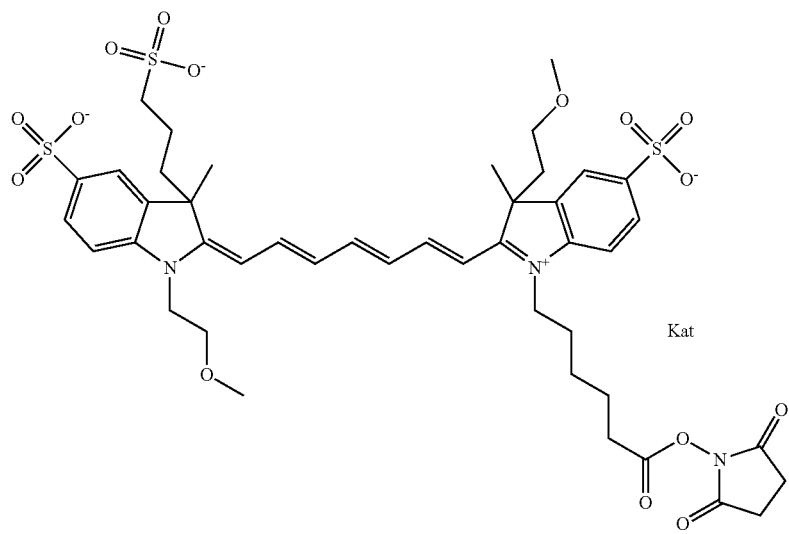 [SMILES: COCCN1/C(=C/C=C/C=C/C=C/C2=[N+](CCCCCC(=O)ON3C(=O)CCC3=O)c3ccc(S(=O)(=O)[O-])cc3C2(C)CCOC)C(C)(CCCS(=O)(=O)[O-])c2cc(S(=O)(=O)[O-])ccc21]
In one embodiment, the compound is an NHS-ester of 755 Compound 1/2 where, according to general formula I, o is 1, shown below:
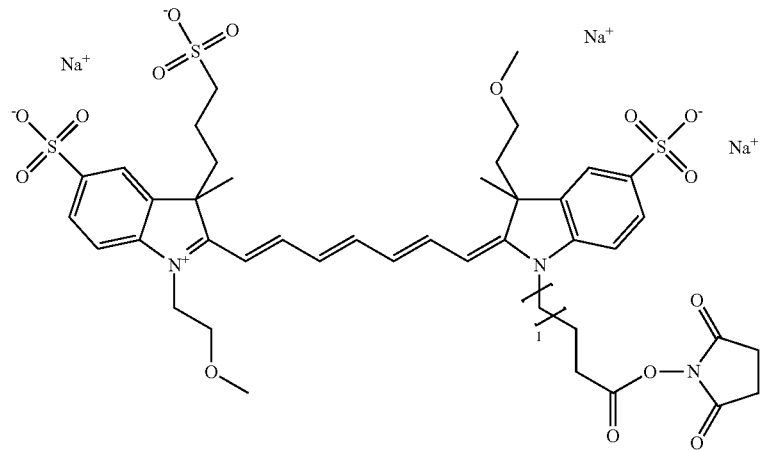
In one embodiment, the compound is an NHS-ester of 755 Compound 1/2 where, according to general formula I, o is 5, shown below:
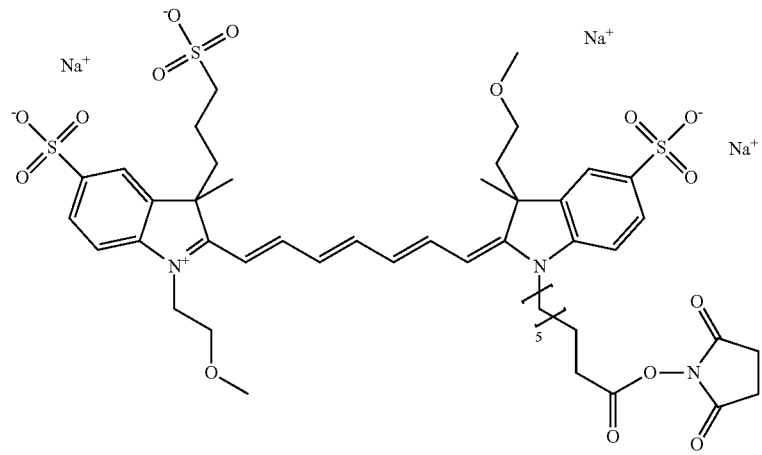

One non-limiting example of a NHS-ester of 755 Compound 1/3, according to general formula III, where m=1 and p=1, is shown below:
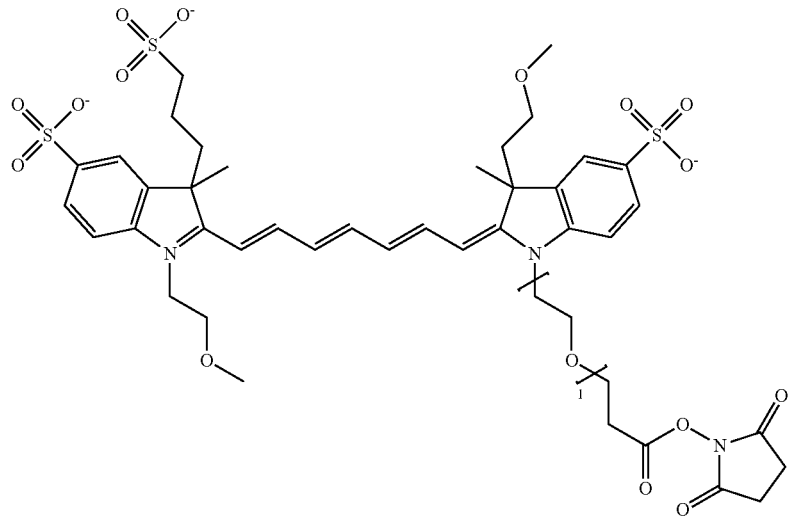
One non-limiting example of a NHS-ester of 755 Compound 1/3, according to general formula III, where m=1 and p=2, is shown below:
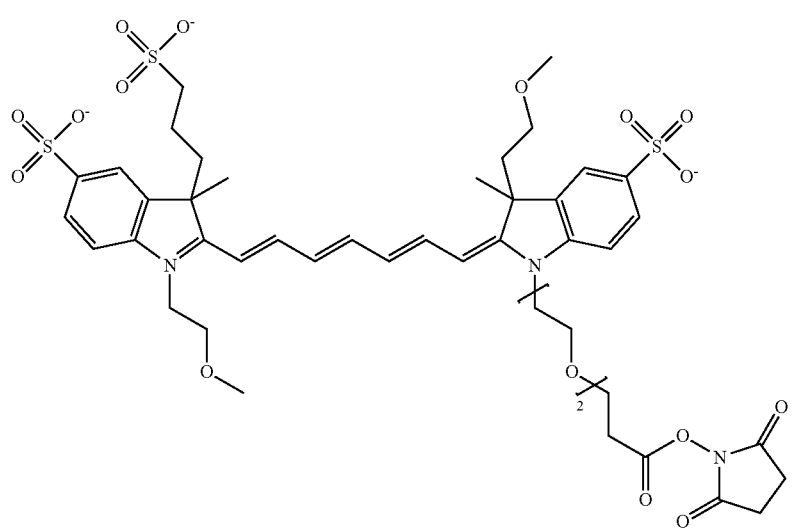
One non-limiting example of a NHS-ester of 755 Compound 1/3, according to general formula III, where m=1 and p=3, is shown below:

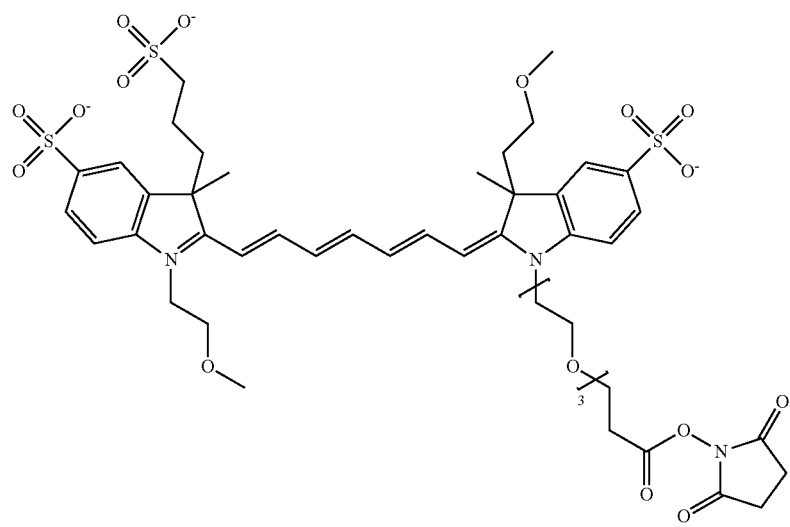
One non-limiting example of a NHS-ester of 755 Compound 1/3, according to general formula III, where m=1 and p=4, is shown below:
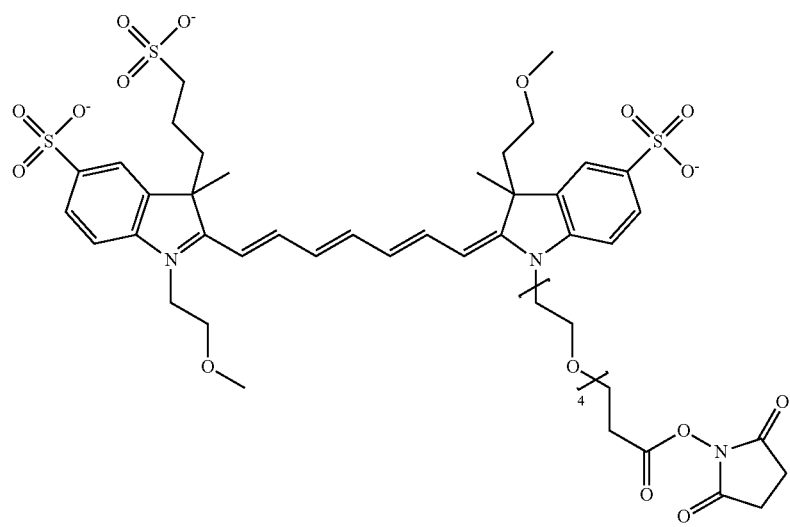
One non-limiting example of a NHS-ester of 755 Compound 1/3, according to general formula III, where m=1 and p=5, is shown below:

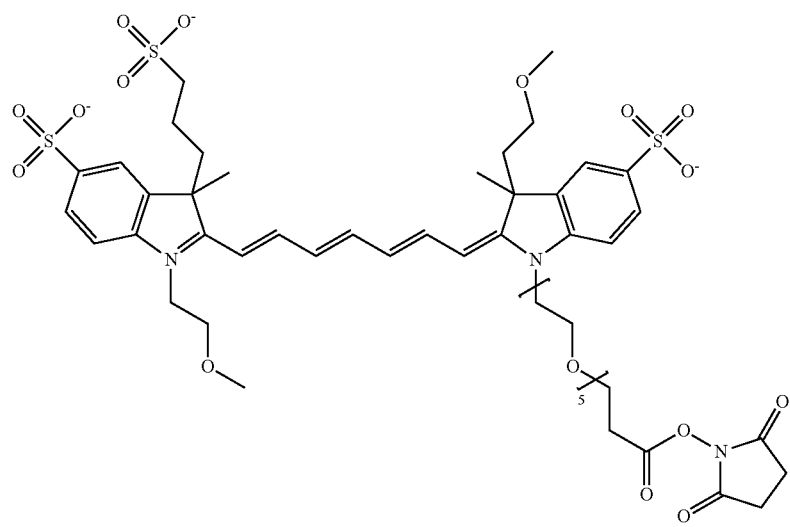
One non-limiting example of a NHS-ester of 755 Compound 1/3, according to general formula III, where m=1 and p=6, is shown below:
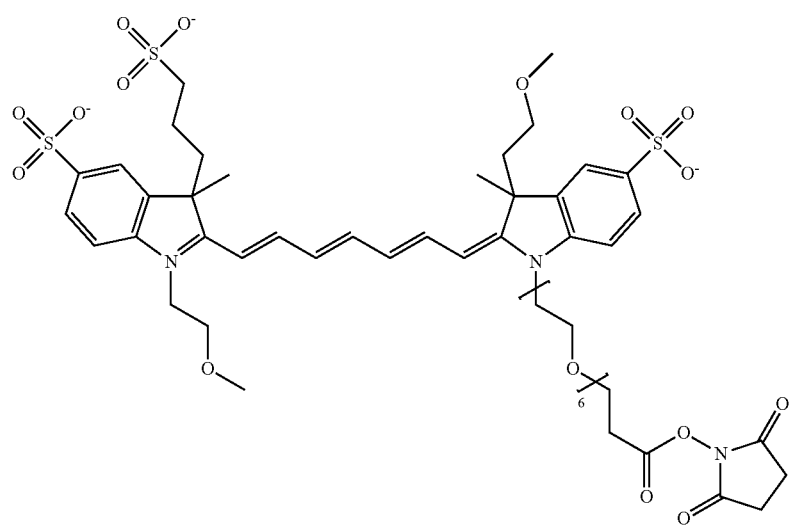
One non-limiting example of a NHS-ester of 755 Compound 2/3, according to general formula III, where m=2 and p=1, is shown below:

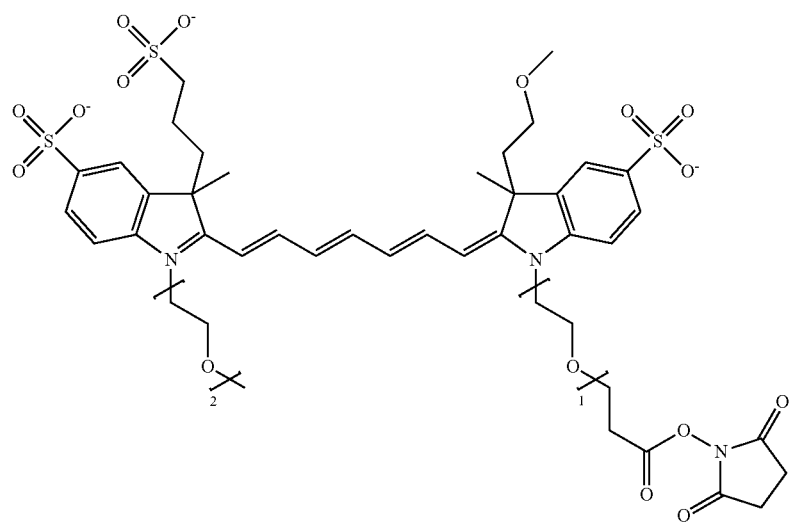
One non-limiting example of a NHS-ester of 755 Compound 2/3, according to general formula III, where m=2 and p=2, is shown below:
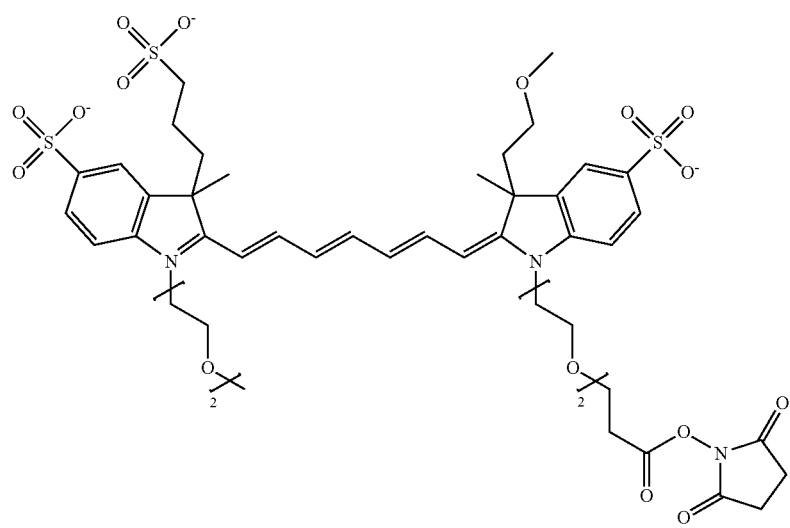
One non-limiting example of a NHS-ester of 755 Compound 2/3, according to general formula III, where m=2 and p=3, is shown below:

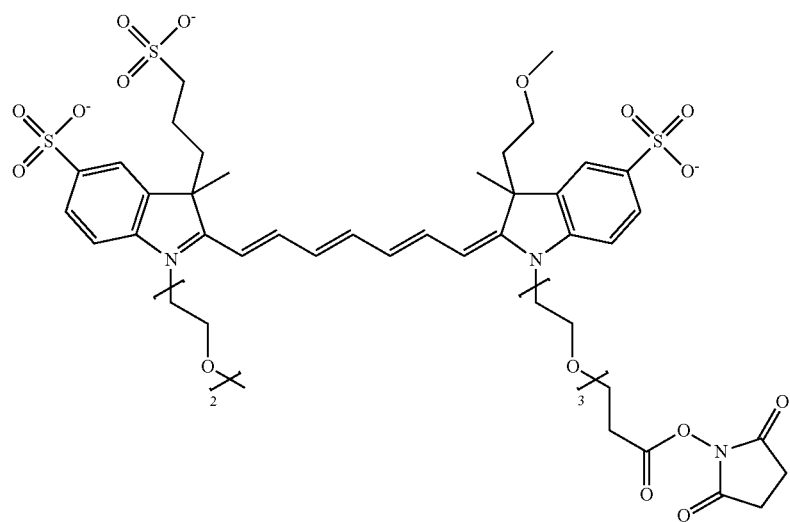
One non-limiting example of a NHS-ester of 755 Compound 3/3, according to general formula III, where m=3 and p=1, is shown below:
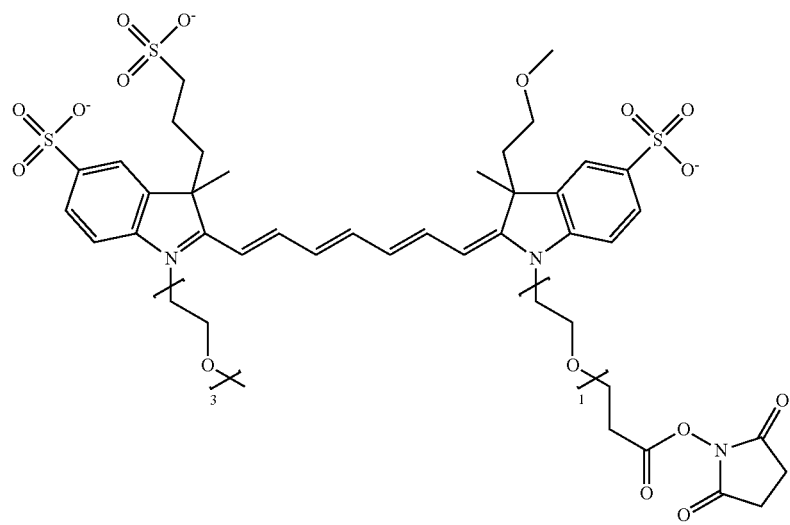
One non-limiting example of a NHS-ester of 755 Compound 3/3, according to general formula III, where m=3 and p=2, is shown below:

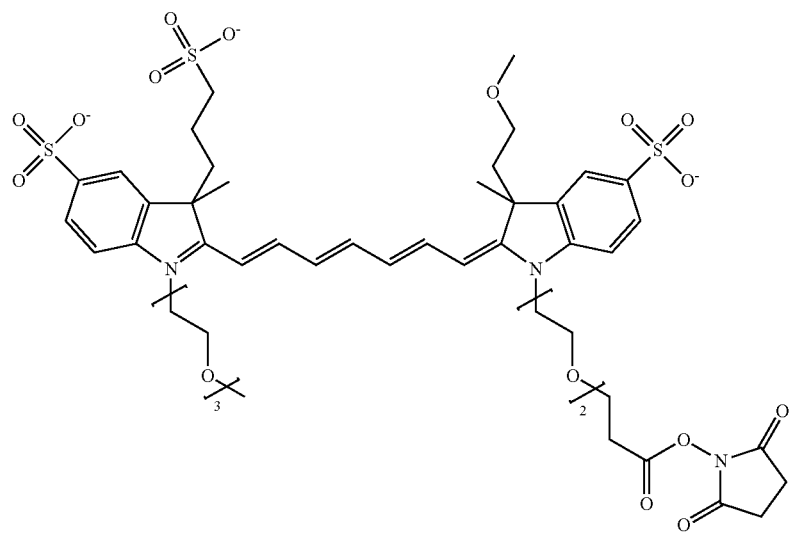
One non-limiting example of a NHS-ester of 755 Compound 3/3, according to general formula III, where m=3 and p=3, is shown below:
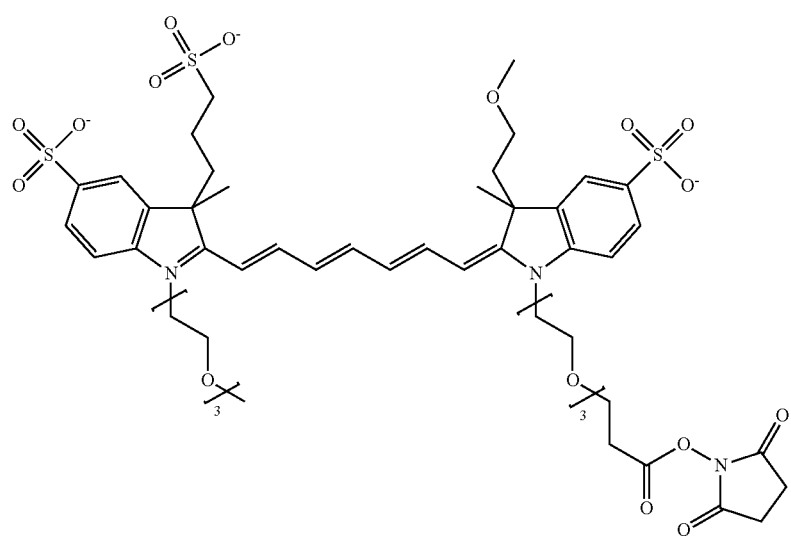
One non-limiting example of a NHS-ester of 755 Compound 4/3, according to general formula III, where m=4 and p=1, is shown below:

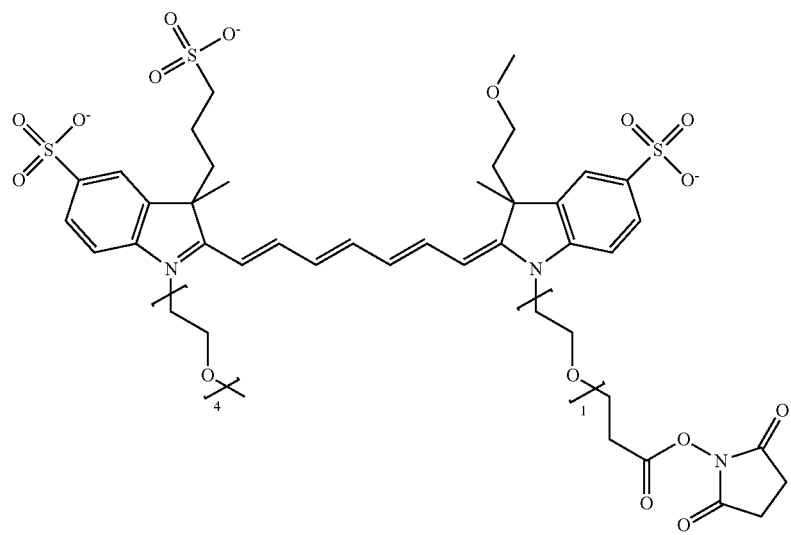
One non-limiting example of a NHS-ester of 755 Compound 5/3, according to general formula III, where m=5 and p=1, is shown below:
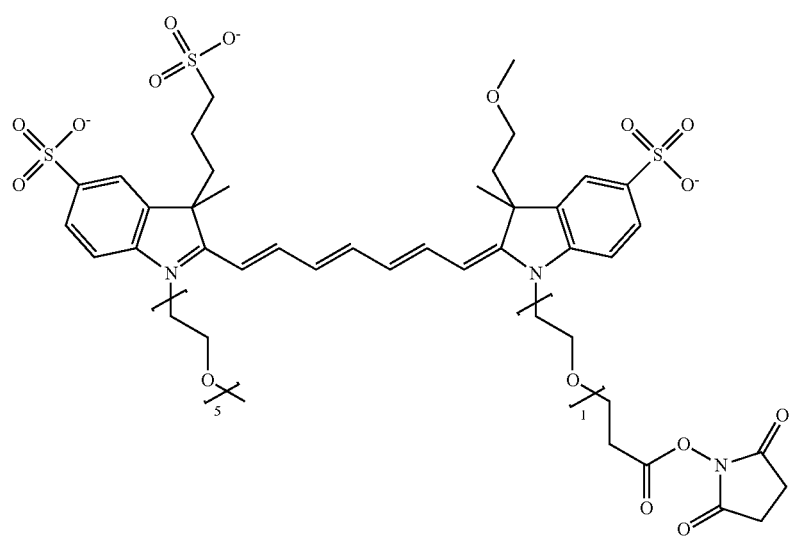
One non-limiting example of a NHS-ester of 755 Compound 6/3, according to general formula III, where m=6 and p=1, is shown below:

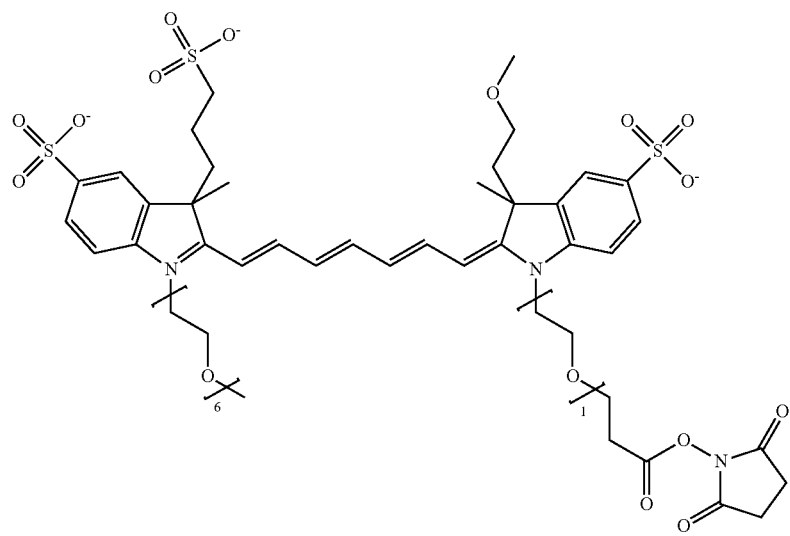
One non-limiting example of an activated 755 Compound 1/2 is a tetrafluorophenyl (TFP)-ester form of 755 Compound 1/2, shown below:
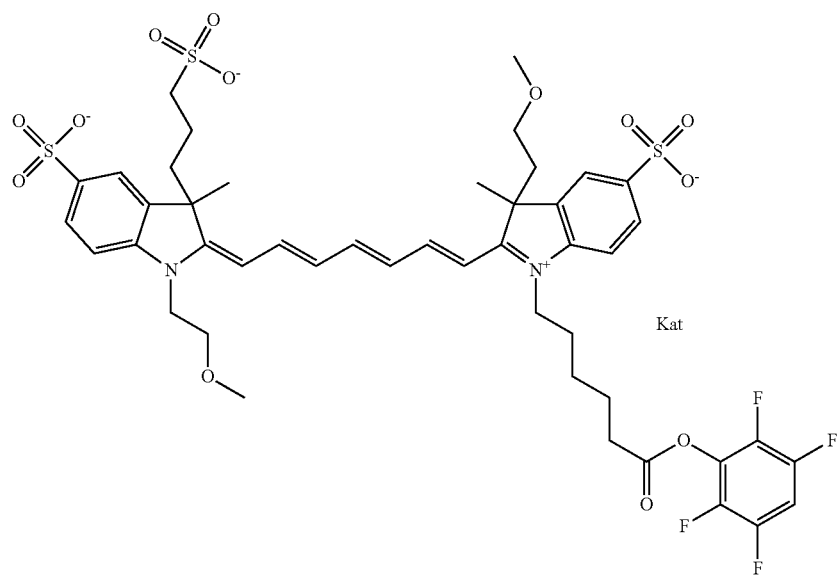 [SMILES: COCCN1/C(=C/C=C/C=C/C=C/C2=[N+](CCCCCC(=O)Oc3c(F)c(F)cc(F)c3F)c3ccc(S(=O)(=O)[O-])cc3C2(C)CCOC)C(C)(CCCS(=O)(=O)[O-])c2cc(S(=O)(=O)[O-])ccc21]
One non-limiting example of an activated 755 Compound 1/2 is a sulfotetrafluorophenyl (STP)-ester form of 755 Compound 1/2, shown below:

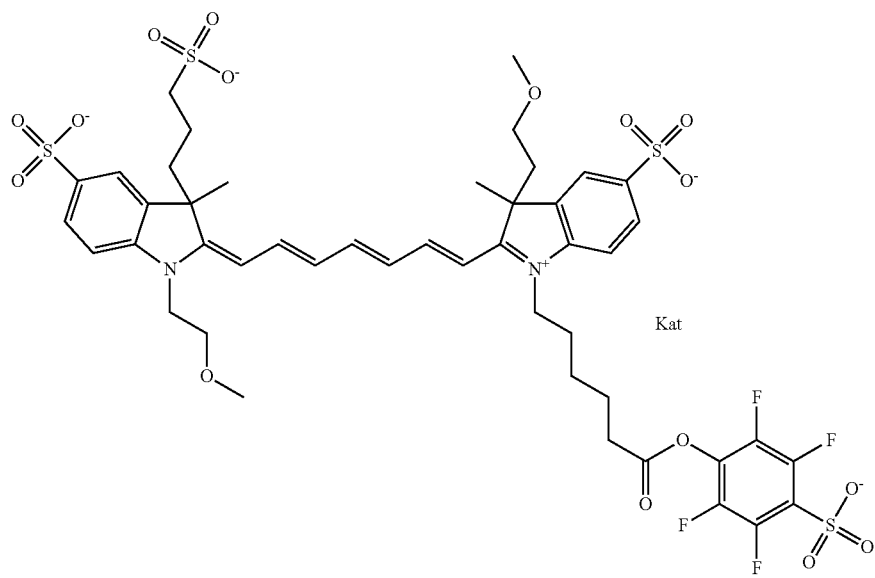 [SMILES: COCCN1/C(=C/C=C/C=C/C=C/C2=[N+](CCCCCC(=O)Oc3c(F)c(F)c(S(=O)(=O)[O-])c(F)c3F)c3ccc(S(=O)(=O)[O-])cc3C2(C)CCOC)C(C)(CCCS(=O)(=O)[O-])c2cc(S(=O)(=O)[O-])ccc21]
One non-limiting example of an activated 755 Compound 1/2 is a hydrazide form of 755 Compound 1/2, shown below:
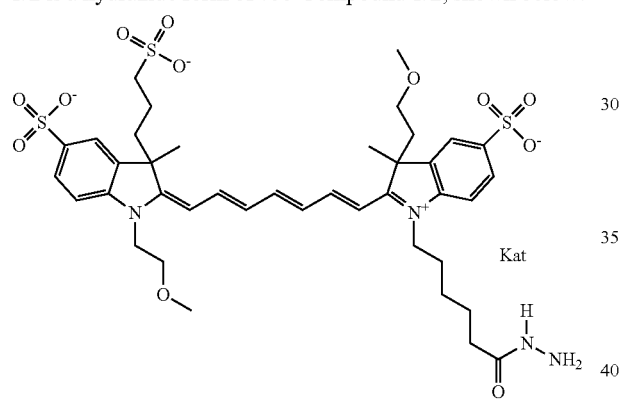
One non-limiting example of an activated 755 Compound 1/2 is a maleimide form of 755 Compound 1/2,
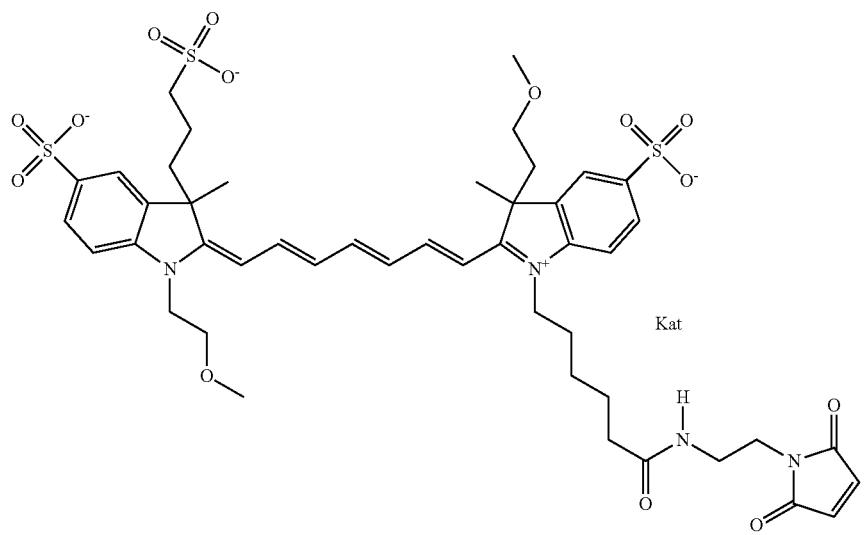 [SMILES: COCCN1/C(=C/C=C/C=C/C=C/C2=[N+](CCCCCC(=O)NCCN3C(=O)C=CC3=O)c3ccc(S(=O)(=O)[O-])cc3C2(C)CCOC)C(C)(CCCS(=O)(=O)[O-])c2cc(S(=O)(=O)[O-])ccc21]

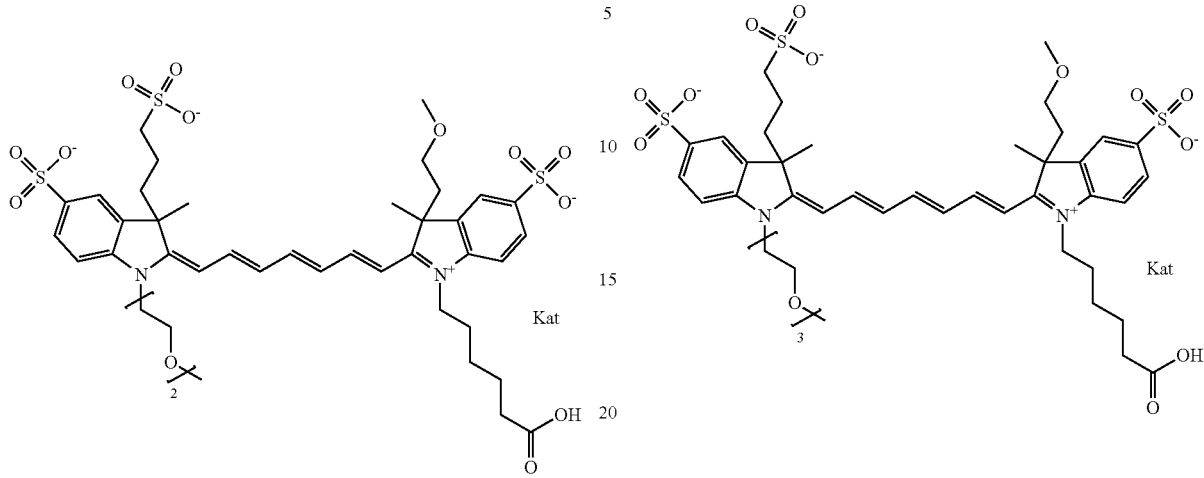

In one embodiment, the compound is 755 Compound 2/2

755 Compound 2/2 (1-(5-carboxypentyl)-2-((1E,3E,5E,7E)-7-(1-(2-(2-methoxyethoxy)ethyl)-3-methyl-5-sulfonato-3-(3-sulfonatopropyl) indolin-2-ylidene)hepta-1,3,5-trienyl)-3-(2-methoxyethyl)-3-methyl-3H-indolium-5-sulfonate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 755 Compound 2/2 is activated as described above, one non-limiting example of which is the NHS-ester form of 755 Compound 2/2, shown below.

In one embodiment, the compound is 755 Compound 3/2

755 Compound 3/2 (1-(5-carboxypentyl)-2-((1E,3E,5E,7E)-7-(1-(2-(2-(2-methoxyethoxy)ethoxy)ethyl)-3-methyl-5-sulfonato-3-(3-sulfonatopropyl)indolin-2-ylidene)hepta-1,3,5-trienyl)-3-(2-methoxyethyl)-3-methyl-3H-indolium-5-sulfonate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 755 Compound 3/2 is activated as described above, one non-limiting example of which is the NHS-ester form of 755 Compound 3/2, shown below.

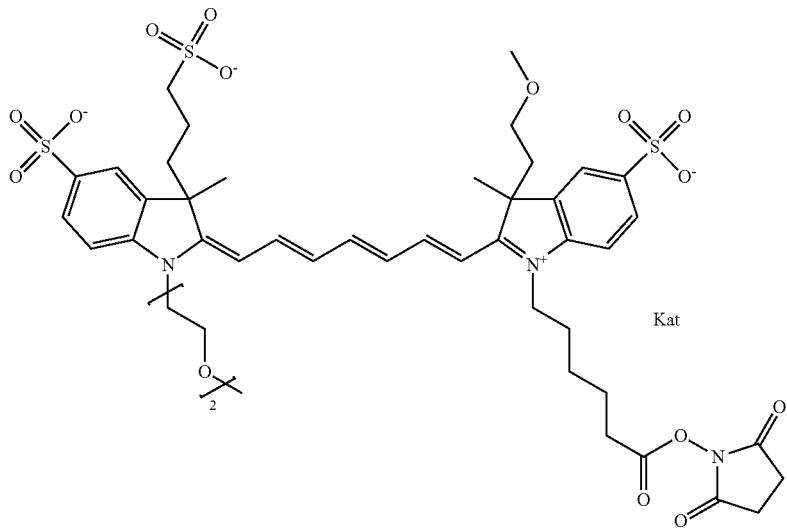

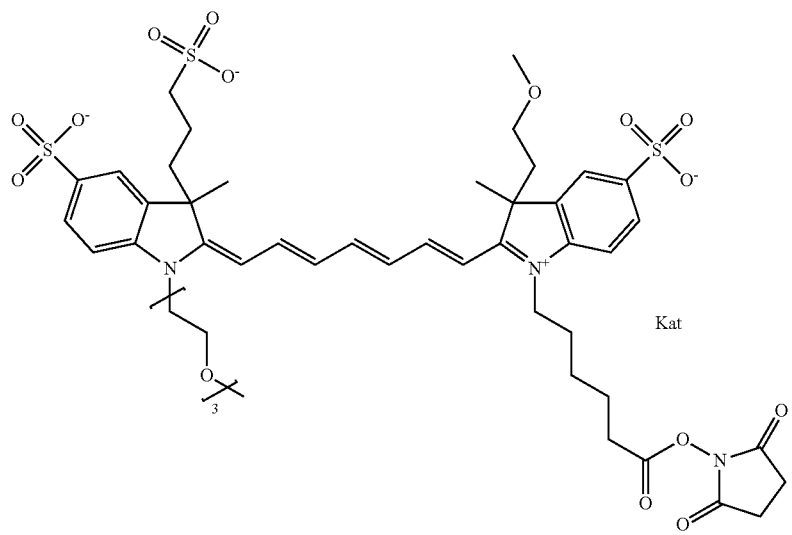

In one embodiment, the compound is 755 Compound 4/2

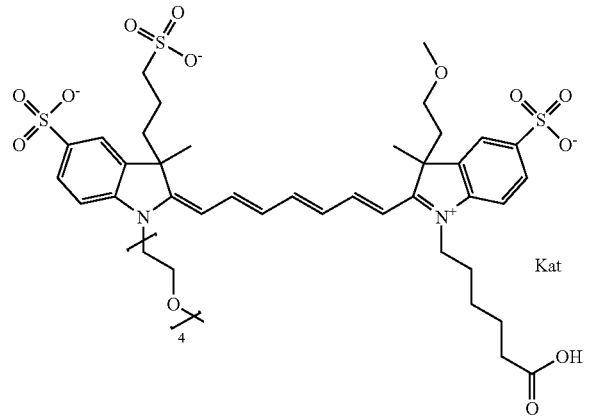

In one embodiment, the compound is 755 Compound 4/2E,3E,5E,7E)-7-(3-methyl-5-sulfonato-3-(3-sulfonatopropyl)-1-(2,5,8,11-tetraoxatridecan-13-yl)indolin-2-ylidene)hepta-1,3,5-trienyl)-3H-indolium-5-sulfonate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 755 Compound 4/2 is activated as described above.

In one embodiment, the compound is 755 Compound 5/2

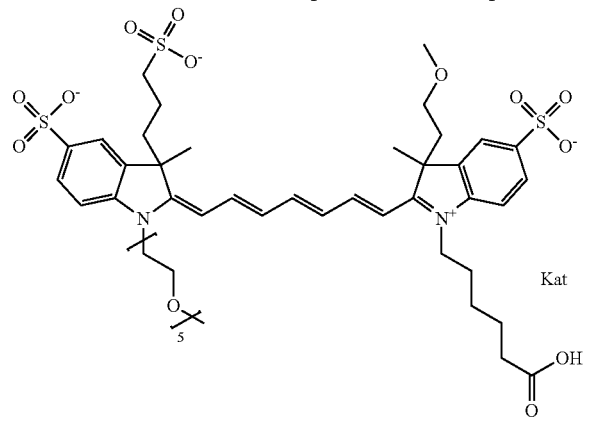

755 Compound 5/2 (2-((1E,3E,5E,7E)-7-(1-(2,5,8,11,14-pentaoxahexadecan-16-yl)-3-methyl-5-sulfonato-3-(3-sulfonatopropyl)indolin-2-ylidene)hepta-1,3,5-trienyl)-1-(5-carboxypentyl)-3-(2-methoxyethyl)-3-methyl-3H-indolium-5-sulfonate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 755 Compound 5/2 is activated as described above.

In one embodiment, the compound is 755 Compound 6/2

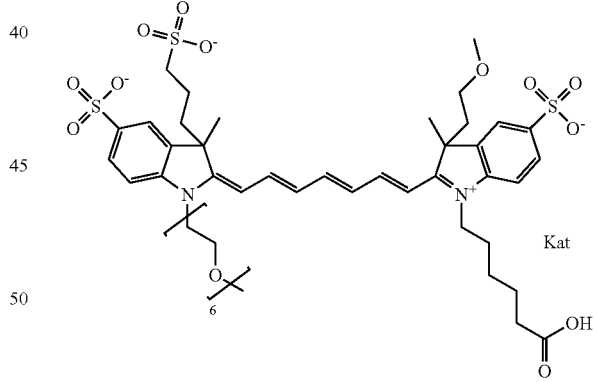

755 Compound 6/2 (1-(5-carboxypentyl)-3-(2-methoxyethyl)-3-methyl-2-((1E,3E,5E,7E)-7-(3-methyl-1-(2,5,8,11,14,17-hexaoxanonadecan-19-yl)-5-sulfonato-3-(3-sulfonatopropyl)indolin-2-ylidene)hepta-1,3,5-trienyl)-3H-indolium-5-sulfonate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 755 Compound 6/2 is activated as described above.

In embodiments, the compound contains one or more substitutions of the polymethine linker. In one embodiment, the compound has general formula VIa with "a" indicating an ethylene glycol, diethylene glycol, or (poly)ethylene glycol group on the left indole N, and the chain on the right indole N terminating in COX:

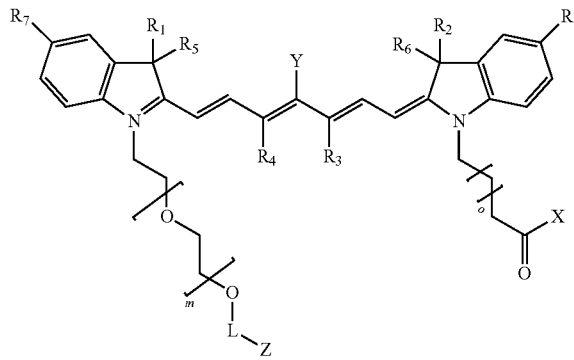

general formula VIb with "b" indicating an ethylene glycol, diethylene glycol, or (poly)ethylene glycol group on the left indole N, and the chain on the right indole N terminating in COH:

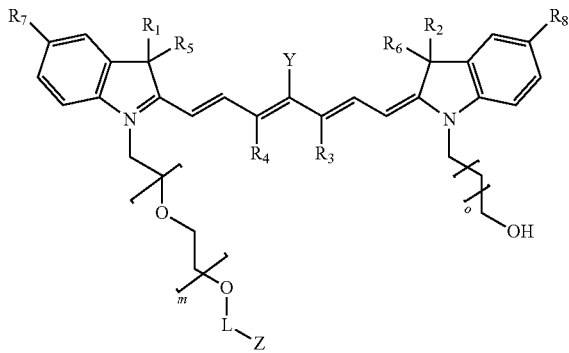

general formula VIc with "c" indicating an ethylene glycol, diethylene glycol, or (poly)ethylene glycol group on the left and right indole N, and the chain on the right indole N terminating in COX:

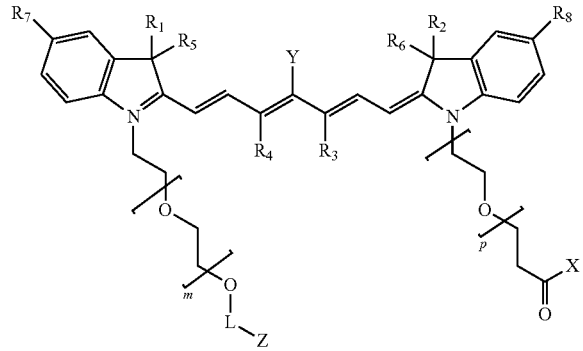

or general formula VId with "d" indicating an ethylene glycol, diethylene glycol, or (poly)ethylene glycol group on the left and right indole N, and the chain on the right indole N terminating in COH:

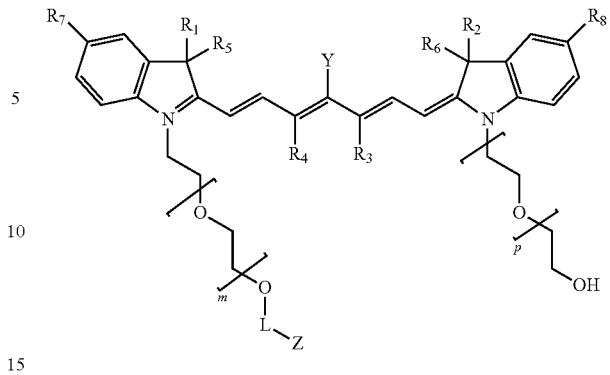

where each of $R^1$, $R^2$, $R^5$, and $R^6$ is the same or different and is independently selected from the group consisting of an aliphatic, heteroaliphatic, sulfoalkyl group, heteroaliphatic with terminal $SO_3$, a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group -L-$SO_2$NH—P-L-Z, and a carboxamide group -L-CONH—P-L-Z; each of $R^7$ and $R^8$ is the same or different and is independently selected from either H, $SO_3$, a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group —$SO_2$NH—P-L-Z, or a carboxamide group —CONH—P-L-Z; where L is selected from the group consisting of a divalent linear (—$(CH_2)_o$—, o=0 to 15), crossed, or cyclic alkane group that can be substituted by at least one atom selected from the group consisting of oxygen, substituted nitrogen, and/or sulfur; where Z is selected from the group consisting of H, $CH_3$, alkyl, a heteroalkyl group, $NH_2$, —COO$^-$, —COOH, —COSH, CO—NH—$NH_2$, —COF, —COCl, —COBr, —COI, —COO-Su (succinimidyl/sulfosuccinimidyl), —COO-STP (4-sulfo-2,3,5,6-tetrafluorophenyl), —COO-TFP (2,3,5,6-tetrafluorophenyl), —COO-benzotriazole, —CO-benzotriazole, —CONR'—CO—$CH_2$—I, —CONR'R", —CONR'-biomolecule, —CONR'-L-COO$^-$, —CONR'-L-COOH, —CONR'-L-COO-Su, —CONR'-L-COO-STP, —CONR'-L-COO-TFP, —CONR'-L-CONR"$_2$, —CONR'-L-CO-biomolecule, —CONR'-L-CO—NH—$NH_2$, —CONR'-L-OH, —CONR'-L-O-phosphoramidite, —CONR'-L-CHO, —CONR'-L-maleimide, and —CONR'-L-NH—CO—$CH_2$—I; R' and R" is selected from the group consisting of H, aliphatic group, and heteroaliphatic group, and the biomolecule is a protein, antibody, nucleotide, oligonucleotide, biotin, or hapten; X is selected from the group consisting of —OH, —SH, —$NH_2$, —NH—$NH_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, and —NR-L-NH—CO—CH2-I, where R is —H or an aliphatic or heteroaliphatic group; Kat is a number of Na$^+$, K$^+$, Ca$^{2+}$, ammonia, or other cation(s) needed to compensate the negative charge brought by the cyanine; m is an integer from 0 to 5 inclusive; p is an integer from 1 to 6 inclusive; each of R3 and R4 is the same or different and is independently hydrogen, an aliphatic group, a heteroaliphatic group, or a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive; or R3 and R4 together form a cyclic structure where R3 and R4 are joined using a divalent structural element selected from the group consisting of $-(CH_2)_q-$, $-(CH_2)_qO(CH_2)_{q'}-$, $-(CH_2)_qS(CH_2)_{q'}-$, $-(CH_2)_qCH=CH-$, $-OCH=CH-$ where each of q and q' is the same or different and is a integer from 2 to 6 inclusive; and Y is selected from the group consisting of hydrogen, alkyl, sulfoalkyl, fluorine, chlorine, bromine, a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, and an oxygen-containing group $OR^{PM}$ where $R^{PM}$ is selected from the group consisting of hydrogen, substituted or unsubstituted alkyl, substituted or unsubstituted heteroalkyl, substituted or unsubstituted cyclic alkyl, substituted or unsubstituted heterocyclic alkyl, substituted or unsubstituted aryl, and substituted or unsubstituted heteroaryl, where the group can be substituted with at least one of hydroxyl, sulfo, carboxy, and/or amino; with the proviso that at least one of $R^1$, $R^2$, $R^3$, $R^4$, $R^5$, $R^6$, $R^7$, and $R^8$ contains a PEG group.

In one embodiment, the compound of general formula VI where each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of $-(CH_2)_q-$ and $CH=CH$, where q is an integer from 1 to 2 inclusive, to result in a 3-, 4-, or 5-membered ring.

In one embodiment, the compound of general formula VI wherein R3 and R4 together form a cyclic structure where R3 and R4 are joined using a divalent structural element of $-(CH_2)_q-$, where q is 3, to result in a 6-membered ring, and Y is $OR^{PM}$ where $R^{PM}$ is a substituted 6-membered aryl group, where the substituted group is sulfo.

One non-limiting example is a substituted polymethine form of 755 Compound 1/2, shown below:

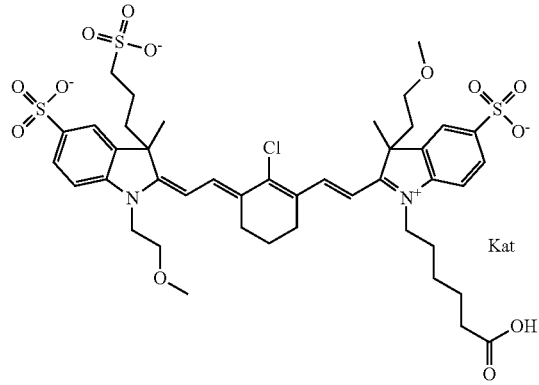 [SMILES: COCCN1/C(=C/C=C2\CCCC(/C=C/C3=[N+](CCCCCC(=O)O)c4ccc(S(=O)(=O)[O-])cc4C3(C)CCOC)=C2Cl)C(C)(CCCS(=O)(=O)[O-])c2cc(S(=O)(=O)[O-])ccc21 ; "Kat"]

One non-limiting example is a substituted polymethine form of 755 Compound 2/2, shown below:

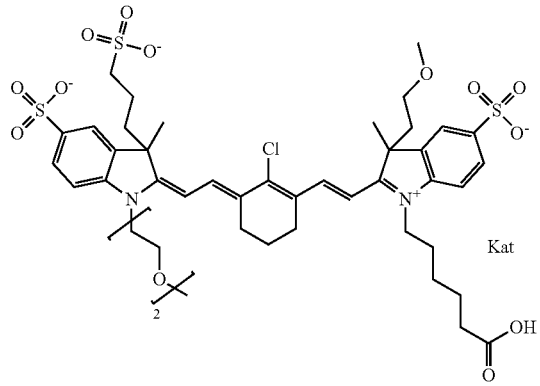

One non-limiting example is a substituted polymethine form of 755 Compound 3/2, shown below:

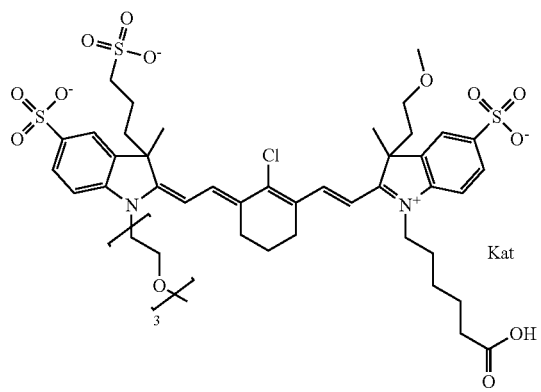

One non-limiting example is a substituted polymethine form of 755 Compound 4/2, shown below:

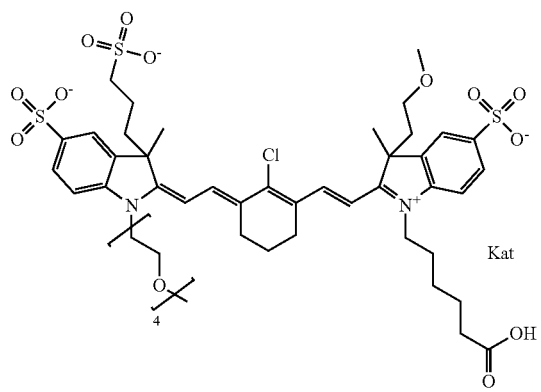

One non-limiting example is a substituted polymethine form of 755 Compound 5/2, shown below:

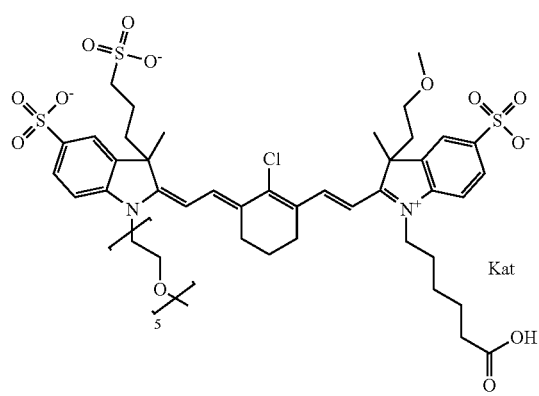

One non-limiting example is a substituted polymethine form of 755 Compound 6/2, shown below:

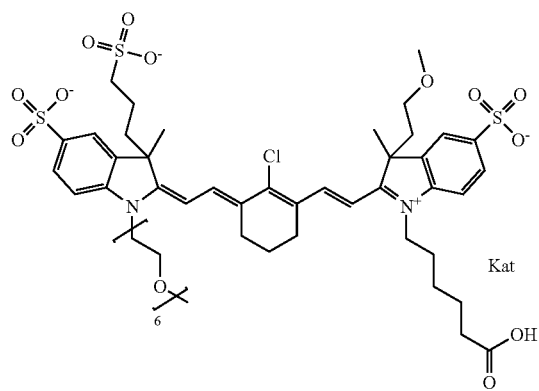

One non-limiting example is a substituted polymethine form of 755 Compound 1/3 having an ethylene glycol, diethylene glycol, or (poly)ethylene glycol as described for general formula VI, such as the compound shown below:

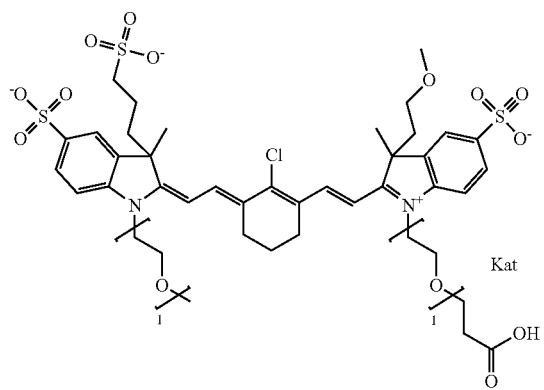

One non-limiting example is a substituted polymethine form of 755 Compound 4/4 having an ethylene glycol, diethylene glycol, or (poly)ethylene glycol as described for general formula VI, such as the compound shown below:

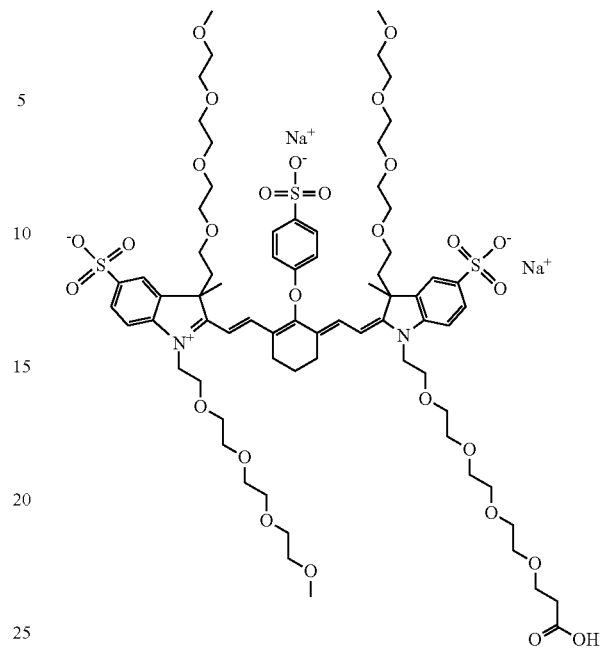

In embodiments, the degree of sulfonation is varied to, e.g., vary the compound's degree of hydrolilicity or hydrophobicity. One non-limiting example is a monosulfonate form of 755 Compound 1/2, shown below, but it is understood that the single sulfo group can be at any of the described positions:

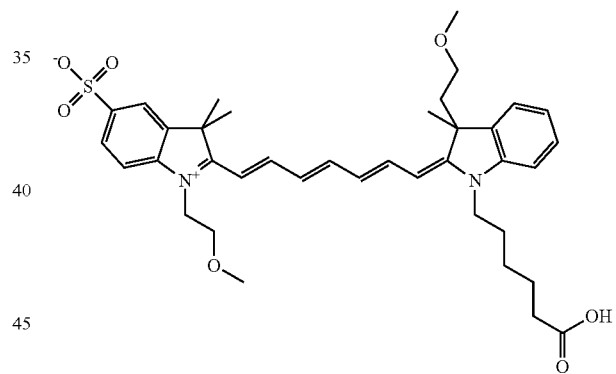

One non-limiting example is a disulfonate form of 755 Compound 1/2, shown below, but it is understood that the each of the two sulfo groups can be at any of the described positions:

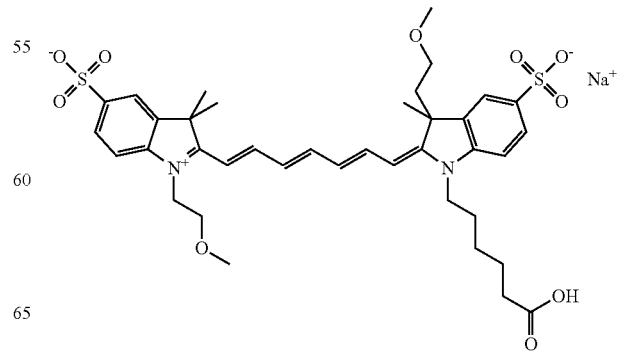

One non-limiting example is a trisulfonate form of 755 Compound 1/2, shown below, but it is understood that the each of the three sulfo groups can be at any of the described positions:

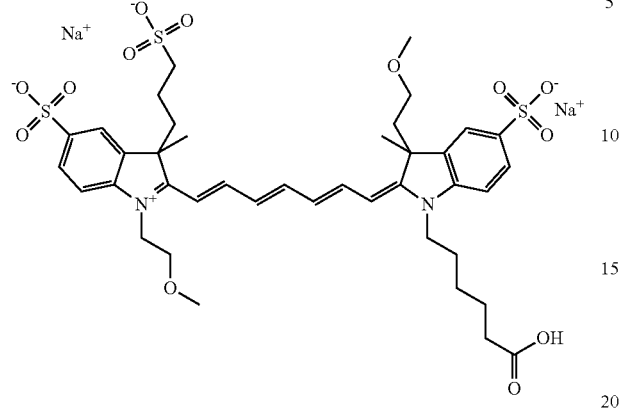

One non-limiting example is a tetrasulfonate form of 755 Compound 1, shown below, but it is understood that the each of the four sulfo groups can be at any of the described positions:

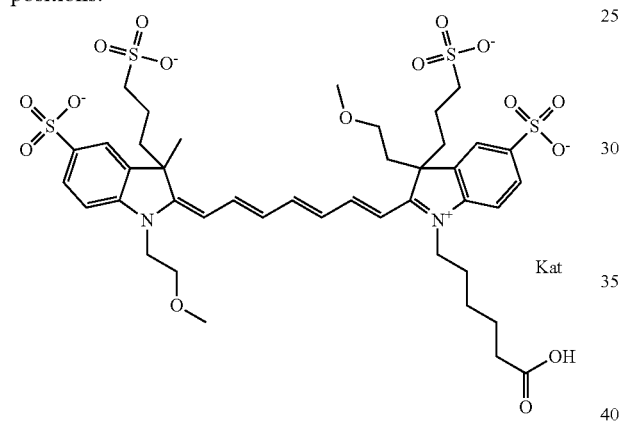

In embodiments, an ethylene glycol group, diethylene glycol group, and/or a (poly)ethylene glycol group, which will collectively be referred to as a PEG group unless specifically defined, may be present at position(s) in addition to such groups being present on the N atom(s) of the indole structure. One non-limiting example of an additionally PEG-substituted compound is a 755 Compound 1/2 according to general formula II where R1 is an ethylene glycol group terminating with a methyl group, shown below:

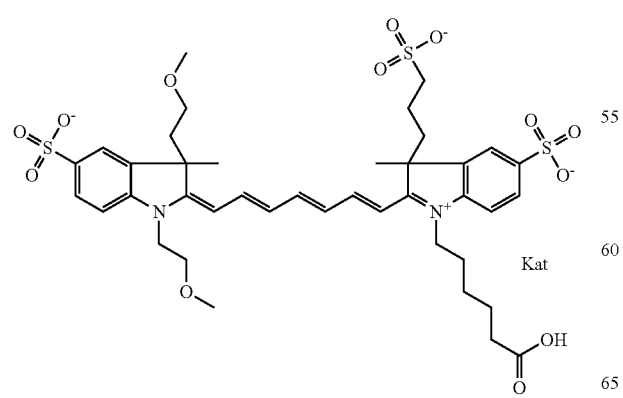

One non-limiting example of an additionally PEG-substituted compound is a 755 Compound 1/2 according to general formula II where R1 is a diethylene glycol group terminating with a methyl group, shown below:

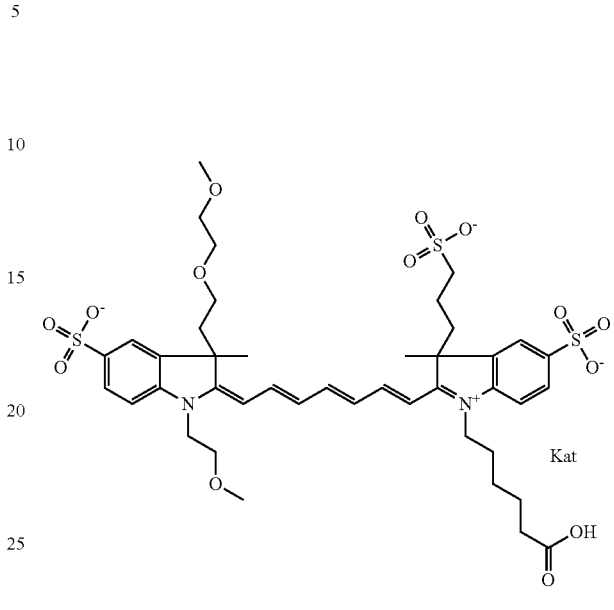

One non-limiting example of an additionally PEG-substituted compound is a 755 Compound 1/2 according to general formula II where R1 is a (poly)ethylene glycol (3) group terminating with a methyl group, shown below:

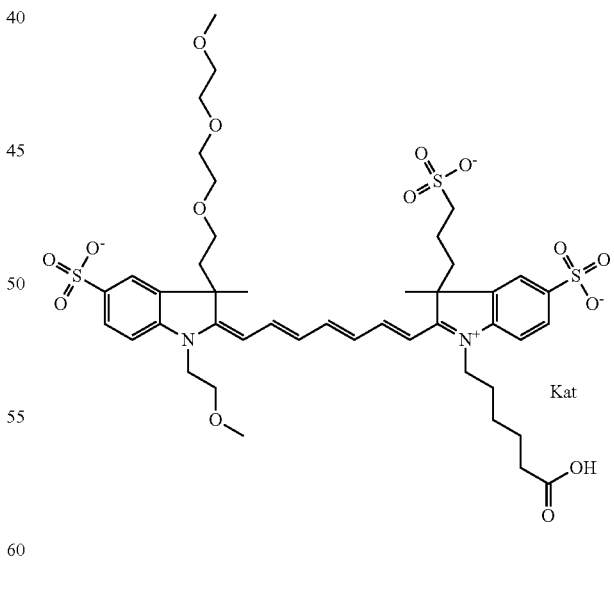

One non-limiting example of an additionally PEG-substituted compound is a 755 Compound 1/2 according to general formula II where R1 is a (poly)ethylene glycol (4) group terminating with a methyl group, shown below:

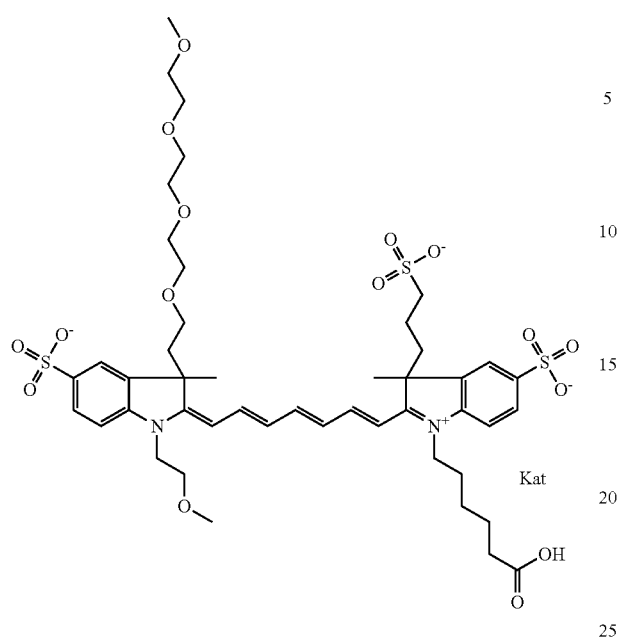

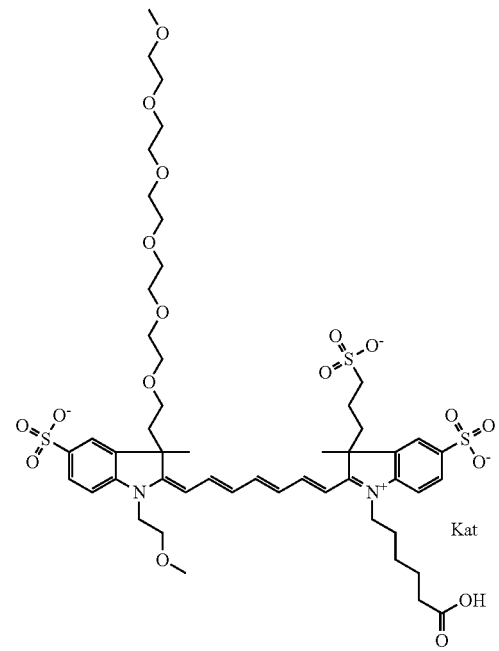

One non-limiting example of an additionally PEG-substituted compound is a 755 Compound 1/2 according to general formula II where R1 is a (poly)ethylene glycol (5) group terminating with a methyl group, shown below:

One non-limiting example of an additionally PEG-substituted compound is a 755 Compound 1/2 according to general formula II where R1 is a sulfonamide group -L-SO₂NH—P—Z where Z is a methyl group, shown below:

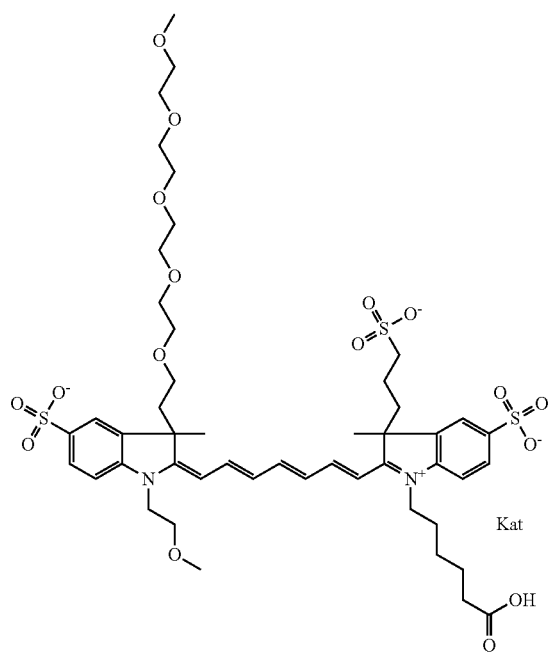

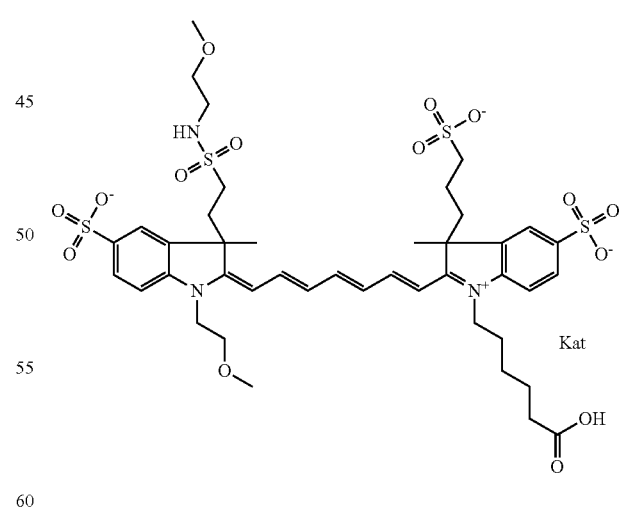

One non-limiting example of an additionally PEG-substituted compound is a 755 Compound 1/2 according to general formula II where R1 is a (poly)ethylene glycol (6) group terminating with a methyl group, shown below:

One non-limiting example of an additionally PEG-substituted compound is a 755 Compound 1/2 according to general formula II where R1 is a carboxamide group -L-CONH—P—Z where Z is a methyl group, shown below:

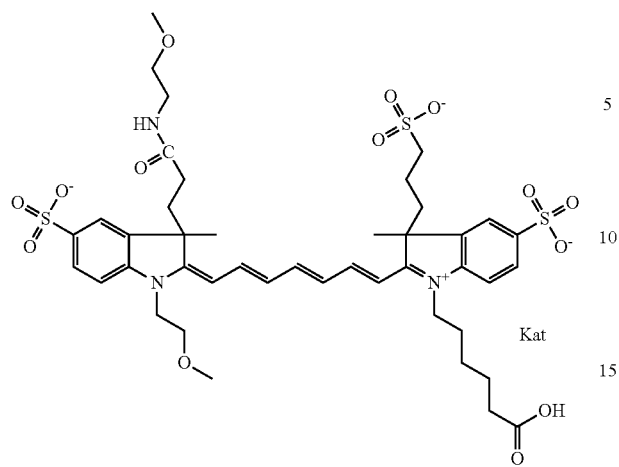

One non-limiting example of an additionally PEG-substituted compound is a 755 Compound 1/2 according to general formula II where R2 is an ethylene glycol group terminating with a methyl group, shown below:

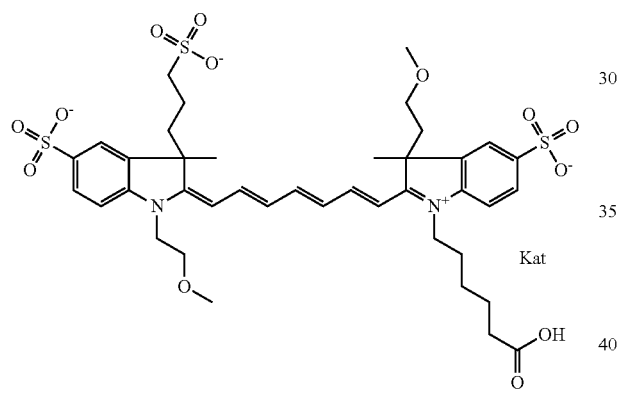

One non-limiting example of an additionally PEG-substituted compound is a 755 Compound 1/2 according to general formula II where R2 is a diethylene glycol group terminating with a methyl group, shown below:

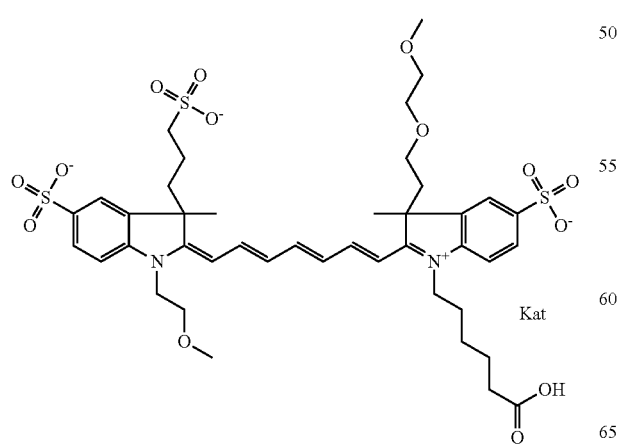

One non-limiting example of an additionally PEG-substituted compound is a 755 Compound 1/2 according to general formula II where R2 is a (poly)ethylene glycol (3) group terminating with a methyl group, shown below:

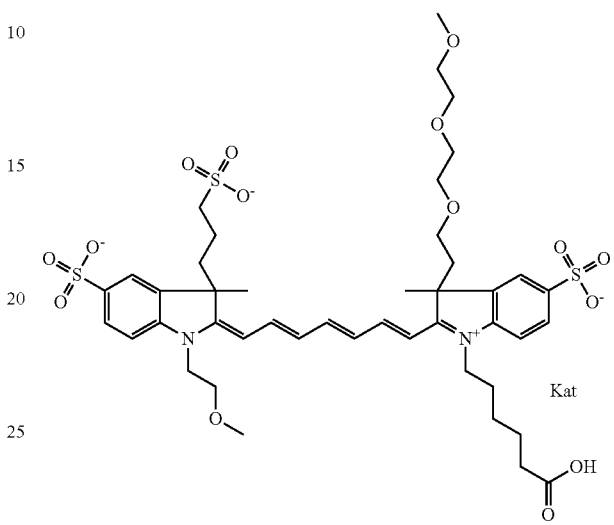

One non-limiting example of an additionally PEG-substituted compound is a 755 Compound 1/2 according to general formula II where R2 is a (poly)ethylene glycol (4) group terminating with a methyl group, shown below:

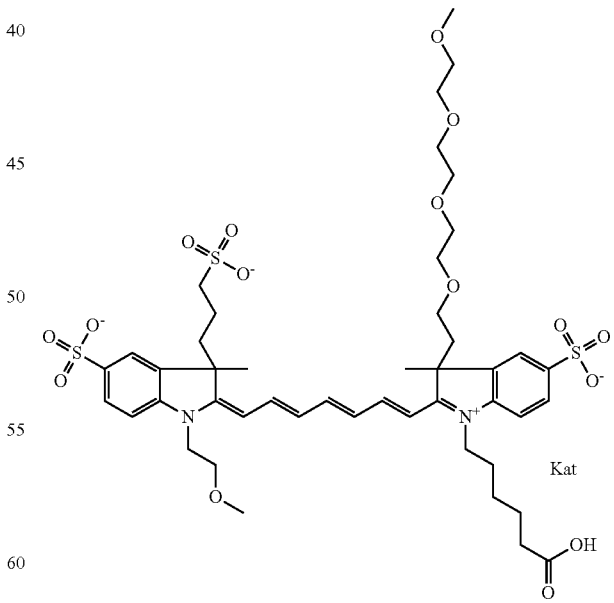

One non-limiting example of an additionally PEG-substituted compound is a 755 Compound 1/2 according to general formula II where R2 is a (poly)ethylene glycol (5) group terminating with a methyl group, shown below:

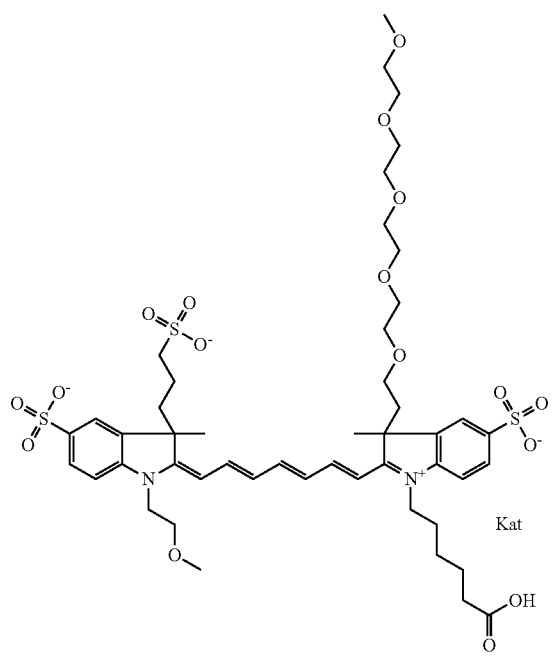

One non-limiting example of an additionally PEG-substituted compound is a 755 Compound 1/2 according to general formula II where R2 is a (poly)ethylene glycol (6) group terminating with a methyl group, shown below:

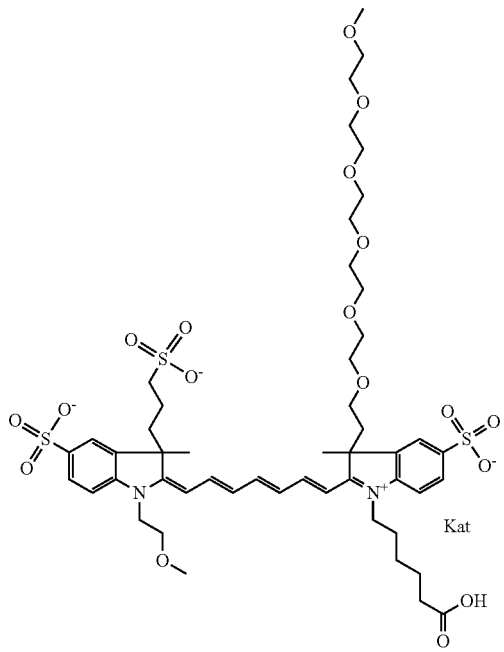

One non-limiting example of an additionally PEG-substituted compound is a 755 Compound 1/2 according to general formula II where R2 is a sulfonamide group -L-SO$_2$NH—P—Z where Z is a methyl group, shown below:

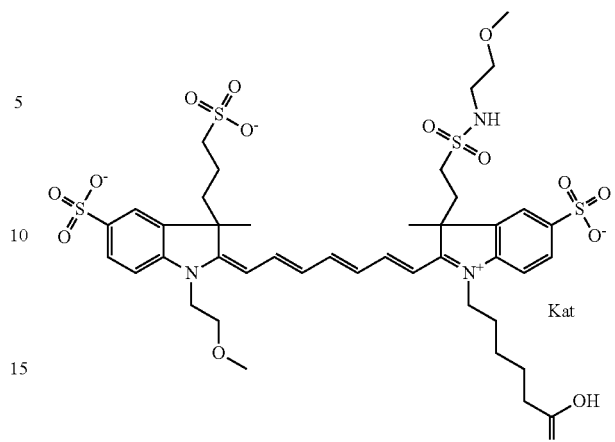

One non-limiting example of an additionally PEG-substituted compound is a 755 Compound 1/2 according to general formula II where R2 is a carboxamide group -L-CONH—P—Z where Z is a methyl group, shown below:

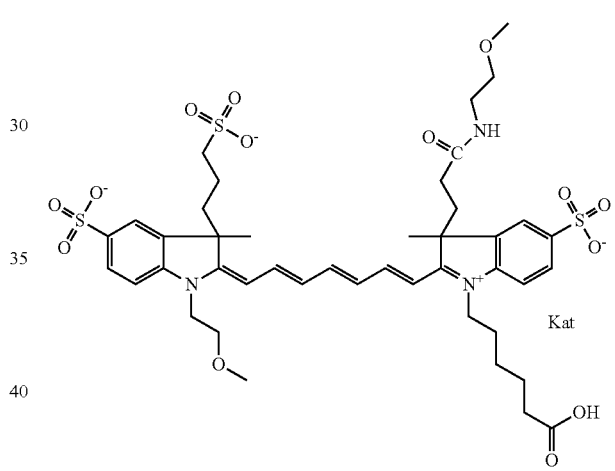

One non-limiting example of an additionally PEG-substituted compound is a 755 Compound 1/3 according to general formula II where both R1 and R2 are an ethylene glycol group terminating with a methyl group, shown below:

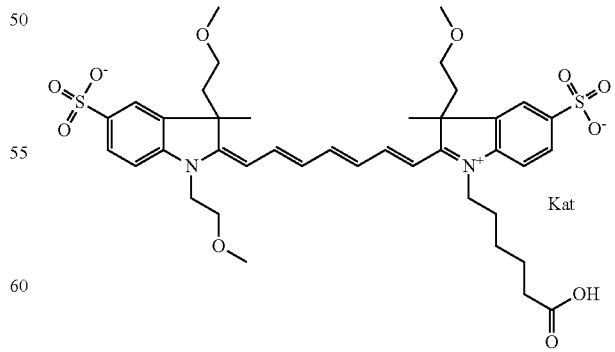

One non-limiting example of an additionally PEG-substituted compound is a 755 Compound 1/3 according to general formula II where both R1 and R2 are a diethylene glycol group terminating with a methyl group, shown below:

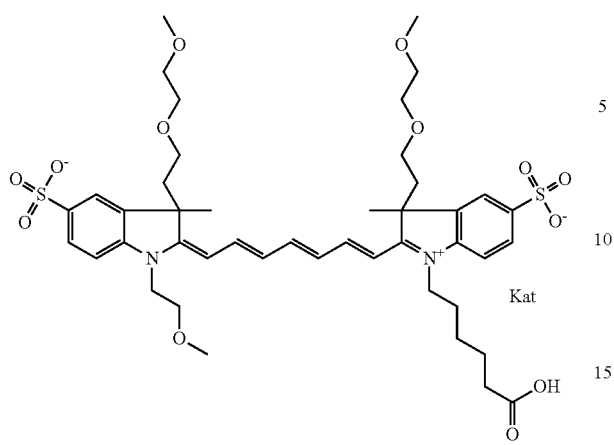

One non-limiting example of an additionally PEG-substituted compound is a 755 Compound 1/3 according to general formula II where both R1 and R2 are a (poly) ethylene glycol (4) group terminating with a methyl group, shown below:

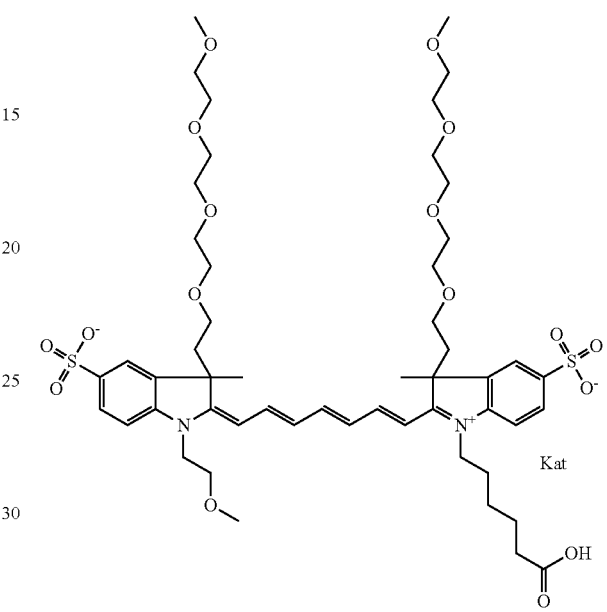

One non-limiting example of an additionally PEG-substituted compound is a 755 Compound 1/3 according to general formula II where both R1 and R2 are a (poly) ethylene glycol (3) group terminating with a methyl group, shown below:

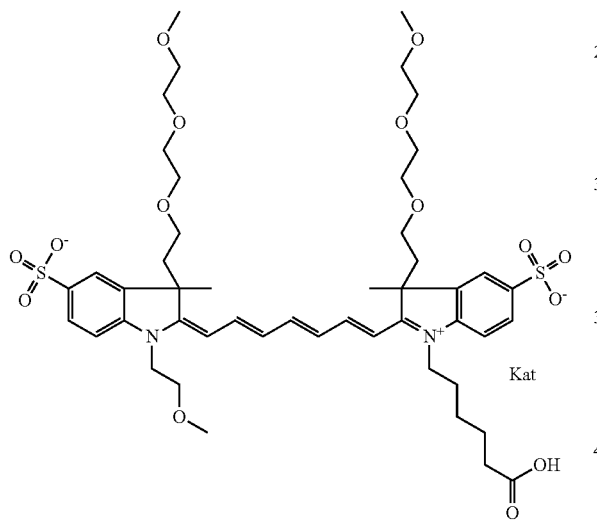

One non-limiting example of an additionally PEG-substituted compound is a 755 Compound 4/4 according to general formula II where both R1 and R2 are a (poly) ethylene glycol (4) group terminating with a methyl group, and R7 and R8 are sulfo, shown below:

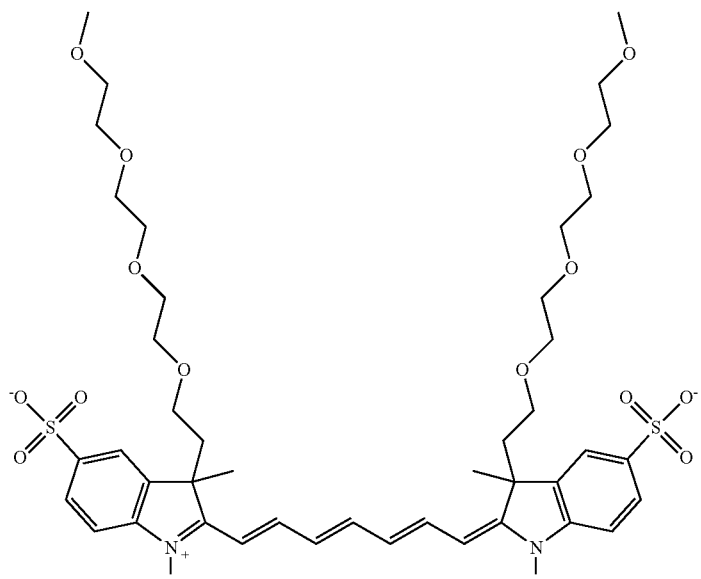

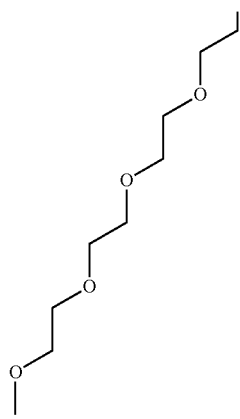
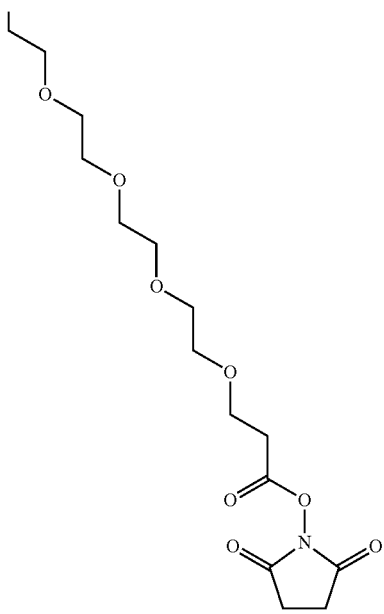
One non-limiting example of an additionally PEG-substituted compound is a 755 Compound 4/4 according to general formula II where both R1 and R2 are a (poly) ethylene glycol (4) group terminating with a methyl group, and R7 and R8 are H, shown below:
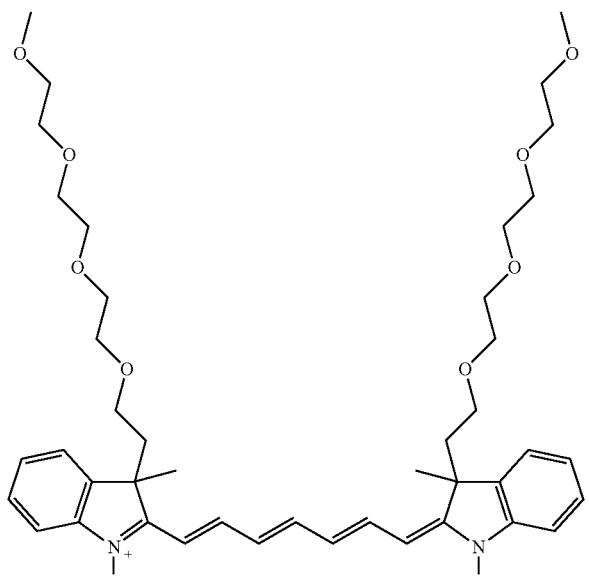

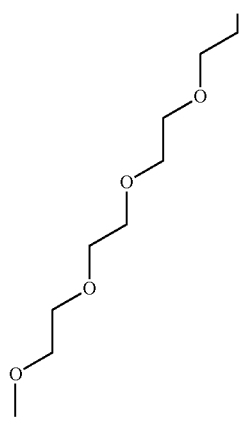

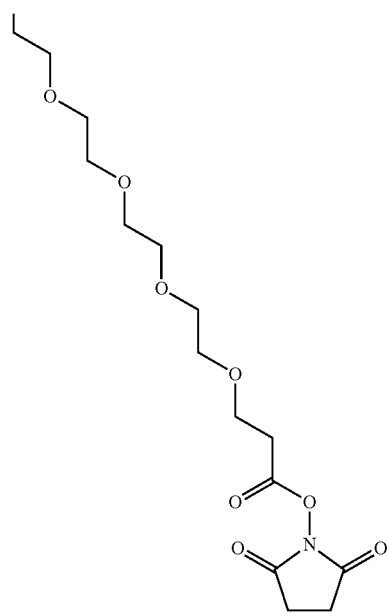

One non-limiting example of an additionally PEG-substituted compound is a 755 Compound 1/3 according to general formula II where both R1 and R2 are a (poly) ethylene glycol (5) group terminating with a methyl group, shown below:

One non-limiting example of an additionally PEG-substituted compound is a 755 Compound 1/3 according to general formula II where both R1 and R2 are a (poly) ethylene glycol (6) group terminating with a methyl group, shown below:

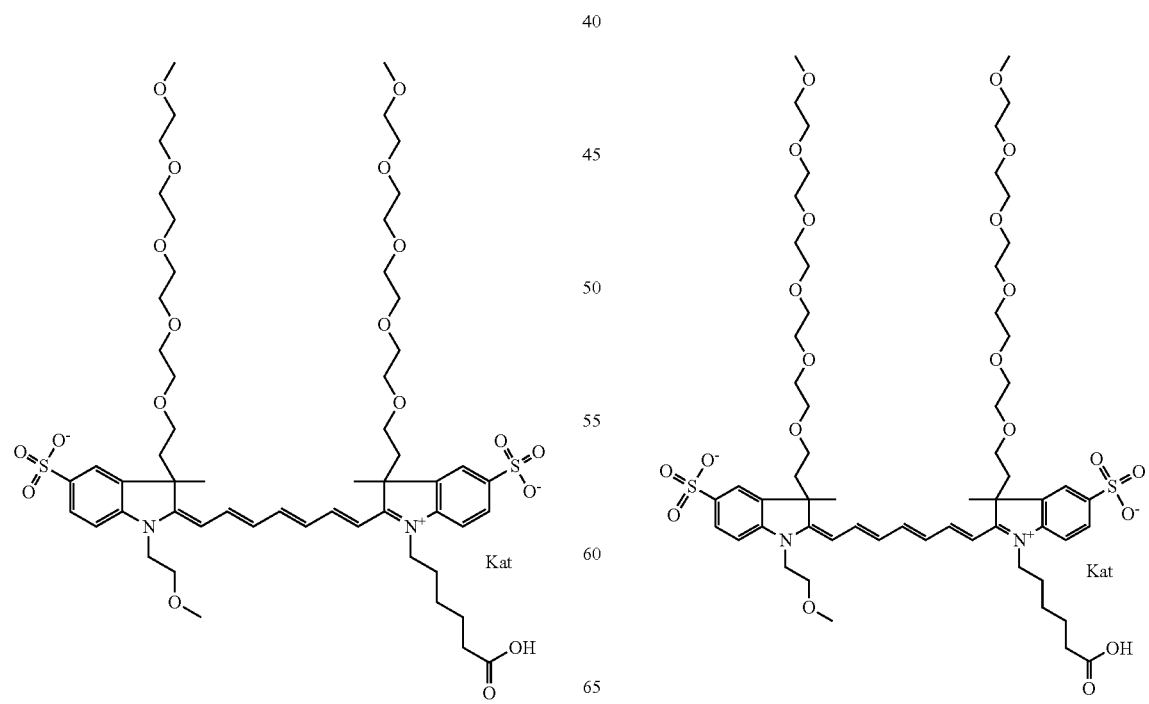

One non-limiting example of an additionally PEG-substituted compound is a 755 Compound 1/3 according to general formula II where both R1 and R2 are a sulfonamide group -L-SO$_2$NH—P—Z where Z is a methyl group, shown below:

general formula II where both R1 and R2 are a carboxamide group -L-CONH—P—Z where Z is a methyl group, shown below:

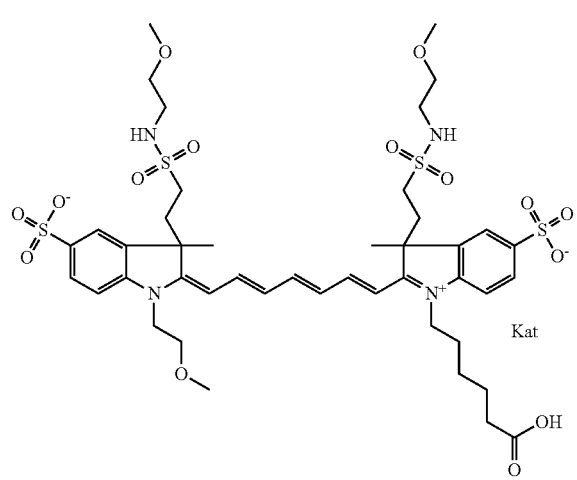

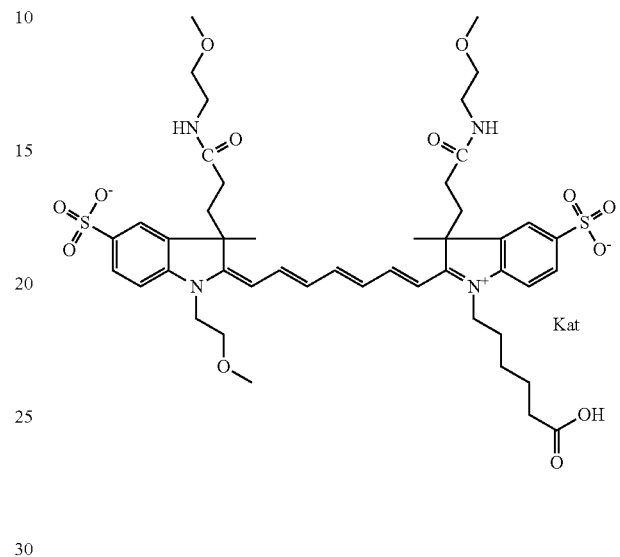

One non-limiting example of an additionally PEG-substituted compound is a 755 Compound 1/3 according to One non-limiting example of an additionally PEG-substituted compound is a 755 Compound 1/2 according to general formula II where R8 is an ethylene glycol group terminating with a methyl group, shown below:

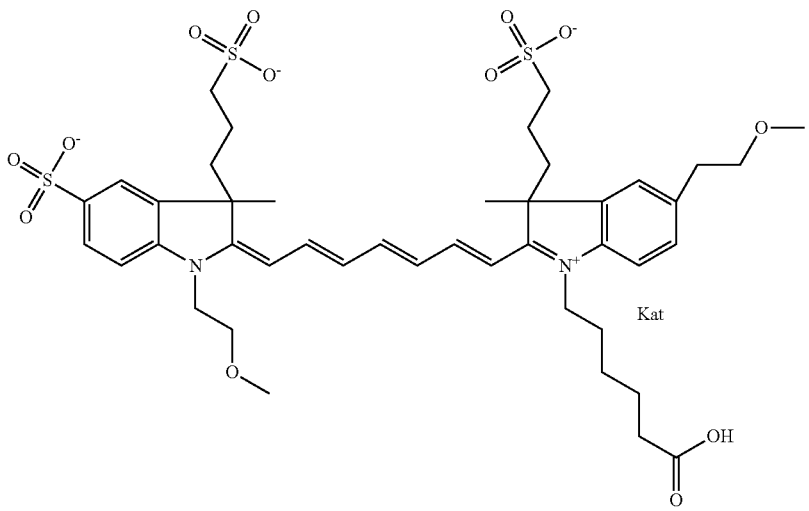

One non-limiting example of an additionally PEG-substituted compound is a 755 Compound 1/2 according to general formula II where R8 is sulfonamide —SO$_2$NH—P—Z where Z is a methyl group, shown below:

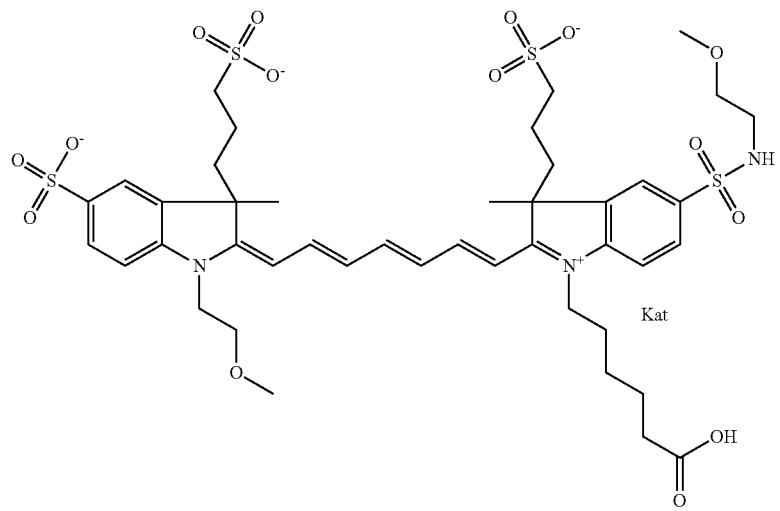

One non-limiting example of an additionally PEG-substituted compound is a 755 Compound 1/2 according to general formula II where R8 is carboxamide —CONH— P—Z where Z is a methyl group, shown below:

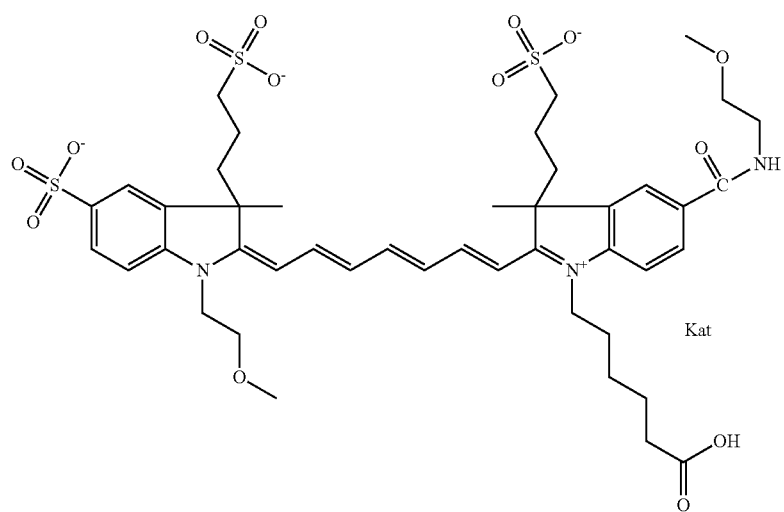

One non-limiting example of an additionally PEG-substituted compound is a 755 Compound 1/2 according to general formula II where R7 is an ethylene glycol group terminating with a methyl group, shown below:

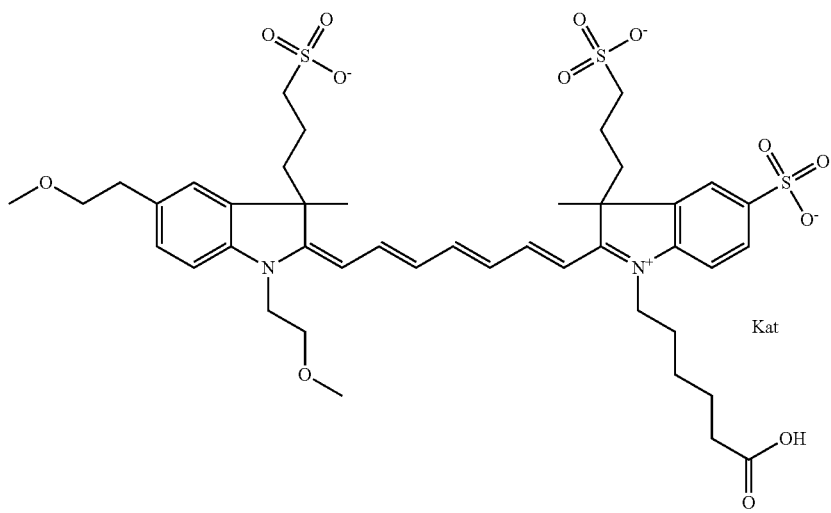

One non-limiting example of an additionally PEG-substituted compound is a 755 Compound 1/2 according to general formula II where R7 is a sulfonamide group —SO$_2$NH—P—Z where Z is a methyl group, shown below:

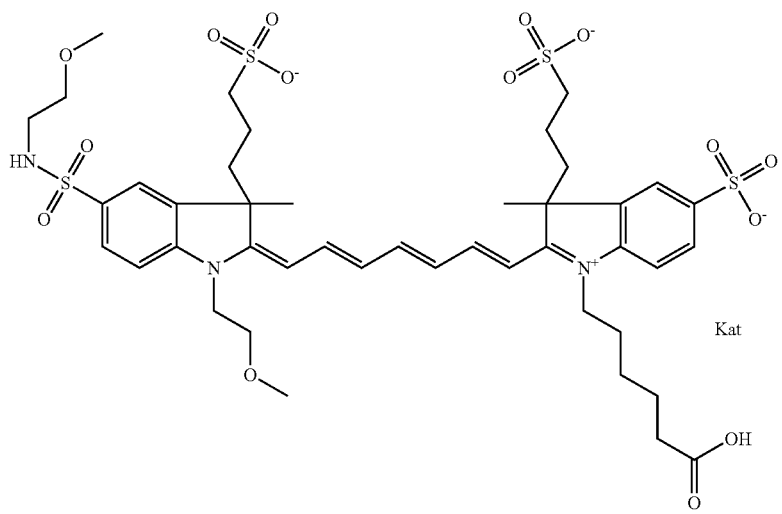

One non-limiting example of an additionally PEG-substituted compound is a 755 Compound 1/2 according to general formula II where R7 is a carboxamide group —CONH—P—Z where Z is a methyl group, shown below:

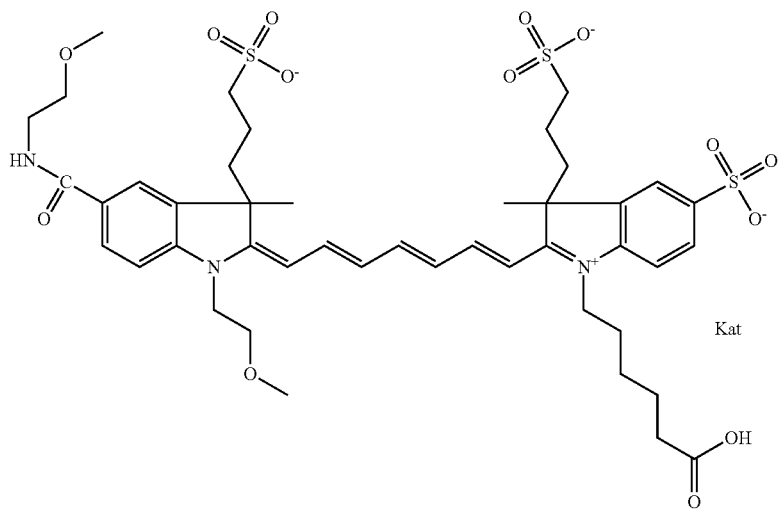

One non-limiting example of an additionally PEG-substituted compound is a 755 Compound 1/3 according to general formula II where both R7 and R8 are an ethylene glycol group terminating with a methyl group, shown below:

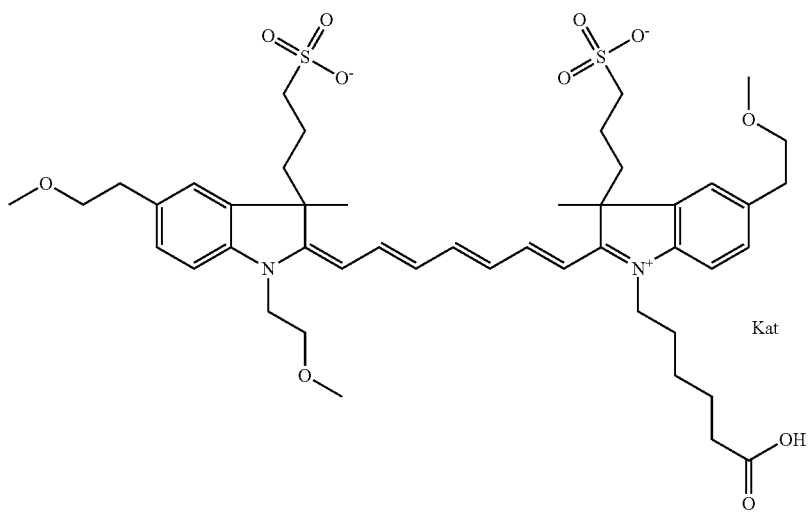

One non-limiting example of an additionally PEG-substituted compound is a 755 Compound 1/3 according to general formula II where both R7 and R8 are a sulfonamide group —SO₂NH—P—Z where Z is a methyl group, shown below:

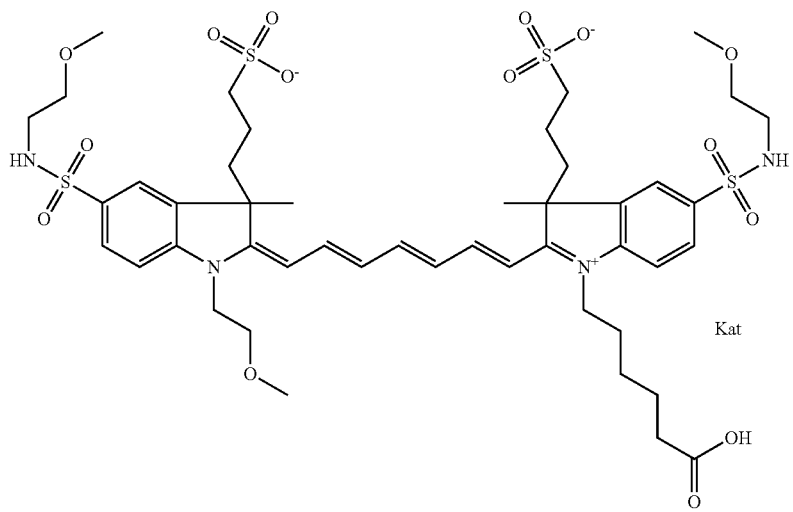

One non-limiting example of an additionally PEG-substituted compound is a 755 Compound 1/3 according to general formula II where both R7 and R8 are a carboxamide group —CONH—P—Z where Z is a methyl group, shown below:

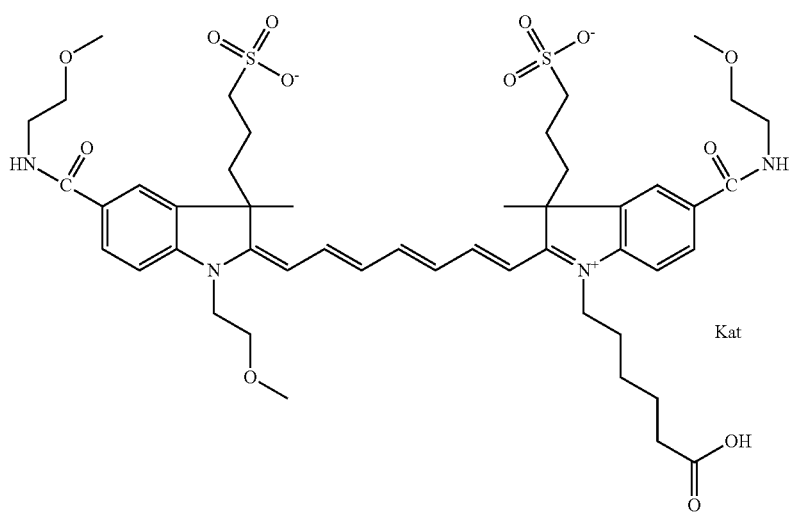

The disclosed compounds are used and are useful as chromophores and/or fluorophores. For example, they can be used for optical labelling and, therefore, for the qualitative and/or quantitative detection of proteins, nucleic acids, oligomers, DNA, RNA, biological cells, lipids, mono-, oligo- and polysaccharides, ligands, receptors, polymers, drugs, polymeric beads, etc.

The inventive compounds, containing the disclosed functionality or functionalities, may be synthesized using methods known in the art, e.g., as described as follows with all references expressly incorporated by reference herein in their entirety. The hydrophilicity or hydrophobicity of the inventive compounds is modified by the number and location of hydrophilic groups, such as sulfo, carboxy, hydroxy, etc., groups. In embodiments, the number and location of hydrophilic groups is symmetrical, such that the number and location of hydrophilic group(s) on one of the indoles of the inventive cyanine compound is also found on the other indole. In various embodiments, at least one hydrophilic group is found on each of the indoles of the inventive cyanine compound. Similarly, solubility, lack of aggregation, reactivity, lack of cross-reactivity, etc., are effected by the number and location of the disclosed functionality or functionalities on the compound.

In one embodiment, short PEG groups are added on opposite sides and opposite ends of indole cyanine compounds to effectively surround the hydrophobic core structure of the molecule. In another embodiment, sulfonate groups are added to the outer phenyl rings of indole cyanine dyes along with the symmetrical placement of short PEG chains on opposite sides and opposite ends.

Adding PEG 1-6, if at the appropriate positions to strategically surround the core dye structure, have significant beneficial effects on the hydrophilicity and performance of these dyes in biological applications. Previous attempts to make dyes more hydrophilic and less "sticky" toward biomolecules included the addition of multiple sulfonates or much longer PEG chains to some locations on dye molecules. However, the addition of too many sulfonates, while having the effect of increasing the relative water solubility of dyes, can create undesirable nonspecific binding character due to negative charge interactions with positively charged biomolecules, particularly proteins. In addition, previous attempts to make dyes more water soluble by adding longer PEG chains to one or two sites on a dye has the detrimental effect of dramatically increasing the molecular weight of the dye, possibly preventing efficient access of dye-labeled antibodies and other dye-labeled targeting molecules to bind with inner cellular targets, while also not fully surrounding and masking the hydrophobic dye core structure. The inventors have discovered that by using short PEG chain modifications at critical sites on a dye structure that the total molecular size of labeled molecules can be limited, while nonspecificity is dramatically reduced by masking the hydrophobic dye core.

In one embodiment, PEG 1-6 group(s) are added on opposite sides and opposite ends of indole cyanine compounds to effectively surround the hydrophobic core structure of the molecule. In another embodiment, sulfonate groups are added to the outer phenyl rings of indole cyanine dyes along with the symmetrical placement of short PEG chains on opposite sides and opposite ends.

The core indocyanine structure without additional functionalities, along with its synthesis, was described by König in U.S. Pat. No. 1,524,791 and BP 434875, and included 3-, 5-, and 7-membered polymethine chains.

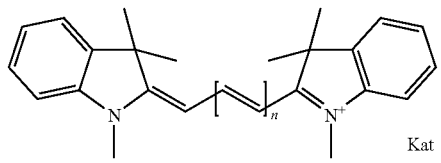

Synthesis of numerous modifications of the core indocyanine structure have been described. Such modifications provided various functionalities, e.g., synthesis of N-isothiocyanato-alkyl- and aromatic-carboxyalkyl-functionalized indocyanines were described in U.S. Pat. Nos. 5,627,027; 6,048,982; 4,981,977; U.S. Publication No. 2006/0199949; Southwick, Anal. Chem. 67 (1995) 1742-48).

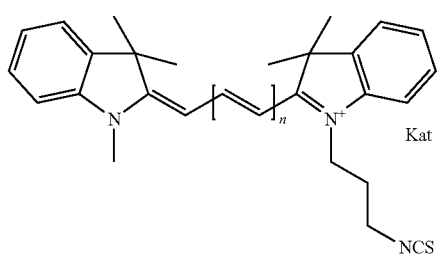

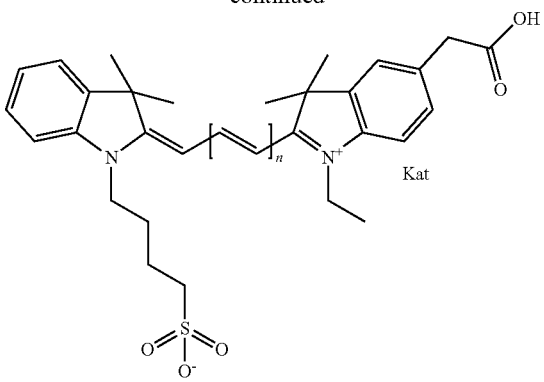

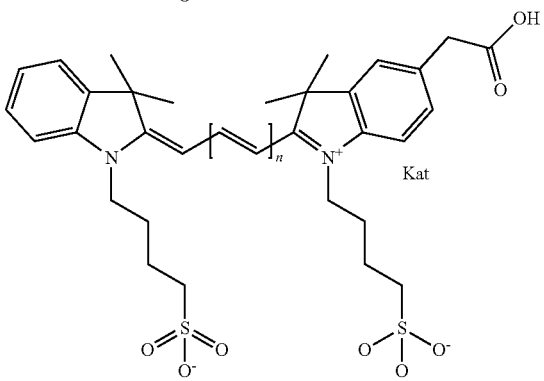

Synthesis of indocyanines with one or two N-carboxyalkyl functionalities were described in U.S. Pat. Nos. 5,268,486; 5,486,616; 5,569,587; 5,569,766; JP 03217837.

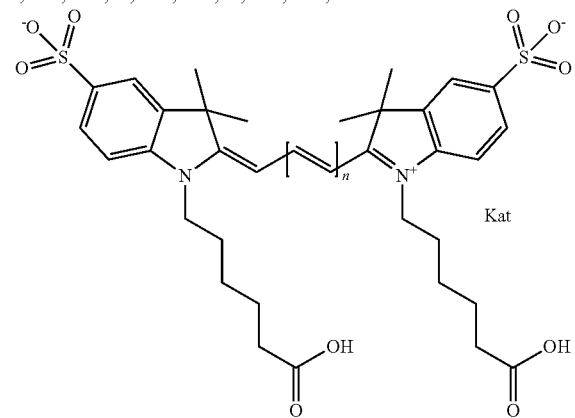

Synthesis of indocyanines containing C-carboxyalkyl groups were described in JP 05-313304; U.S. Publication Nos. 2006/0099638, 2006/0004188; 2002/0077487; 2002/0064794; U.S. Pat. Nos. 6,977,305 and 6,974,873.

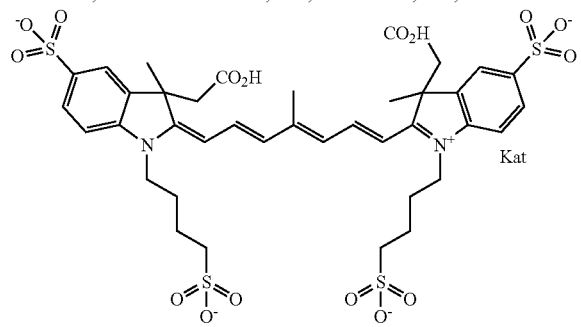

163
-continued
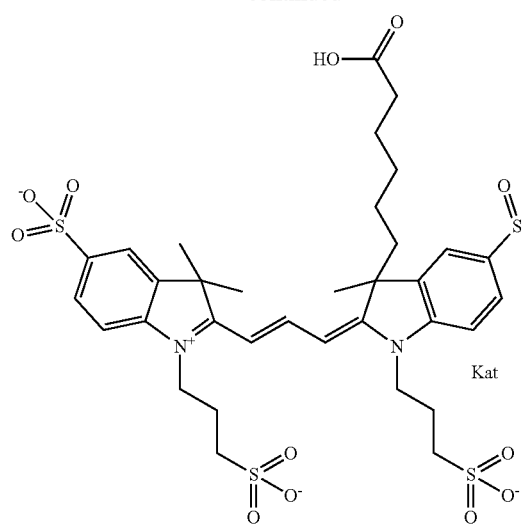
164
-continued
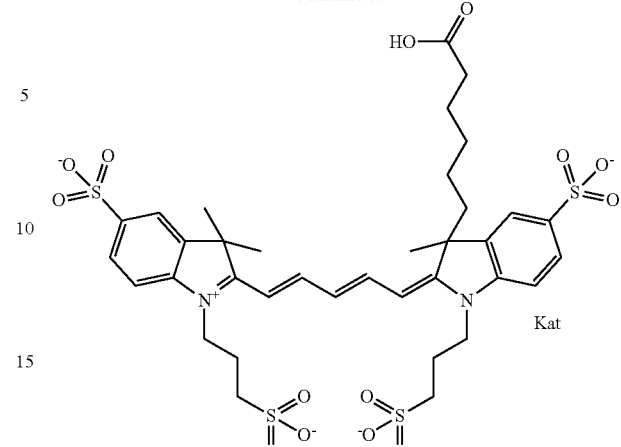
Synthesis of indocyanines with N- and C-sulfoalkyl groups were described in JP 05-313304; WO 2005/044923; U.S. Publication No. 2007/0203343.
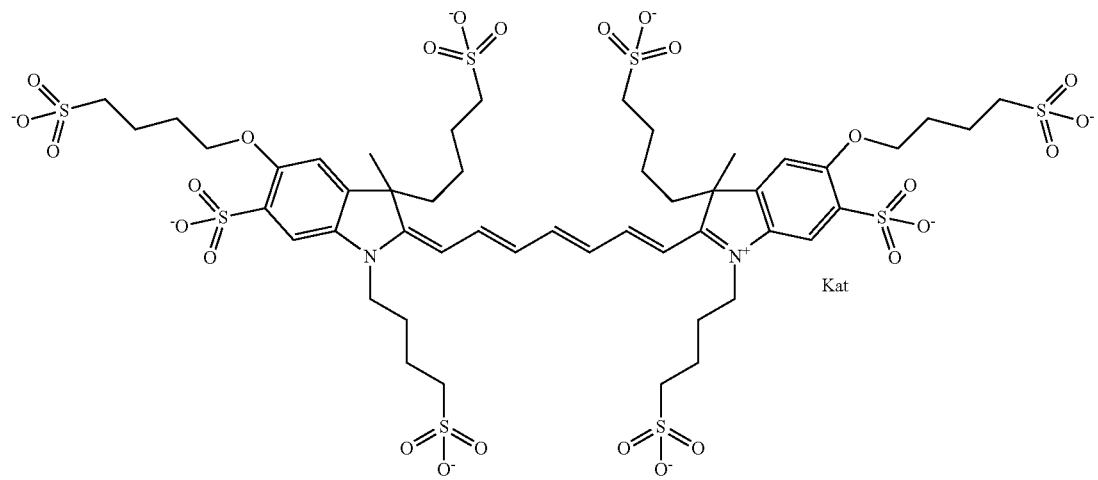
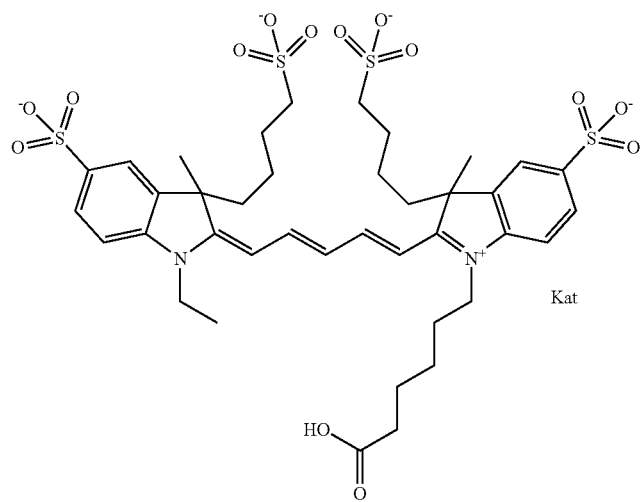

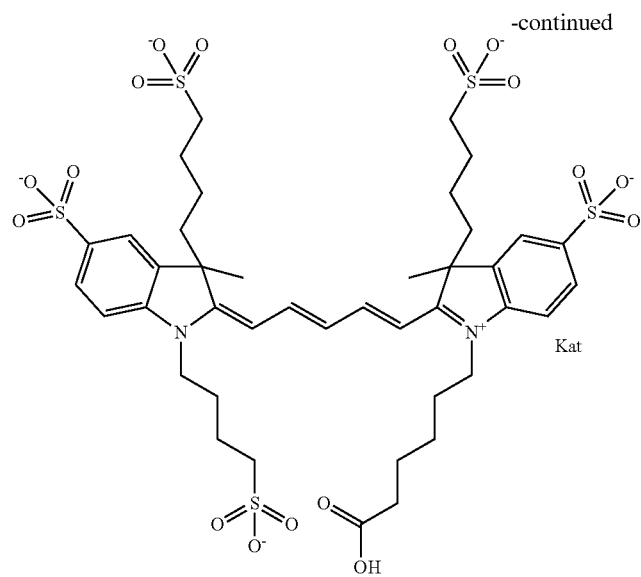
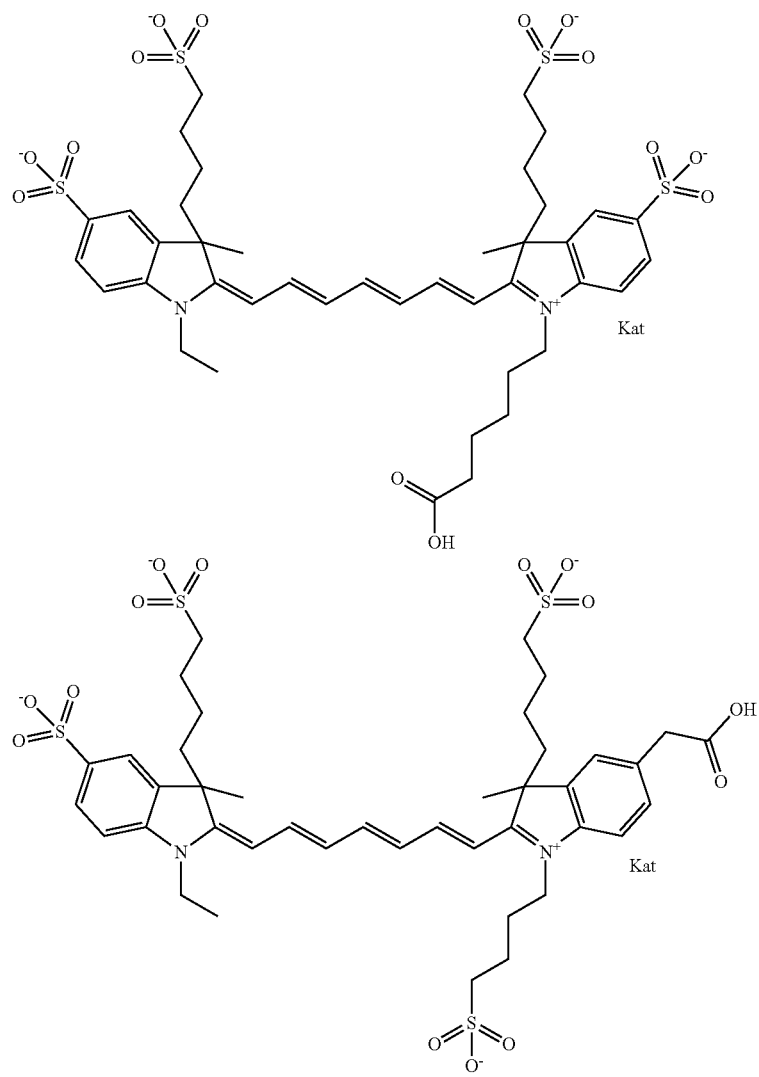

Synthesis of indocyanines with mixed C-carboxyalkyl and C-sulfoalkyl were described in EP 1792949 and U.S. Pat. No. 7,745,640.

Functionalization of the N-carboxyalkyl with an amino-functionalized PEG-alkyl chain, and N- and C-substituted PEG-alkyl chains, were described in U.S. Publication No. 2009/0305410.

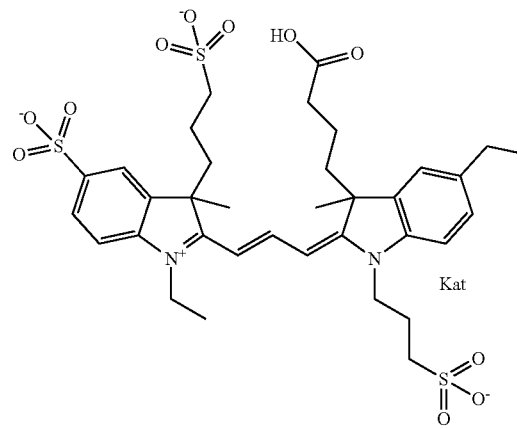

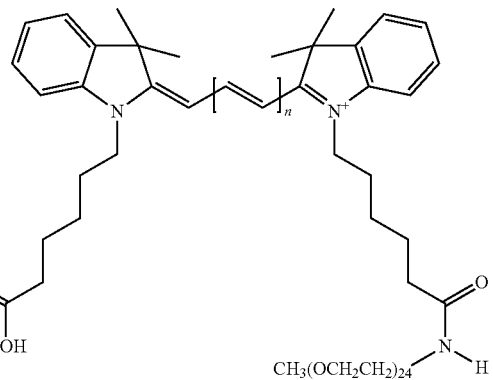

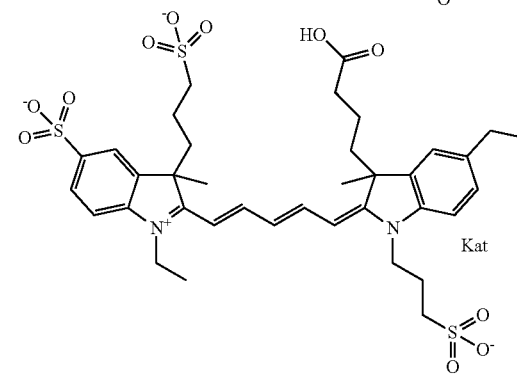

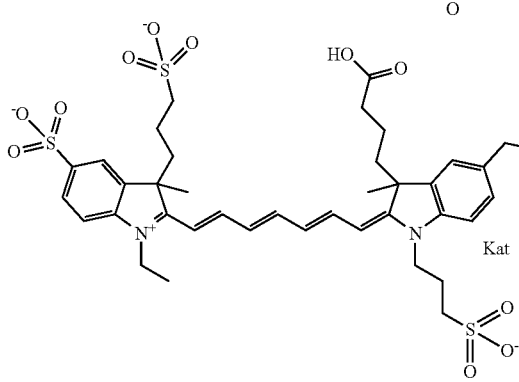

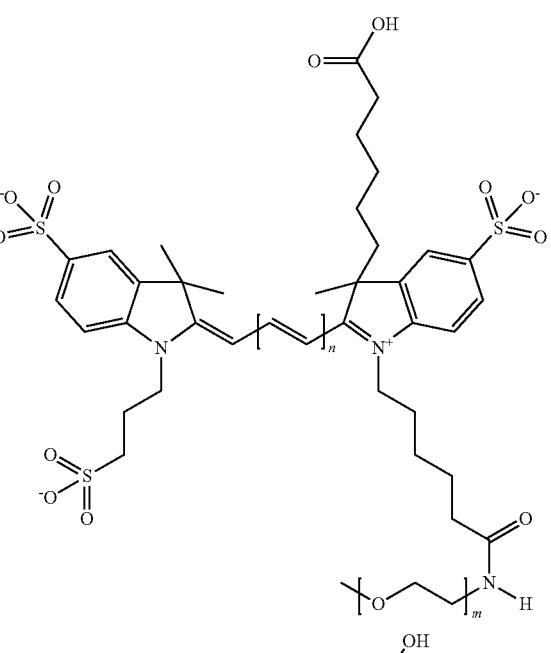

Synthesis of indocyanines having a PEG-containing, N-carboxyalkyl spacer were described in U.S. Pat. No. 6,939,532.

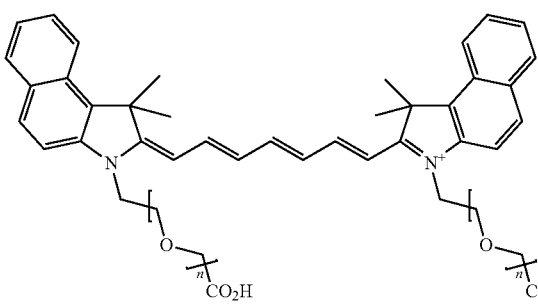

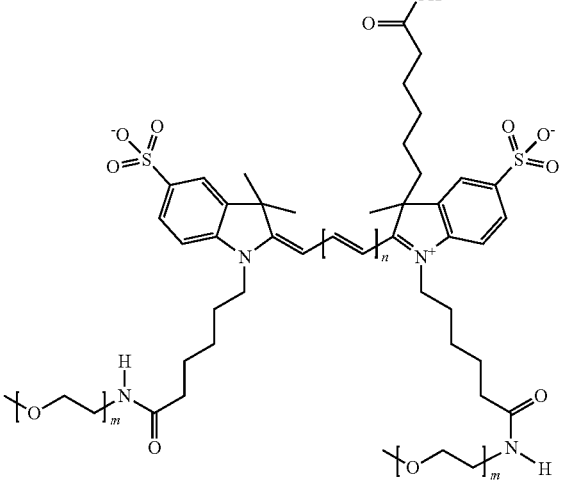

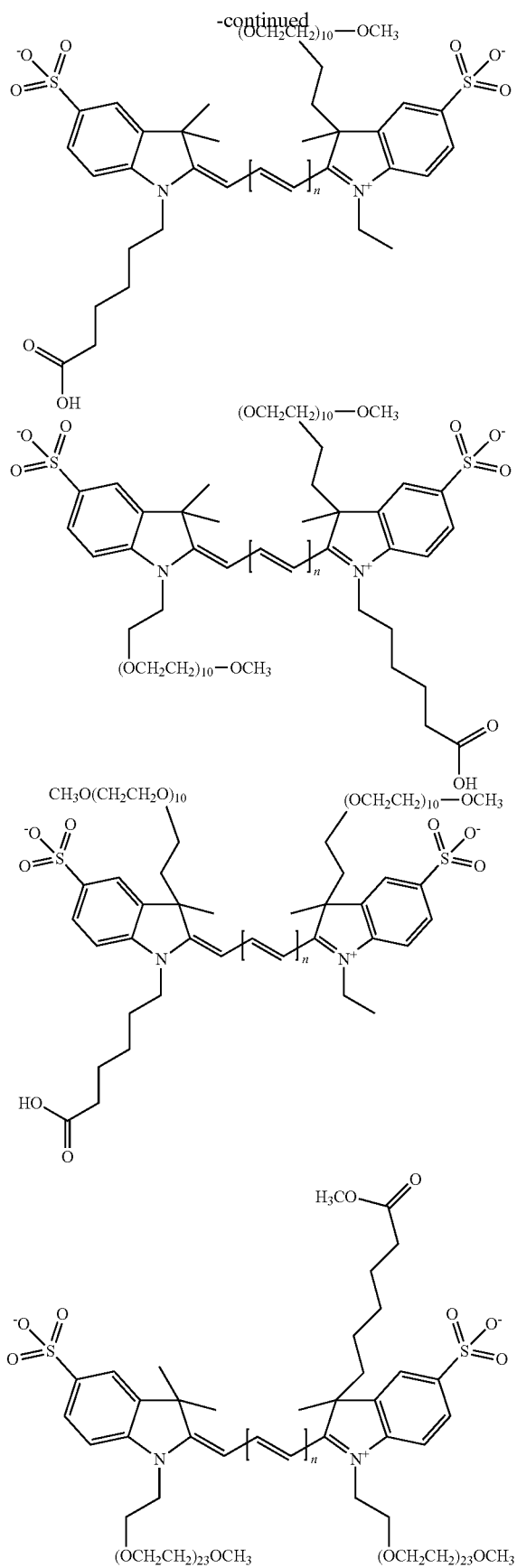

Synthesis of various polymethine bridge substitutions, and other functionalizations of indocyanines, were described in Strekowski, Heterocyclic Polymethine Dyes: Synthesis, Properties and Applications, (2008) Springer-Verlag, Berlin Heidelberg; Gragg, "Synthesis of Near-Infrared Heptamethine Cyanine Dyes" (2010). Chemistry Theses. Paper 28. http://digitalarchive.gsu.edu/chemistry_theses/28; Patonay et al. (2004) Noncovalent Labeling of Biomolecules with Red and Near-Infrared Dyes, Molecules 9 (2004) 40-49; and U.S. Pat. No. 7,172,907.

In one embodiment, the compound is synthesized by a condensation reaction, known to one skilled in the art, of the two differently substituted indole heterocycles separated by a (poly)methine linker or bridge, e.g., C1, C3, or C5. Other synthesis methods are possible. As only one example, one of the indole heterocycles is first reacted with the C1, C3, or C5 linker. The 1:1 condensation product is isolated, and then condensed with the second indole heterocycle to result in the cyanine compound. The sequence of reacting the indole heterocycles is irrelevant. Thus, a plurality of differently functionalized, strongly hydrophilic, diastereomeric compounds that differ in total charge and specificity/reactivity of the active groups used for their immobilization, were prepared.

Conjugates of the compounds were prepared by covalently coupling the compounds to a biomolecule using the functional substituent on the N-position of the indole ring. This functional substituent was activated by routine protein chemistry reaction methods known to one skilled in the art.

The activated compound may be converted to, e.g, and without limitation, aN-hydroxysuccinimide (NHS)-ester, an acid fluoride, a tetrafluorophenyl (TFP)- or sulfotetrafluorophenyl (STP)-ester, an iodoacetyl group, a maleimide, a hydrazide, a sulfonyl chloride, or a phenylazide. Methods for preparing such compounds are known to one skilled in the art. In one embodiment, the activated substituent was then reacted with an amino group on the biomolecule under conditions to conjugate the desired biomolecule.

In one embodiment, a non-activated carboxyl group on the N-position of the indole in the compound was coupled to an amine using a carbodimide.

In one embodiment, a N-hydroxysuccinimidyl ester (X=—NHS) of a compound was formed as follows: 20 μmol dye with X=OH (carboxyalkyl group), 8 mg (40 μmol) dicyclohexylcarbodiimide, and 5 mg (40 μmol) N-hydroxysuccinimide were dissolved in 2 ml DMF and 100l water. Six μl (40 μmol) triethylamine was added. The reaction mixture was stirred at room temperature (about 20° C. to about 22° C.) for 24 hours and then filtered. The solvent was removed and the residue was washed with diethylether. The reaction proceeded quantitatively.

In one embodiment, a maleimide (X=—NH—CH$_2$CH$_2$-maleimide) of a compound is formed as follows: 20 μmol dye with X=—NHS (N-hydroxysuccinimid-ester) was dissolved in 2 ml DMF and 100 μl water and mixed with 7.6 mg (30 μmol) 2-maleimidoethylamine-trifluoracetate and 5 μl (30 μmol) N-ethyldiisopropyl-amine. The reaction mixture is stirred for 3 h at room temperature (about 20° C. to about 22° C.). The solvent was evaporated under reduced pressure. The residue is washed with diethylether and acetone and dried in vacuum. The reaction proceeds quantitatively.

In one embodiment, a iodoacetamide (X=—NH—CH$_2$CH$_2$—NH—CO—CH$_2$—I) of a compound is formed as follows: 20 μmol dye with X=—NHS (N-hydroxysuccinimid-ester) was dissolved in 2 ml DMF and 100 μl water, followed by addition of 40 mg (300 μmol) ethylendiamindihydrochloride and 26 µl (150 µmol) N-ethyldiisopropylamine. The reaction mixture is stirred for 3 h at room temperature (about 20° C. to about 22° C.). The solvent is then evaporated under reduced pressure, the residue was dissolved in methanol, and the ethylendiamindihydrochlorid was removed by filtration. The methanol is evaporated under reduced pressure. The residue is dissolved in 2 ml dry DMF, followed by addition of 7 mg (25 µmol) N-succinimidyl iodoacetate and 4 µl (25 µmol) N-ethyldiisopropylamine. The reaction mixture is stirred for 3 h at room temperature. The solvent was evaporated under reduced pressure and the residue was purified by reverse phase HPLC.

In one embodiment, a hydroxyl group, such as a terminal hydroxyl group, can be subsequently activated to a reactive derivative able to link with, for example, proteins and other molecules. Examples of activating groups include tosyl chloride (TsCl), tresyl chloride (TrCl), disuccinimidyl carbonate (DSC), divinyl sulfone, bis-epoxy compounds, carbonyl diimidazole (CDI), 2-fluoro-1-methylpyridinium (FMP), and trichloro-s-triazine (TsT). In one embodiment, the hydroxyl group is activated to a succinimidyl carbonate, which is reactive with amines.

Coupling between the compound and the biomolecule may be performed as follows. The compound was reacted with the biomolecule in an organic or aqueous solution at pH between pH 5-pH 12 inclusive. The compound need not be dissolved in an organic solvent, such as dimethyl formamide (DMF) or dimethyl sulfoxide (DMSO) prior to adding the biomolecule. In one embodiment, coupling reaction may be performed in a 100% aqueous solution. In one embodiment, the coupling reaction occurs at room temperature (about 20° C. to about 22° C.).

To form a composition (dye), at least one biocompatible excipient was added to the compound(s), as known to one of ordinary skill in the art. Excipients include, but are not limited to, buffers, solubility enhancing agents, stabilizing agents, etc.

In one embodiment, a kit for performing an assay method comprises a disclosed compound, and instructions for performing the method using the compound.

The disclosed activated compounds (i.e., the compound modified with a reactive group) are useful to label macromolecules (e.g., antibodies, streptavidin, etc) using methods known to one skilled in the art, e.g., Hermanson, Bioconjugate Techniques, 2nd Ed., London, Elsevier Inc. 2008. The reaction was carried out for 1-2 h at room temperature (about 20° C. to about 22° C.), and then desalted by dialyzing against several changes of phosphate buffered saline (pH 7.2) or purified by gel filtration to remove the unreacted fluorescent dye. The resulting compound-biomolecule conjugate was used to detect, e.g., specific proteins in immunoassays, sugars in glycoproteins with lectins, protein-protein interactions, oligonucleotides in nucleic acid, hybridization, and in electrophoretic mobility shift assays (EMSA).

The resulting compound-biomolecule conjugates exhibited fluorescent properties. In this embodiment, they were used in optical methods including fluorescence optical qualitative and quantitative determination methods. Examples of such methods include, but are not limited to, microscopy, immunoassays, hybridization methods, chromatographic and electrophoretic methods, fluorescence resonance energy transfer (FRET) systems, bioluminescence reasonance energy transfer (BRET), high throughput screenings, analysis of receptor-ligand interactions on a microarray, etc.

Compounds in any embodiment were used as dyes for optical labelling of organic or inorganic biomolecules, referred to as recognition units. Recognition units are molecules having specificity and/or affinity for a specific group of molecules. Examples include, but are not limited to, antibodies that have affinity for antigens, enzymes that bind and/or react with a specific bond or bonds within a sequence of amino acids in a peptide or react with a substrate, cofactors such as metals that enhance or inhibit specific interactions, lectins that bind specific sugars or sugar sequences (e.g., oligosaccharides, polysaccharides, dextrans, etc.), biotin binding proteins such as avidin and streptavidin that bind biotin and biotinylated molecules, antibody binding proteins such as Protein A, Protein G, Protein A/G and Protein L, sequences of amino acids or metals that have affinity for each other (e.g., histidine sequences that bind nickel or copper, phosphate containing proteins that bind gallium, aluminium, etc.), specific sequences of nucleic acids such as DNA and/or RNA oligonucleotides that have affinity for proteins, specific sequences of amino acids that have affinity for DNA and/or RNA, haptens, carotenoids, hormones (e.g., neurohormones), neurotransmitters, growth factors, toxins, biological cells, lipids, receptor binding drugs or organic or inorganic polymeric carrier materials, fluorescent proteins such as phycobilliproteins (e.g., phycoethrin, allophycocyanin), etc. Ionic interactions between recognition units and the disclosed compounds results in labeling of the recognition units. The recognition unit and compound can be covalently bound. The result is a conjugate for qualitative or quantitative determination of various biomaterials or other organic or inorganic materials using optical methods.

The inventive compounds and/or conjugates are used in optical, including fluorescence optical, qualitative and/or quantitative determination methods to diagnose properties of cells (molecular imaging), in biosensors (point of care measurements), for investigation of the genome, and in miniaturizing technologies. Microscopy, cytometry, cell sorting, fluorescence correlation spectroscopy (FCS), ultra high throughput screening (uHTS), multicolor fluorescence in situ hybridisation (mc-FISH), FRET-systems, BRET-systems, and microarrays (DNA- and protein-chips) are exemplary application fields. As known to one skilled in the art, a microarray is a grid-like arrangement where more than two different molecules are immobilized in a known predefined region on at least one surface, and is useful to evaluate receptor ligand interactions. As known to one skilled in the art, a receptor is a naturally occurring or synthetic molecule that exhibits an affinity to a given ligand. Receptors can be used in a pure form or bound to another specie. Receptors can be coupled covalently or noncovalently to a binding partner either directly or indirectly (e.g., through a coupling mediator). Receptor examples include, but are not limited to, agonists and antagonists for cell membrane receptors, toxins and other poisons, viral epitopes, hormones (e.g., opiates, steroids), hormone receptors, peptides, enzymes, enzyme substrates, drugs acting as cofactors, lectins, sugars, oligonucleotides, nucleic acids, oligosaccharides, cells, cell fragments, tissue fragments, proteins, antibodies, etc. As known to one skilled in the art, a ligand is a molecule that is recognized by a certain receptor. Ligand examples include, but are not limited to, agonists and antagonists for cell membrane receptors, toxins and other poisons, viral epitopes, hormones (e.g., opiates, steroids), hormone receptors, peptides, enzymes, enzyme substrates, drugs acting as cofactors, lectins, sugars, oligonucleotides, nucleic acids, oligosaccharides, proteins, antibodies, etc.

The following non-limiting examples further describe the compounds, methods, compositions, uses, and embodiments.

Example 1 Synthesis of 4-methyl-5-oxohexane sulfonic acid Used to Synthesize Example 2 compound 2,3-dimethyl-3-(3-sulfopropyl)-3H-indole-5-sulfonic acid di-potassium salt and

Example 8 compound 1,2-dimethyl-1-(3-sulfopropyl)-H-benzo[e]indole-6,8-disulfonic acid tripotassium salt

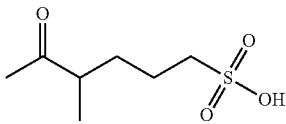

Sodium hydride (2.1 g, 80 wt %=69 mmol) was slurried in 10 ml of dry THF. The suspension was cooled to 0° C. and a solution of ethyl-2-methylacetoacetate (10 g, 69 mmol) in 10 ml of dry THF was added dropwise. The solution was stirred at room temperature for 1 h. A solution of 1,3-propanesultone (8.42 g, 69 mmol) in 10 ml of dry THF was added dropwise. Once the addition was complete, the solution was stirred for 2 h at 40° C. The solution was evaporated to dryness. The residue was dissolved in 100 ml water. The aqueous solution was extracted twice with ethylacetate, then 100 ml concentrated HCl was added and the solution was refluxed for 2 h. The solvent was evaporated in vacuum. The residue was purified by column chromatography (silica, methanol/dichloromethane) to give 4-methyl-5-oxohexane sulfonic acid. Yield 10 g; MS (ESI–): 193.2 [M]$^-$

Example 2 Synthesis of 2,3-dimethyl-3-(3-sulfopropyl)-3H-indole-5-sulfonic acid di-potassium salt Used to Synthesize Example 3 compound 1-(2-methoxy-ethyl)-2,3-dimethyl-5-sulfo-3-(3-sulfo-propyl)-3H-indolium and

Example 4 compound 1-[2-(2-methoxy-ethoxy)-ethyl]-2,3-dimethyl-5-sulfo-3-(3-sulfo-propyl)-3H-indolium and

Example 5 compound 1-{2-[2-(2-methoxy-ethoxy)-ethoxy]-ethyl}-2,3-dimethyl-5-sulfo-3-(3-sulfo-propyl)-3H-indolium and

Example 6 compound 1-(5-carboxypentyl)-2,3-dimethyl-5-sulfo-3-(3-sulfopropyl)-3H-indolium

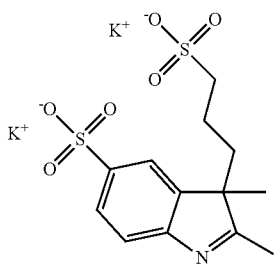

Ten g (51 mmol) 4-hydrazino-benzene sulfonic acid and 9.85 g (51 mmol) 4-methyl-5-oxohexane sulfonic acid were dissolved in 50 ml acetic acid. The solution was heated at 140° C. for 4 h. The solvent was evaporated in vacuum. The oily residue was dissolved in 20 ml methanol, then 50 ml of a saturated solution of KOH in 2-propanol was added to yield a yellow precipitate. The solid was filtered off and dried in vacuum. Yield 11 g, MS (ESI–): 172.5 [M]$^{2-}$

Example 3 Synthesis of 1-(2-methoxy-ethyl)-2,3-dimethyl-5-sulfo-3-(3-sulfo-propyl)-3H-indolium Used to Synthesize 550, 650, 755 Compound 1

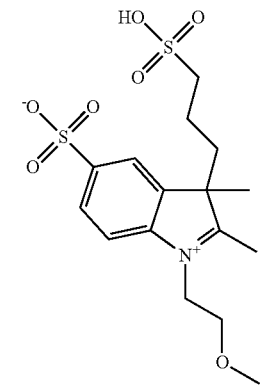

A mixture of 5 g (12.4 mmol) 2,3-dimethyl-3-(3-sulfo-propyl)-3H-indole-5-sulfonic acid dipotassium salt and 5.89 g (25.6 mmol) 2-methoxyethyl-p-toluene sulfonate was heated under argon for 24 h. The residue was purified by column chromatography (reversed phase silica, methanol/water, TFA).

Yield 2.3 g, MS (ESI–): 404.1 [M-H]$^-$

Example 4 Synthesis of 1-[2-(2-methoxy-ethoxy)-ethyl]-2,3-dimethyl-5-sulfo-3-(3-sulfo-propyl)-3H-indolium Used to Synthesize 550, 650, 755 Compound 2

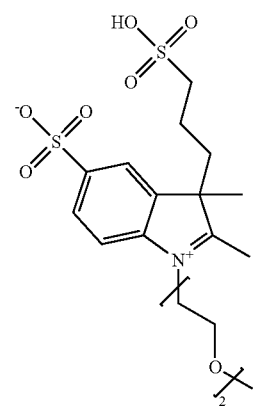

A mixture of 5 g (12.4 mmol) 2,3-dimethyl-3-(3-sulfo-propyl)-3H-indole-5-sulfonic acid dipotassium salt and 7.1 g (25.6 mmol) [2-(2-methoxyethoxy)ethoxy]-p-toluene sulfonate was heated under argon for 24 h. The residue was purified by column chromatography (reversed phase silica, methanol/water, TFA). Yield 2.0 g. MS (ESI–): 448.2 [M-H]$^-$ Example 5 Synthesis of 1-{2-[2-(2-methoxy-ethoxy)-ethoxy]-ethyl}-2,3-dimethyl-5-sulfo-3-(3-sulfo-propyl)-3H-indolium Used to Synthesize 550, 650, 755 Compound 3

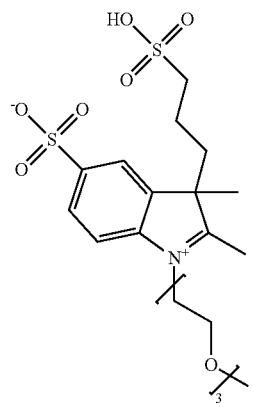

A mixture of 5 g (12.8 mmol) 2,3-dimethyl-3-(3-sulfo-propyl)-3H-indole-5-sulfonic acid dipotassium salt and 8.14 g (25.6 mmol) [2-[2-(2-methoxyethoxy)ethoxy]ethoxy]p-toluene sulfonate was heated under argon for 24 h. The residue was purified by column chromatography (reversed phase silica, methanol/water, TFA). Yield 1.9 g, MS (ESI−): 492.1 [M-H]⁻

Example 6 Synthesis of 1-(5-carboxypentyl)-2,3-dimethyl-5-sulfo-3-(3-sulfopropyl)-3H-indolium Used to Synthesize Example 7 compound 1-(5-carboxypentyl)-3-methyl-2-((E)-2-phenylamino-vinyl)-5-sulfo-3-(3-sulfo-propyl)-3H-indolium and Example 8 compound 1-(5-carboxypentyl)-3-methyl-2-((1E,3E)-4-phenylamino-buta-1,3-dienyl)-5-sulfo-3-(3-sulfopropyl)-3H-indolium and Example 9 compound 1-(5-carboxypentyl)-3-methyl-2-((1E,3E,5E)-6-phenylamino-hexa-1,3,5-trienyl)-5-sulfo-3-(3-sulfopropyl)-3H-indolium

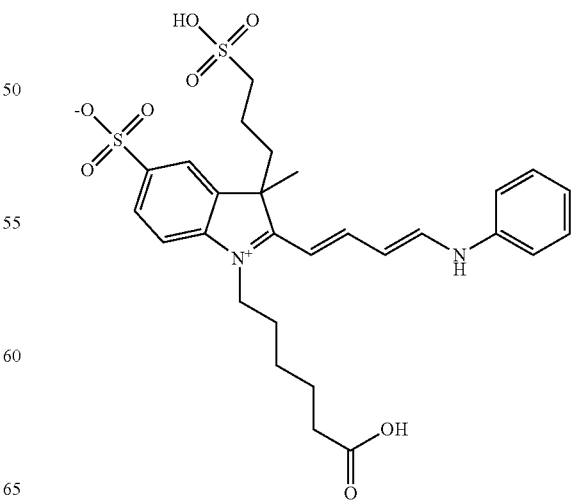

Both 5 g (15.7 mmol) 6-hydrazino-naphthalene-1,3-disulfonic acid and 4.93 g (25 mmol) 4-methyl-5-oxohexane sulfonic acid were dissolved in 50 ml acetic acid. The solution was heated at 140° C. for 4 h. The solvent was evaporated in a vacuum. The oily residue was dissolved in 20 ml methanol, then 50 ml of a saturated solution of KOH in 2-propanol was added to yield a yellow precipitate. The solid was filtered off and dried in vacuum. Yield 4.1 g, MS (ESI−): 158.2 [M]³⁻

Example 7 Synthesis of 1-(5-carboxypentyl)-3-methyl-2-((E)-2-phenylamino-vinyl)-5-sulfo-3-(3-sulfo-propyl)-3H-indolium Used to Synthesize 550 Compounds

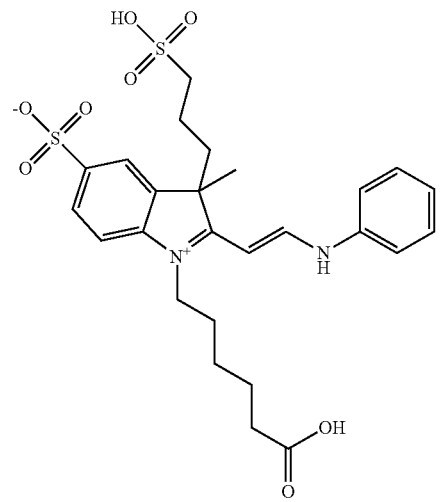

A combination of 0.92 g (2 mmol) 1-(5-carboxypentyl)-2,3-dimethyl-5-sulfo-3-(3-sulfopropyl)-3H-indolium and 0.43 g (2.2 mmol) N,N'-diphenylformamidine was dissolved in 20 ml methanol and stirred for 4 h under reflux. The solvent was removed under vacuum. The residue was washed carefully with ethyl acetate. A dark yellow solid was obtained which was processed without further purification. MS (ESI−): 563.1 [M-H]⁻

Example 8 Synthesis of 1-(5-carboxypentyl)-3-methyl-2-((1E,3E)-4-phenylamino-buta-1,3-dienyl)-5-sulfo-3-(3-sulfopropyl)-3H-indolium Used to Synthesize 650 Compounds A combination of 0.92 g (2 mmol) 1-(5-carboxypentyl)-2,3-dimethyl-5-sulfo-3-(3-sulfopropyl)-3H-indolium and 0.57 g (2.2 mmol) malonaldehyde-bisphenylimine-hydrochloride were dissolved in 10 ml acetic acid and 10 ml acetic anhydride and stirred for 4 h at 120° C. The solvent was removed under vacuum. The residue was washed carefully with ethyl acetate. A dark brown solid was obtained which was processed without further purification. MS (ESI−): 589.2 [M-H]−

Example 9 Synthesis of 1-(5-carboxypentyl)-3-methyl-2-((1E,3E,5E)-6-phenylamino-hexa-1,3,5-trienyl)-5-sulfo-3-(3-sulfopropyl)-3H-indolium Used to Synthesize 755 Compounds

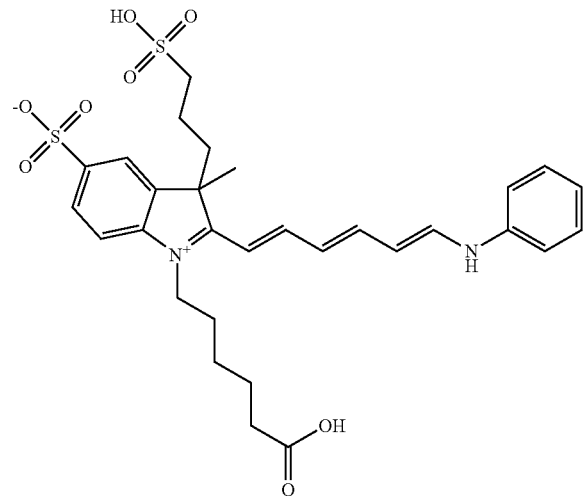

A combination of 0.92 g (2 mmol) 1-(5-carboxypentyl)-2,3-dimethyl-5-sulfo-3-(3-sulfopropyl)-3H-indolium and 0.63 g (2.2 mmol) glutacondianil-hydrochloride were dissolved in 10 ml acetic acid and 10 ml acetic anhydride and stirred for 4 h at 120° C. The solvent was removed under vacuum. The residue was washed carefully with ethyl acetate. A dark solid was obtained which was processed without further purification. MS (ESI−): 615.2 [M-H]−

Example 10 Synthesis of 550 Compound 1

2-{(E)-3-[1-(5-carboxypentyl)-3-methyl-5-sulfo-3-(3-sulfopropyl)-1,3-dihydro-indol-(2E)-ylidene]-propenyl}-1-(2-methoxy-ethyl)-3-methyl-5-sulfo-3-(3-sulfo-propyl)-3H-indolium tri sodium salt

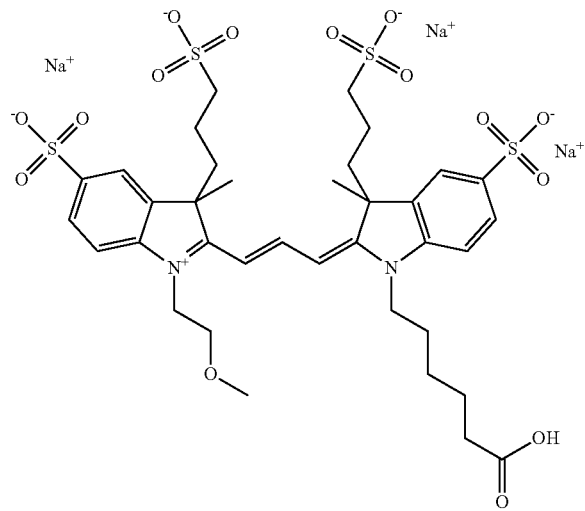

Five hundred sixty-four mg (1 mmol) 1-(5-carboxypentyl)-3-methyl-2-((E)-2-phenylamino-vinyl)-5-sulfo-3-(3-sulfopropyl)-3H-indolium and 404 mg (1 mmol) 1-(2-methoxy-ethyl)-2,3-dimethyl-5-sulfo-3-(3-sulfopropyl)-3H-indolium were dissolved in 20 ml of acetic acid/acetic anhydride (1/1), followed by 200 mg sodium acetate. The solution was stirred under reflux for 15 min. After cooling to room temperature, 20 ml diethylether was added. The resulting precipitate (mixture of the diastereomers 550 Compound 1 (isomer 1) and 550 Compound 1 (isomer 2)) was extracted by suction, washed with ether, and dried.

The residue was purified by column chromatography (RP-18, acetonitrile/water and concentrated HCl) to separate the diastereomers from each other. The diastereomer that first eluted from the column was termed diastereomer 1 (550 Compound 1 (isomer 1)). The diastereomer that eluted second from the column was termed diastereomer 2 (550 Compound 1 (isomer 2)). The diastereomers were separated, followed by neutralization and evaporation. Purification of the single diastereomeric compound was completed on a RP-18 column, acetonitrile/water. The corresponding fractions were pooled and the solvent was removed by distillation. The two products (diastereomers 550 Compound 1 (isomer 1) and 550 Compound 1 (isomer 2)) were dried in high vacuum.

550 Compound 1 (Isomer 1):
  yield: 12%
  UV-vis (PBS): λmax=557 nm, λem=572 nm
  MS (ESI−) [M/z]: 291.2 [M]$^{3-}$; 448.3 [M+Na]$^{2-}$
550 Compound 1 (Isomer 2):
  yield: 23%
  UV-vis (PBS): λmax=557 nm, λem=572 nm
  MS (ESI−) [M/z]: 291.1 [M]$^{3-}$; 448.2 [M+Na]$^{2-}$ Example 11 Synthesis of 550 Compound 2

2-{(E)-3-[1-(5-carboxypentyl)-3-methyl-5-sulfo-3-(3-sulfopropyl)-1,3-dihydro-indol-(2E)-ylidene]-propenyl}-1-[2-(2-methoxy-ethoxy)-ethyl]-3-methyl-5-sulfo-3-(3-sulfo-propyl)-3H-indolium tri sodium salt

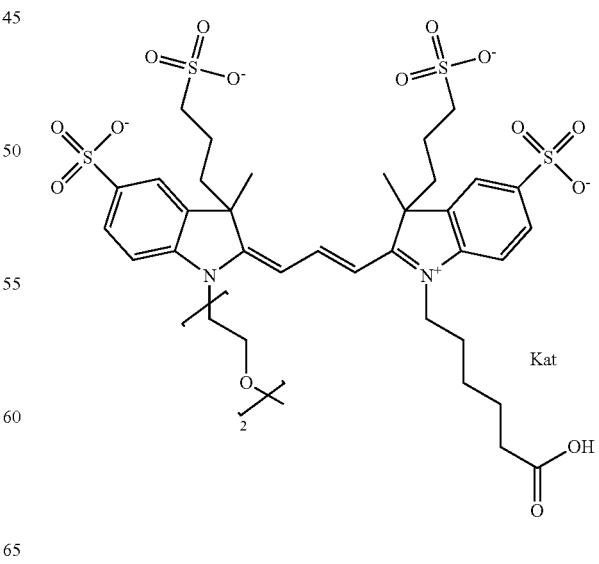

Both 1 mmol 1-(5-carboxypentyl)-3-methyl-2-((E)-2-phenylamino-vinyl)-5-sulfo-3-(3-sulfopropyl)-3H-indolium and 1 mmol 1-[2-(2-methoxy-ethoxy)-ethyl]-2,3-dimethyl-5-sulfo-3-(3-sulfo-propyl)-3H-indolium were dissolved in 20 ml acetic acid/acetic anhydride (1/1) followed by the addition of 200 mg sodium acetate. The solution was stirred under reflux for 15 min. After cooling to room temperature, 20 ml diethylether was added. The resulting precipitate (mixture of the diastereomers 550-1 compound 2 and 550-2 compound 2) was extracted by suction, washed with ether and dried.

The residue was purified by column chromatography (RP-18, acetonitrile/water and concentrated HCl), thereby separating the diastereomers from each other, as described in Example 10.

Example 12 Synthesis of 550 Compound 3

2-{(E)-3-[1-(5-carboxypentyl)-3-methyl-5-sulfo-3-(3-sulfopropyl)-1,3-dihydro-indol-(2E)-ylidene]-propenyl}-1-{2-[2-(2-methoxy-ethoxy)-ethoxy]-ethyl}-3-methyl-5-sulfo-3-(3-sulfo-propyl)-3H-indolium tri sodium salt

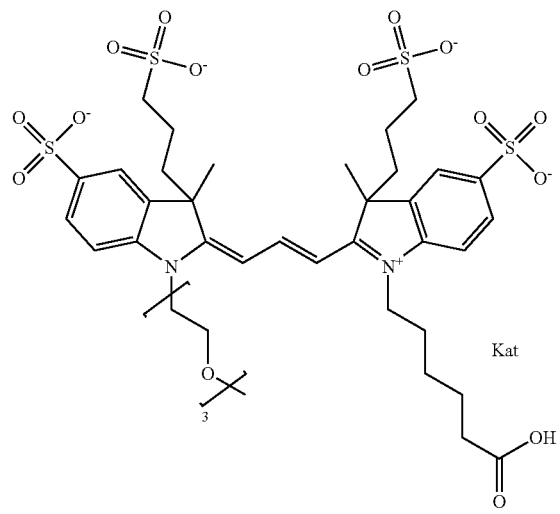

One mmol 1-(5-carboxypentyl)-3-methyl-2-((E)-2-phenylamino-vinyl)-5-sulfo-3-(3-sulfopropyl)-3H-indolium and 1 mmol 1-{2-[2-(2-methoxy-ethoxy)-ethoxy]-ethyl}-2,3-dimethyl-5-sulfo-3-(3-sulfo-propyl)-3H-indolium were dissolved in 20 ml acetic acid/acetic anhydride (1/1) followed by the addition of 200 mg sodium acetate. The solution was stirred under reflux for 15 min. After cooling to room temperature, 20 ml diethylether was added. The resulting precipitate (mixture of the diastereomers 550-1 compound 2 and 550-2 compound 2) was extracted by suction, washed with ether and dried.

The residue was purified by column chromatography (RP-18, acetonitrile/water and concentrated HCl), thereby separating the diastereomers from each other, as described in Example 10.

Example 13 650 Compound 1

Synthesis of 2-{(1E,3E)-5-[1-(5-carboxypentyl)-3-methyl-5-sulfo-3-(3-sulfopropyl)-1,3-dihydro-indol-(2E)-ylidene]-penta-1,3-dienyl}-1-(2-methoxy-ethyl)-3-methyl-5-sulfo-3-(3-sulfopropyl)-3H-indolium tri sodium salt

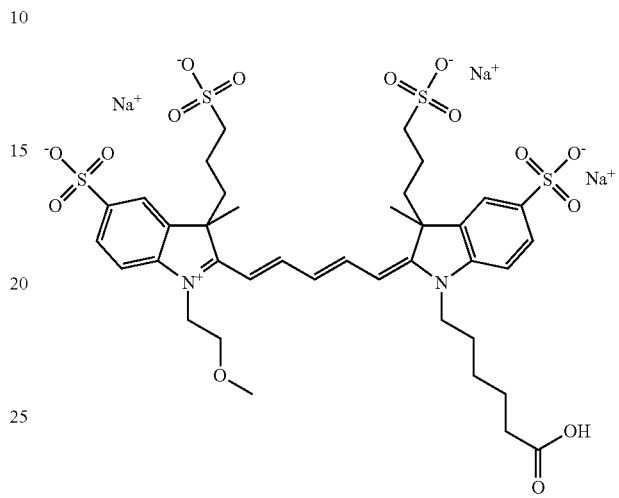

Both 90 mg (1 mmol) 1-(5-carboxypentyl)-3-methyl-2-((1E,3E)-4-phenylamino-buta-1,3-dienyl)-5-sulfo-3-(3-sulfopropyl)-3H-indolium and 404 mg (1 mmol) 1-(2-methoxy-ethyl)-2,3-dimethyl-5-sulfo-3-(3-sulfopropyl)-3H-indolium were dissolved in 20 ml of acetic acid/acetic anhydride (1/1) followed by the addition of 200 mg of sodium acetate. The solution was stirred under reflux for 15 min. After cooling to room temperature, 20 ml diethylether was added. The resulting precipitate (mixture of the diastereomers 650 Compound 1 (isomer 1) and 650 Compound 1 (isomer 2)) was extracted by suction, washed with ether, and dried.

The residue was purified by column chromatography (RP-18, acetonitrile/water and concentrated HCl) to separate the diastereomers from each other. The diastereomer that first eluted from the column was termed diastereomer 1 (650 Compound 1 (isomer 1)). The diastereomer that eluted second from the column was termed diastereomer 2 (650 Compound 1 (isomer 2)). The diastereomers were separated, followed by neutralization and evaporation. Purification of the single diastereomeric compound was completed on a RP-18 column, acetonitrile/water. The corresponding fractions were pooled and the solvent was removed by distillation. The two products (diastereomers 650 Compound 1 (isomer 1) and 650 Compound 1 (isomer 2)) were dried in high vacuum.

650 Compound 1 (Isomer 1):

yield: 11%

UV-vis (PBS): λmax=654 nm, λem=672 nm

MS (ESI−) [M/z]: 299.7 [M]$^{3-}$; 461.0 [M+Na]$^{2-}$

650 Compound 1 (Isomer 2):

yield: 24%

UV-vis (PBS): λmax=654 nm, λem=672 nm

MS (ESI−) [M/z]: 299.6 [M]$^{3-}$; 461.1 [M+Na]$^{2-}$

Example 14 650 Compound 2

Synthesis of 2-{(1E,3E)-5-[1-(5-carboxypentyl)-3-methyl-5-sulfo-3-(3-sulfopropyl)-1,3-dihydro-indol-(2E)-ylidene]-penta-1,3-dienyl}-1-[2-(2-methoxy-ethoxy)-ethyl]-3-methyl-5-sulfo-3-(3-sulfopropyl)-3H-indolium tri sodium salt

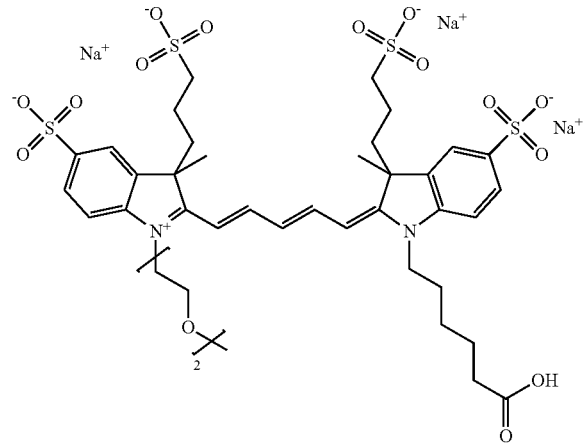

Both 564 mg (1 mmol) 1-(5-carboxypentyl)-3-methyl-2-((1E,3E)-4-phenylamino-buta-1,3-dienyl)-5-sulfo-3-(3-sulfopropyl)-3H-indolium and 449 mg (1 mmol) 1-[2-(2-methoxy-ethoxy)-ethyl]-2,3-dimethyl-5-sulfo-3-(3-sulfopropyl)-3H-indolium were dissolved in 20 ml of acetic acid/acetic anhydride (1/1) followed by the addition of 200 mg of sodium acetate. The synthesis and work-up were carried out according to Example 13.

650-1 Compound 2:
  yield: 11%
  UV-vis (PBS): λmax=654 nm, λem=672 nm
  MS (ESI−) [M/z]: 314.4 [M]$^{3-}$; 483.0 [M+Na]$^{2-}$
650-2 Compound 2:
  yield: 16%
  UV-vis (PBS): λmax=654 nm, λem=672 nm
  MS (ESI−) [M/z]: 314.5 [M]$^{3-}$; 483.1 [M+Na]$^{2-}$

Example 15 650 Compound 3

Synthesis of 2-{(1E,3E)-5-[1-(5-carboxypentyl)-3-methyl-5-sulfo-3-(3-sulfopropyl)-1,3-dihydro-indol-(2E)-ylidene]-penta-1,3-dienyl}-1-{2-[2-(2-methoxy-ethoxy)-ethoxy]-ethyl}-3-methyl-5-sulfo-3-(3-sulfopropyl)-3H-indolium tri sodium salt—650 Compound 3

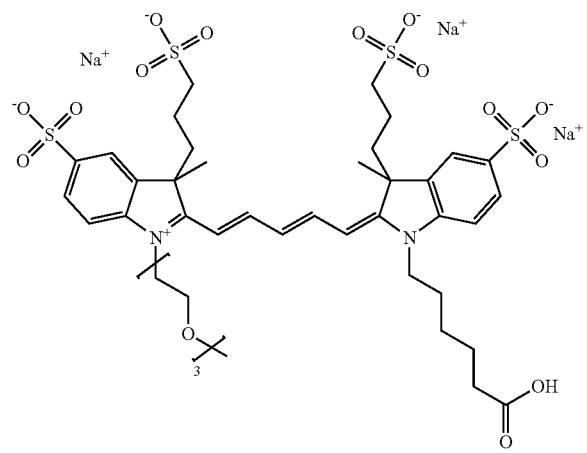

Both 564 mg (1 mmol) 1-(5-carboxypentyl)-3-methyl-2-((1E,3E)-4-phenylamino-buta-1,3-dienyl)-5-sulfo-3-(3-sulfopropyl)-3H-indolium and 493 mg (1 mmol) 1-{2-[2-(2-methoxy-ethoxy)-ethoxy]-ethyl}-2,3-dimethyl-5-sulfo-3-(3-sulfopropyl)-3H-indolium were dissolved in 20 ml acetic acid/acetic anhydride (1/1) followed by the addition of 200 mg sodium acetate. The synthesis and work-up were carried out according to Example 13.

650-1 Compound 3:
  yield: 10%
  UV-vis (PBS): λmax=654 nm, λem=672 nm
  MS (ESI−) [M/z]: 329.2 [M]$^{3-}$; 505.0 [M+Na]$^{2-}$
650-2 Compound 3:
  yield: 23%
  UV-vis (PBS): λmax=654 nm, λem=672 nm
  MS (ESI−) [M/z]: 329.1 [M]$^{3-}$; 505.1 [M+Na]$^{2-}$

Example 16 Synthesis of 755 Compound 1

2-{(1E,3E,5E)-7-[1-(5-Carboxypentyl)-3-methyl-5-sulfo-3-(3-sulfopropyl)-1,3-dihydro-indol-(2E)-ylidene]-hepta-1,3,5-trienyl}-1-(2-methoxy-ethyl)-3-methyl-5-sulfo-3-(3-sulfopropyl)-3H-indolium tri sodium salt

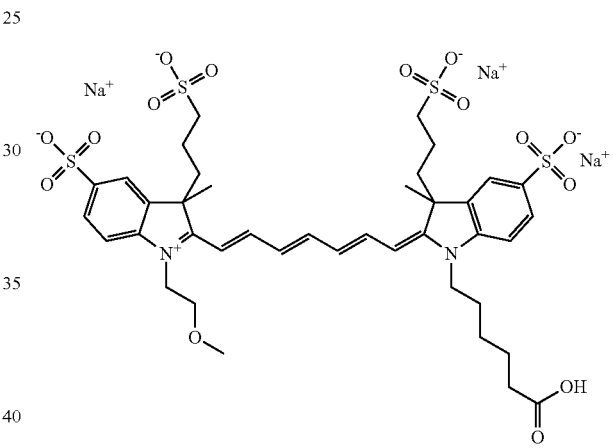

Six hundred and sixteen mg (1 mmol) 1-(5-Carboxypentyl)-3-methyl-2-((1E,3E,5E)-6-phenylamino-hexa-1,3,5-trienyl)-5-sulfo-3-(3-sulfopropyl)-3H-indolium and 404 mg (1 mmol) 1-(2-methoxy-ethyl)-2,3-dimethyl-5-sulfo-3-(3-sulfopropyl)-3H-indolium were dissolved in 20 ml of acetic acid/acetic anhydride (1/1) followed by the addition of 200 mg of sodium acetate. The solution was stirred under reflux for 15 min. After cooling to room temperature, 20 ml diethylether was added. The resulting precipitate (mixture of the diastereomers 755 Compound 1 (isomer 1) and 755 Compound 1 (isomer 2)) was extracted by suction, washed with ether, and dried.

The residue was purified by column chromatography (RP-18, acetonitrile/water and concentrated HCl) to separate the diastereomers from each other. The diastereomer that first eluted from the column was termed diastereomer 1 (755 Compound 1 (isomer 1)). The diastereomer that eluted second from the column was termed diastereomer 2 (755 Compound 1 (isomer 2)). The diastereomers were separated, followed by neutralization and evaporation. Purification of the single diastereomeric compound was completed on a RP-18 column, acetonitrile/water. The corresponding fractions were pooled and the solvent was removed by distillation. The two products (diastereomers 755 Compound 1 (isomer 1) and 755 Compound 1 (isomer 2)) were dried in high vacuum.

755 Compound 1 (Isomer 1):
 yield: 8%
 UV-vis (PBS): $\lambda_{max}$ 752 nm; $\lambda_{em}$=778 nm
 MS (ESI−) [M/z]: 308.4 [M]$^{3-}$; 474.2 [M+Na]$^{2-}$
755 Compound 1 (Isomer 2):
 yield: 16%
 UV-vis (PBS): $\lambda_{max}$=752 nm; $\lambda_{em}$=778 nm
 MS (ESI−) [M/z]: 308.4 [M]$^{3-}$; 474.2 [M+Na]$^{2-}$.

Example 17 Synthesis of 755 Compound 2

2-{(1E,3E,5E)-7-[1-(5-Carboxypentyl)-3-methyl-5-sulfo-3-(3-sulfopropyl)-1,3-dihydro-indol-(2E)-ylidene]-hepta-1,3,5-trienyl}-1-(2-methoxy-ethoxy)-3-methyl-5-sulfo-3-(3-sulfopropyl)-3H-indolium

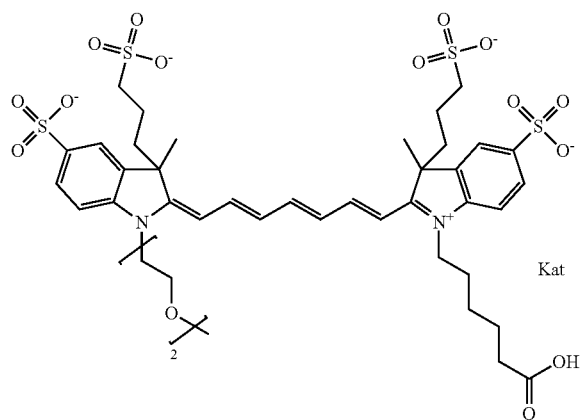

Both 1 mmol 1-(5-Carboxypentyl)-3-methyl-2-((1E,3E,5E)-6-phenylamino-hexa-1,3,5-trienyl)-5-sulfo-3-(3-sulfopropyl)-3H-indolium and 1 mmol 1-[2-(2-methoxy-ethoxy)-ethyl]-2,3-dimethyl-5-sulfo-3-(3-sulfo-propyl)-3H-indolium were dissolved in 20 ml acetic acid/acetic anhydride (1/1) followed by the addition of 200 mg sodium acetate. The solution was stirred under reflux for 15 min. After cooling to room temperature, 20 ml diethylether was added. The resulting precipitate (mixture of the diastereomers 755 compound 2 (isomer 1) and 755 compound 2 (isomer 2)) was extracted by suction, washed with ether and dried. The residue is purified by column chromatography (RP-18, acetonitrile/water and concentrated HCl), thereby separating the diastereomers from each other, as described in Example 16.

Example 18 Synthesis of 755 Compound 3

2-{(1E,3E,5E)-7-[1-(5-Carboxypentyl)-3-methyl-5-sulfo-3-(3-sulfopropyl)-1,3-dihydro-indol-(2E)-ylidene]-hepta-1,3,5-trienyl}-1-{2-[2-(2-methoxy-ethoxy)-ethoxy]-ethyl}-3-methyl-5-sulfo-3-(3-sulfopropyl)-3H-indolium

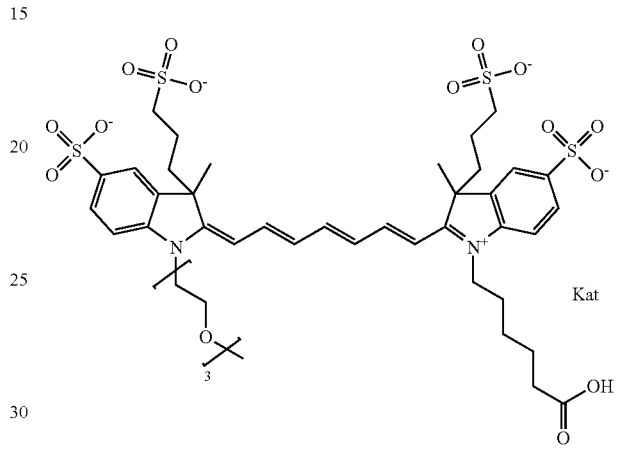

Both 1 mmol 1-(5-carboxypentyl)-3-methyl-2-((1E,3E,5E)-6-phenylamino-hexa-1,3,5-trienyl)-5-sulfo-3-(3-sulfopropyl)-3H-indolium and 1 mmol 1-{2-[2-(2-methoxy-ethoxy)-ethoxy]-ethyl}-2,3-dimethyl-5-sulfo-3-(3-sulfo-propyl)-3H-indolium were dissolved in 20 ml acetic acid/acetic anhydride (1/1) followed by the addition of 200 mg sodium acetate. The solution was stirred under reflux for 15 min. After cooling to room temperature, 20 ml diethylether was added. The resulting precipitate (mixture of the diastereomers 755 compound 3 (isomer 1) and 755 compound 3 (isomer 2)) was extracted by suction, washed with ether and dried. The residue is purified by column chromatography (RP-18, acetonitrile/water and concentrated HCl), thereby separating the diastereomers from each other, as described in Example 16.

Example 19

Properties of 650 Compounds as NHS esters were compared with commercially available dyes, as shown below.

|  | 650 1/1-NHS (tetrasulfonated) | 650 4/4-NHS | 650 1/1-NHS (disulfonated) | Alexa Fluor 647-NHS | CF 647-NHS |
|---|---|---|---|---|---|
| MW (g/mol) | 1066 | 1424.63 | 789.91 | ~1150 | 3241 |
| Ex (nm) | 652 | 658 | 651 | 650 | 650 |
| Em (nm) | 672 | 681 | 665 | 665 | 665 |
| ε (M$^{-1}$cm$^{-1}$) (theoretical) | 250,000 | 250,000 | 250,000 | 239,000 | 240,000 |
| PEG (length/# of chain) | 1/1 | 4/4 | 1/1 | N/A | unknown |
| Sulfonate | 4 | 2 | 2 |  | unknown |

Properties of 755 Compounds as NHS esters were compared with commercially available dyes as shown below:

|  | DyLight 800-NHS | 755 Compound 4/4-NHS |
|---|---|---|
| MW (g/mol) | 1050 | 1684.9 |
| Ex (nm) | 777 | 783 |
| Em (nm) | 794 | 797 |
| ε ($M^{-1}cm^{-1}$) (theoretical) | 270,000 | 270,000 |
| PEG (length/number of PEG groups on compound | N/A | 4/4 |
| Sulfonates | 3 | 3 |

Excitation/emission spectra of 755 Compound 4/4-NHS was within +/−10 nm compared to DyLight 800-NHS.

Example 20

DyLight 650 1/1 and DyLight 650 4/4 were dissolved in dimethylformamide (DMF) at 10 mg/ml, mixed on a vortex mixer for 15 seconds, and observed to determine if the dyes went into solution. The dyes were then allowed to incubate for five minutes and again mixed on a vortex mixer for 30 seconds. DyLight 650 (4/4) dissolved immediately and DyLight 650 (1/1) did not go into solution until it was incubated for five minutes and mixed again.

Example 21

Inventive and commercial compounds, each as the NHS ester, were conjugated to goat anti-mouse (GAM) and goat anti-rabbit (GAR) antibodies. GAM and GAR at 10 mg/ml in phosphate buffered saline (PBS), were dialyzed against 50 mM borate buffer, pH 8.5. The compounds were reconstituted in DMF, and CF 647 was reconstituted in dimethylsulfoxide (DMSO), at 10 mg/ml and combined at 2.5×, 5×, 10×, or 15× molar excess with GAM or GAR for about two hours at room temperature to label the antibodies.

Labeled compounds, also termed dyes or labels, were subjected to PDDR to remove the unlabeled (free) compound; 100-200 µl of the packed resin was used per mg of protein purified. The purified antibody-labeled dyes were then diluted 1:50 in PBS and scanned for absorbance from 700 nm to 230 nm on a UV Cary spectrophotometer to determine the protein concentration, and to determine the mole dye to mole protein ratio. Each conjugate was diluted 1:10 in 50% glycerol and heated in the presence of 10 mM dithiothreitol (DTT) for 5 min at 95° C., then separated by electrophoresis on polyacrylamide gels in the presence of sodium dodecyl sulfate (SDS-PAGE). The gels were scanned using the Typhoon 9400 Imager to verify removal of the unconjugated compound. Labeling efficiency was compared, with results showing degree of labeling below, where 650 Compound 1/1 (4S) denotes four sulfo groups on the compound and 650 Compound 1/1 (2S) denotes two sulfo groups on the compound.

| GAM | 2.5X | 5X | 10X | 15X |
|---|---|---|---|---|
| 650 Compound 4/4-NHS | 2.4 | 4.7 | 9.6 | 14.2 |
| 650 Compound 1/1 (4S)-NHS | 2.6 | 4.4 | 7.9 | 10.0 |
| CF 647-NHS | 1.7 | 2.9 | 4.3 | 5.1 |
| Alexa Fluor 647-NHS | 2.4 | 4.0 | 6.5 | 8.2 |

| GAR | 2.5X | 5X | 10X | 15X |
|---|---|---|---|---|
| 650 Compound 4/4-NHS | 2.3 | 4.6 | 8.5 | 13.4 |
| 650 Compound 1/1 (4S)-NHS | 2.8 | 4.1 | 7.6 | 10.0 |
| CF 647-NHS | 1.7 | 2.6 | 4.2 | 4.9 |
| Alexa Fluor 647-NHS | 2.3 | 3.6 | 6.1 | 7.7 |

Labeling efficiency was the highest for all 650 Compound 4/4 conjugates, followed by 650 Compound 1/1, compared to the other dyes at each molar excess. 650 Compound 1/1 and CF 647 required extra time for complete solubility.

Figure 1B:
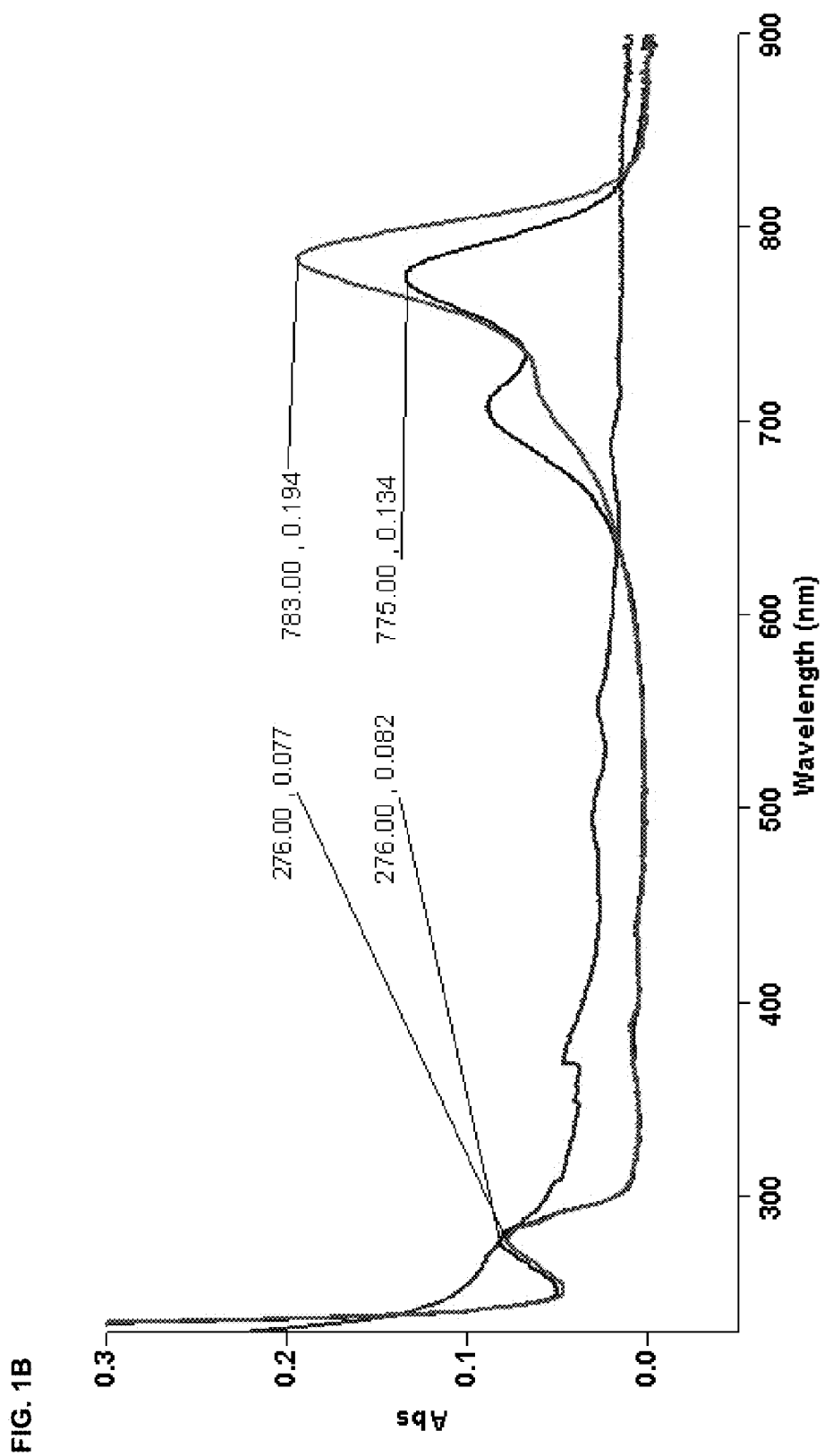
Figure 1C:
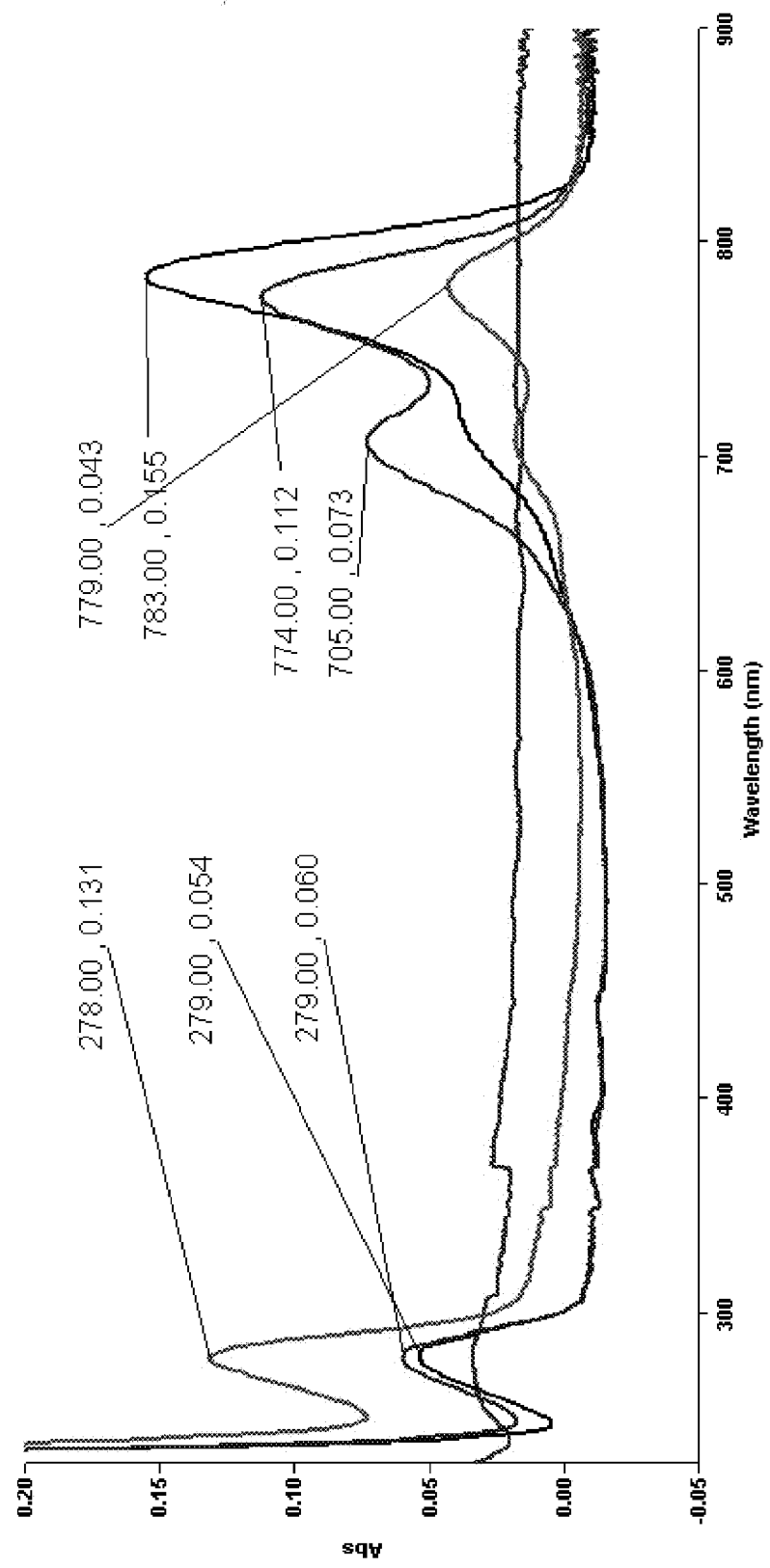

755 Compound 4/4 and DyLight 800, each as the NHS ester, were conjugated to goat anti-mouse (GAM) and goat anti-rabbit (GAR) antibodies as described above. Briefly, 755 Compound 4/4-NHS and DyLight 800-NHS were reconstituted at 10 mg/ml in DMF. Each compound showed good solubility. One mg in 100 µl of GAM or GAR was prepared at 10.0 mg/ml in borate buffer pH 8.5. Ten mg in 1000 µl of GAM was prepared at 10.0 mg/ml in borate buffer pH 8.5. Ten mg in 1000 µl of GAM was prepared at 10.0 mg/ml in PBS pH 7.4. GAM and GAR were labeled with each compound at 2.5×, 5×, 7× (10 mg) and 9× molar excesses. Ten mg GAM was labeled with each compound at 5× and 7× molar excesses in borate buffer. Ten mg GAM was labeled with each compound at 5× and 7× molar excesses in PBS buffer, and incubated for greater than 60 min. Conjugates were purified on Pierce Dye Removal Resin in Harvard columns with 100-200 µl resin per mg of each conjugate. All the conjugates were diluted 1:50 and scanned on UV Cary Spectrophotometer. Absorption maxima for free compounds is shown in FIG. 1A, where free dye 755 Compound 4/4-NHS showed a single absorption peak at 783 nm and free Dye DyLight 800-NHS showed a single absorption peak at 770 nm. Absorption maxima of GAM conjugates with 755 Compound 4/4 (D/P of 2.2) and DyLight 800 (D/P of 1.4), are shown in FIG. 1B, with baseline 100% transmission shown. 755 Compound 4/4-GAM conjugates showed a single absorption peak at 783 nm and DyLight 800-GAM conjugates showed 2 peaks: major at 775 nm and minor at 706 nm. Absorption maxima of GAR conjugates with 755 Compound 4/4 (D/P of 2.2), DyLight 800 (D/P of 1.4), and IR800-GAR (D/P of 2.6; conjugate made using LI-COR IR800 Dye) are shown in FIG. 1C, with baseline 100% transmission shown. 755 Compound 4/4-GAR conjugates showed a single absorption peak at 783 nm, DyLight 800-GAR conjugates showed 2 absorption peaks: major at 774 nm and minor at 705 nm, and IR800-GAR showed a main peak at 779 nm and a minor peak at 709 nm. The secondary peak observed with DyLight 800 at 706 nm is approximately 60% of the main peak at 775 nm, and this secondary peak can affect the readout depending on the instrumentation used.

Labeling efficiency was compared, with results showing degree of labeling (D/P) below.

|  | 2.5X | 5X | 7X | 9X |
|---|---|---|---|---|
| GAM borate buffer |  |  |  |  |
| 755 Compound 4/4-NHS | 0.97 | 1.72 | 2.24 | 2.94 |
| DyLight 800-NHS | 0.74 | 1.12 | 1.41 | 1.91 |
| GAR borate buffer |  |  |  |  |
| 755 Compound 4/4-NHS | 0.84 | 1.64 | 2.22 | 2.91 |
| DyLight 800-NHS | 0.71 | 1.17 | 1.39 | 1.88 |

|  | 2.5X | 5X | 7X | 9X |
| --- | --- | --- | --- | --- |
| GAM borate buffer | | | | |
| 755 Compound 4/4-NHS | | | 1.75 | 2.32 |
| DyLight 800-NHS | | | 1.20 | 1.55 |
| GAM PBS buffer | | | | |
| 755 Compound 4/4-NHS | | | 0.74 | 1.16 |
| DyLight 800-NHS | | | 0.89 | 1.15 |

Conjugation of 755 Compound 4/4 in borate buffer resulted in about 50% higher labeling efficiency than DyLight 800 at similar molar excess. For both dyes, conjugations performed in PBS buffer pH 7.2 showed about two times less labeling efficiency compared to conjugations in borate buffer pH 8.5. DyLight 800 conjugates at 7× molar excess in borate buffer precipitated within three days and 755 Compound 4/4 conjugates had no visible precipitation after three weeks. Use of 755 Compound 4/4 at 5× molar excess avoids dye aggregation and yields a similar D/P as DyLight 800 at 7× molar excess.

Example 22

Performance of the dye-GAM conjugates and dye-GAR conjugates was evaluated in a functional assay. Wells of a 96 white opaque plate were coated with target proteins mouse IgG immunoglobulin or rabbit IgG immunoglobulin. One hundred µl mouse or rabbit IgG at a concentration of 10 µg/ml was applied to the corresponding wells in columns 1 and 2. The target proteins were serially diluted 1:1 from the wells in columns 2 to 11 using 100 µl PBS. One hundred µl of the samples from the wells in column 11 were discarded. One hundred µl PBS was added to the wells in column 12. The plates were incubated overnight at 4° C. and then blocked 2×200 µl with Thermo Scientific SuperBlock® Blocking Buffer. The coated plates were washed 2×200 µl with PBS-Tween and 1×200 µl with PBS. Based on the calculated concentrations, GAM and GAR conjugates were diluted 1:250 (of 1 mg/ml) in PBS buffer. Conjugates diluted in PBS to 4 µg/ml were added to the corresponding plates (100 µl/well) and then incubated for 1 h in the dark. The plates were washed with 2×200 µl with PBS-Tween and 1×200 µl with PBS and filled with PBS buffer (100 µl/well) prior to scanning on Tecan Safire to detect fluorescence intensity.

As shown in FIGS. 2-9, the relative fluorescence units (RFU) or signal-to-background ratio (S/B) of the dyes were compared at various concentrations, using the indicated conjugation conditions.

Figure 2:
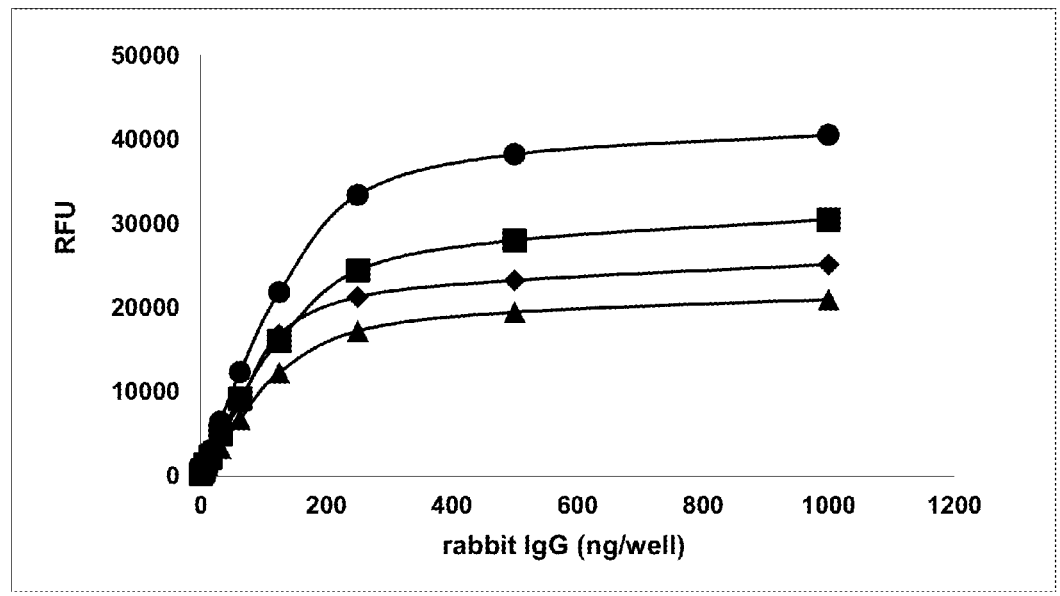
FIG. 2 shows fluorescence plate functional assay results with inventive compounds and commercial dyes in one embodiment.
Figure 3:
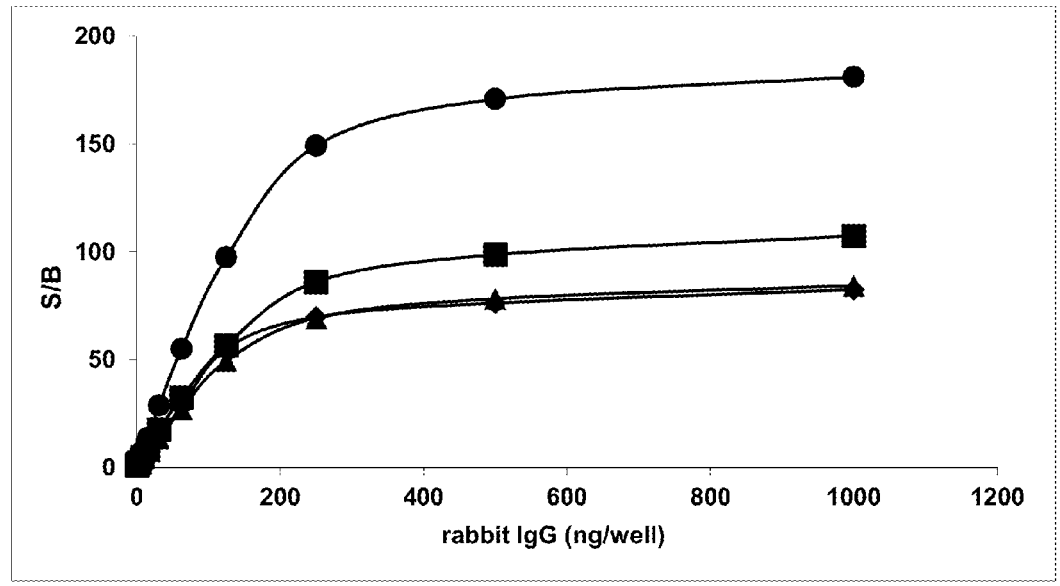
FIG. 3 shows fluorescence plate functional assay results with inventive compounds and commercial dyes in one embodiment.
Figure 4:
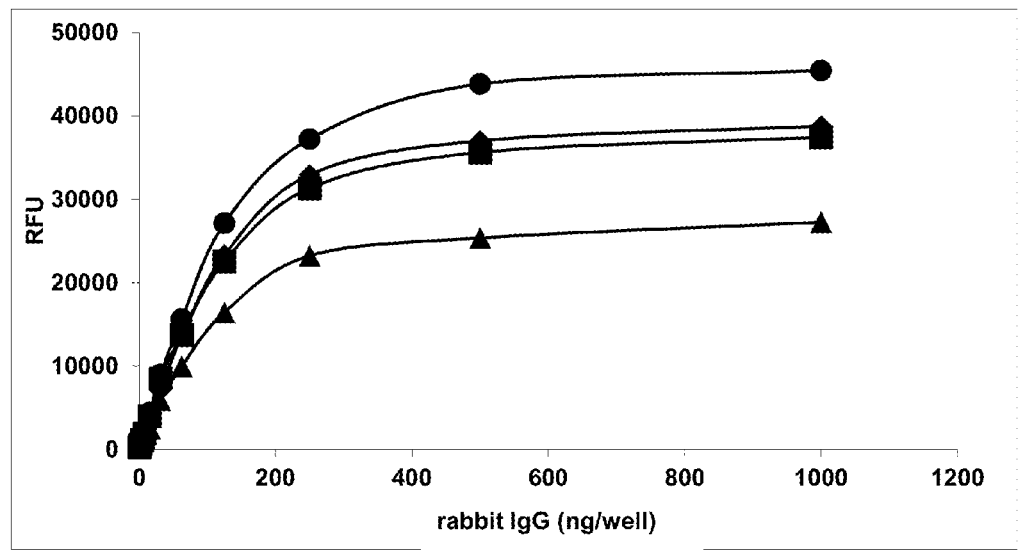
FIG. 4 shows fluorescence plate functional assay results with inventive compounds and commercial dyes in one embodiment.
Figure 5:
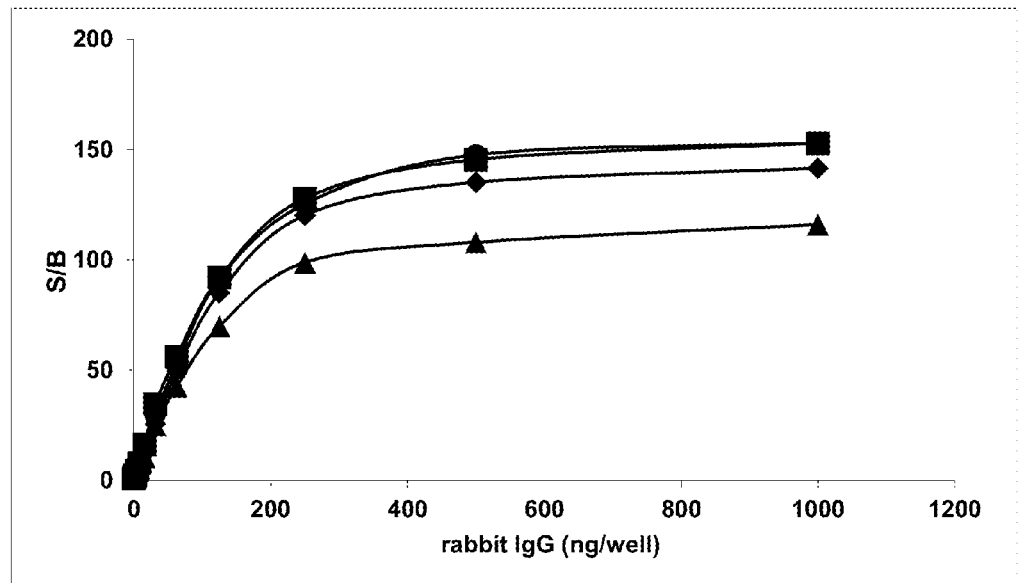
FIG. 5 shows fluorescence plate functional assay results with inventive compounds and commercial dyes in one embodiment.

FIG. 2 shows results of a functional assay using GAR conjugated with either 650 Compound 4/4 (diamonds), 650 Compound 1/1 (circles), CF 647 (triangles), or Alexa Fluor 647 (squares) at a 2.5× molar excess of the dyes, showing relative fluorescence units (RFU) versus amount of target antibody per well (ng/well). FIG. 3 shows the signal-to-background ratio (SB) of the functional assay of FIG. 2, showing either 650 Compound 4/4 (diamonds), 650 Compound 1/1 (circles), CF 647 (triangles), or Alexa Fluor 647 (squares) at a 2.5× molar excess of the dyes. FIG. 4 shows results of a functional assay using GAR conjugated with either 650 Compound 4/4 (diamonds), 650 Compound 1/1 (circles), CF 647 (triangles), or Alexa Fluor 647 (squares) at a 5× molar excess of the dyes, showing relative fluorescence units (RFU) versus amount of target antibody per well (ng/well). FIG. 5 shows the signal-to-background ratio (SB) of the functional assay of FIG. 4, showing either 650 Compound 4/4 (diamonds), 650 Compound 1/1 (circles), CF 647 (triangles), or Alexa Fluor 647 (squares) at a 5× molar excess of the dyes. 650 Compound 1/1-GAR was the best performing conjugate at all molar excesses. Up to 125 ng/well of rabbit IgG, the 650 Compound 4/4-GAR showed similar binding fluorescence as Alexa Fluor 647-GAR but better than CF 647-GAR. CF 647 showed significantly lower performance of all the conjugates.

Figure 6:
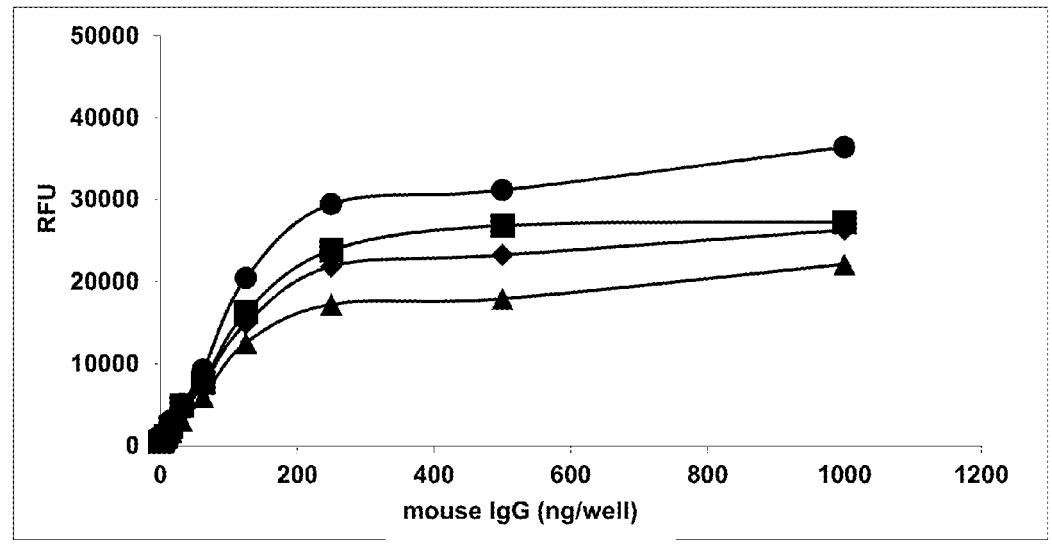
FIG. 6 shows fluorescence plate functional assay results with inventive compounds and commercial dyes in one embodiment.
Figure 7:
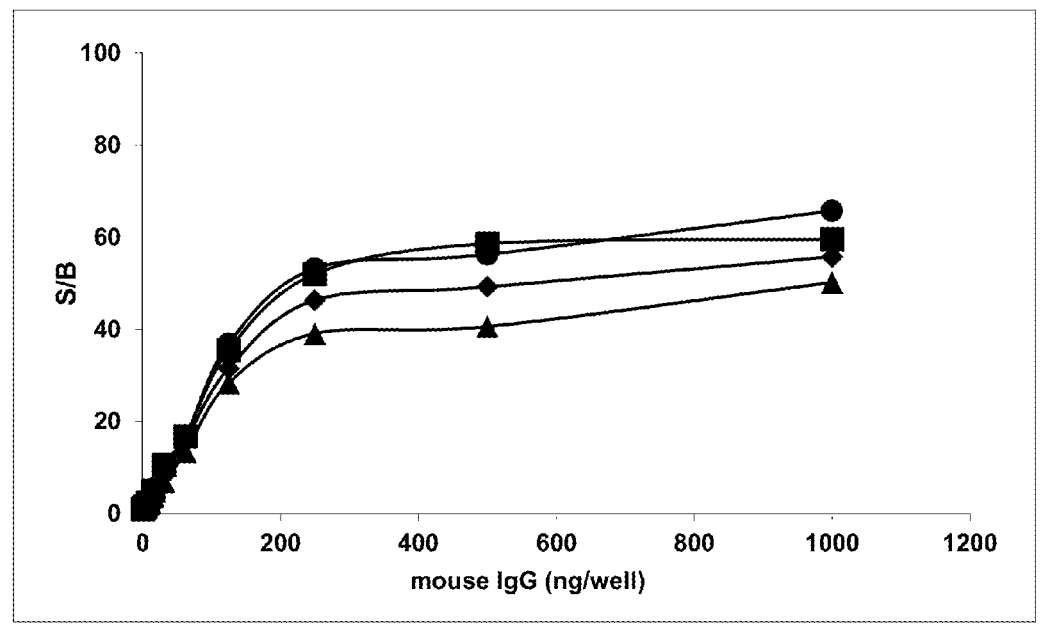
FIG. 7 shows fluorescence plate functional assay results with inventive compounds and commercial dyes in one embodiment.
Figure 8:
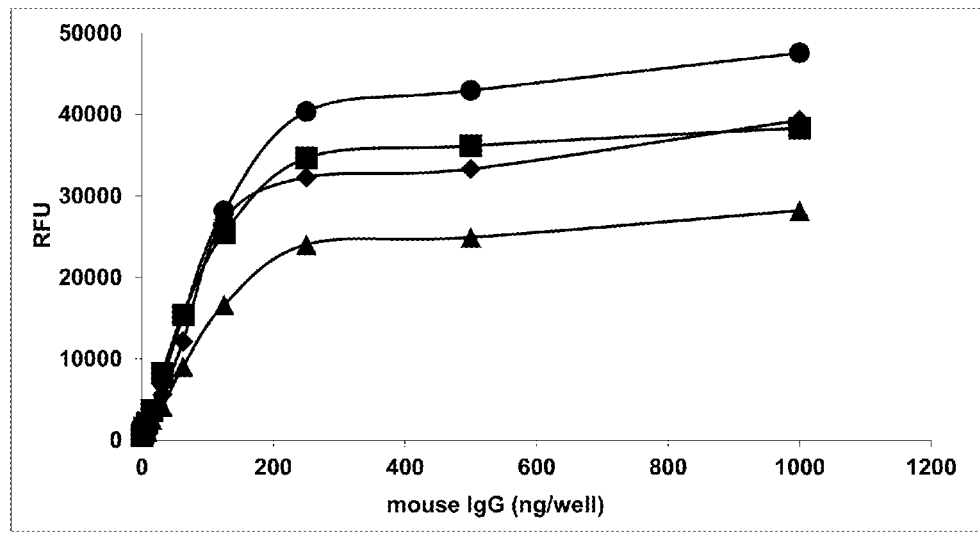
FIG. 8 shows fluorescence plate functional assay results with inventive compounds and commercial dyes in one embodiment.
Figure 9:
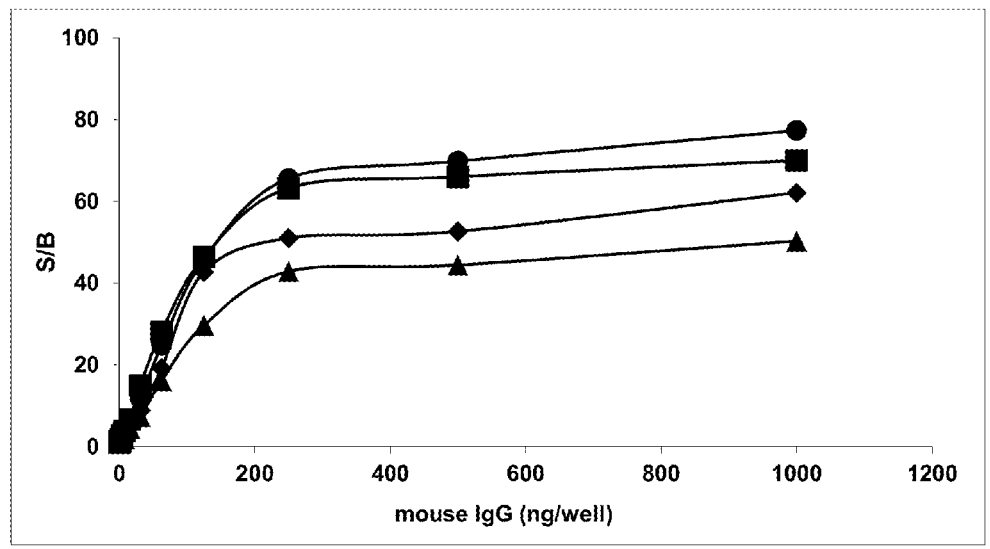
FIG. 9 shows fluorescence plate functional assay results with inventive compounds and commercial dyes in one embodiment.

FIG. 6 shows results of a functional assay using GAM conjugated with either 650 Compound 4/4 (diamonds), 650 Compound 1/1 (circles), CF 647 (triangles), or Alexa Fluor 647 (squares) at a 2.5× molar excess of the dyes, showing relative fluorescence units (RFU) versus amount of target antibody per well (ng/well). FIG. 7 shows the signal-to-background ratio (SB) of the functional assay of FIG. 6, showing either 650 Compound 4/4 (diamonds), 650 Compound 1/1 (circles), CF 647 (triangles), or Alexa Fluor 647 (squares) at a 2.5× molar excess of the dyes. FIG. 8 shows results of a functional assay using GAM conjugated with either 650 Compound 4/4 (diamonds), 650 Compound 1/1 (circles), CF 647 (triangles), or Alexa Fluor 647 (squares) at a 5× molar excess of the dyes, showing relative fluorescence units (RFU) versus amount of target antibody per well (ng/well). FIG. 9 shows the signal-to-background ratio (SB) of the functional assay of FIG. 8, showing either 650 Compound 4/4 (diamonds), 650 Compound 1/1 (circles), CF 647 (triangles), or Alexa Fluor 647 (squares) at a 5× molar excess of the dyes. 650 Compound 1/1-GAM was the best performing conjugate at all molar excesses. Up to 125 ng/well of mouse IgG, 650 Compound 4/4-GAM showed similar binding fluorescence as Alexa Fluor 647-GAM but better than CF 647-GAM. CF-647 showed significantly lower performance of all the conjugates.

Figure 10A:
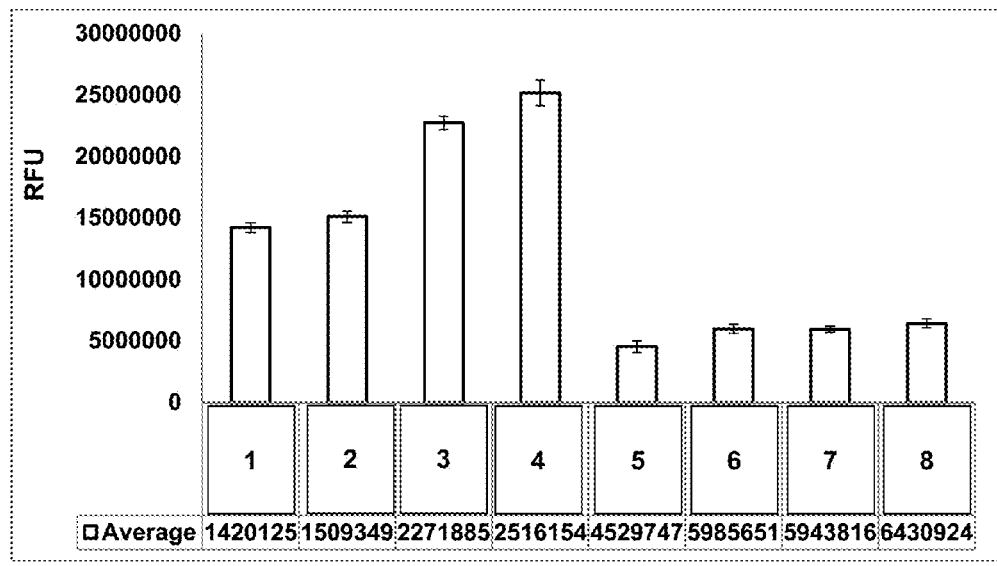
FIGS. 10A-B show the average total unbound fluorescence intensity with inventive compounds and commercial dyes in one embodiment.
Figure 10B:
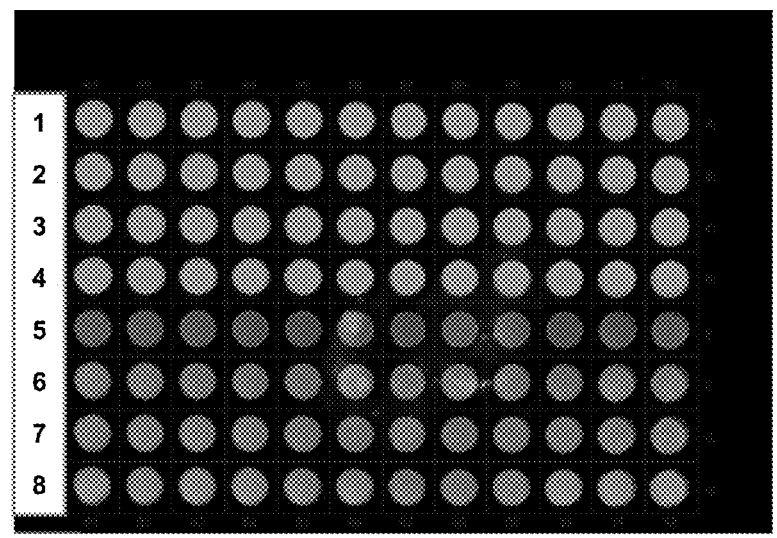
Figure 11A:
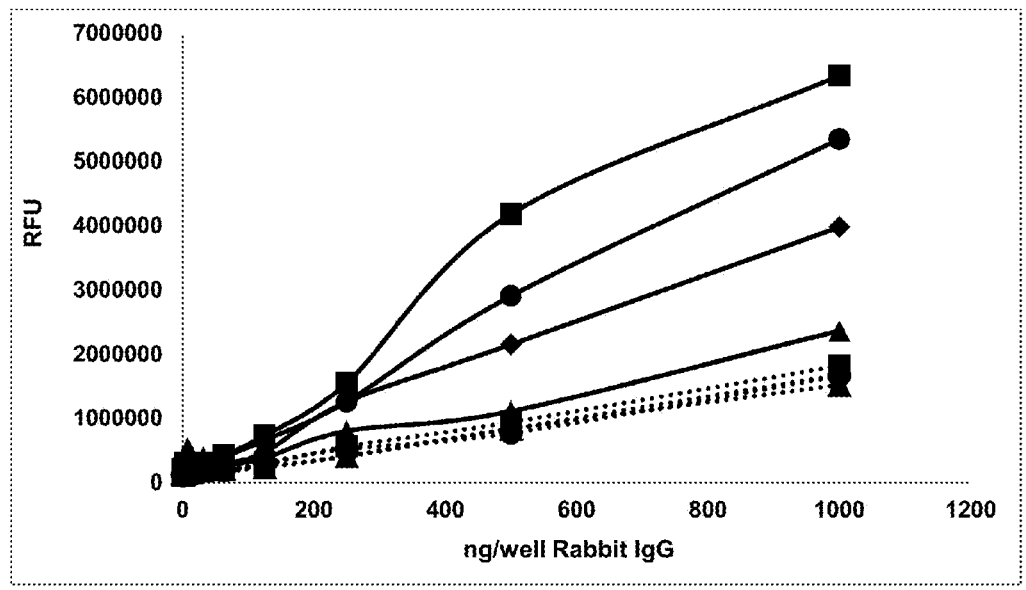
FIGS. 11A-B show the average total unbound fluorescence intensity with inventive compounds and commercial dyes in one embodiment.
Figure 11B:
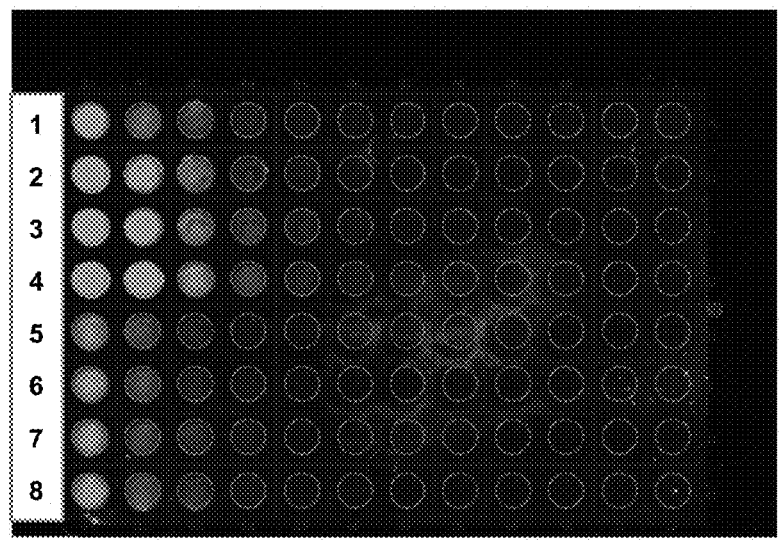

Performance of the dye-GAM conjugates and dye-GAR conjugates was evaluated in a functional fluorescence plate assay, as described above. After incubation, the plates were scanned on LiCor Odyssey at 800 channel (unbound). Plates were washed 2×200 µl with PBS-Tween20 and 1×200 µl with PBS and filled with PBS buffer (100 µl/well) prior to scanning on LiCor Odyssey at 800 channel (bound). Average total unbound fluorescence intensity is shown in FIG. 10A, and the corresponding plate image in FIG. 10B, showing 1 (755 Compound 4/4-GAR; 2.5× molar excess; D/P 0.84), 2 (755 Compound 4/4-GAR; 5× molar excess; D/P 1.64), 3 (755 Compound 4/4-GAR; 7× molar excess; D/P 2.22), 4 (755 Compound 4/4-GAR; 9× molar excess; D/P 2.91), 5 (DyLight 800-GAR; 2.5× molar excess; D/P 0.71), 6 (DyLight 800-GAR; 5× molar excess; D/P 1.17), 7 (DyLight 800-GAR; 7× molar excess; D/P 1.39), and 8 (DyLight 800-GAR; 9× molar excess; D/P 1.88). Average total bound fluorescence intensity is shown in FIG. 11A, with 755 Compound 4/4-GAR (solid lines) and DyLight 800-GAR (dotted lines) at either 2.5× molar excess (triangles), 5× molar excess (diamonds), 7× molar excess (circles), or 9× molar excess (squares). FIG. 11B shows the plate image of FIG. 11A, showing 1 (755 Compound 4/4-GAR; 2.5× molar excess), 2 (755 Compound 4/4-GAR; 5× molar excess), 3 (755 Compound 4/4-GAR; 7× molar excess), 4 (755 Compound 4/4-GAR; 9× molar excess), 5 (DyLight 800-GAR; 2.5× molar excess), 6 (DyLight 800-GAR; 5× molar excess), 7 (DyLight 800-GAR; 7× molar excess), and 8 (DyLight 800-GAR; 9× molar excess). In the above functional fluorescence plate assays, 755 Compound 4/4-GAR showed significantly higher binding fluorescence intensity compared to DyLight 800-GAR conjugates in borate buffer.

Figure 12A:
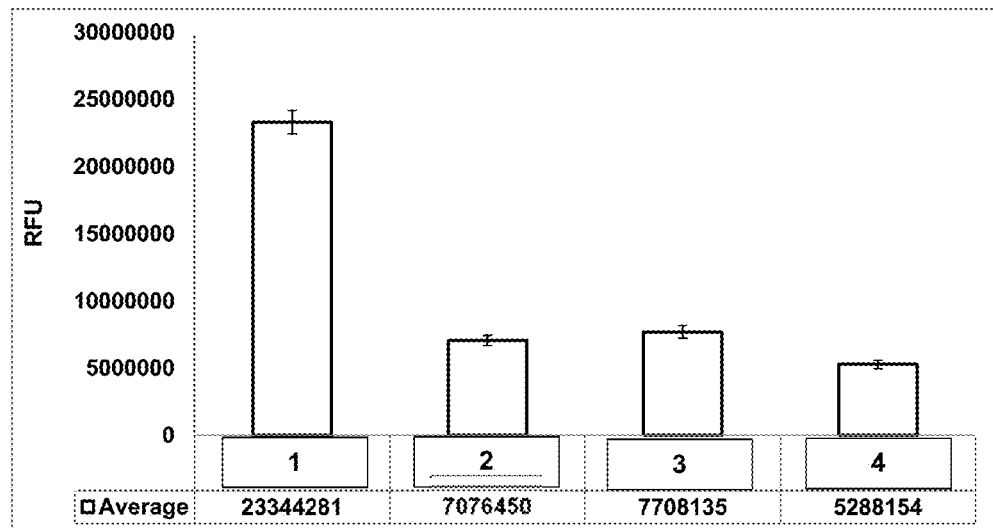
FIGS. 12A-B show the average total unbound fluorescence intensity with inventive compounds and commercial dyes in one embodiment.
Figure 12B:
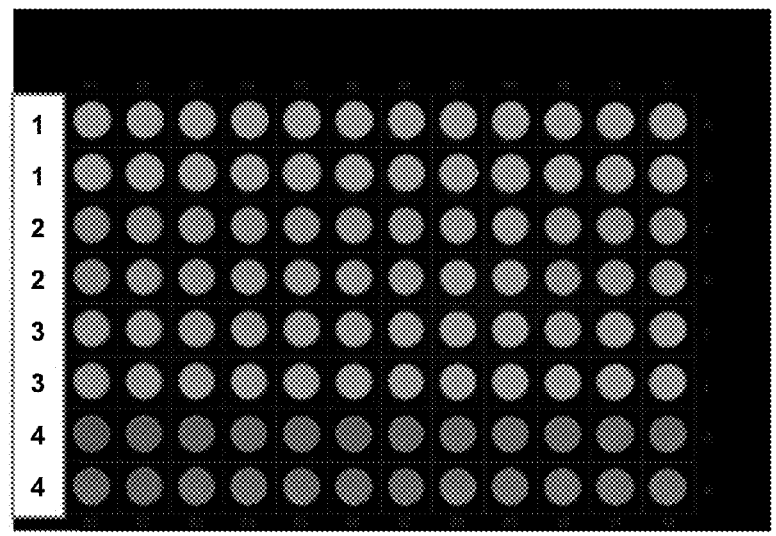
Figure 13A:
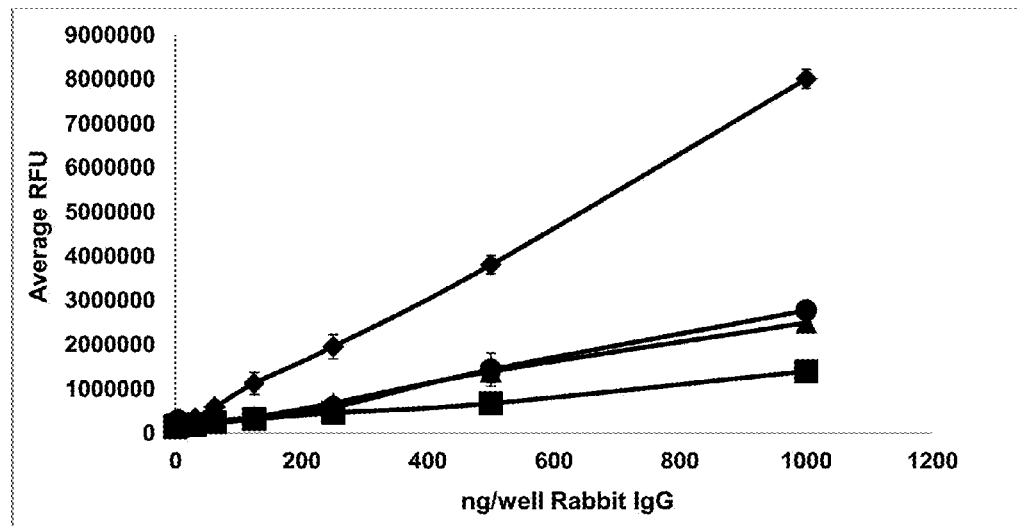
FIGS. 13A-B show the average total unbound fluorescence intensity with inventive compounds and commercial dyes in one embodiment.
Figure 13B:
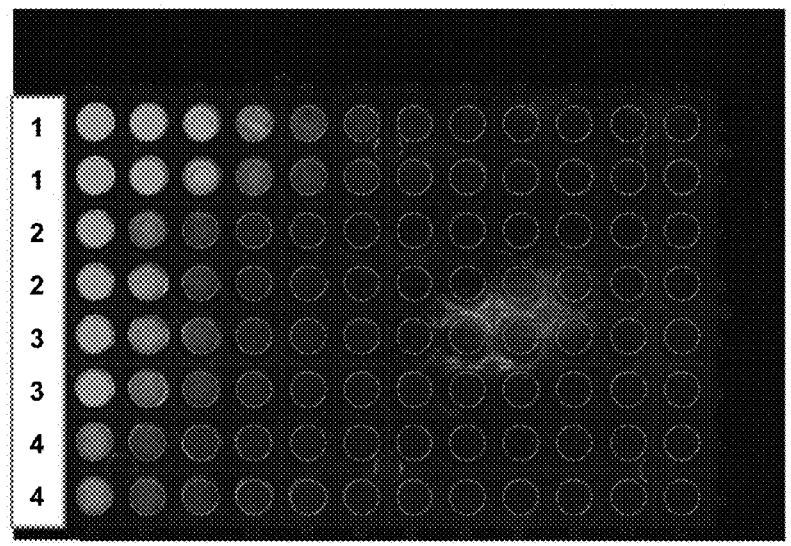
Figure 14A:
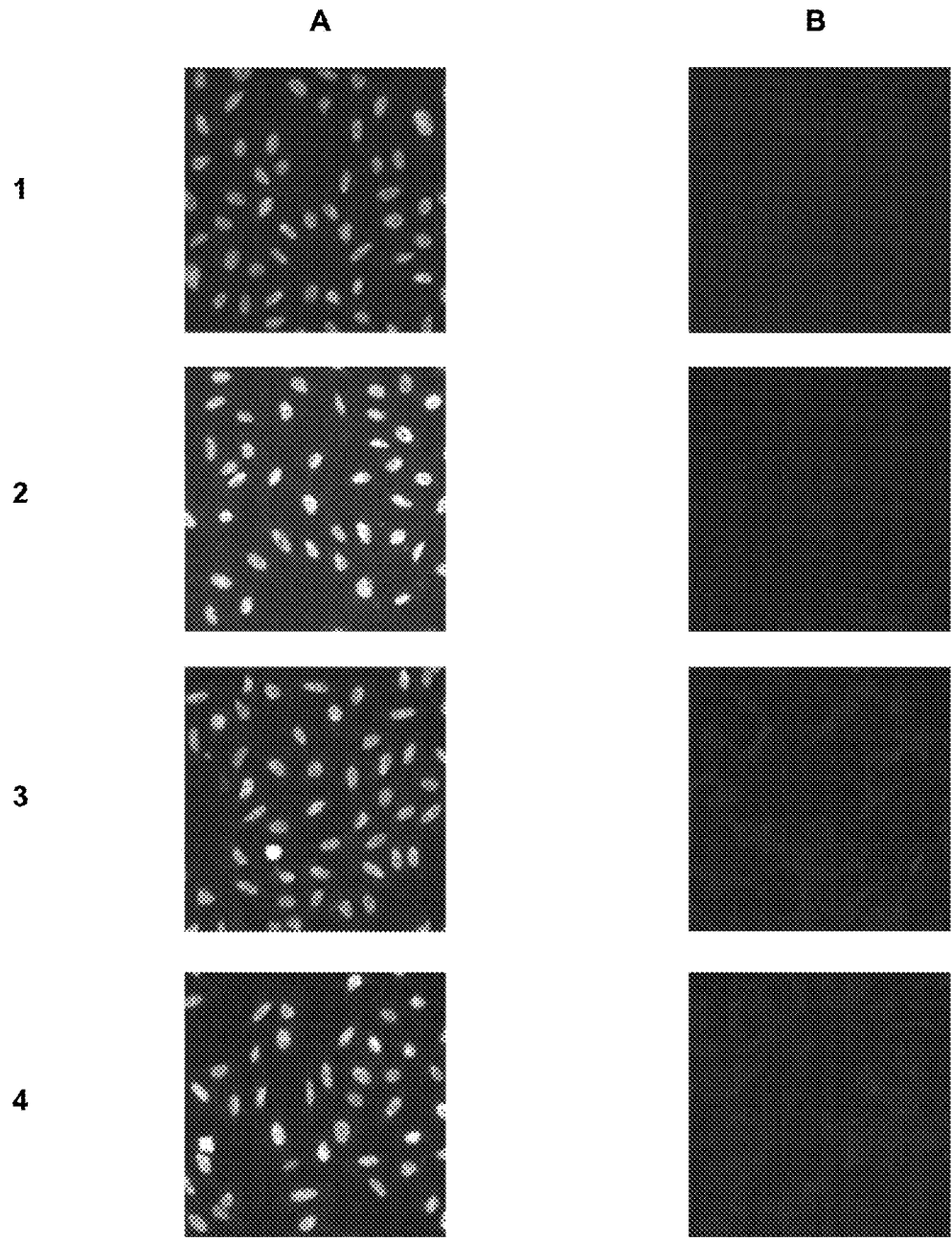
FIGS. 14A-E show immunofluorescence assay results with inventive compounds and commercial dyes in one embodiment.
Figure 14B:
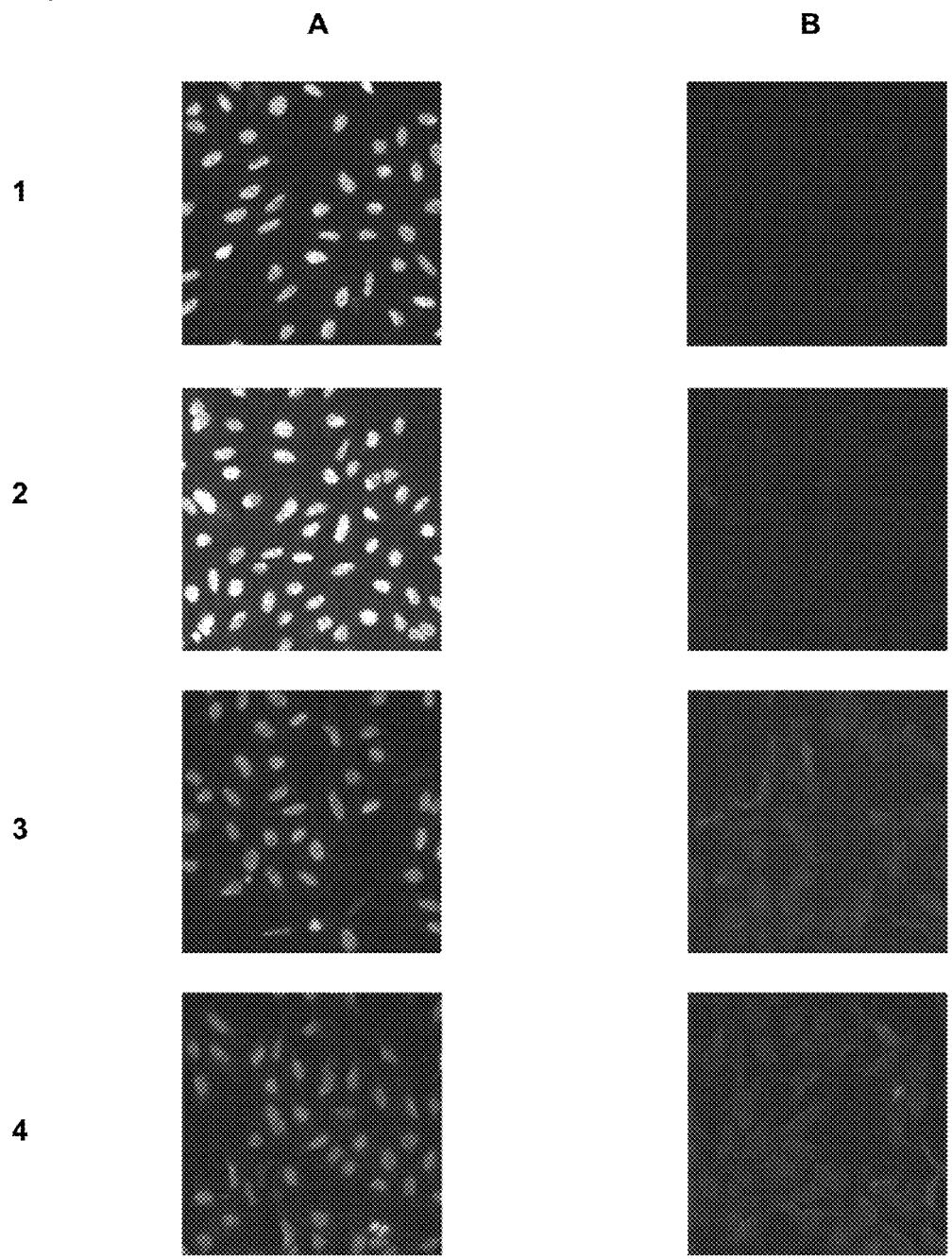
Figure 14C:
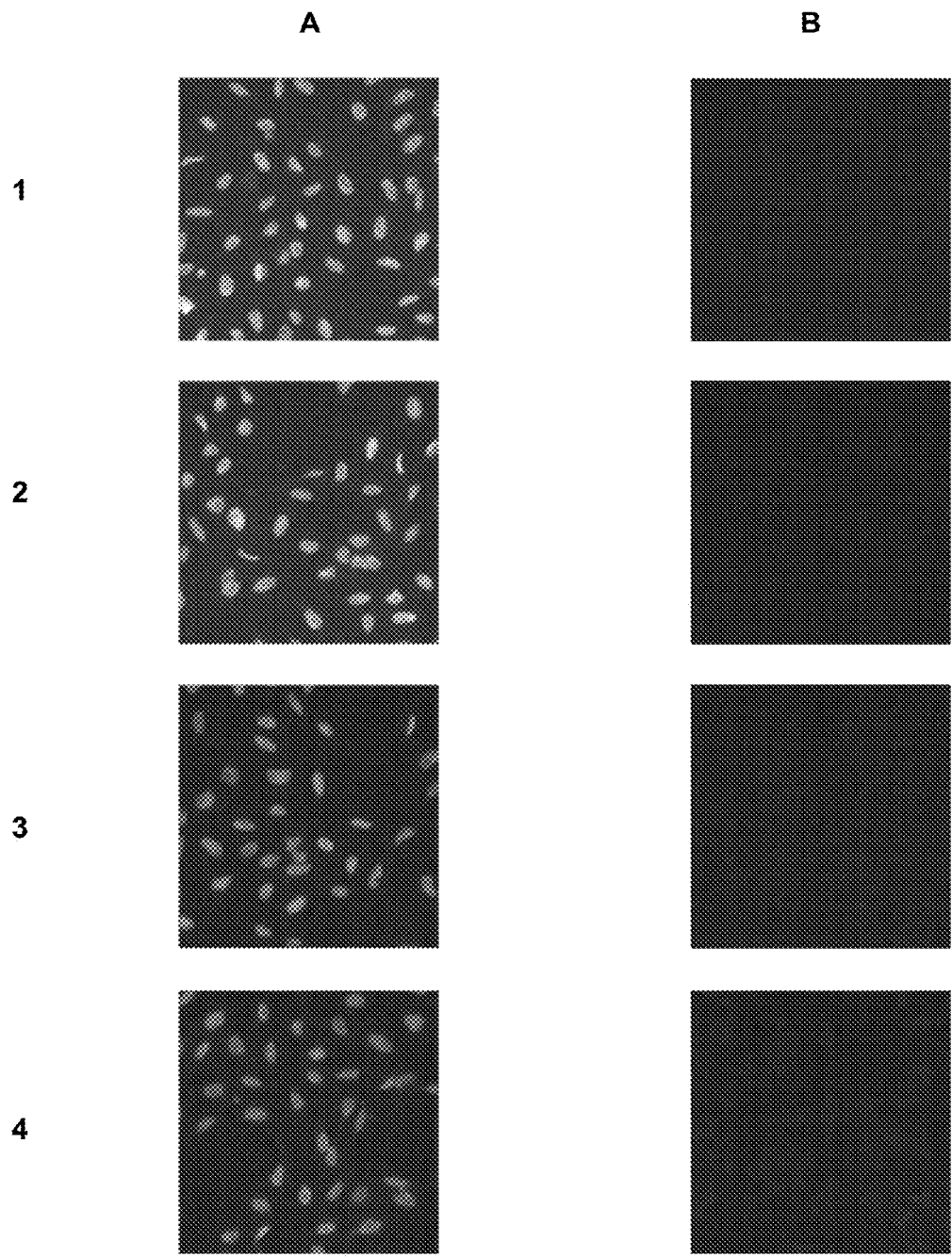
Figure 14D:
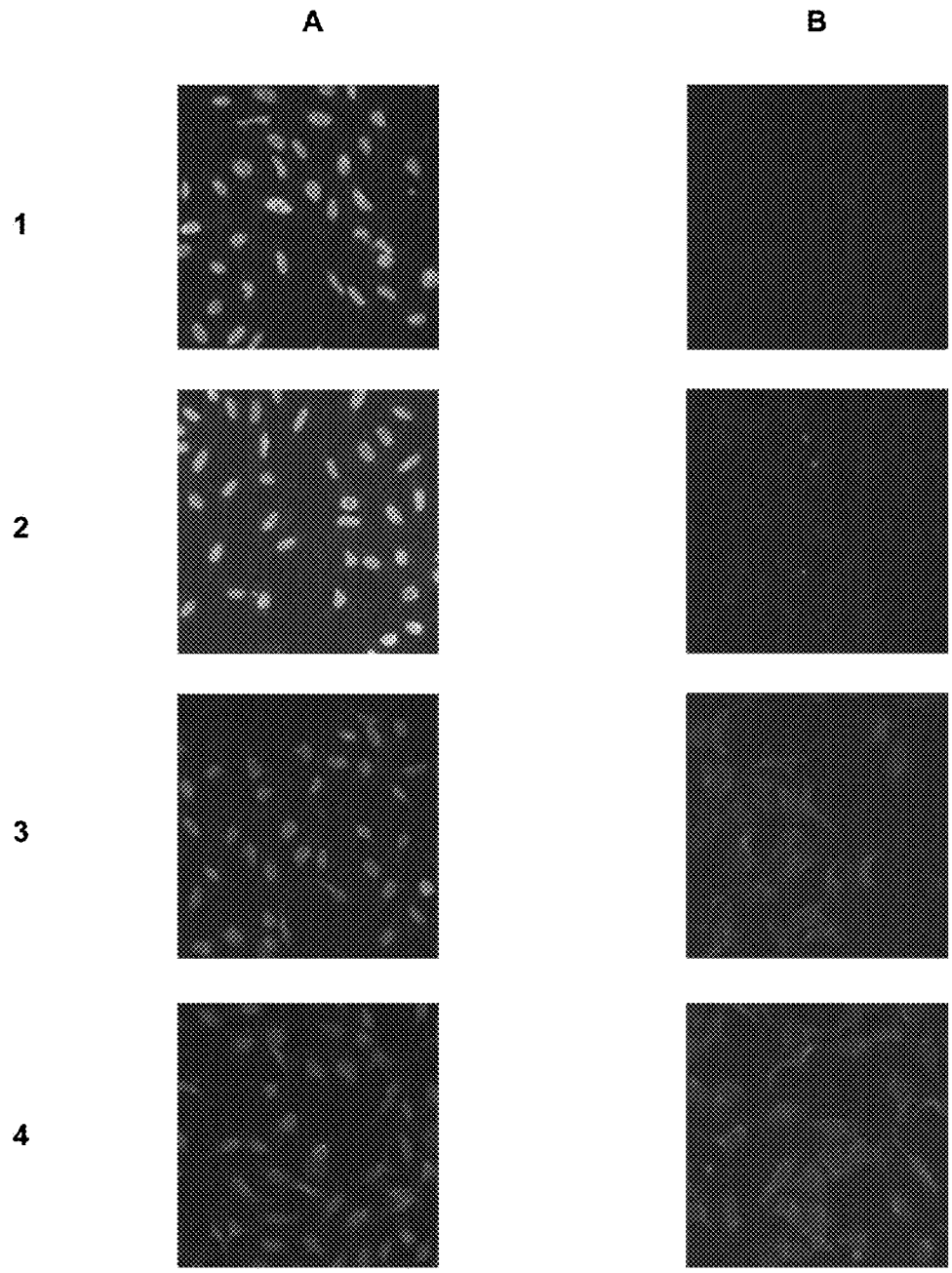
Figure 14E:
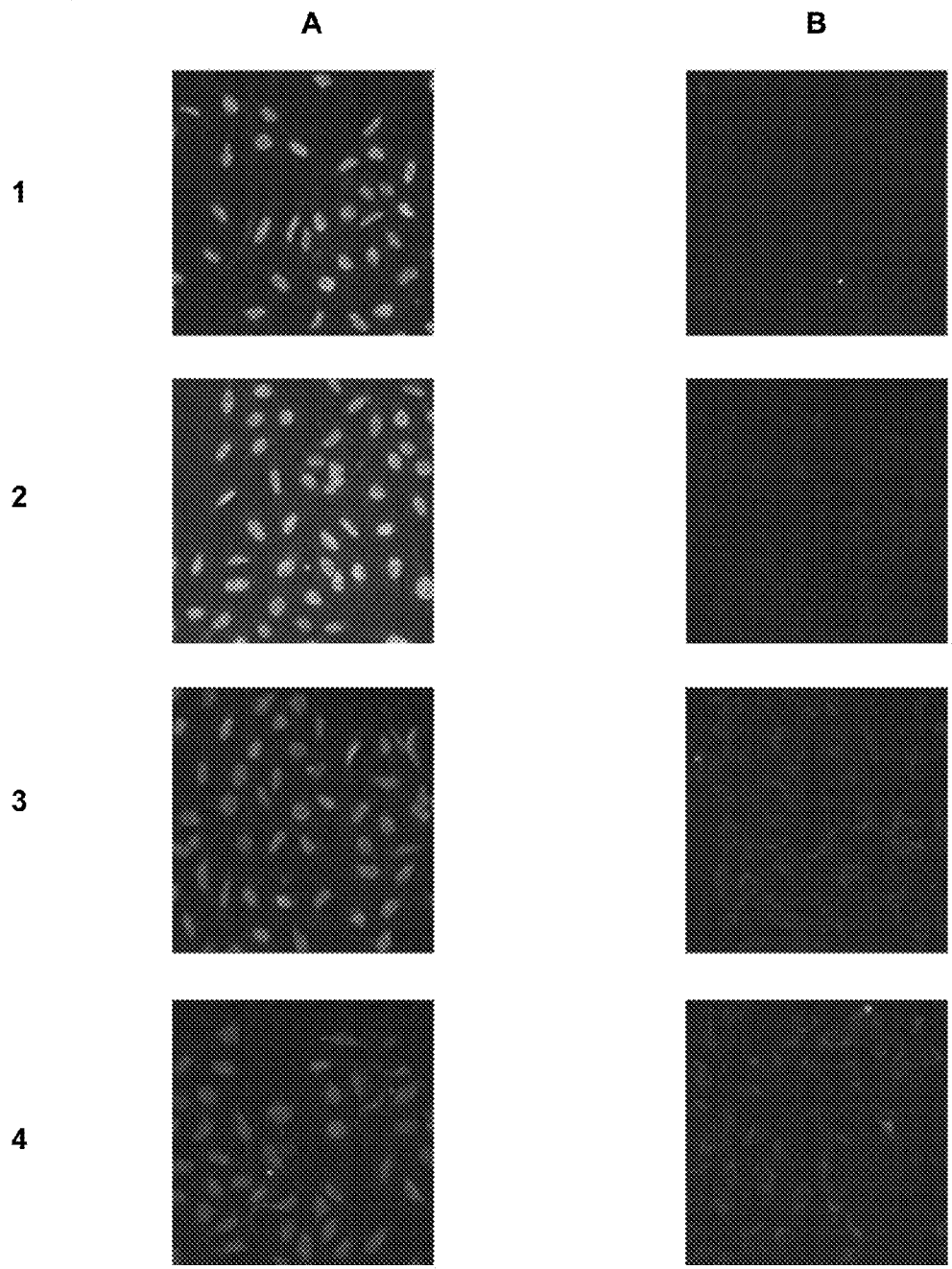

Average total unbound fluorescence intensity is shown in FIG. 12A, and corresponding plate image in FIG. 12B, showing 1 (755 Compound 4/4-GAR; 7× molar excess; D/P 2.22), 2 (DyLight 800-GAR; 7× molar excess; D/P 1.39), 3 (IR800-GAR (Rockland); D/P 2.6), and 4 (DyLight 800-GAR (Rockland); D/P 2.1). Average total bound fluorescence intensity is shown in FIG. 13A, with 755 Compound 4/4-GAR (diamonds; 7× molar excess; D/P 2.24), DyLight 800-GAR (circles; 7× molar excess; D/P 1.39), IR800-GAR (Rockland) (triangles; D/P 2.6), and DyLight 800-GAR (Rockland) (squares; D/P 2.1). FIG. 13B shows the plate image of FIG. 13A, showing 1 (755 Compound 4/4-GAR; 7× molar excess), 2 (DyLight 800-GAR; 7× molar excess), 3 (IR800-GAR (Rockland)), and 4 (DyLight 800-GAR (Rockland)). In the above functional fluorescence plate assays, 755 Compound 4/4-GAR showed significantly higher binding fluorescence intensity compared to DyLight 800-GAR conjugates in borate buffer. At similar D/P of about 2, 755 Compound 4/4-GAR performed better than IR800-GAR (conjugate made by Rockland using IR800 Dye from LiCOR; sold in lyophilized form) and DyLight 800-GAR (conjugate made by Rockland using DyLight 800; sold in lyophilized form). No quenching at high dye molar excesses was observed with 755 Compound 4/4.

Example 23

The inventive compounds and commercial dye were evaluated for immunofluorescence in cell based assays using the following protocol. Plates containing U2OS cells (human osteosarcoma cell line) were fixed in 4% paraformaldehyde in PBS/0.1% Triton X-100 for 15 min at room temperature. The cells were then permeabilized with 2% BSA in PBS/0.1% Triton X-100 for 15 min at room temperature. Negative controls contain only 2% BSA/PBS-0.1% Triton-X100 blocker. Diluted primary antibodies, mouse-anti-protein disulphide isomerase (PDI) or rabbit-anti-HDAC2, diluted in 2% BSA/PBS-0.1% Triton-X100 were added to the plates and incubated for one hour at room temperature. Negative controls contain only 2% BSA/PBS-0.1% Triton-X100 blocker. The plates were washed 3×100 µl with PBS. Based on the calculated protein concentrations, the conjugates made in Example 22 were diluted to 4 µg/ml in PBS/0.1% Triton X-100 and added to the plates (50 µl/well) and incubated one hour in the dark at room temperature. After incubation, the primary antibody solution was removed from the plates, and the plates were washed 3×100 µl with PBS. One hundred µl of 0.1 µg/ml Hoechst dye in PBS was added per well. The plates were then scanned on an ArrayScan® Plate Reader for imaging and quantitation.

FIGS. 14A-E shows results of an immunofluorescence assay using rabbit-anti-HDAC2 as a primary antibody, and either 650 Compound 4/4-GAR (FIG. 14A; column A), 650 Compound 1/1 (4S)-GAR (FIG. 14B; column A), CF 647-GAR (FIG. 14C; column A), Alexa Fluor 647-GAR (FIG. 14D; column A), or 650 Compound 1/1 (2S)-GAR (FIG. 14E; column A) as secondary antibody, with negative controls shown in column B, where the compound was conjugated to GAR (secondary antibody) at 2.5× molar excess (row 1), 5× molar excess (row 2), 10× molar excess (row 3), or 15× molar excess (row 4). Non-specific binding was observed with all the conjugates at high dye molar excesses. 650 Compound 4/4-GAR was not as bright as 650 Compound 1/1-GAR at the lower molar excesses 2.5× and 5×. However, 650 Compound 4/4-GAR did not appear to quench, which was observed with 650 Compound 1/1-GAR. CF 647-GAR and Alexa Fluor 647-GAR conjugates showed lower intensity at all molar excesses.

Figure 15:
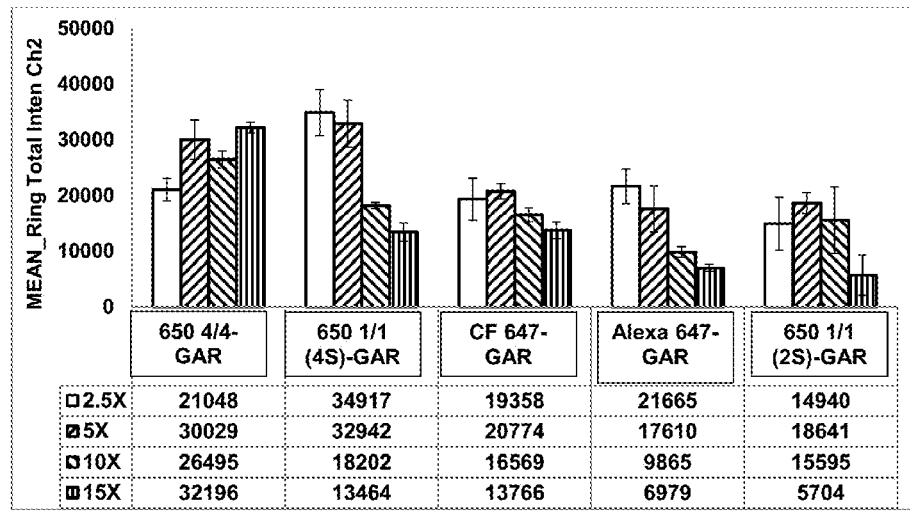
FIG. 15 shows the immunofluorescence assay results of FIG. 14 expressed as fluorescence intensity.
Figure 16:
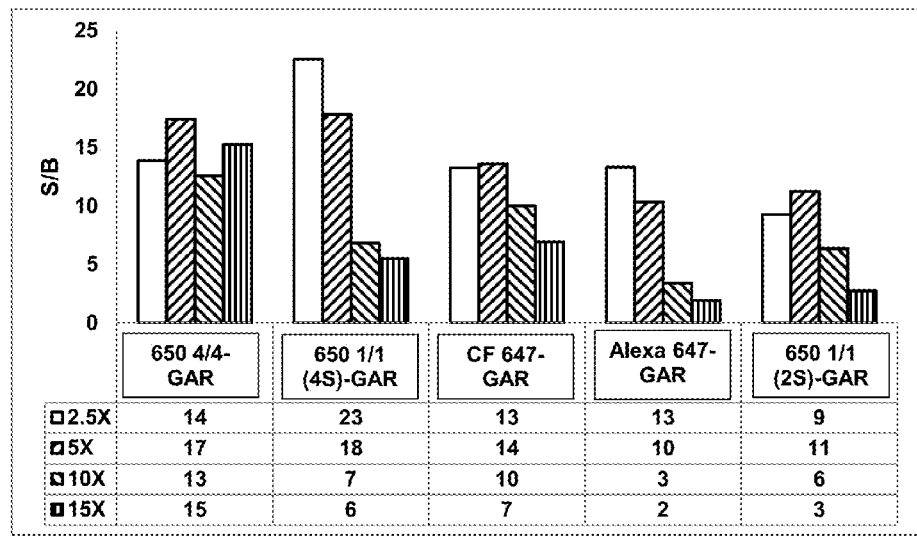
FIG. 16 shows the immunofluorescence assay results of FIG. 14 expressed as signal-to-background ratio.
Figure 17A:
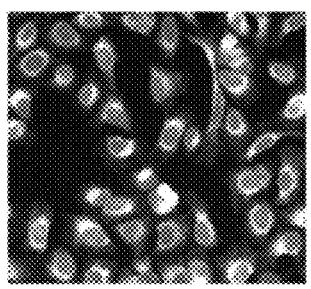
FIGS. 17A-D show immunofluorescence assay results with inventive compounds and commercial dyes in one embodiment.
Figure 17A:
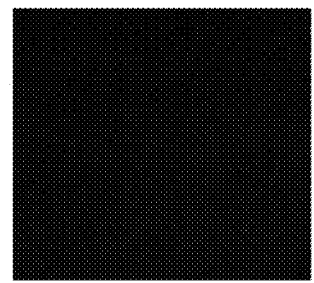
Figure 17A:
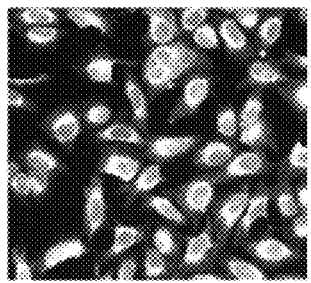
Figure 17A:
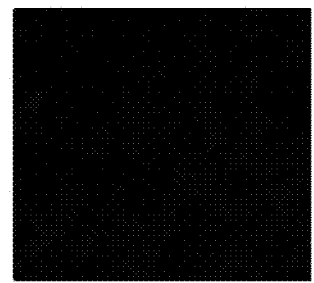
Figure 17A:
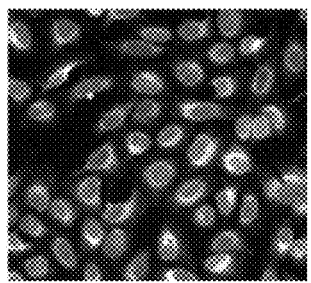
Figure 17A:
Figure 17A:
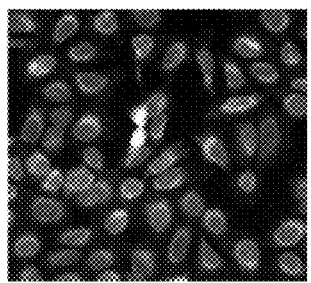
Figure 17A:
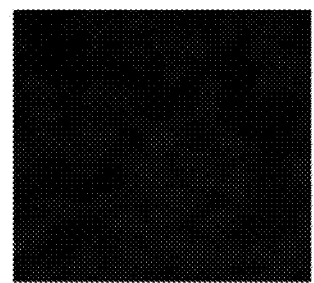
Figure 17B:
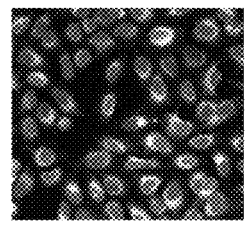
Figure 17B:
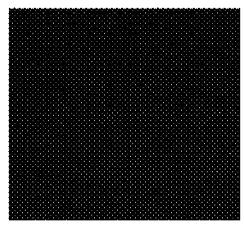
Figure 17B:
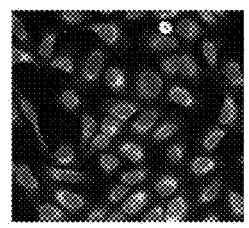
Figure 17B:
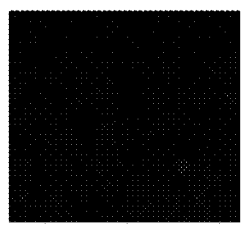
Figure 17B:
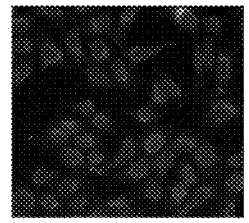
Figure 17B:
Figure 17B:
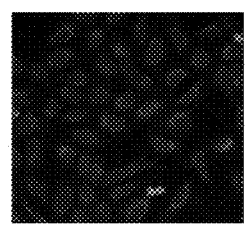
Figure 17B:
Figure 17C:
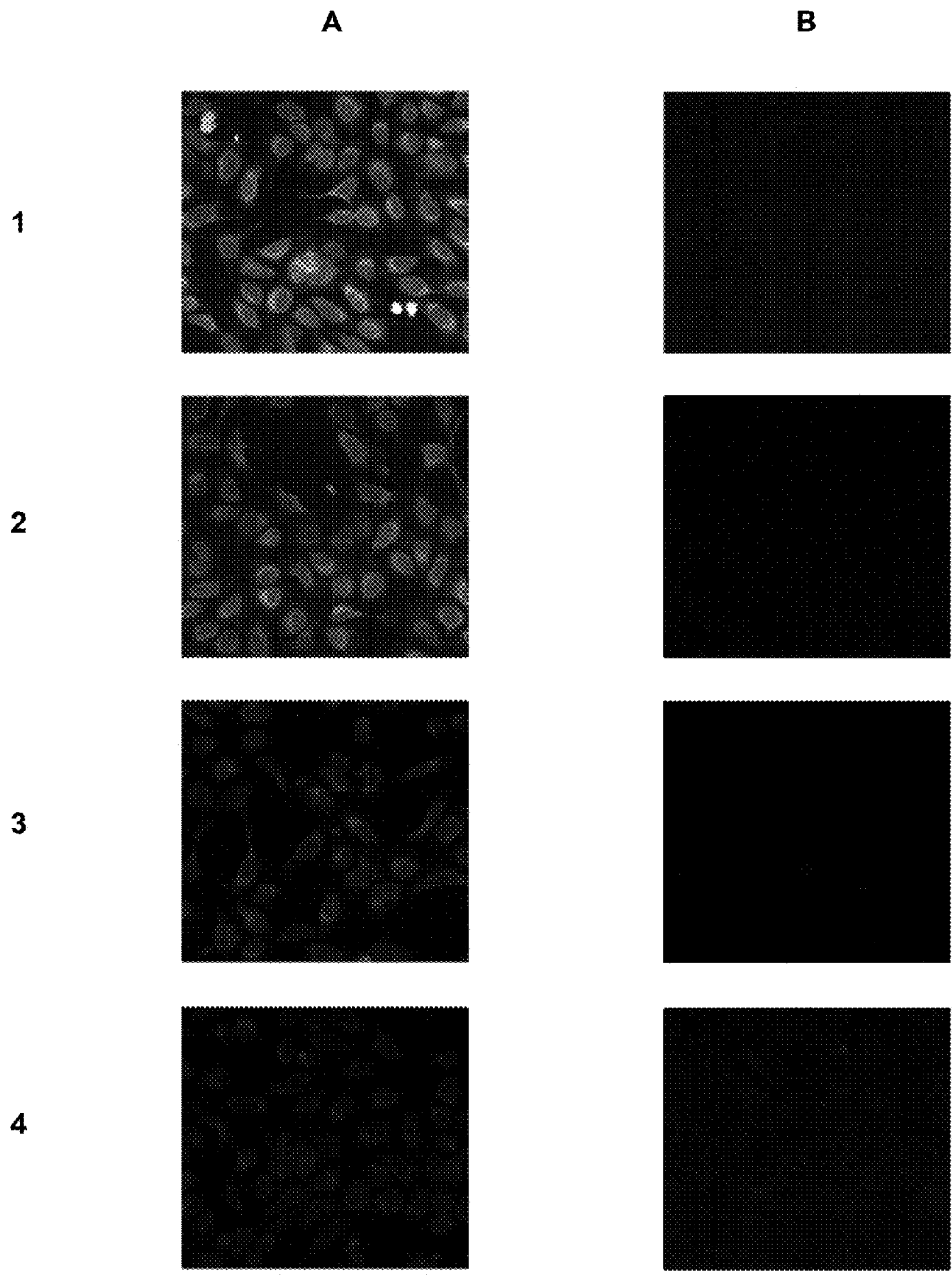
Figure 17D:
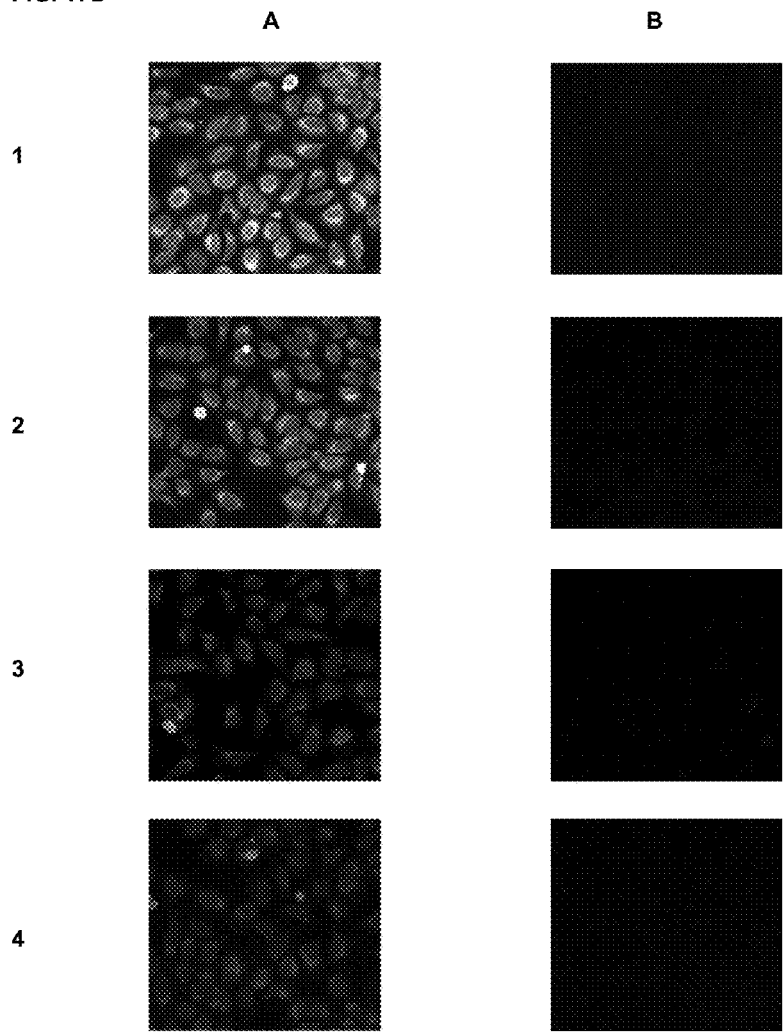

Quantitative analysis of the data of FIGS. 14A-E, expressed as Mean Total Intensity, which is the average total intensity of all pixels within a defined area or defined primary object such as a nucleus, is shown in FIG. 15, and signal to background ratio (S/B) is shown in FIG. 16, at molar excesses of 2.5× (open bars), 5× (upward diagonal lined bars), 10× (downward diagonal lined bars), and 15× (vertical lined bars). 650 Compound 1/1-GAR and 650 Compound 4/4-GAR showed the highest fluorescence intensity. While 650 Compound 4/4-GAR does not appear to quench, 650 Compound 1/1, CF 647, and Alexa Fluor 647 conjugates showed significant quenching at high molar excesses. CF 647-GAR and Alexa 647-GAR conjugates showed lower intensity at all molar excesses.

FIGS. 17A-D show immunofluorescence assay results using mouse-anti-PDI as a primary antibody, and either 650 Compound 4/4-GAR (FIG. 17A; column A), 650 Compound 1/1 (4S)-GAR (FIG. 17B; column A), CF 647-GAR (FIG. 17C; column A), or Alexa Fluor 647-GAR (FIG. 17D; column A) as secondary antibody, with negative controls shown in column B, where the compound was conjugated to GAM (secondary antibody) at 2.5× molar excess (row 1), 5× molar excess (row 2), 10× molar excess (row 3), or 15× molar excess (row 4). No non-specific binding was observed with any the dyes (purified with 200 µl of resin/mg of protein). 650 Compound 4/4-GAM was the brightest at all molar excesses. 650 Compound 1/1, CF 647, and Alexa Fluor 647 conjugates showed significant quenching above 2.5× molar excess. CF 647-GAM and Alexa 647-GAM conjugates showed lower intensity at all molar excesses.

Figure 18:
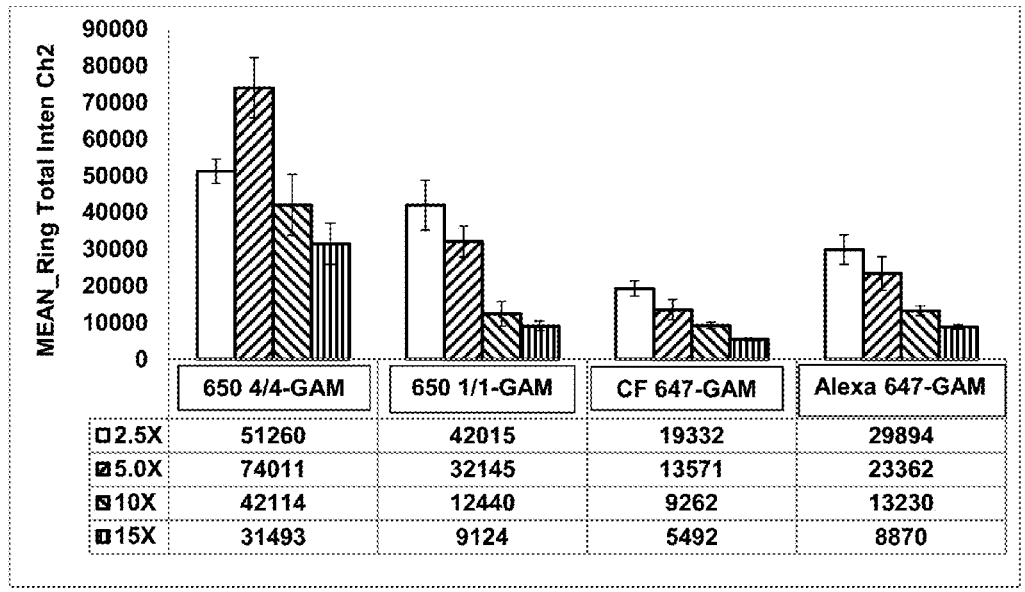
FIG. 18 shows the immunofluorescence assay results of FIG. 17 expressed as fluorescence intensity.
Figure 19:
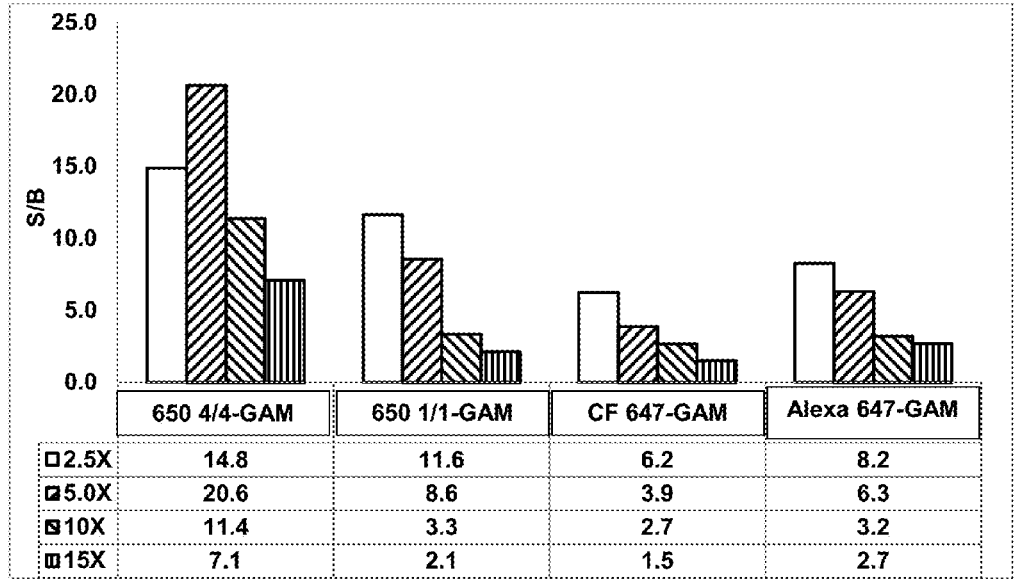
FIG. 19 shows the immunofluorescence assay results of FIG. 17 expressed as signal-to-background ratio.
Figure 20A:
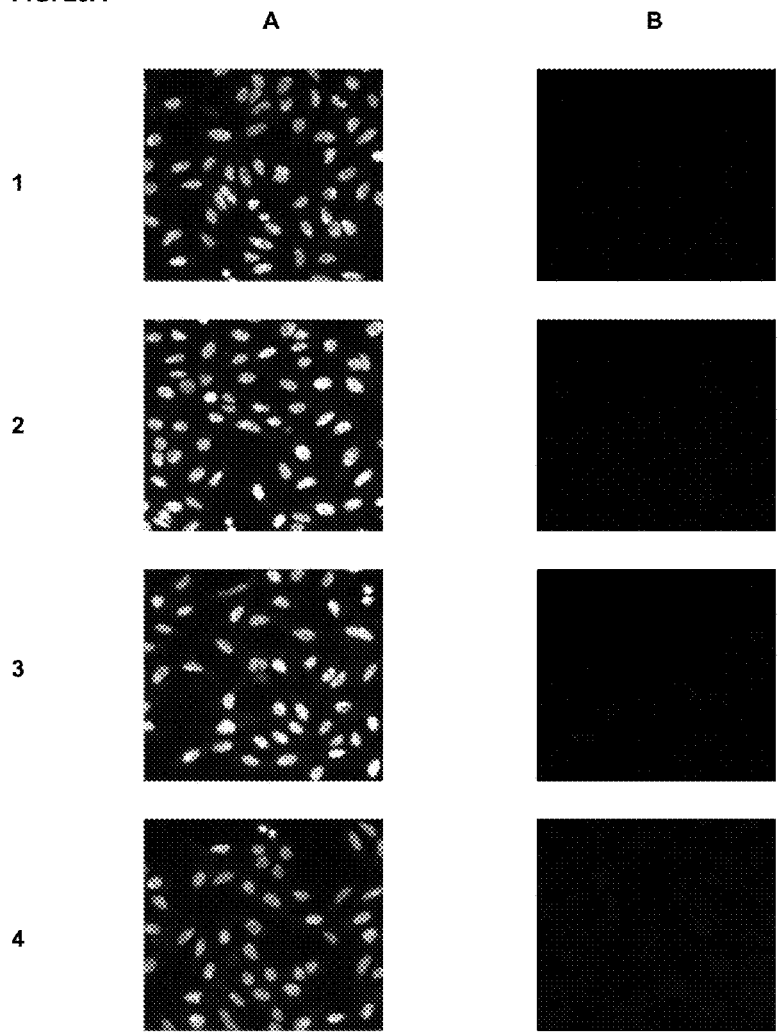
Figure 20C:
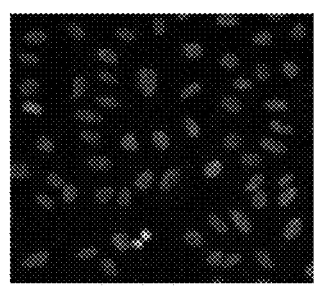
Figure 20C:
Figure 20C:
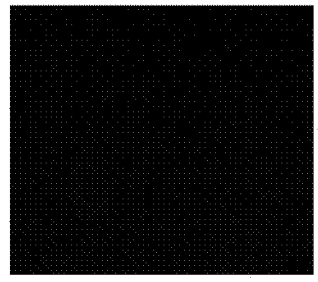
Figure 20C:
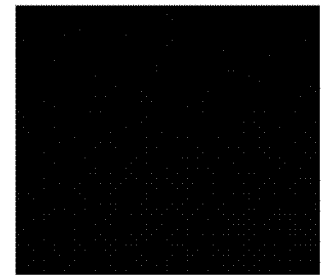
Figure 20C:
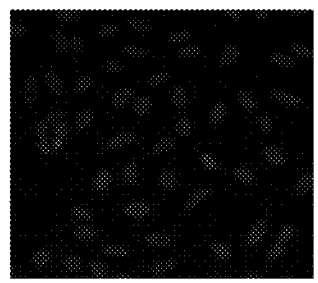
Figure 20C:
Figure 20C:
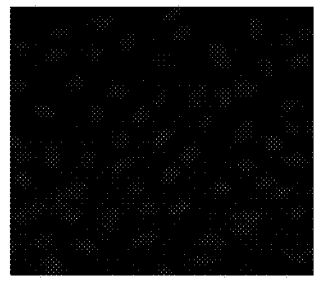
Figure 20C:
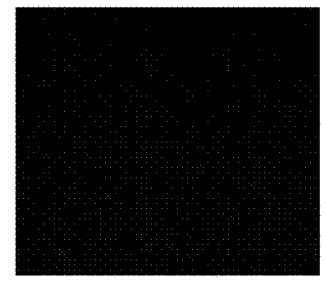
Figure 20D:
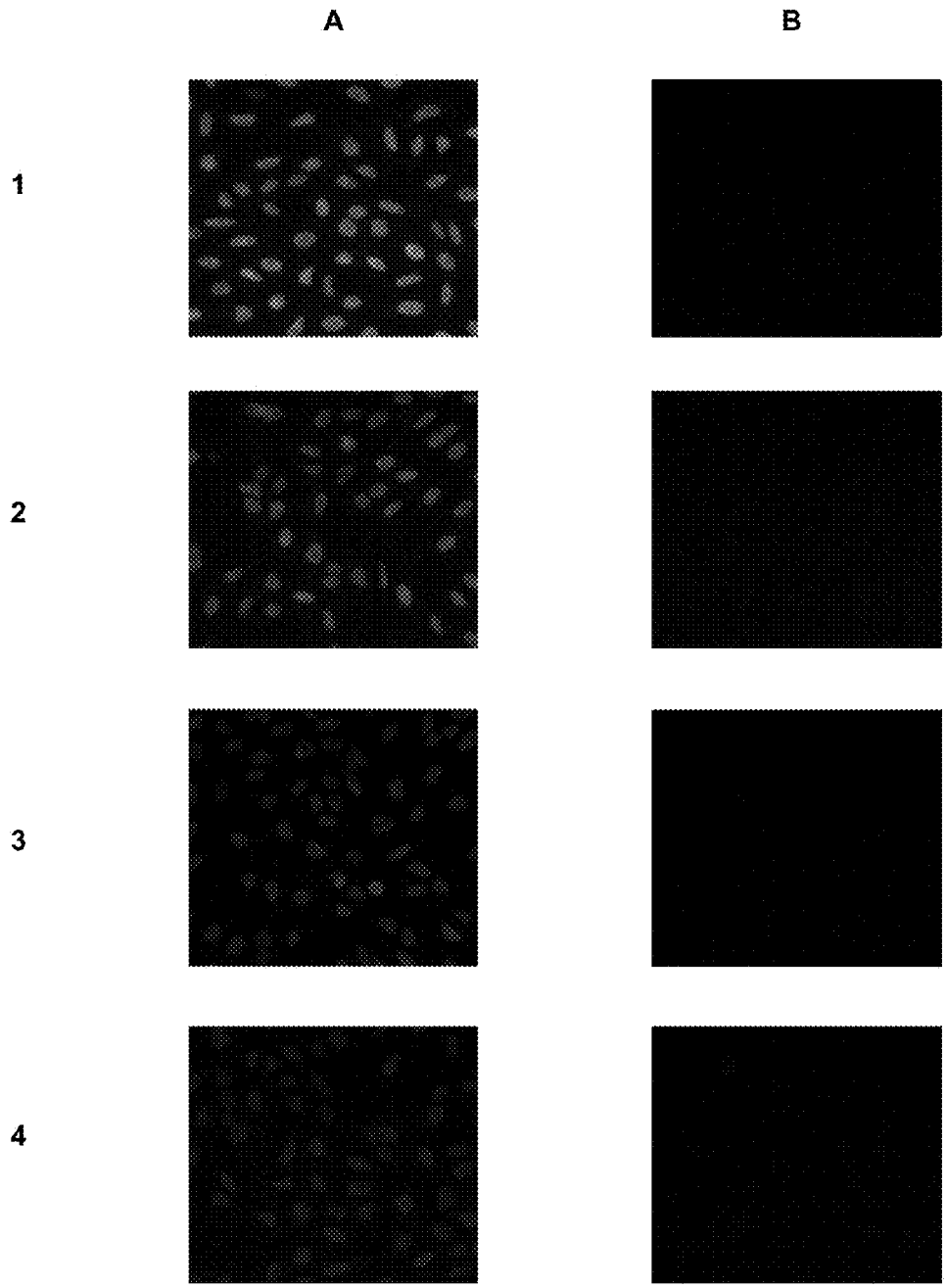

Quantitative analysis of the data of FIGS. 17A-D, expressed as Mean Total Intensity, which is the average total intensity of all pixels within a defined area or defined primary object such as a nucleus, is shown in FIG. 18 and signal to background ratio (S/B) is shown in FIG. 19, at molar excesses of 2.5× (open bars), 5× (upward diagonal lined bars), 10× (downward diagonal lined bars), and 15× (vertical lined bars). 650 Compound 1/1, CF 647, and Alexa Fluor 647 conjugates showing their highest binding intensity at 2.5× dye molar excess. 650 Compound 4/4-GAM was the brightest at all molar excesses. 650 Compound 4/4-GAM showed quenching above 5× molar excess, while 650 Compound 1/1, CF 647, and Alexa Fluor 647 conjugates showed significant quenching above 2.5× molar excess. CF 647-GAM and Alexa 647-GAM conjugates showed lower intensity at all molar excesses.

FIGS. 20A-D shows results of an immunofluorescence assay using rabbit-anti-HDAC2 as a primary antibody, and either 650 Compound 4/4-GAR (FIG. 20A; column A), 650 Compound 1/1 (4S)-GAR (FIG. 20B; column A), CF 647-GAR (FIG. 20C; column A), or Alexa Fluor 647-GAR (FIG. 20D; column A) as secondary antibody, with negative controls shown in column B, where the compound was conjugated to GAR (secondary antibody) at 2.5× molar excess (row 1), 5× molar excess (row 2), 10× molar excess (row 3), or 15× molar excess (row 4). No non-specific binding was observed with any of the conjugates (purified with 200 µl of resin/mg of protein). 650 Compound 4/4-GAR was the brightest at all molar excesses. 650 Compound 1/1, CF 647, and Alexa Fluor 647 conjugates showed significant quenching above 2.5× molar excess. CF 647-GAR and Alexa 647-GAR conjugates showed lower intensity at all molar excesses.

Figure 21:
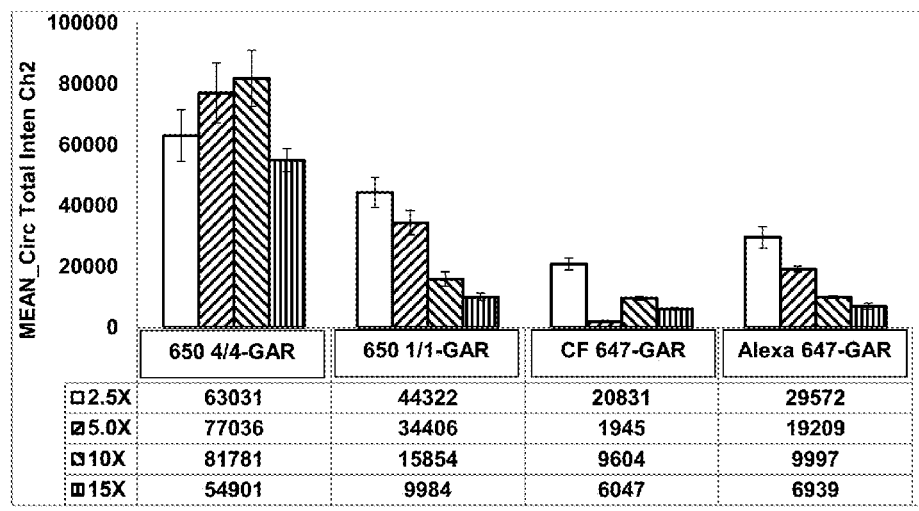
FIG. 21 shows the immunofluorescence assay results of FIG. 20 expressed as fluorescence intensity.
Figure 22:
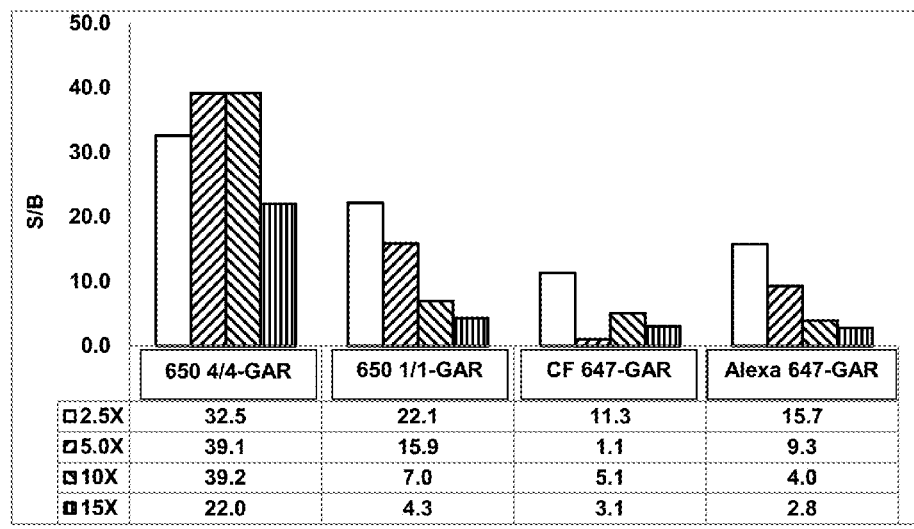
FIG. 22 shows the immunofluorescence assay results of FIG. 20 expressed as signal-to-background ratio.

Quantitative analysis of the data of FIGS. 20A-D, expressed as Mean Total Intensity, which is the average total intensity of all pixels within a defined area or defined primary object such as a nucleus, is shown in FIG. 21 and signal to background ratio (S/B) is shown in FIG. 22, at molar excesses of 2.5× (open bars), 5× (upward diagonal lined bars), 10× (downward diagonal lined bars), and 15× (vertical lined bars). 650 Compound 1/1, CF 647, and Alexa Fluor 647 conjugates showed the highest binding intensity at 2.5× dye molar excess, however 650 Compound 4/4 was the brightest at all molar excesses. While 650 Compound 4/4-GAR did not appear to quench, 650 Compound 1/1, CF 647, and Alexa Fluor 647 conjugates showed significant quenching above 2.5× molar excess. CF 647-GAR and Alexa 647-GAR conjugates showed lower intensity at all molar excesses.

The data indicated that excitation/emission spectra of 650 Compound 4/4-NHS was within +/−10 nm compared to 650 Compound 1/1-NHS, Alexa Fluor 647-NHS, and CF 647-NHS ester. Labeling efficiency of 650 Compound 4/4 was the highest, followed by 650 Compound 1/1, compared to the other dyes at each molar excess. 650 Compound 1/1 and CF 647 required extra time for complete solubility. 650 Compound 1/1-GAM/R was the best performing conjugate at all molar excesses. Up to 125 ng/well of mouse/rabbit IgG, 650 Compound 4/4-GAM showed similar binding fluorescence as 650 Compound 1/1-GAM and Alexa Fluor 647-GAM, but better than CF 647-GAM. CF 647 showed significantly lower performance of all dyes. When purified with 200 µl of resin/mg of protein, the conjugates did not show any non-specific binding. Conjugates made with 650 Compound 4/4 (GAM/R) were the brightest and showed the highest signal to background ratios. 650 Compound 1/1, CF 647, and Alexa Fluor 647 conjugates showed significant quenching above 2.5× molar excess. CF 647 and Alexa Flour 647 conjugates showed lower intensity at all molar excesses.

Example 24

The inventive compounds are evaluated for stability. All compounds are packed under argon in plastic vials. The vials are sealed with a drying pad in an aluminium coated pouch, and then stored at 50° C. for seven days.

Example 25

The inventive compounds are evaluated in direct fluorescence labeling of cell surface proteins using methods known in the art. For example, suitable cell plates, such as IMR90 cells (human lung embryonic fibroblast), are washed and then incubated with the conjugates. The cell plates are then washed and imaged using an appropriate instrument, such as a Thermo Scientific ArrayScan VTI HCS Reader.

Example 26

The inventive compounds are used for in vivo imaging to obtain information about biological tissues that are not readily accessible. The compounds are responsive to light in the near infrared (NIR) region of the spectrum, which is a part of the spectrum that has minimal interference from the absorbance of biological materials. In one embodiment, the compounds are used for fluorescent imaging of targets within animals. For example, in vivo imaging information can be obtained using methods such as X-ray, magnetic resonance imaging, positron emission tomography, ultrasound imaging and probing, and other non-invasive methods used for diagnosing and treating disease. Light in the NIR region, from about 650 nm to about 1000 nm wavelength, can permeate through several centimeters of tissue and therefore, can be used for in vivo imaging. Fluorescent dyes, such as the inventive compounds that are responsive to light in these longer wavelengths, can be used as conjugates with targeting molecules such as antibodies to bind and accumulate in, e.g., diseased tissue such as tumors, and may be used to distinguish healthy from diseased tissue. In some methods, the inventive compound may be attached to a biomolecule, such as a protein, peptide, or a drug, which is localized or retained in the desired tissue environment. Fluorescent in vivo imaging using NIR dyes such as the inventive compounds are diagnostic agents to discretely target disease tissue directly within animals or humans.

For in vivo imaging, the compound or a conjugate of the compound with a targeting agent, is administered to a tissue (e.g., intravenously), permitted to accumulate with excess compound removed by the circulatory system, then the tissue is irradiated with light at an appropriate wavelength. NIR fluorescent light is recorded and/or an image is generated from the data obtained to specifically detect and visualize the targeted cells or tissues. The dose of compound administered can differ depending upon the specific tissue, application, etc., as long as the method achieves a detectable concentration of the compound in the tissue to be assessed.

Example 27

The inventive dyes were evaluated in biodistribution and bioclearance studies. One mg NHS-DyLight 650 4/4 and NHS-DyLight 650 1/1 are reconstituted to 10 mg/ml and diluted to 1 mg/ml in PBS. The dyes are incubated for 30 minutes and then quenched by adding one-tenth volume of 3M N-ethanolamine. One hundred µL of 1 mg/mL of each hydrolyzed dye solution is intravenously injected via the retro orbital plexus of non-tumored nude mice. One mouse is injected for each dye. The animals are imaged on a Carestream MSFX at 0 h, 3 h, 6 h, 12 h, and 24 h post injection. After the final time point, animals are sacrificed and tissues collected for ex vivo imaging. The heart, liver, spleen, lungs, and kidneys are gathered from one mouse from each cohort, and fixed and stained using hematoxalin and eosin. Colorimetric images are acquired at 20× on a Nikon 90i microscope. The results show that the hydrolyzed NHS-DyLight 650 4/4 is removed from the circulatory system, whereas hydrolyzed NHS-DyLight 650 1/1 NHS-Alexa 647 accumulate in the liver.

Example 28

In Vivo Imaging Using 650 Compound 4/4 Conjugated to Anti-HER2 Antibody

650 Compound 4/4-NHS is conjugated to a rabbit anti-HER2 antibody (Genscript USA, Piscataway N.J.) by reconstituting the compound in dimethylformamide (DMF) at 10 mg/ml, then incubated at 10× molar excess with rabbit anti-HER2 antibody (0.1 mg) for 1 h at room temperature to result in a 650 Compound 4/4-anti-HER2 conjugate. The sample is then subjected to PDDR to remove unlabeled (free) 650 Compound 4/4. Ten microgram of the conjugate is injected intravenously (IV) to athymic mice bearing BT474 tumors. The animals are imaged overtime at 1, 24, 48, 72, 96, and 120 hours post-injection using Pearl Impulse Imager from LI-COR Biosciences (LI-COR Instruments, Lincoln Nebr.).

Upon whole body imaging, fluorescence intensity is observed to be distributed over the whole animal during the first hour imagining and diminishes significantly at 72 hours. After 96 hours, the signal is localized and specific to the tumor.

Example 29

In Vivo Imaging Using Either Monosulfonated or Disulfonated 650 Compound 4/4

The compound may be rendered less hydrophilic, i.e., more hydrophobic or less negatively charged, by altering the number of sulfonate groups. Fewer sulfonates render the compound more hydrophobic and less negatively charged. In this embodiment, the compound may be more readily retained in a desired tissue or location if the appropriate number of sulfonates is determined. For example, compound penetration into cells is more efficient if fewer sulfonates are on the compound. The compound may contain one, two, three, or four sulfonate groups. Hydrophobic compounds are also known to more efficiently cross the cell membrane, and therefore are more desirable when the target of interest is located within the cell.

Alendronate, a compound that binds to, and is retained in, LNCap prostate cancer cells, is conjugated with disulfonated or monosulfonated 650 Compound 4/4 by incubating a solution containing 1 mM disulfonated or monosulfonated 650 Compound 4/4-NHS in 1 ml of PBS and 0.5 ml tetrahydrofuran (THF) with 0.1 mM alendronate and 0.2 mM diisopropylethylamine at room temperature overnight. The conjugate is purified using reverse phase HPLC with 0-50% methanol against a 0.1 M ammonium acetate buffer, and is then lyophilized.

LNCap cells are grown orthotopically in nude mice. 650 Compound 1 (isomer 1)-alendronate (5 nmole) is injected into the tumor. Control mice are injected with free 650 Compound 4/4 containing a carboxylic acid residue instead of the reactive NHS ester. X-ray and near infra-red fluorescence images are captured.

Upon imaging the whole mouse, both the monosulfonated and disulfonated 650 Compound 4/4-alendroneate conjugate is retained in mouse tissue but the free dyes are not retained; the conjugate is retained in the LNCap cell-induced tumor for at least 18 hrs.

Example 30

In Vivo Imaging Using Either Monosulfonated or Disulfonated 650 Compound 4/4

A drug delivery nanoparticle system conjugated with disulfonated and monosulfonated 650 Compound 4/4 is prepared as follows. A solution containing 1 mM disulfonated or monosulfonated 650 Compound 4/4-NHS in 1 ml of PBS is incubated overnight at room temperature with 0.1 mM of an anti-cancer drug conjugated with transferrin in the form of a nanoparticle. The resulting 650 Compound 4/4-nanoparticle conjugates are purified by centrifugation, and then lyophilized.

The 650 Compound 4/4-nanoparticle conjugates (1 nmole) are injected intravenously into the tail vein of different mice. Control mice are injected with non-reactive 650 Compound 4/4 dye containing a carboxylic acid residue instead of a reactive NHS ester. X-ray and near infra-red fluorescence images of mouse brain are captured.

Both 650 Compound 4/4-nanoparticle conjugates are found to localize in the mouse brain for greater than about 24 hours after injection. Tumor size progressively decreases after injection of 650 Compound 4/4-nanoparticle conjugate, compared to 650 Compound 4/4-nanoparticle without the anti-cancer drug.

Example 31

The mono-sulfonated derivative could be on any one of six possible positions on the 650 compound, accounting for the stereochemistry around the carbon positions on the rings as well as the non-symmetrical nature of the two ends of each dye. Similarly, the di- and tri-substituted sulfonates could be on multiple possible positions on the inventive compounds.

Example 32

Log P (partition coefficient) and log D (distribution coefficient) of inventive and commercial compounds were determined to assess compound hydrophilicity. The log P value of a compound is the logarithm of a compound's partition coefficient between n-octanol and water $\log(C_{octanol}/C_{water})$, and is a well established measure of a compound's hydrophilicity. Log P is a constant for the molecule under its neutral form. Low hydrophilicity, and thus high log P, causes poor absorption or permeation. For compounds to have a reasonable probability of being well absorbed, their log P is generally <5.0. Lipophilicity is not determined by the partitioning of the neutral species in octanol/water, but by the distribution of both the neutral and positively charged forms of the molecule. Log D is related to hydrophilicity of a compound. The distribution coefficient, given by log D, takes into account all neutral and charged forms of the molecule. Because the charged forms generally do not enter the octanol phase, this distribution varies with pH. In the pH range where the molecule is mostly un-ionized, log D=log P. In the pH range where a significant fraction is ionized, log D becomes a function of log P, pH, and pKa. If one assumes that charged molecules do not enter the octanol at all, log D can be expressed as log D=log P−log(1+10**(pH−pKa)).

The following table provides theoretical calculated log D and log P values for 755 Compound 4/4 and DyLight 800 measured by the ChemAxon program.

| 755 Compound 4/4 | |
|---|---|
| pH | LogD |
| 1.50 | −1.43 |
| 5.00 | −1.77 |
| 6.50 | −1.77 |
| 7.40 | −1.77 |

LogP ionic species = −1.8
LogP nonionic species = 1.0 (3.2 considering tautomerization/resonance)
LogD at pI = 0.2 (2.4 considering tautomerization/resonance)

| DyLight 800 | |
|---|---|
| pH | LogD |
| 1.50 | 1.44 (1.42 considering tautomerization/resonance) |
| 5.00 | −0.31 |
| 6.50 | −0.32 |
| 7.40 | −0.32 |

LogP ionic species = −0.3
LogP nonionic species = 2.4 (4.7 considering tautomerization/resonance)
LogD at pI = 2.8 (5.1 considering tautomerization/resonance)

The log P and log D calculations comparing 755 Compound 4/4 with four PEG$_4$ chains and the DyLight 800 dye from Thermo Fisher with no PEG modifications illustrates the unexpected benefits that even short PEG$_4$ chains have on the hydrophilicity of cyanine-type dyes. Although the literature teaches the hydrophilicity benefits of longer PEG polymer modifications on small dye molecules, it does not suggest that such benefits occur with short PEG chains. The DyLight 800 dye calculation of log D indicated that the three sulfonates on the molecule resulted in a mildly hydrophilicity index of −0.32 around neutral pH. By contrast, 755 Compound 4/4 displayed much better hydrophilicity with a log D determination of −1.77 at the same neutral pH values. This calculated difference in the hydrophilicity corresponded to observed results that the PEGylated dye goes into aqueous solution much more readily that the more hydrophobic DyLight 800 dye. Increased solubility of the PEGylated dye was also seen when dissolving the dyes in a water-miscible organic solvent such as DMF or DMSO. Conjugates of 755 Compound 4/4 with antibody molecules were much more stable in solution at all levels of dye-to-protein ratios than the DyLight 800 conjugates. In fact, DyLight 800-antibody conjugates tended to precipitate out of solution during the conjugation reaction and had stability issues upon storage, whereas 755 Compound 4/4-antibody conjugates did not precipitate during conjugation and did not have storage stability issues. These observations emphasized the unexpected benefits the invention provided for cyanine dye compounds modified with the relatively short PEG chains described herein.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. A compound selected from the group consisting of

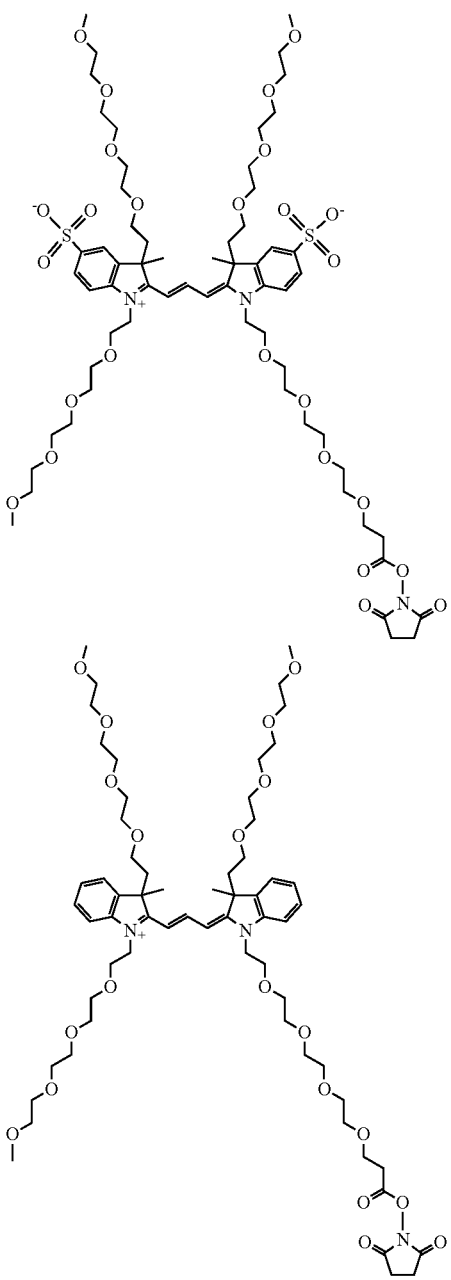

197
-continued
V19-03005
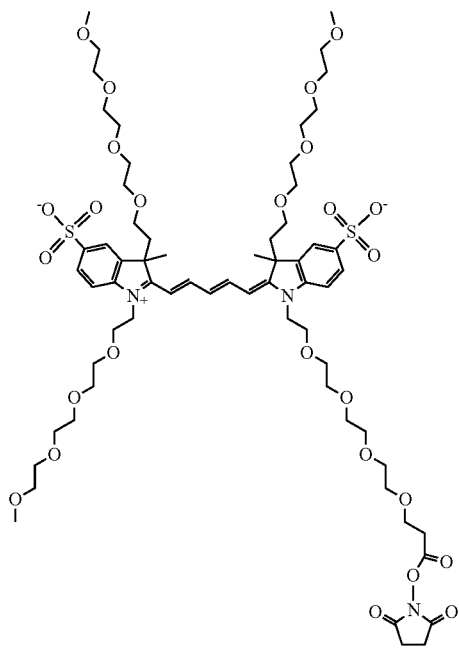
198
-continued
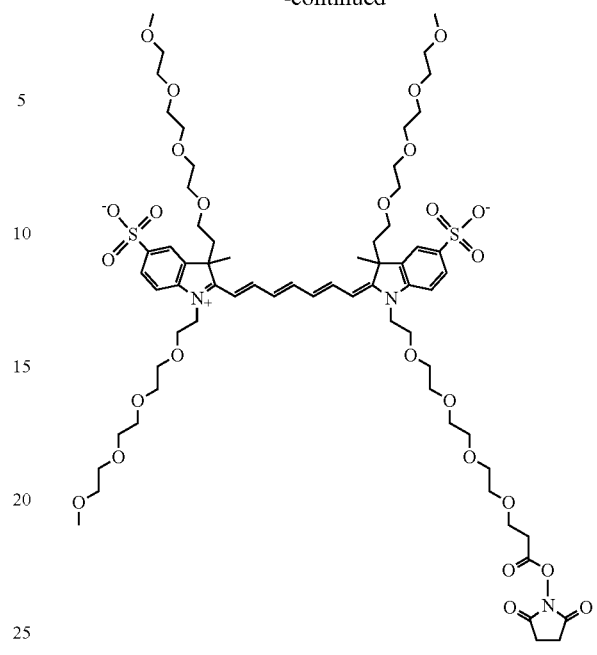
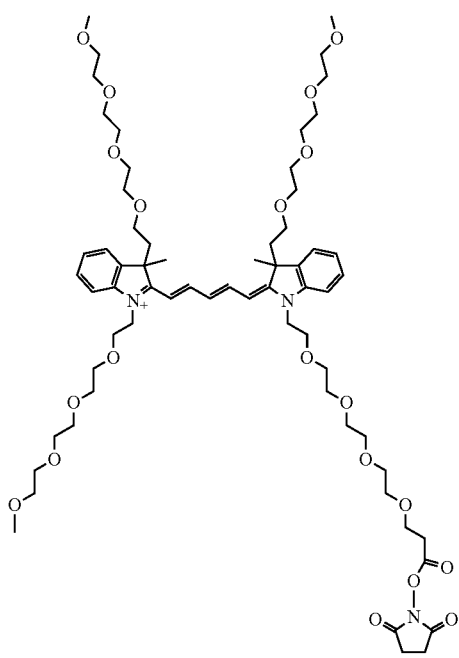 [SMILES: COCCOCCOCCOCC[N+]1=C(/C=C/C=C/C=C2/N(CCOCCOCCOCCOCCC(=O)ON3C(=O)CCC3=O)c3ccccc3C2(C)CCOCCOCCOCCOC)C(C)(CCOCCOCCOCCOC)c2ccccc21]
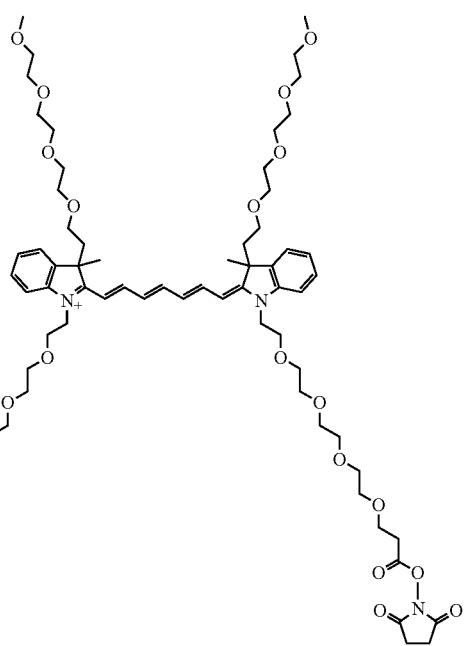
and -continued

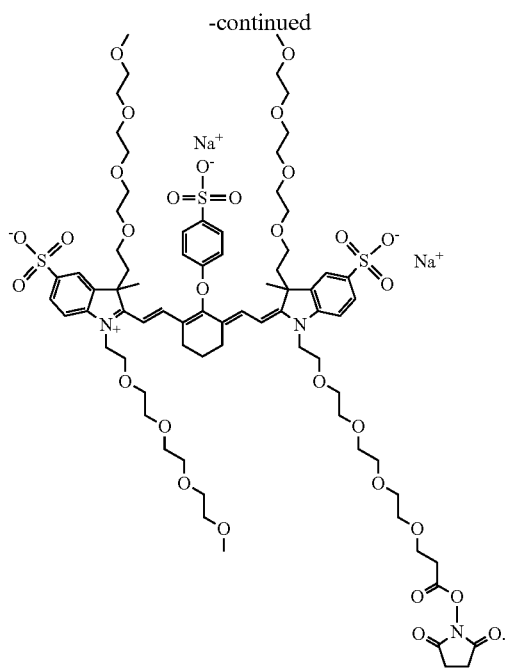

2. A method of labeling at least one biomolecule, the method comprising combining a composition comprising at least one excipient and the compound of claim 1 in an effective concentration to label at least one biomolecule under conditions sufficient for labeling the biomolecule with the compound.

3. The method of claim 2 wherein the biomolecule is selected from the group consisting of a protein, antibody, enzyme, nucleoside triphosphate, oligonucleotide, biotin, hapten, cofactor, lectin, antibody binding protein, carotenoid, carbohydrate, hormone, neurotransmitter, growth factors, toxin, biological cell, lipid, receptor binding drug, fluorescent proteins, organic polymer carrier material, inorganic carrier material, and combinations thereof.

4. The method of claim 2 wherein the compound is V19-03005.

5. A method of detecting at least one biomolecule, the method comprising combining a composition comprising at least one excipient and the compound of claim 1 in an effective concentration to detect at least one biomolecule under conditions sufficient for binding the compound to the biomolecule, and detecting the biomolecule-bound compound.

6. The method of claim 5 wherein the biomolecule is selected from a protein, antibody, enzyme, nucleoside triphosphate, oligonucleotide, biotin, hapten, cofactor, lectin, antibody binding protein, carotenoid, carbohydrate, hormone, neurotransmitter, growth factors, toxin, biological cell, lipid, receptor binding drug, fluorescent proteins, organic polymer carrier material, inorganic carrier material, and combinations thereof.

7. The method of claim 5 wherein the at least one biomolecule is detected in an assay selected from fluorescence microscopy, flow cytometry, in vivo imaging, immunoassay, hybridization, chromatographic assay, electrophoretic assay, microwell plate based assay, fluorescence resonance energy transfer (FRET) system, bioluminescence resonance energy transfer (BRET) system, high throughput screening, or microarray.

8. The method of claim 5 wherein the biomolecule is detected by in vivo imaging comprising administering the biomolecule-bound compound to at least one of a biological sample, tissue, or organism, and detecting the biomolecule within the at least one of a biological sample, tissue, or organism.

9. The method of claim 5 wherein the compound is V19-03005.

10. A kit for labeling and/or detecting at least one biomolecule in a sample, the kit comprising the compound of claim 1 and at least one excipient.

11. The kit of claim 10 wherein the compound is V19-03005.

* * * * *